(12) United States Patent
Narain et al.

(10) Patent No.: US 11,224,641 B2
(45) Date of Patent: *Jan. 18, 2022

(54) ENOLASE 1 (ENO1) COMPOSITIONS AND USES THEREOF

(71) Applicant: Berg LLC, Framingham, MA (US)

(72) Inventors: Niven Rajin Narain, Cambridge, MA (US); Rangaprasad Sarangarajan, Boylston, MA (US); Vivek K. Vishnudas, Bedford, MA (US); Stephane Gesta, Arlington, MA (US); Enxuan Jing, West Roxbury, MA (US)

(73) Assignee: Berg LLC, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/202,989

(22) Filed: Nov. 28, 2018

(65) Prior Publication Data

US 2019/0307863 A1 Oct. 10, 2019

Related U.S. Application Data

(63) Continuation of application No. 14/596,208, filed on Jan. 13, 2015, now Pat. No. 10,188,708.

(60) Provisional application No. 62/100,881, filed on Jan. 7, 2015, provisional application No. 62/009,783, filed on Jun. 9, 2014, provisional application No. 61/926,913, filed on Jan. 13, 2014.

(51) Int. Cl.
| | |
|---|---|
| *A61K 38/51* | (2006.01) |
| *A61K 49/00* | (2006.01) |
| *A61K 38/00* | (2006.01) |
| *A61K 9/00* | (2006.01) |
| *C12N 9/88* | (2006.01) |
| *C12Q 1/54* | (2006.01) |
| *A61K 47/59* | (2017.01) |
| *A61K 47/64* | (2017.01) |

(52) U.S. Cl.
CPC ............ *A61K 38/51* (2013.01); *A61K 9/0019* (2013.01); *A61K 9/0053* (2013.01); *A61K 38/00* (2013.01); *A61K 47/59* (2017.08); *A61K 47/64* (2017.08); *A61K 49/0008* (2013.01); *C12N 9/88* (2013.01); *C12Q 1/54* (2013.01); *C12Y 402/01011* (2013.01); *G01N 2333/988* (2013.01); *G01N 2800/042* (2013.01)

(58) Field of Classification Search
None
See application file for complete search history.

(56) References Cited

U.S. PATENT DOCUMENTS

| | | |
|---|---|---|
| 5,552,524 A | 9/1996 | Basinski et al. |
| 6,329,501 B1 | 12/2001 | Smith et al. |
| 7,645,453 B2 | 1/2010 | Shih et al. |
| 8,003,096 B2 | 8/2011 | Carmeliet et al. |
| 8,071,721 B2 | 12/2011 | Novelli et al. |
| 8,124,073 B2 | 2/2012 | Stefano |
| 10,188,707 B2 | 1/2019 | Narain et al. |
| 10,188,708 B2 | 1/2019 | Narain et al. |
| 2003/0044795 A1 | 3/2003 | Byrajalsen et al. |
| 2003/0203372 A1 | 10/2003 | Ward et al. |
| 2004/0204356 A1 | 10/2004 | Guenzler-Pukall et al. |
| 2004/0219572 A1 | 11/2004 | Chen et al. |
| 2004/0236091 A1 | 11/2004 | Chicz et al. |
| 2005/0191627 A1 | 9/2005 | Yang et al. |
| 2005/0222023 A1 | 10/2005 | Hauser et al. |
| 2006/0263336 A1 | 11/2006 | Caplan |
| 2007/0122810 A1 | 5/2007 | Iwadate et al. |
| 2007/0162985 A1 | 7/2007 | Mose Larsen et al. |
| 2007/0248628 A1 | 10/2007 | Keller et al. |
| 2008/0138913 A1 | 6/2008 | Jeon et al. |
| 2009/0061465 A1 | 3/2009 | Cho et al. |
| 2009/0110662 A1 | 4/2009 | Breitenkamp et al. |
| 2009/0208507 A1 | 8/2009 | Rohlff |
| 2009/0221505 A1 | 9/2009 | Kolonin et al. |
| 2009/0227655 A1 | 9/2009 | Khan |
| 2010/0047256 A1 | 2/2010 | Lundberg et al. |
| 2010/0184948 A1 | 7/2010 | Heemskerk et al. |

(Continued)

FOREIGN PATENT DOCUMENTS

| | | |
|---|---|---|
| CN | 1720052 A | 1/2006 |
| EP | 1284298 A2 | 2/2003 |

(Continued)

OTHER PUBLICATIONS

Giallongo et al., "Molecular cloning and nucleotide sequence of a full-length cDNA for human a enolase", PNAS, 1986, vol. 83, pp. 6741-6745.*

Chen et al., Fusion protein linkers: property, design and functionality. Adv Drug Deliv Rev. Oct. 2013;65(10):1357-69.

Cho et al., ENOblock, a unique small molecule inhibitor of the non-glycolytic functions of enolase, alleviates the symptoms of type 2 diabetes. Scientific Reports. Mar. 8, 2017;7:44186, 16 pages.

(Continued)

*Primary Examiner* — Suzanne M Noakes
(74) *Attorney, Agent, or Firm* — McCarter & English, LLP; Jill Mello

(57) ABSTRACT

The invention provides compositions comprising Eno1 for delivery to a muscle. Further, the invention provides a method for normalizing blood glucose in a subject with elevated blood glucose, comprising administering to the subject enolase 1 (Eno1), thereby normalizing blood glucose in the subject. The invention also provides methods of treating one or more conditions including impaired glucose tolerance, insulin resistance, pre-diabetes, and diabetes, especially type 2 diabetes in a subject, comprising administering to the subject enolase 1 (Eno1), thereby treating the condition in the subject. In certain methods of the invention, the Eno1 is delivered to muscle.

16 Claims, 50 Drawing Sheets

Specification includes a Sequence Listing.

(56) References Cited

U.S. PATENT DOCUMENTS

| | | |
|---|---|---|
| 2011/0053787 A1 | 3/2011 | Brulliard et al. |
| 2011/0130346 A1 | 6/2011 | Wood et al. |
| 2011/0178005 A1 | 7/2011 | Yamka et al. |
| 2011/0269665 A1 | 11/2011 | Kole |
| 2012/0128677 A1 | 5/2012 | Domon et al. |
| 2012/0164146 A1 | 6/2012 | Novelli et al. |
| 2012/0183552 A1 | 7/2012 | Joseloff et al. |
| 2012/0309684 A1 | 12/2012 | Wood et al. |
| 2013/0004427 A1 | 1/2013 | El-Sayed et al. |
| 2013/0078654 A1 | 3/2013 | Lundberg et al. |
| 2014/0030287 A1 | 1/2014 | McNeely et al. |
| 2014/0086895 A1 | 3/2014 | Vittecoq et al. |
| 2016/0375113 A1 | 12/2016 | Narain et al. |
| 2017/0014495 A1 | 1/2017 | Sarangarajan et al. |
| 2019/0307864 A1 | 10/2019 | Narain et al. |

FOREIGN PATENT DOCUMENTS

| | | |
|---|---|---|
| EP | 1350523 A2 | 10/2003 |
| EP | 2194382 A1 | 6/2010 |
| JP | 2003-522183 A | 7/2003 |
| JP | 2004-081111 A | 3/2004 |
| JP | 2009-256324 A | 11/2009 |
| JP | 2010-533171 A | 10/2010 |
| WO | 1996/12737 A2 | 5/1996 |
| WO | 2001/016322 A2 | 3/2001 |
| WO | 2001/016323 A2 | 3/2001 |
| WO | 2001/30973 A2 | 5/2001 |
| WO | 2003/064501 A1 | 8/2003 |
| WO | 2004/043361 A2 | 5/2004 |
| WO | 2004/052284 A2 | 6/2004 |
| WO | 2004/061088 A2 | 7/2004 |
| WO | 2005/019258 A2 | 3/2005 |
| WO | 2006/073254 A1 | 7/2006 |
| WO | 2009/144481 A2 | 12/2009 |
| WO | 2011/147981 A2 | 12/2011 |
| WO | 2012/152882 A1 | 11/2012 |
| WO | 2013/021210 A1 | 2/2013 |
| WO | 2013/030569 A2 | 3/2013 |
| WO | 2013/090732 A2 | 6/2013 |
| WO | 2014/018851 A1 | 1/2014 |
| WO | 2014/070723 A1 | 5/2014 |
| WO | 2015/106295 A2 | 7/2015 |
| WO | 2016/210008 A1 | 12/2016 |

OTHER PUBLICATIONS

Díaz-Ramos et al., alpha-Enolase, a multifunctional protein: its role on pathophysiological situations. J Biomed Biotechnol. 2012;2012:156795. 12 pages.

Elkins et al., X-ray crystal structure of ERK5 (MAPK7) in complex with a specific inhibitor. J Med Chem. Jun. 13, 2013;56(11):4413-21.

Jung et al., A unique small molecule inhibitor of enolase clarifies its role in fundamental biological processes. ACS Chem Biol. 2013;8(6):1271-82.

Koves et al., Mitochondrial overload and incomplete fatty acid oxidation contribute to skeletal muscle insulin resistance. Cell Metabolism. Jan. 2008;7:45-56.

Lee et al., Human alpha-enolase from endothelial cells as a target antigen of anti-endothelial cell antibody in Behçet's disease. Arthritis Rheum. Jul. 2003;48(7):2025-35.

Lu et al., Oxidative and nitrative modifications of alpha-enolase in cardiac proteins from diabetic rats. Free Radic Biol Med. Apr. 1, 2010;48(7):873-81.

Mu et al., Molecular insight into the steric shielding effect of PEG on the conjugated staphylokinase: biochemical characterization and molecular dynamics simulation. PLoS One. Jul. 18, 2013;8(7):e68559, 10 pages.

RCSB, PDB—Protein Data Bank, 3B97, Crystal Structure of Human Enolase 1. 8 pages, Sep. 16, 2008.

Subramanian et al., Structural analysis of alpha-Enolase. Mapping the Functional Domains Involved in Down-regulation of the c-myc Photooncogene. The Journal of Biological Chemistry Feb. 25, 2000;275(8):5958-5965.

Thangarajah et al., The molecular basis for impaired hypoxia-induced VEGF expression in diabetic tissues. Proc Natl Acad Sci U S A. Aug. 11, 2009;106(32):13505-10.

Van Vught et al., Site-specific Functionalization of Proteins and Their Applications to Therapeutic Antibodies. Comput Struct Biotechnol J. Feb. 14, 2014;9:e201402001, 13 pages.

\* cited by examiner

Maximal reduction of blood glucose was observed at 4 hrs after injection of eno1

Basal state | Enhanced Eno1 Activity

Eno1 - Nampt interaction in skeletal muscle myotubes

FIG. 34A

LOCUS    NM_001428        2204 bp    mRNA    linear    PRI 10-JAN-2014

DEFINITION Homo sapiens enolase 1, (alpha) (ENO1), transcript variant 1, mRNA.

ACCESSION   NM_001428 NM_005945

VERSION    NM_001428.3 GI:319996653

```
  1 msilkihare ifdsrgnptv evdlftskgl fraavpsgas tgiyealelr dndktrymgk
 61 gvskavehin ktiapalvsk klnvteqeki dklmiemdgt enkskfgana ilgvslavck
121 agavekgvpl yrhiadlagn sevilpvpaf nvinggshag nklamqefmi lpvgaanfre
181 amrigaevyh nlknvikeky gkdatnvgde ggfapnilen keglellkta igkagytdkv
241 vigmdvaase ffrsgkydld fkspddpsry ispdqladly ksfikdypvv siedpfdqdd
301 wgawqkftas agiqvvgddl tvtnpkriak avnekscncl llkvnqigsv teslqackla
361 qangwgvmvs hrsgetedtf iadlvvglct gqiktgapcr serlakynql lrieeelgsk
421 akfagrnfrn plak
```

FIG. 34B

LOCUS       NM_001428             2204 bp    mRNA    linear   PRI 10-JAN-2014

DEFINITION  Homo sapiens enolase 1, (alpha) (ENO1), transcript variant 1, mRNA.

ACCESSION   NM_001428 NM_005945

VERSION     NM_001428.3  GI:319996653

```
   1 gtggggcccc agagcgacgc tgagtgcgtg cgggactcgg agtacgtgac ggagccccga
  61 gctctcatgc ccgccacgcc gccccgggcc atccccgga gccccggctc cgcacacccc
 121 agttcggctc accggtccta tctggggcca gagtttcgcc cgcaccacta cagggccgct
 181 ggggagtcgg ggcccccag atctgcccgc ctcaagtccg cgggacgtca ccccccttc
 241 cacgctactg cagccgtcgc agtcccaccc cttccggga ggtgagggaa tgagtgacgg
 301 ctctcccgac gaatggcgag gcggagctga ggggcgtgc cccggaggcg ggaagtgggt
 361 ggggctcgcc ttagctaggc aggaagtcgg cgcgggcggc gcggacagta tctgtgggta
 421 cccggagcac ggagatctcg ccggctttac gttcacctcg gtgtctgcag caccctccgc
 481 ttcctctcct aggcgacgag acccagtggc tagaagttca ccatgtctat tctcaagatc
 541 catgccaggg agatctttga ctctcgcggg aatcccactg ttgaggttga tctcttcacc
 601 tcaaaaggtc tcttcagagc tgctgtgccc agtggtgctt caactggtat ctatgaggcc
 661 ctagagctcc gggacaatga taagactcgc tatatgggga agggtgtctc aaaggctgtt
 721 gagcacatca taaaactat tgcgcctgcc ctggttagca gaaactgaa cgtcacagaa
 781 caagagaaga ttgacaaact gatgatcgag atggatggaa cagaaaataa atctaagttt
 841 ggtgcgaacg ccattctggg ggtgtccctt gccgtctgca agctggtgc cgttgagaag
 901 ggggtccccc tgtaccgcca catcgctgac ttggctggca actctgaagt catcctgcca
 961 gtcccggcgt tcaatgtcat caatggcggt tctcatgctg gcaacaagct ggccatgcag
1021 gagttcatga tcctcccagt cggtgcagca aacttcaggg aagccatgcg cattggagca
1081 gaggtttacc acaacctgaa gaatgtcatc aaggagaaat atgggaaaga tgccaccaat
1141 gtgggggatg aaggcgggtt tgctcccaac atcctggaga ataagaagg cctggagctg
1201 ctgaagactg ctattgggaa agctggctac actgataagg tggtcatcgg catggacgta
1261 gcggcctccg agttcttcag gtctgggaag tatgacctgg acttcaagtc tcccgatgac
```

FIG. 34B (continued)

```
1321 cccagcaggt acatctcgcc tgaccagctg gctgacctgt acaagtcctt catcaaggac
1381 tacccagtgg tgtctatcga agatccctttt gaccaggatg actggggagc ttggcagaag
1441 ttcacagcca gtgcaggaat ccaggtagtg ggggatgatc tcacagtgac caacccaaag
1501 aggatcgcca aggccgtgaa cgagaagtcc tgcaactgcc tcctgctcaa agtcaaccag
1561 attggctccg tgaccgagtc tcttcaggcg tgcaagctgg cccaggccaa tggttggggc
1621 gtcatggtgt ctcatcgttc gggggagact gaagatacct tcatcgctga cctggttgtg
1681 gggctgtgca ctgggcagat caagactggt gccccttgcc gatctgagcg cttggccaag
1741 tacaaccagc tcctcagaat tgaagaggag ctgggcagca aggctaagtt tgccggcagg
1801 aacttcagaa accccttggc caagtaagct gtgggcaggc aagcccttcg gtcacctgtt
1861 ggctacacag acccctcccc tcgtgtcagc tcaggcagct cgaggccccc gaccaacact
1921 tgcagggtc cctgctagtt agcgcccac cgccgtggag ttcgtaccgc ttccttagaa
1981 cttctacaga agccaagctc cctggagccc tgttggcagc tctagctttg cagtcgtgta
2041 attggcccaa gtcattgttt ttctcgcctc actttccacc aagtgtctag agtcatgtga
2101 gcctcgtgtc atctccgggg tggccacagg ctagatcccc ggtggttttg tgctcaaaat
2161 aaaaagcctc agtgacccat gagaataaaa aaaaaaaaaa aaaa
```

FIG. 35A

LOCUS     NP_001188412     341 aa     linear   PRI 10-JAN-2014

DEFINITION c-myc promoter-binding protein-1 isoform MBP-1 [Homo sapiens].

ACCESSION NP_001188412

VERSION NP_001188412.1 GI:319996655

```
  1 miemdgtenk skfganailg vslavckaga vekgvplyrh iadlagnsev ilpvpafnvi
 61 nggshagnkl amqefmilpv gaanfreamr igaevyhnlk nvikekygkd atnvgdeggf
121 apnilenkeg lellktaigk agytdkvvig mdvaaseffr sgkydldfks pddpsryisp
181 dqladlyksf ikdypvvsie dpfdqddwga wqkftasagi qvvgddltvt npkriakavn
241 eksdnclllk vnqigsvtes lqacklaqan gwgvmvshrs getedtfiad lvvglctgqi
301 ktgapcrser lakynqllri eeelgskakf agrnfrnpla k
```

FIG. 35B

LOCUS       NM_001201483           2567 bp    mRNA    linear   PRI 10-JAN-2014

DEFINITION  Homo sapiens enolase 1, (alpha) (ENO1), transcript variant 2, mRNA.

ACCESSION   NM_001201483

VERSION     NM_001201483.1  GI:319996654

```
   1 aactaaagaa aagtttcccc atctcccagg agggttctgt gggccctcca gagatcatca
  61 gcctcttcac gggctagaaa ggatccaggg aaggtctaac caatgacctg ccctgaatgg
 121 tgagctgcag gtgtgtcatt tagtgtgatt ttcctgttga ctgactcata ggagccctgc
 181 tctgtggcag agctagcctc tggctgtatt caaattgact tagtgtgtgt gcaacattga
 241 cctttctaga gatagaacat gtggccaaat tacagaaaag cacatagggc tagatcacgc
 301 attctcagtg gggcacccgg aaaactccaa aaaggctgca gggaggggac aatgatgaaa
 361 tcaggttgtg aaacactggg ctggtgtcgc agtggtggtg ctgggtgttc agtcccgctt
 421 taatgctgta agaagcactc tacacacacg aacatgttac catttgaccg ttgtttaatg
 481 gcgtacgtgg ggacttagcc ggagcaggat gatgctgtgc cttgatggta atgagtgctc
 541 agtaagtaag catttgtgga agattgaacg catggcccct gaaatgctct cctctgcttt
 601 cctgccccct cactgtctct cactcgcagt ccttaatcac cggttctctt ctgagtctct
 661 ctcattttc cttcttcatc ctctgctggg caggcgtctc cagacccatt aagtatatta
 721 atgagttcct ggcaccagcc ctgtgcactc aggtaactga ttgaacagcc tttagtctgc
 781 agttggcgtt tccagtgcat ggtcttgcaa actaacctcc agtcagatcg ttctgagcca
 841 gctgctgttt tgtgtggctc taaccctctg gggtcctagg taggagcact cagactgggc
 901 cggaaagtcc tccgattctg gggggaaagg ggagagggg aagaggtccc acagaaggtc
 961 ccttggtggg cttccgcgtc ggcctcaaca gtggttctct ctaacaatgc tgctcaagcc
1021 tgttttaaag ttaatgtcag taatttgatt tgattgttcc ttccaggtgt ctcaaggct
1081 gttgagcaca tcaataaaac tattgcgcct gccctggtta gcaagaaact gaacgtcaca
1141 gaacaagaga agattgacaa actgatgatc gagatggatg gaacagaaaa taaatctaag
1201 tttggtgcga acgccattct gggggtgtcc cttgccgtct gcaaagctgg tgccgttgag
1261 aagggggtcc ccctgtaccg ccacatcgct gacttggctg caactctga agtcatcctg
```

FIG. 35B (continued)

```
1321 ccagtcccgg cgttcaatgt catcaatggc ggttctcatg ctggcaacaa gctggccatg
1381 caggagttca tgatcctccc agtcggtgca gcaaacttca gggaagccat gcgcattgga
1441 gcagaggttt accacaacct gaagaatgtc atcaaggaga atatgggaa agatgccacc
1501 aatgtggggg atgaaggcgg gtttgctccc aacatcctgg agaataaaga aggcctggag
1561 ctgctgaaga ctgctattgg gaaagctggc tacactgata aggtggtcat cggcatggac
1621 gtagcggcct ccgagttctt caggtctggg aagtatgacc tggacttcaa gtctcccgat
1681 gaccccagca ggtacatctc gcctgaccag ctggctgacc tgtacaagtc cttcatcaag
1741 gactacccag tggtgtctat cgaagatccc tttgaccagg atgactgggg agcttggcag
1801 aagttcacag ccagtgcagg aatccaggta gtgggggatg atctcacagt gaccaaccca
1861 aagaggatcg ccaaggccgt gaacgagaag tcctgcaact gcctcctgct caaagtcaac
1921 cagattggct ccgtgaccga gtctcttcag gcgtgcaagc tggcccaggc caatggttgg
1981 ggcgtcatgg tgtctcatcg ttcggggag actgaagata ccttcatcgc tgacctggtt
2041 gtggggctgt gcactgggca gatcaagact ggtgcccctt gccgatctga gcgcttggcc
2101 aagtacaacc agctcctcag aattgaagag gagctgggca gcaaggctaa gtttgccggc
2161 aggaacttca gaaacccctt ggccaagtaa gctgtgggca ggcaagccct tcggtcacct
2221 gttggctaca cagacccctc ccctcgtgtc agctcaggca gctcgaggcc cccgaccaac
2281 acttgcaggg gtccctgcta gttagcgccc caccgccgtg gagttcgtac cgcttcctta
2341 gaacttctac agaagccaag ctccctggag ccctgttggc agctctagct ttgcagtcgt
2401 gtaattggcc caagtcattg tttttctcgc ctcactttcc accaagtgtc tagagtcatg
2461 tgagcctcgt gtcatctccg gggtggccac aggctagatc cccggtggtt ttgtgctcaa
2521 aataaaaagc ctcagtgacc catgagaata aaaaaaaaa aaaaaa
```

FIG. 36A

LOCUS       NM_001975
2423 bp    mRNA    linear   PRI 18-MAY-2014
DEFINITION  Homo sapiens enolase 2 (gamma, neuronal) (ENO2), mRNA.
ACCESSION   NM_001975
VERSION     NM_001975.2  GI:16507966

```
   1 acccgcgctc gtacgtgcgc ctccgccggc agctcctgac tcatcggggg ctccgggtca
  61 catgcgcccg cgcggcccta taggcgcctc ctccgcccgc cgcccgggag ccgcagccgc
 121 cgccgccact gccactcccg ctctctcagc gccgccgtcg ccacgccac cgccaccgcc
 181 actaccaccg tctgagtctg cagtcccgag atcccagcca tcatgtccat agagaagatc
 241 tgggcccggg agatcctgga ctccgcgggg aacccacag tggaggtgga tctctatact
 301 gccaaggtc ttttccgggc tgcagtgccc agtggagcct ctacgggcat ctatgaggcc
 361 ctggagctga gggatggaga caaacagcgt tacttaggca aaggtgtcct gaaggcagtg
 421 gaccacatca actccaccat cgcgccagcc ctcatcagct caggtctctc tgtggtggag
 481 caagagaaac tggacaacct gatgctggag ttggatggga ctgagaacaa atccaagttt
 541 ggggccaatg ccatcctggg tgtgtctctg gccgtgtgta aggcagggc agctgagcgg
 601 gaactgcccc tgtatcgcca cattgctcag ctggccggga actcagacct catcctgcct
 661 gtgccggcct tcaacgtgat caatggtggc tctcatgctg caacaagct ggccatgcag
 721 gagttcatga tcctcccagt gggagctgag agctttcggg atgccatgcg actaggtgca
 781 gaggtctacc atacactcaa gggagtcatc aaggacaaat acggcaagga tgccaccaat
 841 gtgggggatg aaggtggctt tgcccccaat atcctggaga cagtgaagc cttggagctg
 901 gtgaaggaag ccatcgacaa ggctggctac acggaaaaga tcgttattgg catggatgtt
 961 gctgcctcag agttttatcg tgatggcaaa tatgacttgg acttcaagtc tccactgat
1021 ccttcccgat acatcactgg ggaccagctg ggggcactct accaggactt tgtcagggac
1081 tatcctgtgg tctccattga ggacccattt gaccaggatg attgggctgc ctggtccaag
1141 ttcacagcca atgtagggat ccagattgtg ggtgatgacc tgacagtgac caacccaaaa
1201 cgtattgagc gggcagtgga agaaaaggcc tgcaactgtc tgctgctcaa ggtcaaccag
1261 atcggctcgg tcactgaagc catccaagcg tgcaagctgg cccaggagaa tggctggggg
1321 gtcatggtga gtcatcgctc aggagagact gaggacacat tcattgctga cctggtggtg
1381 gggctgtgca caggccagat caagactggt gccccgtgcc gttctgaacg tctggctaaa
1441 tacaaccagc tcatgagaat tgaggaagag ctggggatg aagctcgctt gccggacat
1501 aacttccgta atccagtgt gctgtgattc ctctgcttgc ctggagacgt ggaacctctg
1561 tctcatcctc ctggaacctt gctgtcctga tctgtgatag ttaccccct gagatccct
1621 gagccccagg gtgcccagaa cttcctgat tgacctgctc cgctgctcct tggcttacct
1681 gacctcttgc tgtctctgct cgcctcctt tctgtgccct actcattggg gttccgcact
1741 ttccacttct tcctttctct ttctctcttc cctcagaaac tagaaatgtg aatgaggatt
1801 attataaaag ggggtccgtg gaagaatgat cagcatctgt gatgggagcg tcagggttgg
1861 tgtgctgagg tgttagagag ggaccatgtg tcacttgtgc tttgctcttg tcccacgtgt
1921 cttccacttt gcatatgagc cgtgaactgt gcatagtgct gggatggagg ggagtgttgg
1981 gcatgtgatc acgcctggct aataaggctt tagtgtattt atttatttat ttatttatt
2041 tgttttcat tcatcccatt aatcatttcc cataactca atggcctaaa actggcctga
2101 cttgggggaa cgatgtgtct gtatttcatg tggctgtaga tccaagatg actggggtgg
2161 gaggtcttgc tagaatggga agggtcatag aaagggcctt gacatcagtt cctttgtgtg
2221 tactcactga agcctgcgtt ggtccagagc ggaggctgtg tcctggggg agttttcctc
2281 tatacatctc tccccaaccc taggttccct gttcttcctc cagctgcacc agagcaacct
2341 ctcactcccc atgccacgtt ccacagttgc caccacctct gtggcattga aatgagcacc
2401 tccattaaag tctgaatcag tgc
```

FIG. 36B

LOCUS    NP_001966
434 aa
linear  PRI 18-MAY-2014
DEFINITION  gamma-enolase (Eno2) [Homo sapiens].
ACCESSION  NP_001966
VERSION    NP_001966.1  GI:5803011

```
  1 msiekiware ildsrgnptv evdlytakgl fraavpsgas tgiyealelr dgdkqrylgk
 61 gvlkavdhin stiapaliss glsvveqekl dnlmleldgt enkskfgana ilgvslavck
121 agaaerelpl yrhiaqlagn sdlilpvpaf nvinggshag nklamqefmi lpvgaesfrd
181 amrlgaevyh tlkgvikdky gkdatnvgde ggfapnilen sealelvkea idkagyteki
241 vigmdvaase fyrdgkydld fksptdpsry itgdqlgaly qdfvrdypvv siedpfdqdd
301 waawskftan vgiqivgddl tvtnpkrier aveekacncl llkvnqigsv teaiqackla
361 qengwgvmvs hrsgetedtf iadlvvglct gqiktgapcr serlakynql mrieeelgde
421 arfaghnfrn psvl
```

FIG. 37A

LOCUS        NM_001976
1536 bp    mRNA    linear
PRI 04-MAY-2014
DEFINITION  Homo sapiens enolase 3 (beta, muscle) (ENO3), transcript variant 1, mRNA.
ACCESSION   NM_001976
VERSION     NM_001976.4  GI:301897468

```
   1 ataaatgcgc agcctgagag ggggtgagct gacactgtcc cagctgccac ctagactcgg
  61 agctccatcc aaacctccag cgaagacatc ccaggtcggg tgaatcttcc agccctgggg
 121 gtggaggtag taaaggccat ggccatgcag aaaatctttg cccgggaaat cttggactcc
 181 agggcaacc ccacggtgga ggtggacctg cacacggcca agggccgatt ccgagcagct
 241 gtgcccagtg gggcttccac gggtatctat gaggctctgg aactaagaga cggagacaaa
 301 ggccgctacc tggggaaagg agtcctgaag gctgtggaga acatcaacaa tactctgggc
 361 cctgctctgc tgcaaaagaa actaagcgtt gtggatcaag aaaaagttga caaatttatg
 421 attgagctag atgggaccga gaataagtcc aagtttgggg ccaatgccat cctgggcgtg
 481 tccttggccg tgtgtaaggc gggagcagct gagaagggg tcccctgta ccgccacatc
 541 gcagatctcg ctgggaaccc tgacctcata ctcccagtgc cagccttcaa tgtgatcaac
 601 gggggctccc atgctggaaa caagctggcc atgcaggagt tcatgattct gcctgtggga
 661 gccagctcct tcaaggaagc catgcgcatt ggcgccgagg tctaccacca cctcaagggg
 721 gtcatcaagg ccaagtatgg gaaggatgcc accaatgtgg gtgatgaagg tggcttcgca
 781 cccaacatcc tggagaacaa tgaggccctg gagctgctga agacggccat ccaggcggct
 841 ggttacccag acaaggtggt gatcggcatg gatgtggcag catctgagtt ctatcgcaat
 901 gggaagtacg atcttgactt caagtcgcct gatgatcccg cacggcacat cactggggag
 961 aagctcggag agctgtataa gagctttatc aagaactatc ctgtggtctc catcgaagac
1021 ccctttgacc aggatgactg ggccacttgg acctccttcc tctcgggggt gaacatccag
1081 attgtggggg atgacttgac agtcaccaac cccaagagga ttgcccaggc cgttgagaag
1141 aaggcctgca actgtctgct gctgaaggtc aaccagatcg gctcggtgac cgaatcgatc
1201 caggcgtgca aactggctca gtctaatggc tgggggggtga tggtgagcca ccgctctggg
1261 gagactgagg acacattcat tgctgacctt gtggtggggc tctgcacagg acagatcaag
1321 actggcgccc cctgccgctc ggagcgtctg gccaaataca accaactcat gaggatcgag
1381 gaggctcttg gggacaaggc aatctttgct ggacgcaagt tccgtaaccc gaaggccaag
1441 tgagaagctg gaggctccag gactccactg gacagaccca ggtcttccag acctgcttcc
1501 tgaaataaac actggtgcca accaagaaaa aaaaaa
```

FIG. 37B

LOCUS    NM_053013
1494 bp   mRNA   linear
PRI 03-FEB-2014
DEFINITION  Homo sapiens enolase 3 (beta, muscle) (ENO3), transcript variant 2,
    mRNA.
ACCESSION   NM_053013
VERSION    NM_053013.3  GI:301897476

```
   1 ataaatgcgc agcctgagag ggggtgagct gacactgtcc cagctgccac ctagactcgg
  61 agctccatcc aaacctccag cgaagacatc ccagccatgg ccatgcagaa aatctttgcc
 121 cgggaaatct tggactccag gggcaacccc acggtggagg tggacctgca cacggccaag
 181 ggccgattcc gagcagctgt gcccagtggg gcttccacgg gtatctatga ggctctggaa
 241 ctaagagacg gagacaaagg ccgctacctg gggaaggag tcctgaaggc tgtggagaac
 301 atcaacaata ctctgggccc tgctctgctg caaaagaaac taagcgttgt ggatcaagaa
 361 aaagttgaca aatttatgat tgagctagat gggaccgaga ataagtccaa gtttggggcc
 421 aatgccatcc tgggcgtgtc cttggccgtg tgtaaggcgg gagcagctga aaggggggtc
 481 cccctgtacc gccacatcgc agatctcgct gggaaccctg acctcatact cccagtgcca
 541 gccttcaatg tgatcaacgg gggctccat gctggaaaca agctggccat gcaggagttc
 601 atgattctgc ctgtgggagc cagctccttc aaggaagcca tgcgcattgg cgccgaggtc
 661 taccaccacc tcaagggggt catcaaggcc aagtatggga aggatgccac caatgtgggt
 721 gatgaaggtg gcttcgcacc caacatcctg gagaacaatg aggccctgga gctgctgaag
 781 acggccatcc aggcggctgg ttacccagac aaggtggtga tcggcatgga tgtggcagca
 841 tctgagttct atcgcaatgg gaagtacgat cttgacttca gtcgcctga tgatcccgca
 901 cggcacatca ctggggagaa gctcggagag ctgtataaga gctttatcaa gaactatcct
 961 gtggtctcca tcgaagaccc ctttgaccag gatgactggg ccacttggac ctccttcctc
1021 tcggggtga acatccagat tgtgggggat gacttgacag tcaccaaccc caagaggatt
1081 gccaggccg ttgagaagaa ggcctgcaac tgtctgctgc tgaaggtcaa ccagatcggc
1141 tcggtgaccg aatcgatcca ggcgtgcaaa ctggctcagt ctaatggctg ggggtgatg
1201 gtgagccacc gctctgggga gactgaggac acattcattg ctgaccttgt ggtgggctc
1261 tgcacaggac agatcaagac tggcgccccc tgccgctcgg agcgtctggc caaatacaac
1321 caactcatga ggatcgagga ggctcttggg acaaggcaa tctttgctgg acgcaagttc
1381 cgtaacccga aggccaagtg agaagctgga ggctccagga ctccactgga cagacccagg
1441 tcttccagac ctgcttcctg aaataaacac tggtgccaac caagaaaaaa aaaa
```

FIG. 37C

LOCUS     NP_001967
434 aa           linear
PRI 04-MAY-2014
DEFINITION  beta-enolase (Eno3) isoform 1 [Homo sapiens].
ACCESSION   NP_001967
VERSION     NP_001967.3  GI:301897469

```
  1 mamqkifare ildsrgnptv evdlhtakgr fraavpsgas tgiyealelr dgdkgrylgk
 61 gvlkavenin ntlgpallqk klsvvdqekv dkfmieldgt enkskfgana ilgvslavck
121 agaaekgvpl yrhiadlagn pdlilpvpaf nvinggshag nklamqefmi lpvgassfke
181 amrigaevyh hlkgvikaky gkdatnvgde ggfapnilen nealellkta iqaagypdkv
241 vigmdvaase fyrngkydld fkspddparh itgeklgely ksfiknypvv siedpfdqdd
301 watwtsflsg vniqivgddl tvtnpkriaq avekkacncl llkvnqigsv tesiqackla
361 qsngwgvmvs hrsgetedtf iadlvvglct gqiktgapcr serlakynql mrieealgdk
421 aifagrkfrn pkak
```

FIG. 37D

LOCUS       NM_001193503
1365 bp    mRNA    linear
PRI 26-FEB-2014
DEFINITION  Homo sapiens enolase 3 (beta, muscle) (ENO3), transcript variant 3,
    mRNA.
ACCESSION   NM_001193503
VERSION     NM_001193503.1  GI:301897478

```
   1 ataaatgcgc agcctgagag ggggtgagct gacactgtcc cagctgccac ctagactcgg
  61 agctccatcc aaacctccag cgaagacatc ccagccatgg ccatgcagaa aatctttgcc
 121 cgggaaatct tggactccag gggcaacccc acggtggagg tggacctgca cacggccaag
 181 ggccgattcc gagcagctgt gcccagtggg gcttccacgg gtatctatga ggctctggaa
 241 ctaagagacg gagacaaagg ccgctacctg gggaaagcca agtttggggc caatgccatc
 301 ctgggcgtgt ccttggccgt gtgtaaggcg ggagcagctg agaaggggt cccctgtac
 361 cgccacatcg cagatctcgc tgggaaccct gacctcatac tccagtgcc agccttcaat
 421 gtgatcaacg ggggctccca tgctggaaac aagctggcca tgcaggagtt catgattctg
 481 cctgtgggag ccagctcctt caaggaagcc atgcgcattg gcgccgaggt ctaccaccac
 541 ctcaagggg tcatcaaggc caagtatggg aaggatgcca ccaatgtggg tgatgaaggt
 601 ggcttcgcac ccaacatcct ggagaacaat gaggccctgg agctgctgaa gacggccatc
 661 caggcggctg gttacccaga caaggtggtg atcggcatgg atgtggcagc atctgagttc
 721 tatcgcaatg ggaagtacga tcttgacttc aagtcgcctg atgatccgc acggcacatc
 781 actggggaga agctcggaga gctgtataag agctttatca agaactatcc tgtggtctcc
 841 atcgaagacc cctttgacca ggatgactgg gccacttgga cctccttcct ctcggggtg
 901 aacatccaga ttgtggggga tgacttgaca gtcaccaacc caagaggat gcccaggcc
 961 gttgagaaga aggcctgcaa ctgtctgctg ctgaaggtca accagatcgg ctcggtgacc
1021 gaatcgatcc aggcgtgcaa actggctcag tctaatggct gggggtgat ggtgagccac
1081 cgctctgggg agactgagga cacattcatt gctgaccttg tggtgggct ctgcacagga
1141 cagatcaaga ctggcgcccc ctgccgctcg gagcgtctgg ccaaatacaa ccaactcatg
1201 aggatcgagg aggctcttgg ggacaaggca atctttgctg gacgcaagtt ccgtaacccg
1261 aaggccaagt gagaagctgg aggctccagg actccactgg acagacccag gtcttccaga
1321 cctgcttcct gaaataaaca ctggtgccaa ccaagaaaaa aaaaa
```

FIG. 37E

LOCUS    NP_001180432
391 aa       linear
PRI 26-FEB-2014
DEFINITION  beta-enolase isoform 2 of Eno3 [Homo sapiens].
ACCESSION  NP_001180432
VERSION    NP_001180432.1  GI:301897479

```
  1 mamqkifare ildsrgnptv evdlhtakgr fraavpsgas tgiyealelr dgdkgrylgk
 61 akfganailg vslavckaga aekgvplyrh iadlagnpdl ilpvpafnvi nggshagnkl
121 amqefmilpv gassfkeamr igaevyhhlk gvikakygkd atnvgdeggf apnilennea
181 lellktaiqa agypdkvvig mdvaasefyr ngkydldfks pddparhitg eklgelyksf
241 iknypvvsie dpfdqddwat wtsflsgvni qivgddltvt npkriaqave kkacnclllk
301 vnqigsvtes iqacklaqsn gwgvmvshrs getedtfiad lvvglctgqi ktgapcrser
361 lakynqlmri eealgdkaif agrkfrnpka k
```

ENOLASE 1 (ENO1) COMPOSITIONS AND USES THEREOF

RELATED APPLICATIONS

This application is a continuation of U.S. patent application Ser. No. 14/596,208 filed Jan. 13, 2015 which, in turn, claims priority to U.S. Provisional Patent Application No. 61/926,913 filed on Jan. 13, 2014, U.S. Provisional Patent Application No. 62/009,783 filed on Jun. 9, 2014, and U.S. Provisional Patent Application No. 62/100,881 filed on Jan. 7, 2015, the contents of each of which are incorporated herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 119992_10606_Sequence_Listing. The size of the text file is 58 KB, and the text file was created on Nov. 27, 2018.

BACKGROUND

As the levels of blood glucose rise postprandially, insulin is secreted and stimulates cells of the peripheral tissues (skeletal muscles and fat) to actively take up glucose from the blood as a source of energy. Loss of glucose homeostasis as a result of dysregulated insulin secretion or action typically results in metabolic disorders such as diabetes, which may be co-triggered or further exacerbated by obesity. Because these conditions can reduce the quality of life or even be fatal, strategies to restore adequate glucose clearance from the bloodstream are required.

Although diabetes may arise secondary to any condition that causes extensive damage to the pancreas (e.g., pancreatitis, tumors, administration of certain drugs such as corticosteroids or pentamidine, iron overload (i.e., hemochromatosis), acquired or genetic endocrinopathies, and surgical excision), the most common forms of diabetes typically arise from primary disorders of the insulin signaling system. There are two major types of diabetes, namely type 1 diabetes (also known as insulin dependent diabetes (IDDM)) and type 2 diabetes (also known as insulin independent or non-insulin dependent diabetes (NIDDM)), which share common long-term complications in spite of their different pathogenic mechanisms.

Type 1 diabetes, which accounts for approximately 10% of all cases of primary diabetes, is an organ-specific autoimmune disease characterized by the extensive destruction of the insulin-producing beta cells of the pancreas. The consequent reduction in insulin production inevitably leads to the deregulation of glucose metabolism. While the administration of insulin provides significant benefits to patients suffering from this condition, the short serum half-life of insulin is a major impediment to the maintenance of normoglycemia. An alternative treatment is islet transplantation, but this strategy has been associated with limited success.

Type 2 diabetes, which affects a larger proportion of the population, is characterized by a deregulation in the secretion of insulin and/or a decreased response of peripheral tissues to insulin, i.e., insulin resistance. While the pathogenesis of type 2 diabetes remains unclear, epidemiologic studies suggest that this form of diabetes results from a collection of multiple genetic defects or polymorphisms, each contributing its own predisposing risks and modified by environmental factors, including excess weight, diet, inactivity, drugs, and excess alcohol consumption. Although various therapeutic treatments are available for the management of type 2 diabetes, they are associated with various debilitating side effects. Accordingly, patients diagnosed with or at risk of having type 2 diabetes are often advised to adopt a healthier lifestyle, including loss of weight, change in diet, exercise, and moderate alcohol intake. Such lifestyle changes, however, are not sufficient to reverse the vascular and organ damages caused by diabetes.

SUMMARY OF THE INVENTION

In one aspect, the invention provides compositions comprising enolase 1 (Eno1) or a fragment thereof for delivery to a muscle. In one aspect, the invention provides method for normalizing blood glucose in a subject with elevated blood glucose, comprising administering to the subject a composition comprising Eno1 or a fragment thereof, thereby normalizing blood glucose in the subject. In one aspect, the invention provides methods of treating one or more conditions including impaired glucose tolerance, insulin resistance, pre-diabetes, and diabetes, especially type 2 diabetes, in a subject, comprising administering to the subject a composition comprising Eno1 or a fragment thereof, thereby treating the condition in the subject. In certain methods of the invention, the Eno1 is delivered to muscle.

The invention provides pharmaceutical composition comprising Eno1 or a fragment thereof for delivery to a muscle cell.

In certain embodiments, the Eno1 comprises an Eno1 polypeptide, or a fragment thereof. In certain embodiments, the Eno1 comprises an Eno1 nucleic acid, or a fragment thereof. In certain embodiments, the Eno1 comprises human Eno1, e.g., a human Eno1 polypeptide or human Eno1 nucleic acid, or fragment thereof.

In certain embodiments, the composition further comprises a microparticle. In certain embodiments, the composition further comprises a nanoparticle. In certain embodiments, the Eno1 or the fragment thereof is biologically active. In certain embodiments, the Eno1 or the fragment thereof has at least 90% of the activity of a purified endogenous human Eno1 polypeptide.

In certain embodiments, the composition further comprises an in situ forming composition. In certain embodiments, the composition further comprises a liposome. In certain embodiments, the composition comprises a dendrimer. In certain embodiments, the composition further comprises an expression vector, e.g., encoding the Eno1 or fragment thereof. In certain embodiments, the expression vector comprises a viral vector.

In certain embodiments, the composition comprises a complex comprising Eno1 or a fragment thereof, e.g., an Eno1 polypeptide, e.g., a human Eno1 polypeptide, and a muscle targeting moiety. In certain embodiments, the muscle targeting moiety comprises a skeletal and/or smooth muscle targeting peptide). In certain embodiments, the MTP comprises an amino acid sequence selected from the group consisting of: ASSLNIA (SEQ ID NO: 12); WDANGKT (SEQ ID NO: 13); GETRAPL (SEQ ID NO: 14); CGHHPVYAC (SEQ ID NO: 15); and HAIYPRH (SEQ ID NO: 16). In certain embodiments, the complex comprises a linker, e.g., linking Eno1 and the SMTP. In certain embodiments, the linker is selected from the group consisting of a covalent linker, a non-covalent linkage, and a reversible linker. In certain embodiments, the complex comprises a pharmaceutically acceptable dendrimer. In certain embodiments, the dendrimer is a PAMAM dendrimer. In certain embodiments, the dendrimer is a G5 dendrimer. In certain embodiments, the dendrimer is an uncharged dendrimer. In certain embodiments, the dendrimer is an acylated dendrimer. In certain embodiments, the dendrimer is a PEGylated dendrimer or an acetylated dendrimer. In certain embodiments, the complex comprises a liposome. In certain embodiments, the complex comprises a microparticle or a nanoparticle. In certain embodiments, the composition comprises an in situ forming composition.

In certain embodiments, the Eno1 is released from the complex upon delivery to a muscle cell.

In certain embodiments, the Eno1 or a fragment thereof and the targeting moiety are present in the complex at a ratio of about 1:1 to about 1:30.

In certain embodiments, the composition is formulated for administration by injection or infusion. In certain embodiments, the composition is formulated for oral administration. In certain embodiments, the composition is formulated for parenteral administration. In certain embodiments, the composition is formulated for intramuscular administration, intravenous administration, or subcutaneous administration.

The invention provides methods of decreasing blood glucose in a subject with elevated blood glucose, the method comprising administering to the subject a pharmaceutical composition comprising of Eno1 or a fragment thereof. In certain embodiments, the pharmaceutical composition comprises any of the pharmaceutical compositions provided herein.

The invention provides methods of increasing glucose tolerance in a subject with decreased glucose tolerance, the method comprising administering to the subject a pharmaceutical composition comprising of Eno1. In certain embodiments, the pharmaceutical composition comprises any of the pharmaceutical compositions provided herein.

The invention provides methods of improving insulin response in a subject with decreased insulin sensitivity and/or insulin resistance, the method comprising administering to the subject a pharmaceutical composition comprising of Eno1 or a fragment thereof. In certain embodiments, the pharmaceutical composition comprises any of the pharmaceutical compositions provided herein.

The invention provides methods of treating diabetes in a subject, the method comprising administering to the subject a pharmaceutical composition comprising of Eno1 or a fragment thereof. In certain embodiments, the diabetes is type 2 diabetes. In certain embodiments, the diabetes is pre-diabetes. In certain embodiments, the diabetes is type 1 diabetes. In certain embodiments, the diabetes is gestational diabetes. In certain embodiments, the pharmaceutical composition comprises any of the pharmaceutical compositions provided herein.

The invention provides methods of decreasing an HbA1c level in a subject with an elevated Hb1Ac level, the method comprising administering to the subject a pharmaceutical composition comprising of Eno1 or a fragment thereof. In certain embodiments, the pharmaceutical composition comprises any of the pharmaceutical compositions provided herein.

The invention provides methods of improving blood glucose level control in a subject with abnormal blood glucose level control, the method comprising administering to the subject a pharmaceutical composition comprising of Eno1 or a fragment thereof. In certain embodiments, the pharmaceutical composition comprises any of the pharmaceutical compositions provided herein.

In certain embodiments, the Eno1 or a fragment thereof is administered by injection or infusion. In certain embodiments, the Eno1 or a fragment thereof is administered parenterally. In certain embodiments the Eno1 or a fragment thereof is administered orally. In certain embodiments, the Eno1 or a fragment thereof is administered by a route selected from the group consisting of intramuscular, intravenous, and subcutaneous.

The invention provides methods for diagnosing an elevate blood glucose level in a subject, comprising: (a) detecting the level of Eno1 in a biological sample of the subject, and (b) comparing the level of Eno1 in the biological sample with a predetermined threshold value, wherein the level Eno1 below the predetermined threshold value indicates the presence of elevated blood glucose in the subject. In certain embodiments, the methods further comprise detecting the level of one or more diagnostic indicators of elevated blood glucose. In certain embodiments, the one or more additional diagnostic indicators of elevated blood glucose is selected from the group consisting of HbA1c, fasting blood glucose, fed blood glucose, and glucose tolerance. In certain embodiments, the biological sample is blood or serum. In certain embodiments, the level of Eno1 is determined by immunoassay or ELISA. In certain embodiments, step (a) comprises (i) contacting the biological sample with a reagent that selectively binds to the Eno1 to form a biomarker complex, and (ii) detecting the biomarker complex. In certain embodiments, the reagent is an anti-Eno1 antibody that selectively binds to at least one epitope of Eno1.

In certain embodiments, step (a) comprises determining the amount of Eno1 mRNA in the biological sample. In certain embodiments, an amplification reaction is used for determining the amount of Eno1 mRNA in the biological sample. In certain embodiments, the amplification reaction is (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA). In certain embodiments, a hybridization assay is used for determining the amount of Eno1 mRNA in the biological sample. In certain embodiments, an oligonucleotide that is complementary to a portion of a Eno1 mRNA is used in the hybridization assay to detect the Eno1 mRNA.

In certain embodiments of the invention, diagnosis of elevated blood glucose is diagnostic of a disease or condition selected from the group consisting of type 2 diabetes, pre-diabetes, gestational diabetes, and type 1 diabetes.

The invention provides method for diagnosing the presence of elevated blood glucose in a subject, comprising:

(a) contacting a biological sample with a reagent that selectively binds to Eno1;

(b) allowing a complex to form between the reagent and Eno1;

(c) detecting the level of the complex, and (d) comparing the level of the complex with a predetermined threshold value, wherein the level of the complex above the predetermined threshold value indicates the subject is suffering from elevated blood glucose. In certain embodiments, the reagent is an anti-Eno1 antibody. In certain embodiments, the antibody comprises a detectable label. In certain embodiments, the step of detecting the level of the complex further comprises contacting the complex with a detectable secondary antibody and measuring the level of the secondary antibody. In certain embodiments, the methods further comprise detecting the level of one or more additional indicators of elevated blood glucose. In certain embodiments, the one or more additional indicators of blood glucose is selected from the group consisting of HbA1c level, fasting glucose level, fed glucose level, and glucose tolerance. In certain embodiments, the biological sample is blood or serum.

In certain embodiments of the invention, the level of the complex is determined by immunoassay or ELISA. In certain embodiments, the elevated blood glucose is indicative of pre-diabetes, type 2 diabetes, type 1 diabetes, or gestational diabetes. In certain embodiments, the method further comprises administering a therapeutic regimen where the diagnosis indicates the presence of elevated blood glucose in the subject, wherein the therapeutic regimen is selected from the group consisting of drug therapy and behavioral therapy, or a combination thereof. In certain embodiments, the drug therapy comprises treatment with an agent selected from the group consisting of (a) a meglitinide, (b) a sulfonylurea, (c) a dipeptidy peptidase-4 (DPP-4) inhibitor, (d) a biguanide, (e) a thiazolidinediones, (f) an alpha-glucosidase inhibitor, (g) an amylin mimetic; (h) an incretin mimetics; (i) an insulin; and (j) any combination thereof.

In certain embodiments, any of the preceding methods further comprise selecting a subject suspected of having or being at risk of having elevated blood glucose.

In certain embodiments, any of the preceding methods further comprise obtaining a biological sample from a subject suspected of having or being at risk of having elevated blood glucose.

In certain embodiments, any of the preceding methods further comprise comparing the level of the one or more elevated blood glucose related indicators in the biological sample with the level of the one or more elevated blood glucose related indicators in a control sample selected from the group consisting of: a sample obtained from the same subject at an earlier time point than the biological sample, a sample from a subject with normal blood glucose, a sample from a subject with prediabetes, a sample from a subject with type 2 diabetes, a sample from a subject with gestational diabetes, and a sample from a subject with type 1 diabetes.

The invention provides methods for monitoring elevated blood glucose in a subject, the method comprising:

(1) determining a level of Eno1 in a first biological sample obtained at a first time from a subject having elevated blood glucose;

(2) determining a level of Eno1 in a second biological sample obtained from the subject at a second time, wherein the second time is later than the first time; and (3) comparing the level of Eno1 in the second sample with the level of Eno1 in the first sample, wherein a change in the level of Eno1 is indicative of a change in elevated blood glucose status in the subject.

In certain embodiments, the determining steps (1) and (2) further comprise determining the level of one or more additional indicators of blood glucose is selected from the group consisting of HbA1c level, fasting glucose level, fed glucose level, and glucose tolerance.

In certain embodiments, the subject is treated with drugs for elevated blood glucose prior to obtaining the second sample. In certain embodiments, a decreased level of Eno1 in the second biological sample as compared to the first biological sample is indicative of elevation of blood glucose in the subject. In certain embodiments, an increased or equivalent level of Eno1 in the second biological sample as compared to the first biological sample is indicative of normalization of blood glucose in the subject. In certain embodiments, the method further comprises selecting and/or administering a different treatment regimen for the subject based on the blood glucose level in the subject. In certain embodiments, the treatment regimen is selected from the group consisting of drug therapy and behavioral modification therapy. In certain embodiments, the drug therapy comprises treatment with an agent selected from the group consisting of (a) a meglitinide, (b) a sulfonylurea, (c) a dipeptidy peptidase-4 (DPP-4) inhibitor, (d) a biguanide, (e) a thiazolidinediones, (f) an alpha-glucosidase inhibitor, (g) an amylin mimetic; (h) an incretin mimetics; (i) an insulin; and (j) any combination thereof.

The invention provides methods of treating elevated blood glucose in a subject, comprising: (a) obtaining a biological sample from a subject suspected of having elevated blood glucose, (b) submitting the biological sample to obtain diagnostic information as to the level of Eno1, (c) administering a therapeutically effective amount of an anti-diabetic therapy if the level of Eno1 is above a threshold level.

The invention provides methods of treating elevated blood glucose in a subject, comprising: (a) obtaining diagnostic information as to the level of Eno1 in a biological sample, and (b) administering a therapeutically effective amount of an anti-diabetic therapy if the level of Eno1 is above a threshold level.

The invention provides methods of treating elevated blood glucose in a subject, comprising:

(a) obtaining a biological sample from a subject suspected of having elevated blood glucose for use in identifying diagnostic information as to the level of Eno1, (b) measuring the level of Eno1 in the biological sample, (c) recommending to a healthcare provider to administer a blood glucose lowering therapy if the level of Eno1 is below a threshold level.

In certain embodiments, the method further comprises obtaining diagnostic information as to the level of one or more additional indicators of elevated blood glucose.

In certain embodiments, the method further comprises measuring the level of one or more additional indicators of elevated blood glucose.

In certain embodiments, the one or more additional indicators of elevated blood glucose is selected from the group consisting of HbA1c level, fasting glucose level, fed glucose level, and glucose tolerance.

In certain embodiments, step (c) further comprises administering a therapeutically effective amount of a glucose lowering therapy if the level of Eno1 is below and at least one of the additional indicator of elevated blood glucose is detected. In certain embodiments, step (c) further comprises recommending to a healthcare provider to administer a glucose lowering therapy if the level of Eno1 is below a threshold level and at least one of the additional indicator of elevated blood glucose is present.

In certain embodiments, the biological sample is blood or serum. In certain embodiments, the level of Eno1 is determined by immunoassay or ELISA. In certain embodiments, the level of Eno1 is determined by (i) contacting the biological sample with a reagent that selectively binds to the Eno1 to form a biomarker complex, and (ii) detecting the biomarker complex. In certain embodiments, the reagent is an anti-Eno1 antibody that selectively binds to at least one epitope of Eno1.

In certain embodiments, the level of Eno1 is determined by measuring the amount of Eno1 mRNA in the biological sample. In certain embodiments, an amplification reaction is used for measuring the amount of Eno1 mRNA in the biological sample. In certain embodiments, the amplification reaction is (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA). In certain embodiments, a hybridization assay is used for measuring the amount of Eno1 mRNA in the biological sample. In certain embodiments, an oligonucleotide that is complementary to a portion of a Eno1 mRNA is used in the hybridization assay to detect the Eno1 mRNA.

The invention provides kits for detecting Eno1 in a biological sample comprising at least one reagent for measuring the level of Eno1 in the biological sample, and a set of instructions for measuring the level of Eno1. In certain embodiments, the reagent is an anti-Eno1 antibody. In certain embodiments, the kits further comprise a means to detect the anti-Eno1 antibody. In certain embodiments, the means to detect the anti-Eno1 antibody is a detectable secondary antibody. In certain embodiments, the reagent is an oligonucleotide that is complementary to a Eno1 mRNA. In certain embodiments, the instructions set forth an immunoassay or ELISA for detecting the Eno1 level in the biological sample. In certain embodiments, the instructions set forth an amplification reaction for assaying the level of Eno1 mRNA in the biological sample. In certain embodiments, an amplification reaction is used for determining the amount of Eno1 mRNA in the biological sample. In certain embodiments, the amplification reaction is (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA). In certain embodiments, the instructions set forth a hybridization assay for determining the amount of Eno1 mRNA in the biological sample. In certain embodiments, the kit further comprises at least one oligonucleotide that is complementary to a portion of a Eno1 mRNA. In certain embodiments, the kit further comprises at least one reagent for measuring a level of HbA1c and/or blood glucose in the biological sample. In certain embodiments, the kit further comprises instructions for measuring at least one level selected from the group consisting of HbA1c level, fed blood glucose level, fasting blood glucose level, and glucose tolerance in the subject from which the biological sample was obtained.

The invention provides panels of reagents for use in a method of detecting elevated blood glucose, the panel comprising detection reagents for Eno1 and HbA1c.

The invention provides panels of reagents for use in a method of treating elevated blood glucose, the panel comprising detection reagents for Eno1 and HbA1c.

The invention provides panels of reagents for use in a method of monitoring the treatment of elevated blood glucose, the panel comprising detection reagents for Eno1 and HbA1c.

The invention provides kits containing a the panel of reagents provided herein, and a set of instructions for obtaining diagnostic information as to level of one or more indicators of elevated blood glucose.

The invention provides for the use of a panel of reagents comprising a plurality of detection reagents specific for detecting markers of elevated blood glucose in a method for diagnosing and/or treating elevated blood glucose, wherein at least one detection reagent of the panel is specific for detecting Eno1, and wherein the remaining one or more detection reagents are specific for detecting an indicator of elevated blood glucose marker selected from the group consisting of HbA1c and glucose.

In certain embodiments of the aforementioned methods, glucose flux in a skeletal muscle cell of the subject is increased.

In another aspect, the invention provides a method of increasing glucose flux in a subject, the method comprising administering to the subject a pharmaceutical composition comprising Eno1 or a fragment thereof. In certain embodiments, the pharmaceutical composition administered to the subject is any of the aforementioned pharmaceutical compositions. In another aspect, the invention provides a method of increasing glycolytic activity or capacity in a skeletal muscle cell of a subject, the method comprising administering to the subject a pharmaceutical composition comprising Eno1 or a fragment thereof. In certain embodiments, the pharmaceutical composition administered to the subject is any of the aforementioned pharmaceutical compositions.

In another aspect, the invention provides a method of increasing mitochondrial free fatty acid oxidation in a skeletal muscle cell of a subject, the method comprising administering to the subject a pharmaceutical composition comprising Eno1 or a fragment thereof. In certain embodiments, the pharmaceutical composition administered to the subject is any of the aforementioned pharmaceutical compositions.

In certain embodiments, the subject has any one or more of elevated blood glucose, decreased glucose tolerance, decreased insulin sensitivity and/or insulin resistance, diabetes, elevated Hb1Ac level, and abnormal blood glucose level control.

In certain embodiments of any of the aforementioned methods, the subject is human.

In certain aspects the invention relates to a pharmaceutical composition comprising a therapeutically effective amount of Eno1 or a fragment thereof. In certain embodiments, the pharmaceutical composition is for delivery to a muscle cell. In certain embodiments of the composition, the Eno1 comprises an Eno1 polypeptide or a fragment thereof. In certain embodiments of the composition, the Eno1 comprises an Eno1 nucleic acid or a fragment thereof. In certain embodiments, the composition further comprises an expression vector encoding Eno1 or a fragment thereof. In certain embodiments of the composition, the Eno1 or fragment thereof is biologically active. In certain embodiments of the composition, the Eno1 or fragment thereof has at least 90% of the activity of a purified endogenous human Eno1 polypeptide. In certain embodiments of the composition, the Eno1 is human Eno1. In certain embodiments, the composition further comprises a microparticle. In certain embodiments, the composition further comprises a nanoparticle. In certain embodiments, the composition further comprises an in situ forming composition. In certain embodiments, the composition further comprises a liposome. In certain embodiments, the composition further comprises a muscle targeting moiety. In certain embodiments, the muscle targeting moiety is a skeletal muscle targeting moiety. In certain embodiments, the muscle targeting moiety and the Eno1 polypeptide are in a complex.

In certain embodiments of the compositions described herein, the Eno1 is released from the complex upon delivery to a muscle cell. In certain embodiments of the compositions described herein, the composition is formulated for parenteral administration. In certain embodiments, the composition is formulated for oral administration. In certain embodiments, the composition is formulated for intramuscular administration, intravenous administration, or subcutaneous administration.

In certain aspects the invention relates to a method of decreasing blood glucose in a subject with elevated blood glucose, the method comprising administering to the subject a pharmaceutical composition comprising Eno1 or a fragment thereof, thereby decreasing blood glucose in the subject. In certain embodiments of the aforementioned method, the pharmaceutical composition administered to the subject is any of the compositions described above.

In certain aspects the invention relates to a method of increasing glucose tolerance in a subject with decreased glucose tolerance, the method comprising administering to the subject a pharmaceutical composition comprising Eno1 or a fragment thereof, thereby increasing glucose tolerance in the subject. In certain embodiments of the aforementioned method, the pharmaceutical composition administered to the subject is any of the compositions described above.

In certain aspects the invention relates to a method of improving insulin response in a subject with decreased insulin sensitivity and/or insulin resistance, the method comprising administering to the subject a pharmaceutical composition comprising Eno1 or a fragment thereof, thereby improving insulin response in the subject. In certain embodiments of the aforementioned method, the pharmaceutical composition administered to the subject is any of the compositions described above.

In certain aspects the invention relates to a method of treating diabetes in a subject, the method comprising administering to the subject a pharmaceutical composition comprising Eno1 or a fragment thereof, thereby treating diabetes in the subject. In certain embodiments, the diabetes is type 2 diabetes or type 1 diabetes. In certain embodiments, the diabetes is pre-diabetes. In certain embodiments of the aforementioned method, the pharmaceutical composition administered to the subject is any of the compositions described above.

In certain aspects the invention relates to a method of decreasing an HbA1c level in a subject with an elevated Hb1Ac level, the method comprising administering to the subject a pharmaceutical composition comprising Eno1 or a fragment thereof, thereby decreasing the HbA1c level in the subject. In certain embodiments of the aforementioned method, the pharmaceutical composition administered to the subject is any of the compositions described above.

In certain aspects the invention relates to a method of improving blood glucose level control in a subject with abnormal blood glucose level control, the method comprising administering to the subject a pharmaceutical composition comprising Eno1 or a fragment thereof, thereby improving blood glucose level control in the subject. In certain embodiments of the aforementioned method, the pharmaceutical composition administered to the subject is any of the compositions described above.

In certain embodiments of the aforementioned methods, the glucose flux in a skeletal muscle cell of the subject is increased.

In certain aspects the invention relates to a method of increasing glucose flux in a subject, the method comprising administering to the subject a pharmaceutical composition comprising Eno1 or a fragment thereof, thereby increasing glucose flux in the subject. In certain embodiments of the aforementioned method, the pharmaceutical composition administered to the subject is any of the compositions described above.

In certain aspects the invention relates to a method of increasing glycolytic activity or capacity in a skeletal muscle cell of a subject, the method comprising administering to the subject a pharmaceutical composition comprising Eno1 or a fragment thereof, thereby increasing glycolytic activity or capacity in a skeletal muscle cell of the subject. In certain embodiments of the aforementioned method, the pharmaceutical composition administered to the subject is any of the compositions described above.

In certain aspects the invention relates to a method of increasing mitochondrial free fatty acid oxidation in a skeletal muscle cell of a subject, the method comprising administering to the subject a pharmaceutical composition comprising Eno1 or a fragment thereof, thereby increasing mitochondrial free fatty acid oxidation in a skeletal muscle cell of the subject. In certain embodiments of the aforementioned method, the pharmaceutical composition administered to the subject is any of the compositions described above.

In certain embodiments of the aforementioned methods, the Eno1 is administered parenterally. In certain embodiments, the Eno1 is administered orally. In certain embodiments, the Eno1 is administered by a route selected from the group consisting of intramuscular, intravenous, and subcutaneous. In certain embodiments, the subject has any one or more of elevated blood glucose, decreased glucose tolerance, decreased insulin sensitivity and/or insulin resistance, diabetes, elevated Hb1Ac level, and abnormal blood glucose level control.

In certain embodiments of the aforementioned methods, the methods further comprise selecting a subject having any one or more of elevated blood glucose, decreased glucose tolerance, decreased insulin sensitivity and/or insulin resistance, diabetes, elevated Hb1Ac level, and abnormal blood glucose level control. In certain embodiments, the subject is human.

In certain aspects the invention relates to a method for diagnosing an elevated blood glucose level in a subject, comprising: (a) detecting a level of Eno1 in a biological sample from the subject, and (b) comparing the level of Eno1 in the biological sample with a predetermined threshold value, wherein a level of Eno1 in the sample below the predetermined threshold value indicates the presence of elevated blood glucose in the subject. In certain embodiments, the method further comprises detecting the level of one or more diagnostic indicators of elevated blood glucose. In certain embodiments, the one or more additional diagnostic indicators of elevated blood glucose is selected from the group consisting of HbA1c, fasting blood glucose, fed blood glucose, and glucose tolerance. In certain embodiments, the biological sample is blood or serum. In certain embodiments, the level of Eno1 is detected by immunoassay or ELISA. In certain embodiments of the aforementioned method, step (a) comprises (i) contacting the biological sample with a reagent that selectively binds to the Eno1 to form a biomarker complex, and (ii) detecting the biomarker complex. In certain embodiments, the reagent is an anti-Eno1 antibody that selectively binds to at least one epitope of Eno1. In certain embodiments, step (a) comprises detecting the amount of Eno1 mRNA in the biological sample. In certain embodiments, an amplification reaction is used for detecting the amount of Eno1 mRNA in the biological sample. In certain embodiments, the amplification reaction is (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA). In certain embodiments, a hybridization assay is used for detecting the amount of Eno1 mRNA in the biological sample. In certain embodiments, an oligonucleotide that is complementary to a portion of the Eno1 mRNA is used in the hybridization assay to detect the Eno1 mRNA.

In certain embodiments of the aforementioned method, the presence of elevated blood glucose in the subject is diagnostic of a disease or condition selected from the group consisting of type 2 diabetes, pre-diabetes, gestational diabetes, and type 1 diabetes.

In certain embodiments the aforementioned methods further comprise administering a therapeutic regimen to the subject when the presence of elevated blood glucose is determined, wherein the therapeutic regimen is selected from the group consisting of drug therapy and behavioral therapy, or a combination thereof. In certain embodiments, the drug therapy comprises treatment with an agent selected from the group consisting of (a) a meglitinide, (b) a sulfonylurea, (c) a dipeptidy peptidase-4 (DPP-4) inhibitor, (d) a biguanide, (e) a thiazolidinediones, (f) an alpha-glucosidase inhibitor, (g) an amylin mimetic; (h) an incretin mimetics; (i) an insulin; and (j) any combination thereof. In certain embodiments, the methods further comprise selecting a subject suspected of having or being at risk of having elevated blood glucose. In certain embodiments the methods further comprise obtaining a biological sample from a subject suspected of having or being at risk of having elevated blood glucose.

In certain embodiments, the aforementioned methods further comprise comparing the level of one or more elevated blood glucose related indicators in the biological sample with the level of the one or more elevated blood glucose related indicators in a control sample selected from the group consisting of: a sample obtained from the same subject at an earlier time point than the biological sample, a sample from a subject with normal blood glucose, a sample from a subject with prediabetes, a sample from a subject with type 2 diabetes, a sample from a subject with gestational diabetes, and a sample from a subject with type 1 diabetes.

In certain aspects the invention relates to a method for monitoring elevated blood glucose in a subject, the method comprising: (1) determining a level of Eno1 in a first biological sample obtained at a first time from a subject having elevated blood glucose; (2) determining a level of Eno1 in a second biological sample obtained from the subject at a second time, wherein the second time is later than the first time; and (3) comparing the level of Eno1 in the second sample with the level of Eno1 in the first sample, wherein a change in the level of Eno1 is indicative of a change in elevated blood glucose status in the subject. In certain embodiments, the determining steps (1) and (2) further comprise determining a level of one or more additional indicators of blood glucose selected from the group consisting of HbA1c level, fasting glucose level, fed glucose level, and glucose tolerance. In certain embodiments, the subject is treated with drugs for elevated blood glucose prior to obtaining the second sample. In certain embodiments, a decreased level of Eno1 in the second biological sample as compared to the first biological sample is indicative of elevation of blood glucose in the subject. In certain embodiments, an increased or equivalent level of Eno1 in the second biological sample as compared to the first biological sample is indicative of normalization of blood glucose in the subject. In certain embodiments, the method further comprises selecting and/or administering a different treatment regimen for the subject based on the blood glucose level in the subject. In certain embodiments, the treatment regimen is selected from the group consisting of drug therapy and behavioral modification therapy. In certain embodiments, the drug therapy comprises treatment with an agent selected from the group consisting of (a) a meglitinide, (b) a sulfonylurea, (c) a dipeptidy peptidase-4 (DPP-4) inhibitor, (d) a biguanide, (e) a thiazolidinediones, (f) an alpha-glucosidase inhibitor, (g) an amylin mimetic; (h) an incretin mimetics; (i) an insulin; and (j) any combination thereof.

In certain aspects the invention relates to a kit for detecting Eno1 in a biological sample comprising: (a) at least one reagent for measuring the level of Eno1 in the biological sample; (b) a set of instructions for measuring the level of Eno1 in the biological sample; and (c) a set of instructions for determining the level of blood glucose in the biological sample (e.g., based upon the level of Eno1). In certain embodiments the kit further comprises at least one reagent for measuring a level of HbA1c in the biological sample. In certain embodiments, the kit further comprises instructions for measuring at least one of HbA1c level, fed blood glucose level, fasting blood glucose level, and glucose tolerance in the subject from which the biological sample was obtained.

In certain aspects the invention also relates to a panel of reagents for use in a method of detecting elevated blood glucose, the panel comprising detection reagents for Eno1 and HbA1c.

In certain aspects the invention also relates to a panel of reagents for use in a method of treating elevated blood glucose, the panel comprising detection reagents for Eno1 and HbA1c.

In certain aspects the invention also relates to a panel of reagents for use in a method of monitoring the treatment of elevated blood glucose, the panel comprising detection reagents for Eno1 and HbA1c.

In certain aspects the invention also relates to a kit comprising any of the panels of reagents described above, and a set of instructions for obtaining diagnostic information as to level of one or more indicators of elevated blood glucose.

In certain aspects the invention also relates to use of a panel comprising a plurality of detection reagents specific for detecting markers of elevated blood glucose in a method for diagnosing and/or treating elevated blood glucose, wherein at least one detection reagent of the panel is specific for detecting Eno1, and wherein the remaining one or more detection reagents are specific for detecting an indicator of elevated blood glucose marker selected from the group consisting of HbA1c and glucose.

Other embodiments are provided infra.

BRIEF DESCRIPTION OF THE DRAWINGS

FIG. 17A shows the results from all four dosing regimens. FIG. 17B shows results from the G5-PAMAM dendrimer+SMTP (G5+SMTP) and G5-PAMAM dendrimer+Eno1+SMTP (Eno1+G5+SMTP) 50 ug/kg to show the significant difference in glucose levels at the 30 minute time point.

FIGS. 34A and 34B show the (A) amino acid (SEQ ID NO: 2) and (B) nucleic acid coding sequence (SEQ ID NO: 1) of human Eno1, variant 1 (NCBI Accession No. NM_001428.3).

FIGS. 35A and 35B show the (A) amino acid (SEQ ID NO: 4) and (B) nucleic acid coding sequence (SEQ ID NO: 3) of human Eno1, variant 2 (NCBI Accession No. NM_001201483.1). The human Eno1, variant 2 protein is also referred to as MBP-1.

FIG. 36A shows the nucleic acid sequence of ENO2 mRNA (SEQ ID NO: 5). FIG. 36B shows the amino acid sequence of Eno2 (SEQ ID NO: 6).

FIGS. 37A and 37B show the nucleic acid sequences of variant 1 (SEQ ID NO: 7) and variant 2 (SEQ ID NO: 8), respectively, of ENO3 mRNA. FIG. 37C shows isoform 1 of the Eno3 protein (SEQ ID NO: 9), which is encoded by both variant 1 and variant 2. FIG. 37D shows the nucleic acid sequence of variant 3 of ENO3 mRNA (SEQ ID NO: 10). FIG. 37E shows the amino acid sequence of isoform 2 of Eno3 (SEQ ID NO: 11), which is encoded by variant 3. Variant 3 of the ENO3 mRNA differs in the 5' UTR and lacks two exons in the 5' coding region compared to variant 1. Isoform 2 of the Eno3 protein is shorter than isoform 1, but has the same N- and C-termini.

DETAILED DESCRIPTION AND PREFERRED EMBODIMENTS

Figure 1A:
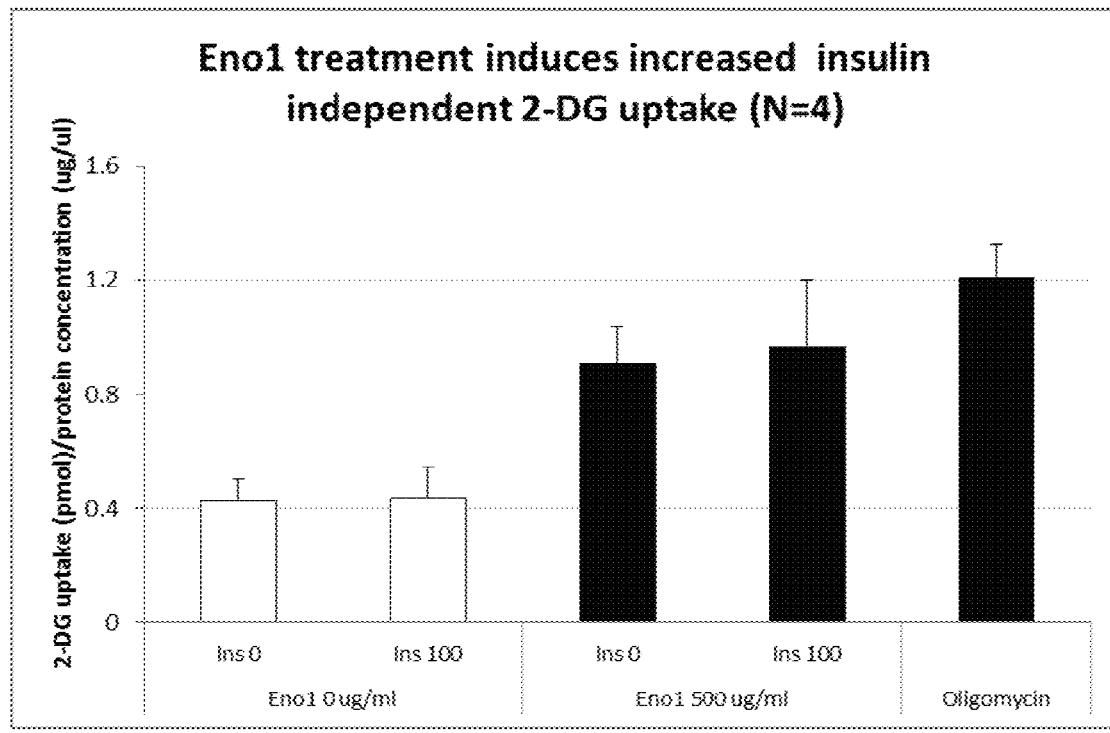
FIG. 1A is a graph showing glucose uptake in smooth muscle myoblasts treated with or without Eno1 and insulin.

A discovery platform technology was used to delineate distinct molecular signatures that drive the pathophysiology of diabetes. Eno1 was identified through this discovery platform technology as a critical node that is significantly modulated in human primary in vitro models of diabetes. Subsequent in vitro and in vivo studies discussed herein confirmed a role for Eno1 in insulin dependent and independent glucose uptake, glucose tolerance, insulin sensitivity, and/or diabetes, e.g., type 1 diabetes, type 2 diabetes, pre-diabetes, and gestational diabetes. More specifically, treatment of human myotubes with Eno1 protein was demonstrated to increase both insulin independent and dependent glucose uptake in myotubes, indicating a role for Eno1 in the treatment of both type 1 and type 2 diabetes and in glucose uptake in both the presence and the absence of insulin and/or insulin response. Further, administration of Eno1 protein, either alone or in the context of a skeletal muscle targeted dendrimer, improved glucose tolerance in a diet induced obesity model in mice, and similar results are expected in genetic models of both type 1 and type 2 diabetes. These results demonstrate that Eno1 is effective in normalizing glucose and insulin response, and thus indicate that Eno1 is useful in improving glucose tolerance and increasing insulin sensitivity/decreasing insulin resistance, thereby treating diabetes.

I. Definitions

Enolase 1, (alpha), also known as ENO1L, alpha-enolase, enolase-alpha, tau-crystallin, non-neural enolase (NNE), alpha enolase like 1, phosphopyruvate hydratase (PPH), plasminogen-binding protein, MYC promoter-binding protein 1 (MPB1), and 2-phospho-D-glycerate hydro-lyase, is one of three enolase isoenzymes found in mammals. Protein and nucleic acid sequences of human Eno1 isoforms are provided herein in FIGS. 34 and 35. The instant application provides human amino acid and nucleic acid sequences for the treatment of human disease. However, it is understood that the compositions and methods of the invention can be readily adapted for treatment of non-human animals by selection of an Eno1 of the species to be treated. Amino acid and nucleic acid sequences of Eno1 for non-human species are known in the art and can be found, for example, at ncbi.nlm.nih.gov/genbank/. In some embodiments, the Eno1 used in the compositions and methods of the invention is a mammalian Eno1. In a preferred embodiment, the Eno1 is human Eno1.

As used herein, "administration of Eno1" unless otherwise indicated is understood as administration of either Eno1 protein or a nucleic acid construct for expression of Eno1 protein. In certain embodiments the Eno1 protein can include an Eno1 protein fragment or a nucleic acid for encoding an Eno1 protein fragment. In certain embodiments, administration of Eno1 is administration of Eno1 protein. In certain embodiments, administration of Eno1 is administration of Eno1 polynucleotide. Protein and nucleic acid sequences of human Eno1 are provided herein. In certain embodiments, administration of Eno1 comprises administration of the first variant or the second variant of human Eno1. In certain embodiments, administration of Eno1 comprises administration of the first variant and the second variant of human Eno1. In certain embodiments, administration of Eno1 comprises administration of the first variant of human Eno1. In certain embodiments, administration of Eno1 comprises administration of the second variant of human Eno1. In certain embodiments, administration of Eno1 comprises administration of only the first variant of human Eno1. In certain embodiments, administration of Eno1 comprises administration of only the second variant of human Eno1.

As used herein, "biologically active" refers to an Eno1 molecule or fragment thereof that has at least one activity of an endogenous Eno1 protein. For example, in some embodiments, the biologically active Eno1 molecule or fragment thereof catalyzes the dehydration of 2-phospho-D-glycerate (PGA) to phosphoenolpyruvate (PEP). In some embodiments, the biologically active Eno1 molecule or fragment thereof catalyzes the hydration of PEP to PGA. In some embodiments, the biologically active Eno1 molecule or fragment thereof increases glucose uptake by a cell, for example a muscle cell, preferably a skeletal muscle cell. In some embodiments, the biologically active Eno1 molecule or fragment thereof reduces blood glucose levels, e.g. fed blood glucose levels or blood glucose levels in a glucose tolerance test. In some embodiments, the biologically active Eno1 molecule or fragment thereof binds to Nampt, for example, extracellular Nampt (eNampt).

As used herein, "administration to a muscle", "delivery to a muscle", or "delivery to a muscle cell" including a skeletal muscle cell, smooth muscle cell, and the like are understood as a formulation, method, or combination thereof to provide an effective dose of Eno1 to a muscle e.g., a muscle cell, to provide a desired systemic effect, e.g., normalization of blood glucose in a subject with abnormal blood glucose, e.g., by increasing glucose tolerance and/or insulin sensitivity, or treating diabetes. In certain embodiments, the Eno1 is formulated for administration directly to, and preferably retention in, muscle. In certain embodiments, the formulation used for administration directly to the muscle (i.e., intramuscular administration) preferably a sustained release formulation of the Eno1 to permit a relatively low frequency of administration (e.g., once per week or less, every other week or less, once a month or less, once every other month or less, once every three months or less, once every four months or less, once every five months or less, once every six months or less). In certain embodiments, the Eno1 is linked to a targeting moiety to increase delivery of the Eno1 to muscle so that the Eno1 need not be delivered directly to muscle (e.g., is delivered subcutaneously or intravenously). It is understood that administration to muscle does not require that the entire dose of Eno1 be delivered to the muscle or into muscle cells. In certain embodiments, at least 5%, at least 10%, at least 15%, at least 20%, at least 25%, at least 30%, at least 35% of the Eno1 is delivered to muscle, preferably skeletal muscle and/or smooth muscle. In certain embodiments, the amount of non-intramuscularly administered muscle-targeted Eno1 delivered to a muscle cell is about 1.5 or more times greater, 2 or more times greater, 3 or more times greater, 4 or more times greater, 5 or more times greater, or 6 or more times greater than the amount of non-targeted Eno1 delivered to muscle. In certain embodiments, the Eno1 is delivered to skeletal muscle. In certain embodiments, the Eno1 is delivered to smooth muscle. In certain embodiments, the Eno1 is delivered to skeletal muscle and smooth muscle. In certain embodiments, is delivered preferentially or in greater amount to skeletal muscle as compared to smooth muscle. In certain embodiments, at least 50%, 60%, 70%, 75%, 80%, 85%, 90%, 95% or greater of the Eno1 delivered to muscle is delivered to skeletal muscle. In certain embodiments, the Eno1 is not delivered to smooth muscle. Assays to determine the relative targeting of a payload by a targeting moiety are known in the art and provided, for example, in Samoylova et al., 1999, *Muscle Nerve*, 22:460-466, incorporated herein by reference.

As used herein, a "muscle targeting moiety" includes, at least, a muscle targeting peptide (MTP), for example a skeletal and/or smooth muscle targeting peptide (SMTP). In certain embodiments, the targeting moiety include ligands to bind integrins αvβ5 or αvβ3 integrins. In certain embodiments, the targeting moiety includes a CD-46 ligand. In certain embodiments, the targeting moiety includes an adenovirus peton protein optionally in combination with an adenovirus 35 fiber protein. In certain embodiments, at least 5%, at least 10%, at least 15%, at least 20%, at least 25%, at least 30%, at least 35% of muscle-targeted Eno1 is delivered to muscle, in some embodiments preferably skeletal and/or smooth muscle, by a muscle-targeting moiety. In certain embodiments, the amount of non-intramuscularly administered muscle-targeted Eno1 delivered to a muscle cell is about 1.5 or more times greater, 2 or more times greater, 3 or more times greater, 4 or more times greater, 5 or more times greater, or 6 or more times greater than the amount of non-targeted Eno1 delivered to muscle.

As used herein, a "muscle targeting peptide" or "MTP" is understood as a peptide sequence that increases the delivery of its payload (e.g., Eno1) to a muscle cell, preferably a skeletal and/or smooth muscle cell. MTPs are known in the art and are provided, for example, in U.S. Pat. No. 6,329,501; US Patent Publication No. 20110130346; and Samoylova et al., 1999, Muscle and Nerve 22: 460-466, each of which is incorporated herein in its entirety. In certain embodiments the MTP is a skeletal muscle targeting peptide. A "skeletal muscle targeting peptide" is a peptide sequence that increases the delivery of its payload (e.g., Eno1) to a skeletal muscle cell. In certain embodiments the MTP is a smooth muscle targeting peptide. A "smooth muscle targeting peptide" is a peptide sequence that increases the delivery of its payload (e.g., Eno1) to a smooth muscle cell. In certain embodiments the MTP increases the delivery of its payload (e.g., Eno1) to a skeletal cell and to a smooth muscle cell. In certain embodiments the MTP, e.g., skeletal muscle targeting peptide and/or smooth muscle targeting peptide, does not increase the delivery of its payload to cardiac muscle cell. MTP, e.g., skeletal muscle, targeting peptides include, but are not limited to peptides comprising the following sequences: ASSLNIA (SEQ ID NO: 12); WDANGKT (SEQ ID NO: 13); GETRAPL (SEQ ID NO: 14); CGHHPVYAC (SEQ ID NO: 15); and HAIYPRH (SEQ ID NO: 16). In a preferred embodiment, the MTP comprises the amino acid sequence ASSLNIA (SEQ ID NO: 12).

As used herein, "payload" is understood as a moiety for delivery to a target cell by a targeting moiety. In certain embodiments, the payload is a peptide, e.g., an Eno1 peptide. In certain embodiments, the payload is a nucleic acid, e.g., a nucleic acid encoding an Eno1 peptide. In certain embodiments, the payload further comprises additional components (e.g., dendrimers, liposomes, microparticles) or agents (e.g., therapeutic agents) for delivery with the Eno1 payload to the target cell.

As used herein, a "linker" is understood as a moiety that juxtaposes a targeting moiety and a payload in sufficiently close proximity such that the payload is delivered to the desired site by the targeting moiety. In certain embodiments, the linker is a covalent linker, e.g., a cross-linking agent including a reversible cross-linking agent; a peptide bond, e.g., wherein the payload is a protein co-translated with the targeting moiety. In certain embodiments, the linker is covalently joined to one of the payload or the targeting moiety and non-covalently linked to the other. In certain embodiments, the linker comprises a dendrimer. In certain embodiments, the dendrimer is covalently linked to the targeting moiety and non-covalently linked to the payload, e.g., Eno1. In certain embodiments, the linker is a liposome or a microparticle, and the targeting moiety is exposed on the surface of the liposome and the payload, e.g., Eno1 is encapsulated in the liposome or microparticle. In certain embodiments, the linker and the Eno1 are present on the surface of the microparticle linker. In certain embodiments, the targeting moiety is present on the surface of a virus particle and the payload comprises a nucleic acid encoding Eno1.

As used herein, "linked", "operably linked", "joined" and the like refer to a juxtaposition wherein the components described are present in a complex permitting them to function in their intended manner. The components can be linked covalently (e.g., peptide bond, disulfide bond, non-natural chemical linkage), through hydrogen bonding (e.g., knob-into-holes pairing of proteins, see, e.g., U.S. Pat. No. 5,582,996; Watson-Crick nucleotide pairing), or ionic binding (e.g., chelator and metal) either directly or through linkers (e.g., peptide sequences, typically short peptide sequences; nucleic acid sequences; or chemical linkers, including the use of linkers for attachment to higher order or larger structures including microparticles, beads, or dendrimers). As used herein, components of a complex can be linked to each other by packaging in and/or on a liposome and/or dendrimer wherein some of the components of the complex can be attached covalently and some non-covalently. Linkers can be used to provide separation between active molecules so that the activity of the molecules is not substantially inhibited (less than 10%, less than 20%, less than 30%, less than 40%, less than 50%) by linking the first molecule to the second molecule. Linkers can be used, for example, in joining Eno1 to a targeting moiety. As used herein, molecules that are linked, but no covalently joined, have a binding affinity (Kd) of less than $10^{-3}$, $10^{-4}$, $10^{-5}$, $10^{-6}$, $10^{-7}$, $10^{-8}$, $10^{-9}$, $10^{-10}$, $10^{-11}$, or $10^{-12}$, or any range bracketed by those values, for each other under conditions in which the reagents of the invention are used, i.e., typically physiological conditions.

In certain embodiments, the payload and the targeting moiety are present in a complex at about a 1:1 molar ratio. In certain embodiments, the targeting moiety is present in a complex with a molar excess of the payload. In certain embodiments, the ratio of payload to targeting moiety is about 0.1:1, about 0.2:1, about 0.3:1, about 0.4:1, about 0.5:1, about 0.6:1, about 0.7:1, about 0.8:1, about 0.9:1, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1.

A "dendrimer" is a polymeric molecule composed of multiple branched monomers that eminate radially from a central core. Due to the structure and synthetic methods used to generate dendrimers, the products from dendrimer synthesis are theoretically monodisperse. When the core of a dendrimer is removed, a number of identical fragments called dendrons remain with the number of dendrons dependent on the multiplicity of the central core. The number of branch points encountered upon moving outward from the core to the periphery defines its generation, e.g., G-1, G-2, G-3, etc., with dendrimers of higher generations being larger, more branched, and having more end groups than dendrimers of lower generations. As used herein, a dendrimer is preferably a pharmaceutically acceptable dendrimer.

As used herein, a "subject with elevated blood glucose" or "increased blood glucose" is understood as a subject who has elevated blood glucose for a sufficient duration and frequency to be considered a pathological condition, i.e., a subject that does not produce enough insulin or is not sufficiently sensitive to insulin so that the glucose level of the subject remains elevated for an extended period after eating a meal, e.g. for more than two hours after eating a meal and/or who has an elevated fasting blood glucose. In certain embodiments, a subject with elevated blood glucose is understood as a subject with one or both of fasting blood glucose of at least 100 mg/dl and 2-hour plasma glucose in a 75-g oral glucose tolerance test of at least 140 mg/dl. In certain embodiments, a subject with elevated blood glucose is understood as a subject with one or more of fasting blood glucose of at least 126 mg/dl; a 2-hour plasma glucose in a 75-g oral glucose tolerance test of at least 200 mg/dl; or a random plasma glucose of at least 200 mg/dl. In certain embodiments, a subject with elevated blood glucose is understood as a pregnant subject with one or more of fasting blood glucose of at least 92 mg/dl; a 1-hour plasma glucose in a 75-g oral glucose tolerance test of at least 180 mg/dl; and a 2-hour plasma glucose in a 75-g oral glucose tolerance test of at least 153 mg/dl. In certain embodiments as used herein, a subject with elevated blood glucose does not include subjects with type 1 diabetes or pancreatic disease that results in an absolute insulin deficiency. In certain embodiments as used herein, a subject with elevated blood glucose includes subjects with type 1 diabetes or pancreatic disease that results in an absolute insulin deficiency.

As used herein, a "subject with elevated HbA1c" or a "subject with elevated A1c" is understood as a subject with an HbA1c level of at least 5.7%. In certain embodiments, the subject has an HbA1c level of at least 6.5%.

As used herein, "diabetes" is intended to refer to either type 1 diabetes or type 2 diabetes, or both type 1 and type 2 diabetes, optionally in combination with gestational diabetes. In certain embodiments, diabetes includes type 2 diabetes. In certain embodiments, diabetes does not include type 1 diabetes. In certain embodiments, diabetes includes gestational diabetes. In certain embodiments, diabetes does not include gestational diabetes. In certain embodiments, diabetes includes pre-diabetes. In certain embodiments, diabetes does not include pre-diabetes. In certain embodiments, diabetes includes pre-diabetes, type 1 diabetes, and type 2 diabetes. In certain embodiments, diabetes includes pre-diabetes and type 2 diabetes.

As used herein, "insulin resistance" and "insulin insensitivity" can be used interchangeably and refers to conditions, especially pathological conditions, wherein the amount of insulin is less effective at lowering blood sugar than in a normal subject resulting in an increase in blood sugar above the normal range that is not due to the absence of insulin. Without being bound by mechanism, the conditions are typically associated with a decrease in signaling through the insulin receptor. Typically, insulin resistance in muscle and fat cells reduces glucose uptake and storage as glycogen and triglycerides, respectively. Insulin resistance in liver cells results in reduced glycogen synthesis and a failure to suppress glucose production and release into the blood.

Insulin resistance is often present in the same subject together with "insulin insufficiency", which also results in an increase in blood sugar, especially a pathological increase in blood sugar, above the normal range that is not due to the absence of insulin. Insulin insufficiency is a condition related to a lack of insulin action in which insulin is present and produced by the body. It is distinct from type 1 diabetes in which insulin is not produced due to the lack of islet cells.

For the purposes of the methods of the instant invention, it is not necessary to distinguish if a subject suffers from insulin resistance/insensitivity, insulin insufficiency, or both.

The term "impaired glucose tolerance" (IGT) or "pre-diabetes" is used to describe a person who, when given a glucose tolerance test, has a blood glucose level that falls between normal and hyperglycemic, i.e., has abnormal glucose tolerance, e.g., pathologically abnormal glucose tolerance. Such a person is at a higher risk of developing diabetes although they are not clinically characterized as having diabetes. For example, impaired glucose tolerance refers to a condition in which a patient has a fasting blood glucose concentration or fasting serum glucose concentration greater than 110 mg/dl and less than 126 mg/dl (7.00 mmol/L), or a 2 hour postprandial blood glucose or serum glucose concentration greater than 140 mg/dl (7.78 mmol/L) and less than 200 mg/dl (11.11 mmol/L). Prediabetes, also referred to as impaired glucose tolerance or impaired fasting glucose is a major risk factor for the development of type 2 diabetes mellitus, cardiovascular disease and mortality. Much focus has been given to developing therapeutic interventions that prevent the development of type 2 diabetes by effectively treating prediabetes (Pharmacotherapy, 24:362-71, 2004).

As used herein, a "pathological" condition reaches a clinically acceptable threshold of disease or condition. A pathological condition can result in significant adverse effects to the subject, particularly in the long term, if the condition is not resolved, e.g., blood glucose and/or HbA1c levels are not normalized. Pathological conditions can be reversed by therapeutic agents, surgery, and/or lifestyle changes. A pathological condition may or may not be chronic. A pathological condition may or may not be reversible. A pathological condition may or may not be terminal.

"Hyperinsulinemia" is defined as the condition in which a subject with insulin resistance, with or without euglycemia, in which the fasting or postprandial serum or plasma insulin concentration is elevated above that of normal, lean individuals without insulin resistance (i.e., >100 mg/dl in a fasting plasma glucose test or >140 mg/dl in an oral glucose tolerance test).

The condition of "hyperglycemia" (high blood sugar) is a condition in which the blood glucose level is too high. Typically, hyperglycemia occurs when the blood glucose level rises above 180 mg/dl. Symptoms of hyperglycemia include frequent urination, excessive thirst and, over a longer time span, weight loss.

The condition of "hypoglycemia" (low blood sugar) is a condition in which the blood glucose level is too low. Typically, hypoglycemia occurs when the blood glucose level falls below 70 mg/dl. Symptoms of hypoglycemia include moodiness, numbness of the extremities (especially in the hands and arms), confusion, shakiness or dizziness. Since this condition arises when there is an excess of insulin over the amount of available glucose it is sometimes referred to as an insulin reaction.

As used herein, an "HbA1c level" or "A1c level" is understood as a hemoglobin A1c (HbA1c) level determined from an HbA1c test, which assesses the average blood glucose levels during the previous two and three months. A person without diabetes typically has an HbA1c value that ranges between 4% and 6%. Prediabetes is characterized by a pathological HbA1c level of 5.7% to 6.5%, with an Hb1Ac level greater than 6.5% being indicative of diabetes. Every 1% increase in HbA1c reflects a blood glucose levels increases by approximately 30 mg/dL and increased risk of complications due to persistent elevated blood glucose. Preferably, the HbA1c value of a patient being treated according to the present invention is reduced to less than 9%, less than 7%, less than 6%, and most preferably to around 5%. Thus, the excess HbA1c level of the patient being treated (i.e., the Hb1Ac level in excess of 5.7%) is preferably lowered by at least 10%, 20%, 30%, 40%, 50%, 60%, 70%, 80%, 90%, or more relative to such levels prior to treatment (i.e., pre-treatment level—post-treatment level/pre-treatment level).

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state. As used herein, treatment can include one or more of reduction of insulin resistance, increasing insulin sensitivity, decreasing insulin deficiency, improving or normalizing HbAc1 levels, improving or normalizing blood glucose levels (e.g., fed blood glucose levels, fasting blood glucose levels, glucose tolerance), and ameliorating at least one sign or symptom of diabetes. Therapeutic goals in the treatment of diabetes, including type 2 diabetes, include HbAc1 levels <6.5%; blood glucose 80-120 mg/dl before meals; and blood glucose <140 mg/dl 2 hours after meals. Therapeutic goals in the treatment of pre-diabetes include reduction of HbA1c, blood glucose levels, and glucose response to normal levels. Treatment does not need to be curative or reach the ideal therapeutic goals of treatment. Treatment outcomes need not be determined quantitatively. However, in certain embodiments, treatment outcomes can be quantitated by considering percent improvement towards a normal value at the end of a range. For example, metabolic syndrome is characterized by an excess of some measures (e.g., blood glucose levels, HbA1c levels) and a deficiency in other measures (e.g., insulin response). A subject with a fasting blood glucose level of 150 mg/dl would have excess fasting blood glucose of 50 mg/dl (150 mg/dl-100 mg/dl, the maximum normal blood glucose level). Reduction of excess blood glucose by 20% would be an 10 mg/dl reduction in excess blood glucose. Similar calculations can be made for other values.

As used herein, "reducing glucose levels" means reducing excess of glucose by at least 10%, 20%, 30%, 40%, 50%, 60%, 70%, 80%, 90%, 95%, or more to achieve a normalized glucose level, i.e., a glucose level no greater than 150 mg/dl. Desirably, glucose levels prior to meals are reduced to normoglycemic levels, i.e., between 150 to 60 mg/dL, between 140 to 70 mg/dL, between 130 to 70 mg/dL, between 125 to 80 mg/dL, and preferably between 120 to 80 mg/dL. Such reduction in glucose levels may be obtained by increasing any one of the biological activities associated with the clearance of glucose from the blood. Accordingly, an agent having the ability to reduce glucose levels may increase insulin production, secretion, or action. Insulin action may be increased, for example, by increasing glucose uptake by peripheral tissues and/or by reducing hepatic glucose production. Alternatively, the agent may reduce the absorption of carbohydrates from the intestines, alter glucose transporter activity (e.g., by increasing GLUT4 expression, intrinsic activity, or translocation), increase the amount of insulin-sensitive tissue (e.g., by increasing muscle cell or adipocyte cell differentiation), or alter gene transcription in adipocytes or muscle cells (e.g., altered secretion of factors from adipocytes expression of metabolic pathway genes). Desirably, the agent increases more than one of the activities associated with the clearance of glucose.

By "alter insulin signaling pathway such that glucose levels are reduced" is meant to alter (by increasing or reducing) any one of the activities involved in insulin signaling such that the overall result is an increase in the clearance of glucose from plasma and normalizes blood glucose. For example, altering the insulin signaling pathway thereby causing an increase in insulin production, secretion, or action, an increasing glucose uptake by peripheral tissues, a reducing hepatic glucose production, or a reducing the absorption of carbohydrates from the intestines.

A "therapeutically effective amount" is that amount sufficient to treat a disease in a subject. A therapeutically effective amount can be administered in one or more administrations.

A number of treatments for type 2 diabetes are known in the art including both drug and behavioral interventions. Drugs for treatment of type 2 diabetes include, but are not limited to meglitinides (repaglinide (Prandin) and nateglinide (Starlix); sulfonylureas (glipizide (Glucotrol), glimepiride (Amaryl), and glyburide (DiaBeta, Glynase)); Dipeptidy peptidase-4 (DPP-4) inhibitors (saxagliptin (Onglyza), sitagliptin (Januvia), and linagliptin (Tradjenta)); biguanides (metformin (Fortamet, Glucophage)); thiazolidinediones (rosiglitazone (Avandia) and pioglitazone (Actos)); and alpha-glucosidase inhibitors (acarbose (Precose) and miglitol (Glyset)). Insulins are typically used only in treatment of later stage type 2 diabetes and include rapid-acting insulin (insulin aspart (NovoLog), insulin glulisine (Apidra), and insulin lispro (Humalog)); short-acting insulin (insulin regular (Humulin R, Novolin R)); intermediate-acting insulin (insulin NPH human (Humulin N, Novolin N)), and long-acting insulin (insulin glargine (Lantus) and insulin detemir (Levemir)). Treatments for diabetes can also include behavior modification including exercise and weight loss which can be facilitated by the use of drugs or surgery. Treatments for elevated blood glucose and diabetes can be combined. For example, drug therapy can be combined with behavior modification therapy.

By "diagnosing" and the like, as used herein, refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. Diagnostic methods provide an indicator that a disease is or is not present. A single diagnostic test typically does not provide a definitive conclusion regarding the disease state of the subject being tested.

As used herein, "monitoring" is understood as assessing at least one sign or symptom of a disease in a subject at a first time point and at a later second time point, comparing the severity of the sign(s) or symptom(s) of the condition, and determining of the condition became more or less severe over time.

The terms "administer", "administering" or "administration" include any method of delivery of a pharmaceutical composition or agent into a subject's system or to a particular region in or on a subject. In certain embodiments, the agent is administered enterally or parenterally. In certain embodiments of the invention, an agent is administered intravenously, intramuscularly, subcutaneously, intradermally, intranasally, orally, transcutaneously, or mucosally. In certain preferred embodiments, an agent is administered by injection or infusion, e.g., intravenously, intramuscularly, subcutaneously. In certain embodiments, administration includes the use of a pump. In certain embodiments, the agent is administered locally or systemically. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, etc.

As used herein, the term "co-administering" refers to administration of Eno1 prior to, concurrently or substantially concurrently with, subsequently to, or intermittently with the administration of an agent for the treatment of diabetes, pre-diabetes, glucose intolerance, or insulin resistance. The Eno1 formulations provided herein, can be used in combination therapy with at least one other therapeutic agent for the treatment of diabetes, pre-diabetes, glucose intolerance, or insulin resistance. Eno1 and/or pharmaceutical formulations thereof and the other therapeutic agent can act additively or, more preferably, synergistically. In one embodiment, Eno1 and/or a formulation thereof is administered concurrently with the administration of another therapeutic agent for the treatment of diabetes, pre-diabetes, glucose intolerance, or insulin resistance. In another embodiment, Eno1 and/or a pharmaceutical formulation thereof is administered prior or subsequent to administration of another therapeutic agent for the treatment of diabetes, pre-diabetes, glucose intolerance, or insulin resistance.

The term "sample" as used herein refers to a collection of similar fluids, cells, or tissues isolated from a subject. The term "sample" includes any body fluid (e.g., urine, serum, blood fluids, lymph, gynecological fluids, cystic fluid, ascetic fluid, ocular fluids, and fluids collected by bronchial lavage and/or peritoneal rinsing), ascites, tissue samples or a cell from a subject. Other subject samples include tear drops, serum, cerebrospinal fluid, feces, sputum, and cell extracts. In a particular embodiment, the sample is urine or serum. In certain embodiments, the sample comprises cells. In other embodiments, the sample does not comprise cells.

The term "control sample," as used herein, refers to any clinically relevant comparative sample, including, for example, a sample from a healthy subject not afflicted with any of impaired glucose tolerance, increased blood glucose, insulin resistance, diabetes, or prediabetes; or a sample from a subject from an earlier time point in the subject, e.g., prior to treatment, at an earlier stage of treatment. A control sample can be a purified sample, protein, and/or nucleic acid provided with a kit. Such control samples can be diluted, for example, in a dilution series to allow for quantitative measurement of analytes in test samples. A control sample may include a sample derived from one or more subjects. A control sample may also be a sample made at an earlier time point from the subject to be assessed. For example, the control sample can be a sample taken from the subject to be assessed before the onset abnormal blood glucose levels or A1c levels, at an earlier stage of disease, or before the administration of treatment or of a portion of treatment. The control sample may also be a sample from an animal model, or from a tissue or cell lines derived from the animal model of impaired glucose tolerance, increased blood glucose, insulin resistance, diabetes, or prediabetes. The level of Eno1 activity or expression in a control sample that consists of a group of measurements may be determined, e.g., based on any appropriate statistical measure, such as, for example, measures of central tendency including average, median, or modal values.

The term "control level" refers to an accepted or pre-determined level of a sign of a impaired glucose tolerance, increased blood glucose, insulin resistance, diabetes, or pre-diabetes in a subject or a subject sample. The following levels are considered to be normal levels:

Fasting blood glucose less than or equal to 100 mg/dl.
HbA1c less than or equal to 5.7%.
Oral glucose tolerance test less than or equal to 140 mg/dl.
Levels above these levels are understood to be pathological levels.

As used herein, a "predetermined threshold value" of a biomarker refers to the level of the biomarker (e.g., the expression level or quantity (e.g., ng/ml) in a biological sample) or other indicator of elevated blood glucose in a corresponding control/normal sample or group of control/normal samples obtained from normal or healthy subjects, e.g., subjects that do not have abnormal blood glucose. The predetermined threshold value may be determined prior to or concurrently with measurement of marker levels in a biological sample. The control sample may be from the same subject at a previous time or from different subjects.

As used herein, a sample obtained at an "earlier time point" is a sample that was obtained at a sufficient time in the past such that clinically relevant information could be obtained in the sample from the earlier time point as compared to the later time point. In certain embodiments, an earlier time point is at least four weeks earlier. In certain embodiments, an earlier time point is at least six weeks earlier. In certain embodiments, an earlier time point is at least two months earlier. In certain embodiments, an earlier time point is at least three months earlier. In certain embodiments, an earlier time point is at least six months earlier. In certain embodiments, an earlier time point is at least nine months earlier. In certain embodiments, an earlier time point is at least one year earlier. Multiple subject samples (e.g., 3, 4, 5, 6, 7, or more) can be obtained at regular or irregular intervals over time and analyzed for trends in changes in marker levels. Appropriate intervals for testing for a particular subject can be determined by one of skill in the art based on ordinary considerations.

As used herein, the term "obtaining" is understood to refer to manufacturing, purchasing, or otherwise coming into possession of.

As used herein, "detecting", "detection" and the like are understood to refer to an assay performed for identification of a specific analyte in a sample, e.g., Eno1 expression or activity level in a sample. The amount of analyte or activity detected in the sample can be none or below the level of detection of the assay or method. Detecting or detection can also include measuring of glucose and/of HbAc1 levels.

The terms "modulate" or "modulation" refer to upregulation (i.e., activation or stimulation), downregulation (i.e., inhibition or suppression) of a level, or the two in combination or apart. A "modulator" is a compound or molecule that modulates, and may be, e.g., an agonist, antagonist, activator, stimulator, suppressor, or inhibitor.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

As used herein, the term "amplification" refers to any known in vitro procedure for obtaining multiple copies ("amplicons") of a target nucleic acid sequence or its complement or fragments thereof. In vitro amplification refers to production of an amplified nucleic acid that may contain less than the complete target region sequence or its complement. Known in vitro amplification methods include, e.g., transcription-mediated amplification, replicase-mediated amplification, polymerase chain reaction (PCR) amplification, ligase chain reaction (LCR) amplification and strand-displacement amplification (SDA including multiple strand-displacement amplification method (MSDA)). Replicase-mediated amplification uses self-replicating RNA molecules, and a replicase such as Q-β-replicase (e.g., Kramer et al., U.S. Pat. No. 4,786,600). PCR amplification is well known and uses DNA polymerase, primers and thermal cycling to synthesize multiple copies of the two complementary strands of DNA or cDNA (e.g., Mullis et al., U.S. Pat. Nos. 4,683,195, 4,683,202, and 4,800,159). LCR amplification uses at least four separate oligonucleotides to amplify a target and its complementary strand by using multiple cycles of hybridization, ligation, and denaturation (e.g., EP Pat. App. Pub. No. 0 320 308). SDA is a method in which a primer contains a recognition site for a restriction endonuclease that permits the endonuclease to nick one strand of a hemimodified DNA duplex that includes the target sequence, followed by amplification in a series of primer extension and strand displacement steps (e.g., Walker et al., U.S. Pat. No. 5,422,252). Two other known strand-displacement amplification methods do not require endonuclease nicking (Dattagupta et al., U.S. Pat. Nos. 6,087,133 and 6,124,120 (MSDA)). Those skilled in the art will understand that the oligonucleotide primer sequences of the present invention may be readily used in any in vitro amplification method based on primer extension by a polymerase. (see generally Kwoh et al., 1990, Am. Biotechnol. Lab. 8:14-25 and (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 2000, Molecular Cloning—A Laboratory Manual, Third Edition, CSH Laboratories). As commonly known in the art, the oligos are designed to bind to a complementary sequence under selected conditions.

As used herein, the term "antigen" refers to a molecule, e.g., a peptide, polypeptide, protein, fragment, or other biological moiety, which elicits an antibody response in a subject, or is recognized and bound by an antibody.

As used herein, the term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As use herein, the phrase "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

The phrase "specific identification" is understood as detection of a marker of interest with sufficiently low background of the assay and cross-reactivity of the reagents used such that the detection method is diagnostically useful. In certain embodiments, reagents for specific identification of a marker bind to only one isoform of the marker. In certain embodiments, reagents for specific identification of a marker bind to more than one isoform of the marker. In certain embodiments, reagents for specific identification of a marker bind to all known isoforms of the marker.

As used herein, the phrase "subject suspected of having elevated blood glucose" refers to a subject that presents one or more signs or symptoms indicative of or correlated with elevated blood glucose or is being screened for a elevated blood glucose (e.g., during a routine physical). A subject suspected of having elevated blood glucose may also have one or more risk factors. A subject suspected of having elevated blood glucose has generally not been tested for abnormal glucose levels, metabolism, or response. However, a "subject suspected of having elevated blood glucose" encompasses an individual who has received an initial diagnosis (e.g., a single incidence of elevated, but not confirmed, blood glucose) but for whom the degree of elevated glucose is not known. The term further includes people who once had elevated blood glucose (e.g., an individual treated for elevated blood glucose who maintained a normal blood glucose and/or HbA1c levels for an extended period, e.g., at least 3 months, at least 6 months, etc.).

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

IIA. Enolase 1

Enolase 1, (alpha), also known as ENO1L, alpha-enolase, enolase-alpha, tau-crystallin, non-neural enolase (NNE), alpha enolase like 1, phosphopyruvate hydratase (PPH), plasminogen-binding protein, MYC promoter-binding protein 1 (MPB1), and 2-phospho-D-glycerate hydro-lyase, is one of three enolase isoenzymes found in mammals. Each isoenzyme is a homodimer composed of 2 alpha, 2 gamma, or 2 beta subunits, and functions as a glycolytic enzyme. Alpha-enolase in addition, functions as a structural lens protein (tau-crystallin) in the monomeric form. Alternative splicing of this gene results in a shorter isoform that has been shown to bind to the c-myc promoter and function as a tumor suppressor. Several pseudogenes have been identified, including one on the long arm of chromosome 1. Alpha-enolase has also been identified as an autoantigen in Hashimoto encephalopathy. Further information regarding human Eno1 can be found, for example, in the NCBI gene database under Gene ID No. 2023 (see, ncbi.nlm.nih.gov/gene/2023, incorporated herein by reference in the version available on the date of filing this application).

Eno1 Variants

Two isoforms of human Eno1 are known. Protein and mRNA sequences of *Homo sapiens* enolase 1, (alpha) (ENO1), transcript variant 1, mRNA can be found at GenBank Accession No. NM_001428 (see ncbi.nlm.nih.gov/nuccore/NM_001428.3, which is incorporated by reference in the version available on the date of filing the instant application). This variant encodes the longer isoform, which is localized to the cytosol, and has alpha-enolase activity. It has been reported that the monomeric form of this isoform functions as a structural lens protein (tau-crystallin), and the dimeric form as an enolase. In a preferred embodiment of the invention, Eno1 is the transcript variant 1 of Eno1.

Protein and mRNA sequences of the *Homo sapiens* enolase 1, (alpha) (ENO1), transcript variant 2, mRNA can be found at GenBank Accession No. NM_001201483 (see ncbi.nlm.nih.gov/nuccore/NM_001201483.1, which is incorporated by reference in the version available on the date of filing the instant application). This variant differs at the 5' end compared to variant 1, and initiates translation from an in-frame downstream start codon, resulting in a shorter isoform (MBP-1). This isoform is localized to the nucleus, and functions as a transcriptional repressor of c-myc protooncogene by binding to its promoter. In certain embodiments of the invention, Eno1 is the transcript variant 2 of Eno1.

Several additional variants of the Eno1 protein have been described, for example, in the UniProtKB/Swiss-Prot database under Accession No. P06733. Examples of Eno1 protein variants are shown in Table 1 below.

TABLE 1

Eno1 variants.

| | AA residue | Modification |
|---|---|---|
| AA modification | 2 | N-acetylserine |
| AA modification | 5 | N6-acetyllysine |
| AA modification | 44 | Phosphotyrosine |
| AA modification | 60 | N6-acetyllysine; alternate |
| AA modification | 60 | N6-succinyllysine; alternate |
| AA modification | 64 | N6-acetyllysine |
| AA modification | 71 | N6-acetyllysine |
| AA modification | 89 | N6-acetyllysine; alternate |
| AA modification | 89 | N6-succinyllysine; alternate |
| AA modification | 92 | N6-acetyllysine |
| AA modification | 126 | N6-acetyllysine |
| AA modification | 193 | N6-acetyllysine |
| AA modification | 199 | N6-acetyllysine |
| AA modification | 202 | N6-acetyllysine |
| AA modification | 228 | N6-acetyllysine; alternate |
| AA modification | 228 | N6-succinyllysine; alternate |
| AA modification | 233 | N6-acetyllysine; alternate |
| AA modification | 233 | N6-malonyllysine; alternate |
| AA modification | 254 | Phosphoserine |
| AA modification | 256 | N6-acetyllysine |
| AA modification | 263 | Phosphoserine |
| AA modification | 272 | Phosphoserine |
| AA modification | 281 | N6-acetyllysine |
| AA modification | 285 | N6-acetyllysine |
| AA modification | 287 | Phosphotyrosine |
| AA modification | 335 | N6-acetyllysine |
| AA modification | 343 | N6-acetyllysine |
| AA modification | 406 | N6-acetyllysine |
| AA modification | 420 | N6-acetyllysine; alternate |
| AA modification | 420 | N6-malonyllysine; alternate |
| AA modification | 420 | N6-succinyllysine; alternate |
| Natural variant | 177 | N → K. Corresponds to variant rs11544513 [dbSNP\|Ensembl]. |
| Natural variant | 325 | P → Q. Corresponds to variant rs11544514 [dbSNP\|Ensembl]. |
| Mutagenesis | 94 | M → I: MBP1 protein production. No MBP1 protein production; when associated with I-97. |
| Mutagenesis | 97 | M → I: MBP1 protein production. No MBP1 protein production; when associated with I-94. |
| Mutagenesis | 159 | Dramatically decreases activity levels |
| Mutagenesis | 168 | Dramatically decreases activity levels |
| Mutagenesis | 211 | Dramatically decreases activity levels |
| Mutagenesis | 345 | Dramatically decreases activity levels |
| Mutagenesis | 384 | L → A: Loss of transcriptional repression and cell growth inhibition; when associated with A-388. |
| Mutagenesis | 388 | L → A: Loss of transcriptional repression and cell growth inhibition; when associated with A-384. |
| Mutagenesis | 396 | Dramatically decreases activity levels |

In certain embodiments of the invention, Eno1 is one of the variants listed in Table 1.

Eno1 Activity

Figure 33:
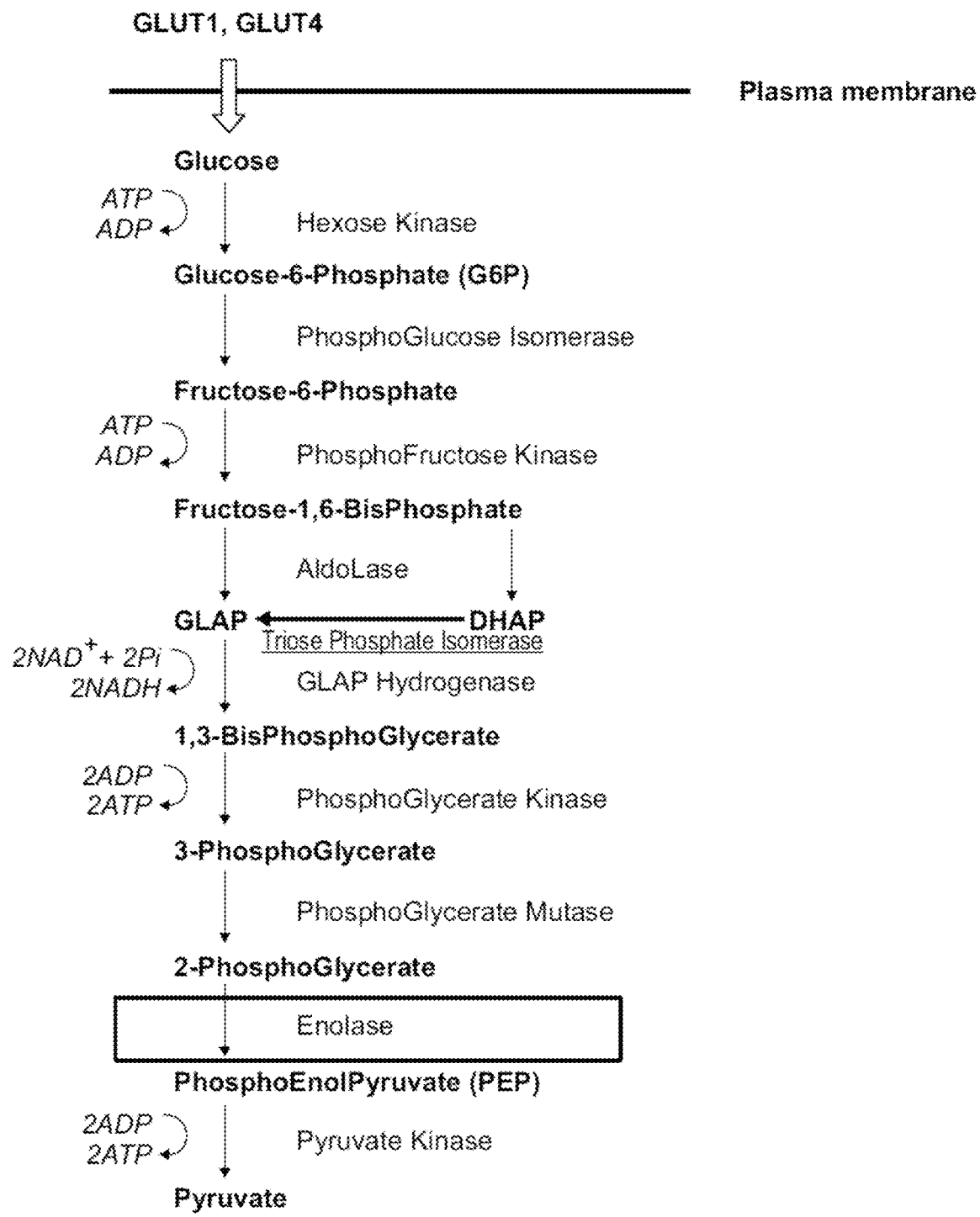
FIG. 33 shows a schematic of the glycolysis pathway.

Eno1 is a key glycolytic enzyme that catalyzes the dehydration of 2-phospho-D-glycerite (PGA) to phosphoenolpyruvate (PEP) in the last steps of the catabolic glycolytic pathway. Diaz-Ramos et al., 2012, J Biomed Biotechnol. 2012: 156795 and FIG. 33. Enolase enzymes catalyse the dehydration of PGA to PEP in the Emden Mayerhoff-Parnas glycolytic pathway (catabolic direction). In the anabolic pathway (reverse reaction) during gluconeogenesis, Eno1 catalyses hydration of PEP to PGA. Accordingly Eno1 is also known as phosphopyruvate hydratase. Metal ions are cofactors impairing the increase of enolase activity; hence Eno1 is also called metal-activated metalloenzyme. Magnesium is a natural cofactor causing the highest activity and is required for the enzyme to be catalytically active. The relative activation strength profile of additional metal ions involved in the enzyme activity appears in the following order $Mg^{2+}>Zn^{2+}>Mn^{2+}>Fe(II)^{2+}>Cd^{2+}>Co^{2+}, Ni^{2+}, Sm^{3+}, Tb^{3+}$ and most other divalent metal ions. In reactions catalyzed by enolases, the alpha-proton from a carbon adjacent to a carboxylate group of PGA, is abstracted, and PGA is conversed to enolate anion intermediate. This intermediate is further processed in a variety of chemical reactions, including racemization, cycloisomerization and beta-elimination of either water or ammonia. See Atlas of Genetics and Cytogenetics in Oncology and Haematology database, atlasgeneticsoncology.org/Genes/GC_ENO1.html.

Enzymatically active enolase exists in a dimeric (homo- or heterodimers) form and is composed of two subunits facing each other in an antiparallel fashion. The crystal structure of enolase from yeast and human has been determined and catalytic mechanisms have been proposed. Diaz-Ramos et al., cited above. The five residues that participate in catalytic activity of this enzyme are highly conserved throughout evolution. Studies in vitro revealed that mutant enolase enzymes that differ at positions Glu168, Glu211, Lys345, Lys396 or His159, demonstrate dramatically decreased activity levels. An integral and conserved part of enolases are two Mg2+ ions that participate in conformational changes of the active site of enolase and enable binding of a substrate or its analogues. Atlas of Genetics and Cytogenetics in Oncology database, cited above. In certain embodiments, the compositions of the invention comprise a metal ion cofactor. The metal ion cofactor can provide increased stability of the Eno1 in the composition and/or increased activity of the Eno1 in vivo. In one embodiment, the metal ion cofactor is divalent. In one embodiment, the divalent metal ion cofactor is $Mg^{2+}$, $Zn^{2+}$, $Mn^{2+}$, $Fe(II)^{2+}$, $Cd^{2+}$, $Co^{2+}$, or $Ni^{2+}$. In one embodiment, the metal ion cofactor is trivalent, e.g. $Sm^{3+}$ or $Tb^{3+}$.

Eno1 activity may be determined, for example, using the pyruvate kinase (PK)/lactate dehydrogenase (LDH) assay. The reaction for this enolase assay is shown below.

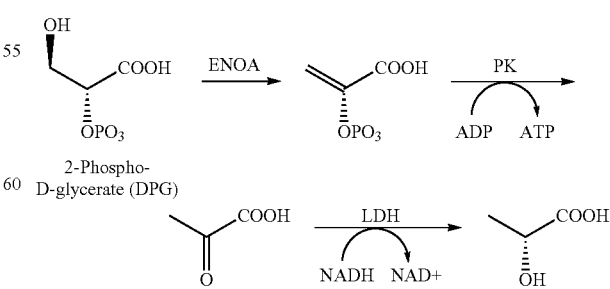

The rate of reaction of NADH to $NAD^+$ conversion may be determined by measuring the decrease of fluorescence of NADH, for example by using a PTI Quantamaster 40 spectrophotometer from Photon Technology International, Inc. (pti-nj.com). Kits for measuring Eno1 activity by a colorimetric pyruvate kinase/lactate dehydrogenase assay are also commercially available, for example, from ABCAM (Cambridge, Mass.; Cat. No. ab117994). The ABCAM Eno1 activity assay is further described in Example 5 below.

Eno1 activity may also be determined by measuring the effect of Eno1 on glucose uptake in human skeletal muscle myotubes (HSMM) as described in Example 2.

In certain embodiments, the Eno1 or the fragment thereof has at least 10%, 20%, 30%, 40%, 50%, 60%, 70%, 80%, 90%, 100%, 110%, 120%, 130%, 140%, 150%, 160%, 170%, 180%, 190%, 200%, 300%, 400% or 500% of the activity of a purified endogenous human Eno1 polypeptide. In certain embodiments, the activity of the Eno1, the fragment thereof, and the purified endogenous human Eno1 polypeptide are determined by the pyruvate kinase/lactate dehydrogenase assay or the HSMM glucose uptake assay described above.

In certain embodiments, the Eno1 polypeptide in complex with a dendrimer as described herein has at least 10%, 20%, 30%, 40%, 50%, 60%, 70%, 80%, 90%, 100%, 110%, 120%, 130%, 140%, 150%, 160%, 170%, 180%, 190%, 200%, 300%, 400% or 500% of the activity of a purified endogenous Eno1 polypeptide that is not in complex with a dendrimer. In certain embodiments, the activity of the Eno1 polypeptide in complex with a dendrimer and the activity of the purified endogenous Eno1 polypeptide that is not in complex with a dendrimer are determined by the pyruvate kinase/lactate dehydrogenase assay or the HSMM glucose uptake assay described above.

In certain embodiments the Eno1 polypeptide in complex with a dendrimer and a targeting peptide as described herein has at least 10%, 20%, 30%, 40%, 50%, 60%, 70%, 80%, 90%, 100%, 110%, 120%, 130%, 140%, 150%, 160%, 170%, 180%, 190%, 200%, 300%, 400% or 500% of the activity of a purified endogenous ENO1 polypeptide that is not in complex with a dendrimer or a targeting peptide. In certain embodiments the activity of the Eno1 polypeptide in complex with a dendrimer and a targeting peptide and the activity of the purified endogenous ENO1 polypeptide that is not in complex with a dendrimer or a targeting peptide are determined by the pyruvate kinase/lactate dehydrogenase assay or the HSMM glucose uptake assay described above.

In one embodiment, the Eno1 or the fragment thereof in the composition of the invention, wherein the composition comprises a metal ion cofactor (e.g., a divalent metal ion cofactor, e.g., $Mg^{2+}$, $Zn^{2+}$, $Mn^{2+}$, $Fe(II)^{2+}$, $Cd^{2+}$, $Co^{2+}$, or $Ni^{2+}$, or a trivalent metal ion cofactor, e.g. $Sm^{3+}$ or $Tb^{3+}$) has at least 10%, 20%, 30%, 40%, 50%, 60%, 70%, 80%, 90%, 100%, 110%, 120%, 130%, 140%, 150%, 160%, 170%, 180%, 190%, 200%, 300%, 400% or 500% of the activity of a purified endogenous human Eno1 polypeptide. In certain embodiments, the activity of the Eno1 or the fragment thereof in the composition comprising a metal ion cofactor as described above and the activity of the purified endogenous human Eno1 polypeptide are determined by the pyruvate kinase/lactate dehydrogenase assay or the HSMM glucose uptake assay described above.

Glucose Flux

The regulation of muscle glucose uptake involves a three-step process consisting of: (1) delivery of glucose to muscle, (2) transport of glucose into the muscle by the glucose transporter GLUT4 and (3) phosphorylation of glucose within the muscle by a hexokinase (HK). The physiological regulation of muscle glucose uptake requires that glucose travels from the blood to the interstitium to the intracellular space and is then phosphorylated to G6P. Blood glucose concentration, muscle blood flow and recruitment of capillaries to muscle determine glucose movement from the blood to the interstitium. Plasma membrane GLUT4 content controls glucose transport into the cell. Muscle hexokinase (HK) activity, cellular HK compartmentalization and the concentration of the HK inhibitor, G6P, determine the capacity to phosphorylate glucose. These three steps—delivery, transport and phosphorylation of glucose—comprise glucose flux, and all three steps are important for glucose flux control. However steps downstream of glucose phosphorylation may also affect glucose uptake. For example, acceleration of glycolysis or glycogen synthesis could reduce G6P, increase HK activity, increase the capacity for glucose phosphorylation and potentially stimulate muscle glucose uptake. Wasserman et al., 2010, J Experimental Biology, Vol. 214, pp. 254-262.

The present invention is based, at least in part, on the discovery that Eno1 affects several components of the glucose flux pathway, including increasing expression of the glucose transporters GLUT1 and GLUT4 and the hexokinase HK2, and increasing levels of the glycolysis pathway intermediates G6P and PEP, thus indicating that Eno1 treatment acts to increase glucose flux.

The present invention is also based, at least in part, on the discovery that Eno1 is differentially regulated in muscle cells from normal subjects and muscle cells from subjects with type 2 diabetes. The invention is further based on the surprising discovery that treatment of muscle cells with Eno1 increases glucose uptake into the cells and administration of Eno1 to mice with diet induced obesity normalizes glucose tolerance and insulin response.

Accordingly, the invention provides methods for treatment of elevated blood glucose typically related to diabetes including at least type 1 diabetes, pre-diabetes, type 2 diabetes, and gestational diabetes by administration of Eno1 to the subject. Further, the invention provides methods for diagnosing and/or monitoring (e.g., monitoring of disease progression or treatment) and/or prognosing an elevated blood glucose state, e.g., diabetes, in a mammal. The invention also provides methods for treating or for adjusting treatment regimens based on diagnostic information relating to the levels of Eno1 in the blood or serum of a subject with elevated blood glucose. The invention further provides panels and kits for practicing the methods of the invention.

The invention also provides methods for increasing glucose flux in a subject comprising administering to the subject a pharmaceutical composition comprising Eno1 or a fragment thereof. In certain embodiments, the pharmaceutical composition administered to the subject is any of the pharmaceutical compositions described herein. The invention also provides a method of increasing glucose flux in a skeletal muscle cell of a subject, the method comprising administering to the subject a pharmaceutical composition comprising Eno1 or a fragment thereof. In certain embodiments, the pharmaceutical composition administered to the subject is any of the pharmaceutical compositions described herein.

The invention also provides a method of increasing glycolytic activity in a skeletal muscle cell of a subject, the method comprising administering to the subject a pharmaceutical composition comprising Eno1 or a fragment thereof. In certain embodiments, the pharmaceutical composition administered to the subject is any of the pharmaceutical compositions described herein.

The invention also provides a method of increasing mitochondrial free fatty acid oxidation in a skeletal muscle cell of a subject, the method comprising administering to the subject a pharmaceutical composition comprising Eno1 or a fragment thereof. In certain embodiments, the pharmaceutical composition administered to the subject is any of the pharmaceutical compositions described herein.

"Increasing glucose flux" as used herein is understood as increasing at least one or more of (1) delivery of glucose to muscle, (2) transport of glucose into the muscle, and (3) phosphorylation of glucose within the muscle. In particular embodiments, increasing glucose flux includes increasing glycolytic activity or mitochondrial free fatty acid oxidation in a muscle cell.

IIA. Enolase 2 and Enolase 3

Enolase 2 (Eno2) is also known as gamma enolase, neuronal enolase, neuron-specific enolase (NSE), or HEL-S-279 and is encoded by the ENO2 gene. Eno2 is a phosphopyruvate phosphatase, a glycolytic enzyme. Eno2 is a homodimer and is found in mature neurons of the central nervous system (CNS) and cells of neuronal origin. Neurons under stress of various types release Eno2 into the systemic circulation. Yee, et al., 2012, Invest. Ophthalmol. Vis. Sci. Vol. 53, No. 10, pp. 6389-6392. The nucleic acid sequence of the ENO2 mRNA and the amino acid sequence of Eno2 are shown in FIGS. 36A and 36B, respectively.

Enolase 3 (Eno3) is also known as beta enolase, muscle enolase, muscle-specific enolase (MSE), or GSD13 and is encoded by the ENO3 gene. Eno3 catalyzes the interconversion of 2-phosphoglycerate and phosphoenolpyruvate. Eno3 is found in adult skeletal muscle cells where it may play a role in muscle development and regeneration. In adult human muscle, over 90% of enolase activity is accounted for by Eno3. Mutations in the gene encoding Eno3 have been associated with glycogen storage disease. Comi et al., 2001, Ann Neurol. Vol. 50, No. 2, pp. 202-207. Three variants of ENO3 mRNA have been identified, variants 1, 2 and 3. Variants 1 and 2 encode isoform 1 of the Eno3 protein, and variant 3 encodes isoform 2 of the Eno3 protein. Variant 3 of the ENO3 mRNA differs in the 5' UTR and lacks two exons in the 5' coding region compared to variant 1. Isoform 2 of the Eno3 protein is shorter than isoform 1, but has the same N- and C-termini. The nucleic acid sequences of variants 1, 2 and 3 and amino acid sequences of isoforms 1 and 2 of Eno3 are shown in FIGS. 37A-37E.

Eno2 and/or Eno3 may alternatively also be used in the methods, pharmaceutical compositions, panels, and kits described herein for Eno1. For example, Eno2 and/or Eno3 may be used in methods for treatment of elevated blood glucose typically related to diabetes including at least type 1 diabetes, pre-diabetes, type 2 diabetes, and gestational diabetes by administration of a pharmaceutical composition comprising Eno2 and/or Eno3 to the subject. Further, Eno2 and/or Eno3 may be used in methods for diagnosing and/or monitoring (e.g., monitoring of disease progression or treatment) and/or prognosing an elevated blood glucose state, e.g., diabetes, in a mammal. Eno2 and/or Eno3 may also be used in methods for treating or for adjusting treatment regimens based on diagnostic information relating to the levels of Eno2 or Eno3 in the blood or serum of a subject with elevated blood glucose, and for panels and kits for practicing the methods of the invention. The invention also relates to pharmaceutical compositions comprising Eno2 and/or Eno3, e.g. for delivery to a muscle cell.

III. Diabetes Diagnosis and Classification

Diabetes mellitus (DM), often simply referred to as diabetes, is a group of metabolic diseases in which a person has high blood sugar, either because the body does not produce enough insulin or because cells do not respond to the insulin that is produced. This high blood sugar produces the classical symptoms of polyuria (frequent urination), polydipsia (increased thirst), and polyphagia (increased hunger).

Type 2 diabetes results from insulin resistance, a condition in which cells fail to use insulin properly, sometimes combined with an absolute insulin deficiency. The defective responsiveness of body tissues to insulin is believed, at least in part, to involve the insulin receptor. However, the specific defects are not known.

In the early stage of type 2 diabetes, the predominant abnormality is reduced insulin sensitivity. At this stage, hyperglycemia can be reversed by a variety of measures and medications that improve insulin sensitivity or reduce glucose production by the liver. Prediabetes indicates a condition that occurs when a person's blood glucose levels are higher than normal but not high enough for a diagnosis of type 2 diabetes.

Type 2 diabetes is due to insufficient insulin production from beta cells in the setting of insulin resistance. Insulin resistance, which is the inability of cells to respond adequately to normal levels of insulin, occurs primarily within the muscles, liver, and fat tissue. In the liver, insulin normally suppresses glucose release. However in the setting of insulin resistance, the liver inappropriately releases glucose into the blood. The proportion of insulin resistance verses beta cell dysfunction differs among individuals with some having primarily insulin resistance and only a minor defect in insulin secretion and others with slight insulin resistance and primarily a lack of insulin secretion.

Other potentially important mechanisms associated with type 2 diabetes and insulin resistance include: increased breakdown of lipids within fat cells, resistance to and lack of incretin, high glucagon levels in the blood, increased retention of salt and water by the kidneys, and inappropriate regulation of metabolism by the central nervous system. However not all people with insulin resistance develop diabetes, since an impairment of insulin secretion by pancreatic beta cells is also required.

Type 1 diabetes results from the body's failure to produce insulin, and presently requires treatment with injectable insulin. Type 1 diabetes is characterized by loss of the insulin-producing beta cells of the islets of Langerhans in the pancreas, leading to insulin deficiency. Most affected people are otherwise healthy and of a healthy weight when onset occurs. Sensitivity and responsiveness to insulin are usually normal, especially in the early stages. However, particularly in late stages, insulin resistance can occur, including insulin resistance due to immune system clearance of administered insulin.

A. Diagnostic Criteria

Criteria for diagnosis and classification of diabetes mellitus were published by the American Diabetes Association in *Diabetes Care,* 36:S67-74, 2013, incorporated herein by reference, which provides a more detailed definition of the various types of diabetes. Diagnostic criteria for diabetes are discussed further below. The reference classifies type 1 diabetes or type 2 diabetes as follows:

I. Type 1 diabetes (β-cell destruction, usually leading to absolute insulin deficiency)
   A. Immune mediated
   B. Idiopathic
II. Type 2 diabetes (may range from predominantly insulin resistance with relative insulin deficiency to a predominantly secretory defect with insulin resistance)
III. Other specific types
IV. Gestational diabetes mellitus Methods for performing diagnostic or assessment methods are provided therein. The diagnostic criteria for diabetes provided therein are as follows:

Criteria for the Diagnosis of Diabetes

HbA1c ≥6.5%. The test should be performed in a laboratory using a method that is National Glycohemoglobin Standardization Program (NGSP) certified and standardized to the Diabetes Control and Complications Trial (DCCT) assay.*
OR
Fasting plasma glucose (FPG) ≥126 mg/dl (7.0 mmol/l). Fasting is defined as no caloric intake for at least 8 h.*
OR
2-h plasma glucose ≥200 mg/dl (11.1 mmol/l) during an oral glucose tolerance test (OGTT). The test should be performed as described by the World Health Organization, using a glucose load containing the equivalent of 75 g anhydrous glucose dissolved in water.*
OR
In a patient with classic symptoms of hyperglycemia or hyperglycemic crisis, a random plasma glucose ≥200 mg/dl (11.1 mmol/l).

*In the absence of unequivocal hyperglycemia, criteria 1-3 should be confirmed by repeat testing.

The diagnostic criteria for increased risk of diabetes/pre-diabetes provided therein are as follows:

Criteria for Increased Risk of Diabetes (Pre-Diabetes)*

Fasting Plasma Glucose (FPG) 100 mg/dl (5.6 mmol/l) to 125 mg/dl (6.9 mmol/l) [Impaired Fasting Glucose - IFG]
2-h Plasma Glucose (PG) in the 75-g oral glucose tolerance test (OGTT) 140 mg/dl (7.8 mmol/l) to 199 mg/dl (11.0 mmol/l) [Impaired Glucose Tolerance - IGT]
A1C 5.7-6.4%

*For all three tests, risk is continuous, extending below the lower limit of the range and becoming disproportionately greater at higher ends of the range.

The diagnostic criteria for gestational diabetes provided therein are as follows:

Screening for and Diagnosis of Gestational Diabetes Mellitus (GDM)

Perform a 75-g OGTT, with plasma glucose measurement fasting and at 1 and 2 h, at 24-28 weeks of gestation in women not previously diagnosed with overt diabetes.
The OGTT should be performed in the morning after an overnight fast of at least 8 h.
The diagnosis of GDM is made when any of the following plasma glucose values are exceeded:
Fasting: ≥92 mg/dl (5.1 mmol/l)
1 h: ≥180 mg/dl (10.0 mmol/l)
2 h: ≥153 mg/dl (8.5 mmol/l)

The blood glucose measurements for the diagnosis and/or monitoring of elevated blood glucose or diabetes can be cumbersome due to the specific timing requirements relative to eating, e.g., a fasting blood glucose or the amount of time required to perform the test, e.g., as with an oral glucose tolerance test. Moreover, the diagnostic criteria explicitly require that in absence of unequivocal hyperglycemia, criteria 1-3 should be confirmed by repeat testing. The use of an HbA1c level as a diagnostic indicator can be advantageous as it provides an indication of blood glucose levels over time, i.e., for about the prior 1-2 months, and does not require special scheduling to perform the test. Similarly, an Eno1 level can be determined without particular scheduling requirements or food consumption limitations or requirements.

Accordingly, in some aspects the invention relates to a method for diagnosing the presence of elevated blood glucose in a subject, comprising: (a) contacting a biological sample with a reagent that selectively binds to Eno1; (b) allowing a complex to form between the reagent and Eno1; (c) detecting the level of the complex, and (d) comparing the level of the complex with a predetermined threshold value, wherein a level of the complex in the sample below the predetermined threshold value indicates the subject is suffering from elevated blood glucose. In certain embodiments, the reagent that selectively binds to Eno1 is an anti-Eno1 antibody. In certain embodiments, the antibody comprises a detectable label.

In some embodiments of the method described above, the step of detecting the level of the complex further comprises contacting the complex with a detectable secondary antibody and measuring the level of the secondary antibody. The method may also further comprise detecting the level of one or more additional indicators of elevated blood glucose. The one or more additional indicators of blood glucose may be selected from the group consisting of HbA1c level, fasting glucose level, fed glucose level, and glucose tolerance.

In some embodiments of the aforementioned method, the biological sample is blood or serum. In some embodiments, the level of the complex is detected by immunoassay or ELISA. In some embodiments, the presence of elevated blood glucose in the subject is indicative of a disease or condition selected from the group consisting of pre-diabetes, type 2 diabetes, type 1 diabetes, and gestational diabetes.

B. Secondary Pathologies of Diabetes, Insulin Resistance, and Insulin Insufficiency Abnormal glucose regulation resulting from diabetes, both type 1 and type 2, insulin resistance, and insulin insufficiency are associated with secondary pathologies, many of which result from poor circulation. Such secondary pathologies include macular degeneration, peripheral neuropathies, ulcers and decrease wound healing, and decreased kidney function. It has been suggested that maintaining glucose levels and/or HbAc1 levels within normal ranges decreases the occurrence of these secondary pathologies. It is understood that normalization of blood glucose, insulin, and HbAc1 levels will reduce the development of secondary pathologies by limiting the primary pathology, e.g., impaired glucose tolerance, increased blood glucose. In certain embodiments, Eno1 is not used for the treatment of secondary pathologies associated with impaired glucose tolerance, increased blood glucose, insulin resistance, insulin insufficiency, diabetes, or pre-diabetes. In certain embodiments, Eno1 is used for the treatment of secondary pathologies associated with impaired glucose tolerance, increased blood glucose, insulin resistance, insulin insufficiency, diabetes, or pre-diabetes.

IV. Dosages and Modes of Administration

Techniques and dosages for administration vary depending on the type of compound (e.g., protein and/or nucleic acid, alone or complexed with a microparticle, liposome, or dendrimer) and are well known to those skilled in the art or are readily determined.

Therapeutic compounds of the present invention may be administered with a pharmaceutically acceptable diluent, carrier, or excipient, in unit dosage form. Administration may be parenteral, intravenous, subcutaneous, oral, topical, or local. In certain embodiments, administration is not oral. In certain embodiments, administration is not topical. In certain preferred embodiments, administration is systemic. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, subcutaneous delivery, etc.

The composition can be in the form of a pill, tablet, capsule, liquid, or sustained release tablet for oral administration; or a liquid for intravenous, subcutaneous, or parenteral administration; or a polymer or other sustained release vehicle for systemic administration.

Methods well known in the art for making formulations are found, for example, in "Remington: The Science and Practice of Pharmacy" (20th ed., ed. A. R. Gennaro, 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The compound may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids and the like; polymeric acids such as tannic acid, carboxymethyl cellulose, and the like; and inorganic acid such as hydrochloric acid, hydrobromic acid, sulfuric acid phosphoric acid, and the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The dosage and the timing of administering the compound depend on various clinical factors including the overall health of the subject and the severity of the symptoms of disease, e.g., diabetes, pre-diabetes.

A. Formulations for Long Acting Injectable Drugs

Biologics and other agents subject to high rates of first pass clearance may not be amenable to oral administration and require administration by parenteral routes. However, compliance with treatment regimens for injectable drugs can be low as subjects are often adverse to self-administering agents by injection, e.g., subcutaneous injection, particularly when the disease does not make the subject feel sick. Other routes of administration by injection, e.g., intravenous, intramuscular, typically require administration by a trained professional, making frequent administration of the agent inconvenient and often painful.

Formulations have been created to provide sustained delivery of injectable agents including, but not limited to, oil-based injections, injectable drug suspensions, injectable microspheres, and injectable in situ systems. Long-acting injectable formulations offer many advantages when compared with conventional formulations of the same compounds. These advantages include, at least, the following: a predictable drug-release profile during a defined period of time following each injection; better patient compliance; ease of application; improved systemic availability by avoidance of first-pass metabolism; reduced dosing frequency (i.e., fewer injections) without compromising the effectiveness of the treatment; decreased incidence of side effects; and overall cost reduction of medical care.

1. Oil-Based Injectable Solutions and Injectable Drug Suspensions.

Conventional long-acting injections consist either of lipophilic drugs in aqueous solvents as suspensions or of lipophilic drugs dissolved in vegetable oils. Commercially available oil based injectable drugs for intramuscular administration include, but are not limited to, haloperidol deconate, fluphenazine deconate, testosterone enanthate, and estradiol valerate. Administration frequency for these long-acting formulations is every few weeks or so. In the suspension formulations, the rate-limiting step of drug absorption is the dissolution of drug particles in the formulation or in the tissue fluid surrounding the drug formulation. Poorly water-soluble salt formations can be used to control the dissolution rate of drug particles to prolong the absorption. However, several other factors such as injection site, injection volume, the extent of spreading of the depot at the injection site, and the absorption and distribution of the oil vehicle per se can affect the overall pharmacokinetic profile of the drug. Modulation of these factors to provide the desired drug release profile is within the ability of those of skill in the art.

2. Polymer-Based Microspheres and In-Situ Formings.

The development of polymer-based long-acting injectables is one of the most suitable strategies for macromolecules such as peptide and protein drugs. Commercially available microsphere preparations include, but are not limited to, leuprolide acetate, triptorelin pamoate, octreotide acetate, lanreotide acetate, risperidone, and naltrexone. Commercially available in situ forming implants include leuprolide acetate, and in situ forming implants containing paclitaxel and bupivacaine are in clinical trials. These formulations are for intramuscular administration. Advantages of polymer-based formulations for macromolecules include: in vitro and in vivo stabilization of macromolecules, improvement of systemic availability, extension of biological half life, enhancement of patient convenience and compliance, and reduction of dosing frequency.

The most crucial factor in the design of injectable microspheres and in situ formings is the choice of an appropriate biodegradable polymer. The release of the drug molecule from biodegradable microspheres is controlled by diffusion through the polymer matrix and polymer degradation. The nature of the polymer, such as composition of copolymer ratios, polymer crystallinities, glass-transition temperature, and hydrophilicities plays a critical role in the release process. Although the structure, intrinsic polymer properties, core solubility, polymer hydrophilicity, and polymer molecular weight influence the drug-release kinetics, the possible mechanisms of drug release from microsphere are as follows: initial release from the surface, release through the pores, diffusion through the intact polymer barrier, diffusion through a water-swollen barrier, polymer erosion, and bulk degradation. All these mechanisms together play a part in the release process. Polymers for use in microsphere and in situ formings include, but are not limited to a variety of biodegradable polymers for controlled drug delivery intensively studied over the past several decades include polylactides (PLA), polyglycolides (PGA), poly(lactide-co-glycolide) (PLGA), poly(ε-caprolactone) (PCL), polyglyconate, polyanhydrides, polyorthoesters, poly(dioxanone), and polyalkylcyanoacrylates. Thermally induced gelling systems used in in situ formings show thermo-reversible sol/gel transitions and are characterized by a lower critical solution temperature. They are liquid at room temperature and produce a gel at and above the lower critical solution temperature. In situ solidifying organogels are composed of water-insoluble amphiphilic lipids, which swell in water and form various types of lyotropic liquid crystals.

B. Targeted Drug Delivery

Delivery of drugs to their site of action can increase the therapeutic index by reducing the amount of drug required to provide the desired systemic effect. Drugs can be delivered to the site of action by administration of the drug to the target tissue using a method or formulation that will limit systemic exposure, e.g., intramuscular injection, intrasinovial injection, intrathecal injection, intraocular injection. A number of the sustained delivery formulations discussed above are for intramuscular administration and provide local delivery to muscle tissue. Alternatively, targeting moieties can be associated with or linked to therapeutic payloads for administration to the target site. Targeting moieties can include any of a number of moieties that bind to specific cell types.

1. Targeting Moieties

Certain embodiments of the invention include the use of targeting moieties include relatively small peptides (e.g., 25 amino acids or less, 20 amino acids or less, 15 amino acids or less, 10 amino acids or less), muscle targeting peptides (MTP) including smooth muscle and/or skeletal muscle targeting peptides, αvβ3 integrin ligands (e.g., RGD peptides and peptide analogs), αvβ5 integrin ligands, or CD46 ligands as discussed above. It is understood that such peptides can include one or more chemical modifications to permit formation of a complex with Eno1, to modify pharmacokinetic and/or pharmacodynamic properties of the peptides. In certain embodiments, the targeting moiety can be a small molecule, e.g., RGD peptide mimetics. In certain embodiments, the targeting moiety can include a protein and optionally a fiber protein from an adenovirus 35. In certain embodiments, the viral proteins are present on a virus particle. In certain embodiments, the viral proteins are not present on a viral particle. In certain embodiments, the targeting moiety can be an antibody, antibody fragment, antibody mimetic, or T-cell receptor.

2. Targeted Complexes

Targeted Eno1 complexes can be administered by a route other than intramuscular injection (e.g., subcutaneous injection, intravenous injection) while providing delivery of the Eno1 to muscle. Targeted complexes can include one or more targeting moieties attached either directly or indirectly to Eno1. Formation of the targeted complex does not substantially or irreversibly inhibit the activity of Eno1 and its effect on normalizing blood glucose levels and insulin response. In certain embodiments, use of a targeted complex can reduce the total amount of Eno1 required to provide an effective dose. Some exemplary, non-limiting, embodiments of targeted complexes are discussed below.

In certain embodiments, the payload and the targeting moiety are present in a complex at about a 1:1 molar ratio. In certain embodiments, the targeting moiety is present in a complex with a molar excess of the payload (e.g., 2:1, 3:1, 4:1, 5:1, 6:1, 7:1; 8:1, 9:1, 10:1, 11:1, 12:1, 13:1, 14:1, 15:1, 16:1, 17:1; 18:1, 19:1, 20:1, 21:1, 22:1, 23:1, 24:1, 25:1, 26:1, 27:1; 28:1, 29:1, 30:1, or more; or any range bracketed by any two values). In certain embodiments, the payload to targeting moiety is about 1:5-1:15; about 1:7-1:13, about 1:8-1:12.

It is understood that the compositions and methods of the invention include the administration of more than one, i.e., a population of, targeting moiety-payload complexes. Therefore, it is understood that the number of targeting moieties per payload can represent an average number of targeting moieties per payload in a population of complexes. In certain embodiments, at least 70% of the complexes have the selected molar ratio of targeting moieties to payload. In certain embodiments, at least 75% of the complexes have the selected molar ratio of targeting moieties to payload. In certain embodiments, at least 80% of the complexes have the selected molar ratio of targeting moieties to payload. In certain embodiments, at least 85% of the complexes have the selected molar ratio of targeting moieties to payload. In certain embodiments, at least 90% of the complexes have the selected molar ratio of targeting moieties to payload.

a. Linkers

A number of chemical linkers are known in the art and available from commercial sources (e.g., Pierce Thermo Fisher Scientific Inc., see, e.g., piercenet.com/cat/crosslinking-reagents). Such agents can be used to chemically link, reversibly or irreversibly, one or more targeting moieties to Eno1. Linkers can also be used to attach targeting moieties and Eno1 to a structure, e.g., microparticle, dendrimer, rather than attaching the targeting moiety directly to Eno1. In certain embodiments, the linker attaching Eno1 to the targeted complex is reversible so that the Eno1 is released from the complex after administration, preferably substantially at the muscle.

b. Peptide Bonds

As used herein, targeted complexes can include the translation of Eno1 with a peptide targeting moiety. Methods to generate expression constructs including an amino acid sequence for targeting Eno1 is well within the ability of those of skill in the art.

c. Liposomes

Liposomal delivery systems are known in the art including formulations to limit systemic exposure, thereby reducing systemic exposure and off target effects. For example, Doxil® is a composition in which doxorubicin encapsulated in long-circulating pegylated liposomes that further comprise cholesterol for treatment of certain types of cancer.

Various liposomal formulations of amphotericin B including Ambisome®, Abelcet®, and Amphotec® are formulated for intravenous administration in liposomes or a lipid complex containing various phospholipids, cholesterol, and cholesteryl sulfate. Visudine® is verteporfin formulated as a liposome in egg phosphotidyl glycerol and DMPC for intravenous administration. Liposomal formulations are also known for intramuscular injection. Epaxal® is an inactivated hepatitis A virus and Inflexal V® is an inactivated hemaglutinine of influenza virus strains A and B. Both viral preparations are formulated in combinations of DOPC and DOPE. Such liposomes, or other physiologically acceptable liposomes, can be used for the packaging of Eno1 and subsequent surface decoration with targeting moieties to delivery Eno1 to the muscle. Additional moieties to modulate intracellular trafficking of the liposome can also be included. Upon uptake of the liposome into the cell, the liposome releases the Eno1 thereby allowing it to have its therapeutic effect.

d. Dendrimers

Dendrimers can be used as a scaffold for the attachment of multiple targeting moieties with one or more molecules of Eno1. In certain embodiments, the dendrimer is decorated with targeting moieties prior to coupling with Eno1.

e. Microparticles

Microparticles can be used as a scaffold for the attachment of multiple targeting moieties with one or more molecules of Eno1 either attached to or encapsulated in the microparticle. In certain embodiments, the microparticle is decorated with targeting moieties prior to coupling with Eno1.

f. Viral Vectors

Viral tropisms have long been studied and are used to direct viruses to the cell type of interest. Parker et al., 2013 (*Gene Therapy,* 20:1158-64) have developed an adenovirus serotype 5 capsite with the fiber and peton of serotype 35 to enhance delivery to skeletal and/or smooth muscle cells. Such viral vectors and other viral vectors can be used for the delivery of Eno1 expression constructs to muscle cells.

C. Dendrimers

Dendrimers can be used in the context of the invention as the backbone for targeted complexes for the delivery of non-intramuscularly administered Eno1 to muscle. Alternatively, dendrimers can be used to modulate the pharmacokinetic and pharmacodynamic properties of intramuscularly administered Eno1. In the compositions and methods of the invention, dendrimers are understood to be pharmaceutically acceptable dendrimers.

Dendrimer-based platforms have achieved attention for use in pharmaceutical applications Similar to other polymeric carriers, dendrimers can be synthesized to avoid structural toxicity and immunogenicity. The dendrimer's ability to mimic the size, solubility, and shape of human proteins makes the technology an ideal choice for many therapeutic and diagnostic applications. Being 1-10 nanometers in size enables dendrimers to efficiently diffuse across the vascular endothelium, internalize into cells, and be rapid cleared by the kidneys. This helps to avoid long-term toxicities and reduces the need for a rapidly degradable platform. The availability of multiple reactive surface groups enables the dendrimer to carry a higher payload of functional molecules, enhancing targeted delivery to the site of action, thereby increasing efficacy.

Dendrimers have been produced or are under commercial development for several biomedical applications. A topical, polylysine dendrimer-based microbicide, VivaGel™, has been developed by Starpharma. SuperFect® is a dendrimer-based material used for gene transfection. Dendrimer based diagnostic tools include Gadomer-17, a magnetic resonance imaging (MRI) contrast agent containing a polylysine dendrimer functionalized with gadolinium chelates, and Stratus® CS, a biosensor for cardiac markers to rapidly diagnosis heart attacks.

Dendrimers are defined by their core-shell structure, where the dendrimer approximately doubles in size and number of functional surface groups with each additional shell (or generation) added to the core. Shells are synthesized by alternating monomer reactions by means well known in the art. Specialized dendrimer backbones can be synthesized by varying the monomer units. The biological properties of the dendrimer are largely influenced by the chemical backbone and surface termination. For a dendrimer to be an appropriate vehicle for drug delivery in vivo, they must be non-toxic, non-immunogenic, and be capable of targeting and reaching specific locations by crossing the appropriate barriers while being stable enough to remain in circulation. The vast majority of the dendrimers synthesized and published in literature are insoluble in physiological conditions or are incapable of remaining soluble after the addition of functional molecules and are inappropriate for biological applications. However, several classes of dendrimers have been shown to be useful scaffolds for biomedical applications; examples include polyesters, polylysine, and polypropyleneimine (PPI or DAB) dendrimers.

The most widely used dendrimers in biomedical applications are poly(amidoamine) (PAMAM) dendrimers. The polyamide backbone synthesized from repeating reactions of methyl acrylate and ethylene-diamine helps the macromolecule maintain water solubility and minimizes immunogenicity. PAMAM dendrimers of different generation also are able to mimic the size and properties of globular proteins readily found in the body. The amine-terminated surface of full generation PAMAM dendrimers allows for easy surface modification, enabling the platform to carry and solubilize hydrophobic therapeutic molecules, such as methotrexate, in physiological conditions. PAMAM dendrimers exhibit little non-specific toxicity if the surface amines have been neutralized or appropriately modified (e.g., acylated).

Active targeting uses a molecule, such as targeting moiety, to mediate delivery of its payload (drug or otherwise) to cells by binding to cell-specific molecules. Targeting moieties, such as those provided herein, frequently bind through receptors highly expressed on target cells. The interactions between the targeting ligand and cell-surface receptor allow the therapeutic agent or payload to selectively reach muscle cells and even be ushered inside via receptor-mediated processes.

The multivalent effect associated with the display of multiple binding ligands on the dendrimer surface enhances the uptake of the dendritic scaffold compared to single ligands. Multivalent interactions, caused by the simultaneous binding of multiple ligands, allow for the dendrimers to increase the binding avidities of the platform, even when individual ligands have low affinities for the targeted receptor. The PAMAM platform has been successfully used as a scaffold for the attachment of multivalent targeting molecules including antibodies, peptides, T-antigens, and folic acid. The targeting ligands anchor the dendrimers to locations where specific receptors are expressed on cell surfaces. Targeted dendrimer-drug conjugates to deliver a higher dose specifically to targeted cells while avoiding normal cells, thus avoiding the potential systemic toxicity.

Neutralizing the surface amines of PAMAM dendrimers with acetyl groups minimizes toxicity and non-specific dendrimer uptake. The acetyl capping of the dendrimer also allows for increased clearance from the body, minimizing effects from long-term treatment. PEGylation of amino-terminated PAMAM dendrimers reduces immunogenicity and increases solubility. PEG terminated dendrimers have an increased half-life the blood stream as compared to the cationic parent material. Hydroxyl and methoxyl terminated polyester dendrimers have been shown to be nontoxic in vivo up at concentrations up to 40 mg/kg. The differences in toxicities between cationic and anionic dendrimers have also been confirmed in vivo. Using a zebrafish embryo model, carboxyl terminated dendrimer was significantly less toxic than G4 amine-terminated dendrimer. In the same study, surface modification with RGD also reduced toxicity.

It will be understood that all of the dendrimers described above and herein may be used in the Eno1 compositions of the invention and their methods of use.

In certain embodiments, the ratio of the number of dendrimer molecules to the number of Eno1 molecules in the complex comprising dendrimer and Eno1 is between about 1:1 and about 10:1, e.g., about 1:1, about 2:1, about 3:1, about 4:1, about 5:1, about 6:1, about 7:1, about 8:1, about 9:1, or about 10:1. In one embodiment, the ratio of the number of dendrimer molecules to the number of Eno1 molecules in the complex comprising dendrimer and Eno1 is between about 3:1 and 7:1, e.g., 3:1, 4:1, 5:1, 6:1, or 7:1. In one embodiment, the ratio of the number of dendrimer molecules to the number of Eno1 molecules in the complex comprising dendrimer and Eno1 is between 4:1 and 6:1, e.g., 3:1, 4:1, or 5:1. In one embodiment, the ratio of the number of dendrimer molecules to the number of Eno1 molecules in the complex comprising dendrimer and Eno1 is between 3:1 and 5:1, e.g., 3:1, 4:1, or 5:1. In yet another embodiment, the ratio of the number of dendrimer molecules to the number of Eno1 molecules in the complex comprising dendrimer and Eno1 is between 4:1 and 5:1. In another embodiment, the ratio of the number of dendrimer molecules to the number of Eno1 molecules in the complex comprising dendrimer and Eno1 is between 3:1 and 4:1. In a further preferred embodiment, the ratio of the number of dendrimer molecules to the number of Eno1 molecules in the complex comprising dendrimer and Eno1 is about 5:1.

Optimal ratios of dendrimer to Eno1 in the complex may be tested and selected by assaying the Eno1 activity of the dendrimer/Eno1 complexes (e.g., as compared to uncomplexed Eno1) by using any routine methods known in the art, such as, for example, the pyruvate kinase (PK)/lactate dehydrogenase (LDH) assay or any other assays described herein. Optimal ratios of dendrimer to Eno1 may also be tested and selected by assessing the effect of the dendrimer/Eno1 complexes on glucose uptake in an in vitro assay, for example, by measuring glucose uptake in human skeletal muscle myotubes (HSMM) as described herein in Example 2 or any similar assays known in the art. Optimal ratios of dendrimer to Eno1 may also be tested and selected by measuring the effect of the dendrimer/Eno1 complexes on blood glucose levels in vivo, for example, by measuring the effect of the dendrimer/Eno1 complex on blood glucose in diabetic mouse models, as described herein in Examples 7 and 8, or any similar models or assays known in the art. Optimal ratios of dendrimer to Eno1 in the complex will preferably retain Eno1 activity in vitro and/or in vivo, and/or provide delivery of Eno1 to cells.

It is understood that the compositions and methods of the invention include the administration of more than one, i.e., a population of dendrimer-Eno1-targeting peptide complexes. Therefore, it is understood that the number of dendrimer per Eno1 molecules can represent an average number of dendrimer per Eno1 in a population of complexes. In certain embodiments, at least 70% of the complexes have the selected molar ratio of dendrimer to Eno1. In certain embodiments, at least 75% of the complexes have the selected molar ratio of dendrimer to Eno1. In certain embodiments, at least 80% of the complexes have the selected molar ratio of dendrimer to Eno1. In certain embodiments, at least 85% of the complexes have the selected molar ratio of dendrimer to Eno1. In certain embodiments, at least 90% of the complexes have the selected molar ratio of dendrimer to Eno1.

In certain embodiments, the ratio of the number of dendrimer molecules to the number of targeting peptides in the dendrimer/Eno1/targeting peptide complex is between 1:0.1 and 1:10, between 1:1 and 1:10, between 1:1 and 1:5, or between 1:1 and 1:3. In certain embodiments the ratio of the number of dendrimer molecules to the number of targeting peptides is about 1:1, 1:2, 1:3, 1:4, 1:5, 1:6, 1:7, 1:8, 1:9 or 1:10. In a preferred embodiment, the ratio of the number of dendrimer molecules to the number of targeting peptides in the dendrimer/Eno1/targeting peptide complex is about 1:1. In a preferred embodiment, the ratio of the number of dendrimer molecules to the number of targeting peptides in the dendrimer/Eno1/targeting peptide complex is about 1:2. In a preferred embodiment, the ratio of the number of dendrimer molecules to the number of targeting peptides in the dendrimer/Eno1/targeting peptide complex is about 1:3.

In certain embodiments, the ratio of the number of targeting peptides to the number of dendrimer molecules in the dendrimer/Eno1/targeting peptide complex is at least 1:1, at least 2:1, at least 3:1, at least 4:1, at least 5:1, at least 6:1, at least 7:1, at least 8:1, at least 9:1 or at least 10:1. In one embodiment, the ratio of the number of targeting peptides to the number of dendrimer molecules in the dendrimer/Eno1/targeting peptide complex is at least 3:1.

It is understood that the compositions and methods of the invention include the administration of more than one, i.e., a population of targeting peptide-Eno1-dendrimer complexes. Therefore, it is understood that the number of targeting peptides per dendrimer can represent an average number of targeting peptides per dendrimer in a population of complexes. In certain embodiments, at least 70% of the complexes have the selected molar ratio of targeting peptides to dendrimer. In certain embodiments, at least 75% of the complexes have the selected molar ratio of targeting peptides to dendrimer. In certain embodiments, at least 80% of the complexes have the selected molar ratio of targeting peptide to dendrimer. In certain embodiments, at least 85% of the complexes have the selected molar ratio of targeting peptide to dendrimer. In certain embodiments, at least 90% of the complexes have the selected molar ratio of targeting peptide to dendrimer.

Optimal ratios of dendrimer to targeting peptide may be selected by measuring the targeting of the dendrimer/Eno1/targeting peptide complex to specific tissues in vivo, for example, by measuring the targeting of a detectably labeled dendrimer/Eno1/targeting peptide complex in vivo, as described herein in Example 6.

V. Detection and Measurement of Indicators of Blood Glucose Levels and Control

Methods for detection and measurement of indicators of elevated blood glucose and blood glucose control vary depending on the nature of the indicator to be measured. Elevated blood glucose, and thereby loss of blood glucose level control and severity of diabetes can be measured directly, e.g., by determining the amount of glucose in the blood, or indirectly, e.g., by detecting the amount of glycated hemoglobin (HbA1c), a reaction product of hemoglobin and glucose. The invention further provides methods for detecting blood glucose control using Eno1.

The present invention contemplates any suitable means, techniques, and/or procedures for detecting and/or measuring the blood glucose level indicators of the invention. The skilled artisan will appreciate that the methodologies employed to measure the indicators of the invention will depend at least on the type of indicator being detected or measured (e.g., glucose, ketones, mRNA, or polypeptide including a glycated polypeptide) and the biological sample (e.g., whole blood, serum). Certain biological sample may also require certain specialized treatments prior to measuring the biomarkers of the invention, e.g., the preparation of mRNA in the case where an mRNA biomarker, e.g., Eno1 mRNA, is being measured.

A. Direct and Indirect Measurement of Blood Glucose and Blood Glucose Control Using Established Indicators Blood glucose monitoring is a way of testing the concentration of glucose in the blood (glycemia) directly at a single point in time. Particularly important in the care of diabetes mellitus, a blood glucose test is performed by piercing the skin (typically, on the finger) to draw blood, then applying the blood to a chemically active disposable 'test-strip'. Different manufacturers use different technology, but most systems measure an electrical characteristic, and use this to determine the glucose level in the blood. The test is usually referred to as capillary blood glucose. Commercially available blood glucose monitors for periodic or continuous use are known in the art. Glucose monitors for periodic detection of blood glucose levels include, but are not limited to, TRUEResult Blood Glucose Meter (TRUE), ACCU-CHEK Glucose Meter (ACCU-CHEK), OneTouch Glucose Meter (ONETOUCH), and FreeStyle Lite Blood Glucose (FREE-STYLE LITE). It is understood that a directly measured normal blood glucose level will vary depending on the amount of time since food was last consumed with a normal fasting blood glucose level being lower than a normal fed blood glucose level. Direct blood glucose monitoring is also used in glucose tolerance tests to monitor response to consumption of a high dose of glucose and the rate of glucose clearance from the blood.

Glycated hemoglobin (hemoglobin A1c, HbA1c, A1C, Hb1c, HbA1c) is a form of hemoglobin that is measured primarily to identify the average plasma glucose concentration over prolonged periods of time, i.e., an indirect measurement of blood glucose. HbA1c is formed in a non-enzymatic glycation pathway by hemoglobin's exposure to plasma glucose. When normal levels of glucose are present, a normal amount of glycated hemoglobin, measured as a percent of total hemoglobin, or a specific blood concentration, is produced. When blood glucose levels are high, elevated levels of glycated hemoglobin are produced. Glycation is an irreversible reaction. Therefore, the amount of glycated hemoglobin within the red cell reflects the average level of glucose to which the cell has been exposed. Measuring glycated hemoglobin assesses the effectiveness of therapy by monitoring long-term serum glucose regulation rather than a snapshot image as provided by glucose monitoring. The HbA1c level is proportional to average blood glucose concentration over the previous four weeks to three months. HbA1c levels can be measured, for example, using high-performance liquid chromatography (HPLC) or immunoassay. Methods for detection and measurement of protein analytes are discussed in detail below.

B. Detection of Nucleic Acid Indicators

In certain embodiments, the invention involves the detection of nucleic acid biomarkers, e.g., Eno1 mRNA biomarkers, optionally in combination with other indicators of blood glucose, to monitor diabetes and/or glucose control in a subject e.g., direct measurement of blood glucose, ketones, and/or HbA1c.

In various embodiments, the diagnostic/prognostic methods of the present invention generally involve the determination of expression levels of Eno1 in a blood sample. Determination of gene expression levels in the practice of the inventive methods may be performed by any suitable method. For example, determination of gene expression levels may be performed by detecting the expression of mRNA expressed from a gene of interest and/or by detecting the expression of a polypeptide encoded by the gene.

For detecting nucleic acids encoding Eno1, any suitable method can be used, including, but not limited to, Southern blot analysis, northern blot analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds), 1990, Academic Press: New York), reverse transcriptase PCR (RT-PCR), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan®, etc.

In other embodiments, gene expression levels of Eno1 may be determined by amplifying complementary DNA (cDNA) or complementary RNA (cRNA) produced from mRNA and analyzing it using a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state mRNA level of a large number of genes simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

In one particular embodiment, the invention comprises a method for identification of a subject suffering from abnormal blood glucose by amplifying and detecting nucleic acids corresponding to Eno1, optionally in combination with one or more additional indicators of elevated blood glucose.

Nucleic acid used as a template for amplification can be isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to any of the Eno1 nucleotide sequences identified herein are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (AFFYMAX technology; Bellus, 1994). Following detection, one may compare the results seen in a given patient with a statistically significant reference group of normal patients and patients with elevated blood glucose, e.g., patients with pre-diabetes, type 2 diabetes, gestational diabetes, or type 1 diabetes. In this way, it is possible to correlate the amount of nucleic acid detected with various clinical states.

The term primer, as defined herein, is meant to encompass any nucleic acid that is capable of priming the synthesis of a nascent nucleic acid in a template-dependent process. Typically, primers are oligonucleotides from ten to twenty, preferably fifteen to twenty nucleotides in length, but longer sequences may be employed. Primers may be provided in double-stranded or single-stranded form, although the single-stranded form is preferred.

A number of template dependent processes are available to amplify the nucleic acid sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

In PCR, two primer sequences are prepared which are complementary to regions on opposite complementary strands of the target nucleic acid sequence. An excess of deoxynucleoside triphosphates are added to a reaction mixture along with a DNA polymerase, e.g., Taq polymerase. If the target nucleic acid sequence is present in a sample, the primers will bind to the target nucleic acid and the polymerase will cause the primers to be extended along the target nucleic acid sequence by adding on nucleotides. By raising and lowering the temperature of the reaction mixture, the extended primers will dissociate from the target nucleic acid to form reaction products, excess primers will bind to the target nucleic acid and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art.

Another method for amplification is the ligase chain reaction ("LCR"), disclosed in European Application No. 320 308, incorporated herein by reference in its entirely. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[α-thio]-triphosphates in one strand of a restriction site also may be useful in the amplification of nucleic acids in the present invention. Walker et al. (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences also may be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other contemplated nucleic acid amplification procedures include transcription-based amplification systems (TAS), including nucleic acid sequence based amplification (NASBA) and 3SR. Kwoh et al. (1989); Gingeras et al., PCT Application WO 88/10315, incorporated herein by reference in their entirety. In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of $E.$ $coli$ DNA polymerase 1), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR™." Frohman (1990) and Ohara et al. (1989), each herein incorporated by reference in their entirety.

Methods based on ligation of two (or more) oligonucleotides in the presence of nucleic acid having the sequence of the resulting "di-oligonucleotide", thereby amplifying the di-oligonucleotide, also may be used in the amplification step of the present invention. Wu et al. (1989), incorporated herein by reference in its entirety.

Oligonucleotide probes or primers of the present invention may be of any suitable length, depending on the particular assay format and the particular needs and targeted sequences employed. In a preferred embodiment, the oligonucleotide probes or primers are at least 10 nucleotides in length (preferably, 10, 11, 12, 13, 14, 15, 16, 17, 18, 19, 20, 21, 22, 23, 24, 25, 26, 27, 28, 29, 30, 31, 32 . . . ), preferably at least 15 nucleotides in length (15, 16, 17, 18, 19, 20, 21, 22, 23, 24, 25, 26, 27, 28, 29, 30, 31, 32 . . . ) and they may be adapted to be especially suited for a chosen nucleic acid amplification system and/or hybridization system used. Longer probes and primers are also within the scope of the present invention as well known in the art. Primers having more than 30, more than 40, more than 50 nucleotides and probes having more than 100, more than 200, more than 300, more than 500 more than 800 and more than 1000 nucleotides in length are also covered by the present invention. Of course, longer primers have the disadvantage of being more expensive and thus, primers having between 15 and 30 nucleotides in length are usually designed and used in the art. As well known in the art, probes ranging from 10 to more than 2000 nucleotides in length can be used in the methods of the present invention. As for the % of identity described above, non-specifically described sizes of probes and primers (e.g., 16, 17, 31, 24, 39, 350, 450, 550, 900, 1240 nucleotides, . . . ) are also within the scope of the present invention. In one embodiment, the oligonucleotide probes or primers of the present invention specifically hybridize with an Eno1 RNA (or its complementary sequence) or an Eno1 mRNA. More preferably, the Eno1 primers and probes are chosen to detect an Eno1 RNA which is associated with elevated blood glucose or abnormal blood glucose regulation related to, e.g., pre-diabetes, type 2 diabetes, type 1 diabetes, or gestational diabetes.

In other embodiments, the detection means can utilize a hybridization technique, e.g., where a specific primer or probe is selected to anneal to a target biomarker of interest, e.g., Eno1, and thereafter detection of selective hybridization is made. As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1994, in Current Protocols in Molecular Biology, John Wiley & Sons Inc., N.Y.).

To enable hybridization to occur under the assay conditions of the present invention, oligonucleotide primers and probes should comprise an oligonucleotide sequence that has at least 70% (at least 71%, 72%, 73%, 74% or more), preferably at least 75% (75%, 76%, 77%, 78%, 79%, 80%, 81%, 82%, 83%, 84%, 85%, 86%, 87%, 88%, 89% or more) and more preferably at least 90% (90%, 91%, 92%, 93%, 94%, 95%, 96%, 97%, 98%, 99%, 100%) identity to a portion of an Eno1 polynucleotide. Probes and primers of the present invention are those that hybridize under stringent hybridization conditions and those that hybridize to Eno1 homologs under at least moderately stringent conditions. In certain embodiments probes and primers of the present invention have complete sequence identity to Eno1 gene sequences (e.g., cDNA or mRNA). It should be understood that other probes and primers could be easily designed and used in the present invention based on the Eno1 sequences disclosed herein by using methods of computer alignment and sequence analysis known in the art (cf. Molecular Cloning: A Laboratory Manual, Third Edition, edited by Cold Spring Harbor Laboratory, 2000).

C. Detection of Polypeptide Indicators of Blood Glucose of Blood Glucose Control The present invention contemplates any suitable method for detecting polypeptide indicators of blood glucose including Eno1 and HbA1c. In certain embodiments, the detection method is an immunodetection method involving an antibody that specifically binds to one or more of Eno1 and hemoglobin, especially specifically to glycated hemoglobin. The steps of various useful immunodetection methods have been described in the scientific literature, such as, e.g., Nakamura et al. (1987), which is incorporated herein by reference.

In general, the immunobinding methods include obtaining a sample suspected of containing a protein or peptide indicator of elevated blood glucose, and contacting the sample with an antibody in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a protein or peptide indicator of elevated blood glucose, and contact the sample with an antibody, and then detect or quantify the amount of immune complexes formed under the specific conditions.

In terms of detection of an indicator of blood glucose, the biological sample analyzed may be any sample that is suspected of containing a protein or peptide indicator of blood glucose, such as, Eno1 or HbA1c. The biological sample may be, for example, blood, in the case of HbA1c, or blood or serum in the case of Eno1.

Contacting the chosen biological sample with the antibody (e.g., as a detection reagent that binds Eno1, HbA1c, or hemoglobin in a biological sample) under conditions effective and for a period of time sufficient to allow the formation of immune complexes (primary immune complexes). Generally, complex formation is a matter of simply adding the composition to the biological sample and incubating the mixture for a period of time long enough for the antibodies to form immune complexes with, i.e., to bind to, any antigens present. After this time, the sample-antibody composition, such as a tissue section, ELISA plate, dot blot or western blot, is generally washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The antibody (e.g., anti-Eno1 antibody, anti-hemoglobin or anti-glycated hemoglobin antibody) employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the bound antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of conditions such as elevated blood glucose, loss of blood glucose control, and diabetes. Here, a biological or clinical sample suspected of containing either the encoded protein or glycated peptide is used. However, these embodiments also have applications to non-clinical samples, such as in the tittering of antigen or antibody samples, in the selection of hybridomas, and the like.

The present invention, in particular, contemplates the use of ELISAs as a type of immunodetection assay. It is contemplated that the biomarker proteins or peptides of the invention will find utility as immunogens in ELISA assays in diagnosis and prognostic monitoring abnormal blood glucose and diabetes. Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections can be useful. However, it will be readily appreciated that detection is not limited to such techniques, and western blotting, dot blotting, and the like also may be used.

In one exemplary ELISA, antibodies binding to the protein indicators of the invention are immobilized onto a selected surface exhibiting protein affinity, such as a well in a polystyrene microtiter plate. Then, a test composition suspected of containing an indicator of blood glucose levels, such as a blood or serum sample, is added to the wells. After binding and washing to remove non-specifically bound immunocomplexes, the bound antigen may be detected. Detection is generally achieved by the addition of a second antibody specific for the indicator protein, that is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label.

In another exemplary ELISA, the samples suspected of containing the blood glucose indicator proteins are immobilized onto the well surface and then contacted with specific antibodies for binding the indicators. After binding and washing to remove non-specifically bound immunocomplexes, the bound antigen is detected. Where the initial antibodies are linked to a detectable label, the immunocomplexes may be detected directly. Again, the immunocomplexes may be detected using a second antibody that has binding affinity for the first antibody, with the second antibody being linked to a detectable label.

Irrespective of the format employed, ELISAs have certain features in common, such as coating, incubating or binding, washing to remove non-specifically bound species, and detecting the bound immunocomplexes. These are described as follows.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

In ELISAs, it is customary to use a secondary or tertiary detection means rather than a direct procedure. Thus, after binding of a protein or antibody to the well, coating with a non-reactive material to reduce background, and washing to remove unbound material, the immobilizing surface is contacted with the control biological sample, e.g., blood or serum from a subject with normal blood glucose and/or sufficient blood glucose control to be tested under conditions effective to allow immunocomplex (antigen/antibody) formation. Detection of the immunocomplex then requires a labeled secondary binding ligand or antibody, or a secondary binding ligand or antibody in conjunction with a labeled tertiary antibody or third binding ligand.

The phrase "under conditions effective to allow immunocomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to about 4 hours, at temperatures preferably on the order of 25 to 27° C., or may be overnight at about 4° C. or so.

Following all incubation steps in an ELISA, the contacted surface is washed so as to remove non-complexed material. A preferred washing procedure includes washing with a solution such as PBS/Tween or borate buffer. Following the formation of specific immunocomplexes between the test sample and the originally bound material, and subsequent washing, the occurrence of even minute amounts of immunocomplexes may be determined.

To provide a detecting means, the second or third antibody has an associated label to allow detection. Preferably, the label is an enzyme that generates color development upon incubating with an appropriate chromogenic substrate. Thus, for example, the first or second immunocomplex is contacted and incubated with a urease, glucose oxidase, alkaline phosphatase or hydrogen peroxidase-conjugated antibody for a period of time and under conditions that favor the development of further immunocomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple. Quantitation is then achieved by measuring the degree of color generation, e.g., using a visible spectra spectrophotometer.

The protein biomarkers/indicators of the invention (e.g., Eno1, HbA1c) can also be measured, quantitated, detected, and otherwise analyzed using protein mass spectrometry methods and instrumentation. Protein mass spectrometry refers to the application of mass spectrometry to the study of proteins. Although not intending to be limiting, two approaches are typically used for characterizing proteins using mass spectrometry. In the first, intact proteins are ionized and then introduced to a mass analyzer. This approach is referred to as "top-down" strategy of protein analysis. The two primary methods for ionization of whole proteins are electrospray ionization (ESI) and matrix-assisted laser desorption/ionization (MALDI). In the second approach, proteins are enzymatically digested into smaller peptides using a protease such as trypsin. Subsequently these peptides are introduced into the mass spectrometer and identified by peptide mass fingerprinting or tandem mass spectrometry. Hence, this latter approach (also called "bottom-up" proteomics) uses identification at the peptide level to infer the existence of proteins.

Whole protein mass analysis of the biomarkers of the invention can be conducted using time-of-flight (TOF) MS, or Fourier transform ion cyclotron resonance (FT-ICR). These two types of instruments are useful because of their wide mass range, and in the case of FT-ICR, its high mass accuracy. The most widely used instruments for peptide mass analysis are the MALDI time-of-flight instruments as they permit the acquisition of peptide mass fingerprints (PMFs) at high pace (1 PMF can be analyzed in approx. 10 sec). Multiple stage quadrupole-time-of-flight and the quadrupole ion trap also find use in this application.

Protein indicators can also be measured in complex mixtures of proteins and molecules that co-exist in a biological medium or sample, however, fractionation of the sample may be required and is contemplated herein. It will be appreciated that ionization of complex mixtures of proteins can result in situation where the more abundant proteins have a tendency to "drown" or suppress signals from less abundant proteins in the same sample. In addition, the mass spectrum from a complex mixture can be difficult to interpret because of the overwhelming number of mixture components. Fractionation can be used to first separate any complex mixture of proteins prior to mass spectrometry analysis. Two methods are widely used to fractionate proteins, or their peptide products from an enzymatic digestion. The first method fractionates whole proteins and is called two-dimensional gel electrophoresis. The second method, high performance liquid chromatography (LC or HPLC) is used to fractionate peptides after enzymatic digestion. In some situations, it may be desirable to combine both of these techniques. Any other suitable methods known in the art for fractionating protein mixtures are also contemplated herein.

Gel spots identified on a 2D Gel are usually attributable to one protein. If the identity of the protein is desired, usually the method of in-gel digestion is applied, where the protein spot of interest is excised, and digested proteolytically. The peptide masses resulting from the digestion can be determined by mass spectrometry using peptide mass fingerprinting. If this information does not allow unequivocal identification of the protein, its peptides can be subject to tandem mass spectrometry for de novo sequencing.

Characterization of protein mixtures using HPLC/MS may also be referred to in the art as "shotgun proteomics" and MuDPIT (Multi-Dimensional Protein Identification Technology). A peptide mixture that results from digestion of a protein mixture is fractionated by one or two steps of liquid chromatography (LC). The eluent from the chromatography stage can be either directly introduced to the mass spectrometer through electrospray ionization, or laid down on a series of small spots for later mass analysis using MALDI.

Protein indicators (e.g., Eno1 or Hb1Ac) can be identified using MS using a variety of techniques, all of which are contemplated herein. Peptide mass fingerprinting uses the masses of proteolytic peptides as input to a search of a database of predicted masses that would arise from digestion of a list of known proteins. If a protein sequence in the reference list gives rise to a significant number of predicted masses that match the experimental values, there is some evidence that this protein was present in the original sample. It will be further appreciated that the development of methods and instrumentation for automated, data-dependent electrospray ionization (ESI) tandem mass spectrometry (MS/MS) in conjunction with microcapillary liquid chromatography (LC) and database searching has significantly increased the sensitivity and speed of the identification of gel-separated proteins. Microcapillary LC-MS/MS has been used successfully for the large-scale identification of individual proteins directly from mixtures without gel electrophoretic separation (Link et al., 1999; Opitek et al., 1997).

Several recent methods allow for the quantitation of proteins by mass spectrometry. For example, stable (e.g., non-radioactive) heavier isotopes of carbon (13C) or nitrogen (15N) can be incorporated into one sample while the other one can be labeled with corresponding light isotopes (e.g. 12C and 14N). The two samples are mixed before the analysis. Peptides derived from the different samples can be distinguished due to their mass difference. The ratio of their peak intensities corresponds to the relative abundance ratio of the peptides (and proteins). The most popular methods for isotope labeling are SILAC (stable isotope labeling by amino acids in cell culture), trypsin-catalyzed 18O labeling, ICAT (isotope coded affinity tagging), iTRAQ (isobaric tags for relative and absolute quantitation). "Semi-quantitative" mass spectrometry can be performed without labeling of samples. Typically, this is done with MALDI analysis (in linear mode). The peak intensity, or the peak area, from individual molecules (typically proteins) is here correlated to the amount of protein in the sample. However, the individual signal depends on the primary structure of the protein, on the complexity of the sample, and on the settings of the instrument. Other types of "label-free" quantitative mass spectrometry, uses the spectral counts (or peptide counts) of digested proteins as a means for determining relative protein amounts.

In one embodiment, any one or more of the protein indicators (e.g., Eno1, HbA1c) can be identified and quantified from a complex biological sample using mass spectroscopy in accordance with the following exemplary method, which is not intended to limit the invention or the use of other mass spectrometry-based methods.

In the first step of this embodiment, (A) a biological sample, e.g., a biological sample suspected of having increased blood glucose, which comprises a complex mixture of protein (including at least one indicator of interest) is fragmented and labeled with a stable isotope X. (B) Next, a known amount of an internal standard is added to the biological sample, wherein the internal standard is prepared by fragmenting a standard protein that is identical to the at least one target biomarker of interest, and labeled with a stable isotope Y. (C) This sample obtained is then introduced in an LC-MS/MS device, and multiple reaction monitoring (MRM) analysis is performed using MRM transitions selected for the internal standard to obtain an MRM chromatogram. (D) The MRM chromatogram is then viewed to identify a target peptide biomarker derived from the biological sample that shows the same retention time as a peptide derived from the internal standard (an internal standard peptide), and quantifying the target protein indicator in the test sample by comparing the peak area of the internal standard peptide with the peak area of the target peptide indicator.

Any suitable biological sample may be used as a starting point for LC-MS/MS/MRM analysis, including biological samples derived blood, urine, saliva, hair, cells, cell tissues, biopsy materials, and treated products thereof; and protein-containing samples prepared by gene recombination techniques. Preferred embodiments of the invention include the use of blood or serum samples.

Each of the above steps (A) to (D) is described further below.

Step (A) (Fragmentation and Labeling). In step (A), the target protein indicator is fragmented to a collection of peptides, which is subsequently labeled with a stable isotope X. To fragment the target protein, for example, methods of digesting the target protein with a proteolytic enzyme (protease) such as trypsin, and chemical cleavage methods, such as a method using cyanogen bromide, can be used. Digestion by protease is preferable. It is known that a given mole quantity of protein produces the same mole quantity for each tryptic peptide cleavage product if the proteolytic digest is allowed to proceed to completion. Thus, determining the mole quantity of tryptic peptide to a given protein allows determination of the mole quantity of the original protein in the sample. Absolute quantification of the target protein can be accomplished by determining the absolute amount of the target protein-derived peptides contained in the protease digestion (collection of peptides). Accordingly, in order to allow the proteolytic digest to proceed to completion, reduction and alkylation treatments are preferably performed before protease digestion with trypsin to reduce and alkylate the disulfide bonds contained in the target protein.

Subsequently, the obtained digest (collection of peptides, comprising peptides of the target biomarker in the biological sample) is subjected to labeling with a stable isotope X. Examples of stable isotopes X include 1H and 2H for hydrogen atoms, 12C and 13C for carbon atoms, and 14N and 15N for nitrogen atoms. Any isotope can be suitably selected therefrom. Labeling by a stable isotope X can be performed by reacting the digest (collection of peptides) with a reagent containing the stable isotope. Preferable examples of such reagents that are commercially available include mTRAQ® (produced by Applied Biosystems), which is an amine-specific stable isotope reagent kit. mTRAQ® is composed of 2 or 3 types of reagents (mTRAQ®-light and mTRAQ®-heavy; or mTRAQ®-DO, mTRAQ®-D4, and mTRAQ®-D8) that have a constant mass difference there between as a result of isotope-labeling, and that are bound to the N-terminus of a peptide or the primary amine of a lysine residue.

Step (B) (Addition of the Internal Standard). In step (B), a known amount of an internal standard is added to the sample obtained in step (A). The internal standard used herein is a digest (collection of peptides) obtained by fragmenting a protein (standard protein) consisting of the same amino acid sequence as the target protein (target biomarker) to be measured, and labeling the obtained digest (collection of peptides) with a stable isotope Y. The fragmentation treatment can be performed in the same manner as above for the target protein. Labeling with a stable isotope Y can also be performed in the same manner as above for the target protein. However, the stable isotope Y used herein must be an isotope that has a mass different from that of the stable isotope X used for labeling the target protein digest. For example, in the case of using the aforementioned mTRAQ (registered trademark) (produced by Applied Biosystems), when mTRAQ-light is used to label a target protein digest, mTRAQ-heavy should be used to label a standard protein digest.

Step (C) (LC-MS/MS and MRM Analysis). In step (C), the sample obtained in step (B) is first placed in an LC-MS/MS device, and then multiple reaction monitoring (MRM) analysis is performed using MRM transitions selected for the internal standard. By LC (liquid chromatography) using the LC-MS/MS device, the sample (collection of peptides labeled with a stable isotope) obtained in step (B) is separated first by one-dimensional or multi-dimensional high-performance liquid chromatography. Specific examples of such liquid chromatography include cation exchange chromatography, in which separation is conducted by utilizing electric charge difference between peptides; and reversed-phase chromatography, in which separation is conducted by utilizing hydrophobicity difference between peptides. Both of these methods may be used in combination.

Subsequently, each of the separated peptides is subjected to tandem mass spectrometry by using a tandem mass spectrometer (MS/MS spectrometer) comprising two mass spectrometers connected in series. The use of such a mass spectrometer enables the detection of several fmol levels of a target protein. Furthermore, MS/MS analysis enables the analysis of internal sequence information on peptides, thus enabling identification without false positives. Other types of MS analyzers may also be used, including magnetic sector mass spectrometers (Sector MS), quadrupole mass spectrometers (QMS), time-of-flight mass spectrometers (TOFMS), and Fourier transform ion cyclotron resonance mass spectrometers (FT-ICRMS), and combinations of these analyzers.

Subsequently, the obtained data are put through a search engine to perform a spectral assignment and to list the peptides experimentally detected for each protein. The detected peptides are preferably grouped for each protein, and preferably at least three fragments having an m/z value larger than that of the precursor ion and at least three fragments with an m/z value of, preferably, 500 or more are selected from each MS/MS spectrum in descending order of signal strength on the spectrum. From these, two or more fragments are selected in descending order of strength, and the average of the strength is defined as the expected sensitivity of the MRR transitions. When a plurality of peptides is detected from one protein, at least two peptides with the highest sensitivity are selected as standard peptides using the expected sensitivity as an index.

Step (D) (Quantification of the Target Protein in the Test Sample). Step (D) comprises identifying, in the MRM chromatogram detected in step (C), a peptide derived from the target protein (a target biomarker of interest) that shows the same retention time as a peptide derived from the internal standard (an internal standard peptide), and quantifying the target protein in the test sample by comparing the peak area of the internal standard peptide with the peak area of the target peptide. The target protein can be quantified by utilizing a calibration curve of the standard protein prepared beforehand.

The calibration curve can be prepared by the following method. First, a recombinant protein consisting of an amino acid sequence that is identical to that of the target biomarker protein is digested with a protease such as trypsin, as described above. Subsequently, precursor-fragment transition selection standards (PFTS) of a known concentration are individually labeled with two different types of stable isotopes (i.e., one is labeled with a stable isomer used to label an internal standard peptide (labeled with IS), whereas the other is labeled with a stable isomer used to label a target peptide (labeled with T). A plurality of samples are produced by blending a certain amount of the IS-labeled PTFS with various concentrations of the T-labeled PTFS. These samples are placed in the aforementioned LC-MS/MS device to perform MRM analysis. The area ratio of the T-labeled PTFS to the IS-labeled PTFS (T-labeled PTFS/IS-labeled PTFS) on the obtained MRM chromatogram is plotted against the amount of the T-labeled PTFS to prepare a calibration curve. The absolute amount of the target protein contained in the test sample can be calculated by reference to the calibration curve.

D. Antibodies and Labels (e.g., Fluorescent Moieties and Dyes)

In some embodiments, the invention provides methods and compositions that include labels for the highly sensitive detection and quantitation of the biomolecules of the invention, e.g., Eno1 alone or in combination with at least one other indicator of blood glucose and blood glucose control, e.g., HbA1c, ketones, or direct measurement of blood glucose. One skilled in the art will recognize that many strategies can be used for labeling target molecules to enable their detection or discrimination in a mixture of particles (e.g., labeled anti-Eno1 antibody or labeled secondary antibody, or labeled oligonucleotide probe that specifically hybridizes to Eno1 mRNA). The labels may be attached by any known means, including methods that utilize non-specific or specific interactions of label and target. Labels may provide a detectable signal or affect the mobility of the particle in an electric field. In addition, labeling can be accomplished directly or through binding partners.

In some embodiments, the label comprises a binding partner that binds to the indicator of interest, where the binding partner is attached to a fluorescent moiety. The compositions and methods of the invention may utilize highly fluorescent moieties, e.g., a moiety capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. Moieties suitable for the compositions and methods of the invention are described in more detail below.

In some embodiments, the invention provides a label for detecting a biological molecule comprising a binding partner for the biological molecule that is attached to a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the moiety comprises a plurality of fluorescent entities, e.g., about 2 to 4, 2 to 5, 2 to 6, 2 to 7, 2 to 8, 2 to 9, 2 to 10, or about 3 to 5, 3 to 6, 3 to 7, 3 to 8, 3 to 9, or 3 to 10 fluorescent entities. In some embodiments, the moiety comprises about 2 to 4 fluorescent entities. In some embodiments, the biological molecule is a protein or a small molecule. In some embodiments, the biological molecule is a protein. The fluorescent entities can be fluorescent dye molecules. In some embodiments, the fluorescent dye molecules comprise at least one substituted indolium ring system in which the substituent on the 3-carbon of the indolium ring contains a chemically reactive group or a conjugated substance. In some embodiments, the dye molecules are Alexa Fluor molecules selected from the group consisting of Alexa Fluor 488, Alexa Fluor 532, Alexa Fluor 647, Alexa Fluor 680 or Alexa Fluor 700. In some embodiments, the dye molecules are Alexa Fluor molecules selected from the group consisting of Alexa Fluor 488, Alexa Fluor 532, Alexa Fluor 680 or Alexa Fluor 700. In some embodiments, the dye molecules are Alexa Fluor 647 dye molecules. In some embodiments, the dye molecules comprise a first type and a second type of dye molecules, e.g., two different Alexa Fluor molecules, e.g., where the first type and second type of dye molecules have different emission spectra. The ratio of the number of first type to second type of dye molecule can be, e.g., 4 to 1, 3 to 1, 2 to 1, 1 to 1, 1 to 2, 1 to 3 or 1 to 4. The binding partner can be, e.g., an antibody.

In some embodiments, the invention provides a label for the detection of a biological indicators of the invention, wherein the label comprises a binding partner for the indicator and a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the fluorescent moiety comprises a fluorescent molecule. In some embodiments, the fluorescent moiety comprises a plurality of fluorescent molecules, e.g., about 2 to 10, 2 to 8, 2 to 6, 2 to 4, 3 to 10, 3 to 8, or 3 to 6 fluorescent molecules. In some embodiments, the label comprises about 2 to 4 fluorescent molecules. In some embodiments, the fluorescent dye molecules comprise at least one substituted indolium ring system in which the substituent on the 3-carbon of the indolium ring contains a chemically reactive group or a conjugated substance. In some embodiments, the fluorescent molecules are selected from the group consisting of Alexa Fluor 488, Alexa Fluor 532, Alexa Fluor 647, Alexa Fluor 680 or Alexa Fluor 700. In some embodiments, the fluorescent molecules are selected from the group consisting of Alexa Fluor 488, Alexa Fluor 532, Alexa Fluor 680 or Alexa Fluor 700. In some embodiments, the fluorescent molecules are Alexa Fluor 647 molecules. In some embodiments, the binding partner comprises an antibody. In some embodiments, the antibody is a monoclonal antibody. In other embodiments, the antibody is a polyclonal antibody.

In various embodiments, the binding partner for detecting an indicator of interest, e.g., Eno1 or HbA1c, is an antibody or antigen-binding fragment thereof. The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. An "antigen-binding fragment" of an antibody refers to the part of the antibody that participates in antigen binding. The antigen binding site is formed by amino acid residues of the N-terminal variable ("V") regions of the heavy ("H") and light ("L") chains. It will be appreciated that the choice of epitope or region of the molecule to which the antibody is raised will determine its specificity, e.g., for various forms of the molecule, if present, or for total (e.g., all, or substantially all of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest, HyTest Ltd., Turku Finland; Abcam Inc., Cambridge, Mass., USA, Life Diagnostics, Inc., West Chester, Pa., USA; Fitzgerald Industries International, Inc., Concord, Mass. 01742-3049 USA; BiosPacific, Emeryville, Calif.).

In some embodiments, the antibody is a polyclonal antibody. In other embodiments, the antibody is a monoclonal antibody.

Antibodies may be prepared by any of a variety of techniques known to those of ordinary skill in the art (see, for example, Harlow and Lane, Antibodies: A Laboratory Manual, Cold Spring Harbor Laboratory, 1988). In general, antibodies can be produced by cell culture techniques, including the generation of monoclonal antibodies as described herein, or via transfection of antibody genes into suitable bacterial or mammalian cell hosts, in order to allow for the production of recombinant antibodies.

Monoclonal antibodies may be prepared using hybridoma methods, such as the technique of Kohler and Milstein (Eur. J. Immunol. 6:511-519, 1976), and improvements thereto. These methods involve the preparation of immortal cell lines capable of producing antibodies having the desired specificity. Monoclonal antibodies may also be made by recombinant DNA methods, such as those described in U.S. Pat. No. 4,816,567. DNA encoding antibodies employed in the disclosed methods may be isolated and sequenced using conventional procedures. Recombinant antibodies, antibody fragments, and/or fusions thereof, can be expressed in vitro or in prokaryotic cells (e.g. bacteria) or eukaryotic cells (e.g. yeast, insect or mammalian cells) and further purified as necessary using well known methods.

More particularly, monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells. The methods for generating monoclonal antibodies (MAbs) generally begin along the same lines as those for preparing polyclonal antibodies.

Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals. Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasma blast stage, and the latter because peripheral blood is easily accessible. Often, a panel of animals will have been immunized and the spleen of the animal with the highest antibody titer will be removed and the spleen lymphocytes obtained by homogenizing the spleen with a syringe.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

The selected hybridomas are then serially diluted and cloned into individual antibody-producing cell lines, which clones may then be propagated indefinitely to provide MAbs. The cell lines may be exploited for MAb production in two basic ways. A sample of the hybridoma may be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines also can be cultured in vitro, where the MAbs are naturally secreted into the culture medium from which they can be readily obtained in high concentrations. MAbs produced by either means can be further purified, if desired, using filtration, centrifugation and various chromatographic methods such as HPLC or affinity chromatography.

Large amounts of the monoclonal antibodies of the present invention also can be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention may be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention may be synthesized using an automated peptide synthesizer.

Antibodies can also be derived from a recombinant antibody library that is based on amino acid sequences that have been designed in silico and encoded by polynucleotides that are synthetically generated. Methods for designing and obtaining in silico-created sequences are known in the art (Knappik et al., J. Mol. Biol. 296:254:57-86, 2000; Krebs et al., J. Immunol. Methods 254:67-84, 2001; U.S. Pat. No. 6,300,064).

Digestion of antibodies to produce antigen-binding fragments thereof can be performed using techniques well known in the art. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment, which comprises both antigen-binding sites. "Fv" fragments can be produced by preferential proteolytic cleavage of an IgM, IgG or IgA immunoglobulin molecule, but are more commonly derived using recombinant techniques known in the art. The Fv fragment includes a non-covalent $V_H$::$V_L$ heterodimer including an antigen-binding site which retains much of the antigen recognition and binding capabilities of the native antibody molecule (Inbar et al., Proc. Natl. Acad. Sci. USA 69:2659-2662 (1972); Hochman et al., Biochem. 15:2706-2710 (1976); and Ehrlich et al., Biochem. 19:4091-4096 (1980)).

Antibody fragments that specifically bind to the polypeptide indicators disclosed herein can also be isolated from a library of scFvs using known techniques, such as those described in U.S. Pat. No. 5,885,793.

A wide variety of expression systems are available in the art for the production of antibody fragments, including Fab fragments, scFv, VL and VHs. For example, expression systems of both prokaryotic and eukaryotic origin may be used for the large-scale production of antibody fragments. Particularly advantageous are expression systems that permit the secretion of large amounts of antibody fragments into the culture medium. Eukaryotic expression systems for large-scale production of antibody fragments and antibody fusion proteins have been described that are based on mammalian cells, insect cells, plants, transgenic animals, and lower eukaryotes. For example, the cost-effective, large-scale production of antibody fragments can be achieved in yeast fermentation systems. Large-scale fermentation of these organisms is well known in the art and is currently used for bulk production of several recombinant proteins.

Antibodies that bind to the polypeptide biomarkers employed in the present methods are well known to those of skill in the art and in some cases are available commercially or can be obtained without undue experimentation.

In still other embodiments, particularly where oligonucleotides are used as binding partners to detect and hybridize to mRNA biomarkers or other nucleic acid based biomarkers, the binding partners (e.g., oligonucleotides) can comprise a label, e.g., a fluorescent moiety or dye. In addition, any binding partner of the invention, e.g., an antibody, can also be labeled with a fluorescent moiety. A "fluorescent moiety," as that term is used herein, includes one or more fluorescent entities whose total fluorescence is such that the moiety may be detected in the single molecule detectors described herein. Thus, a fluorescent moiety may comprise a single entity (e.g., a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

Typically, the fluorescence of the moiety involves a combination of quantum efficiency and lack of photobleaching sufficient that the moiety is detectable above background levels in a single molecule detector, with the consistency necessary for the desired limit of detection, accuracy, and precision of the assay. For example, in some embodiments, the fluorescence of the fluorescent moiety is such that it allows detection and/or quantitation of a molecule, e.g., a marker, at a limit of detection of less than about 10, 5, 4, 3, 2, 1, 0.1, 0.01, 0.001, 0.00001, or 0.000001 pg/ml and with a coefficient of variation of less than about 20, 15, 14, 13, 12, 11, 10, 9, 8, 7, 6, 5, 4, 3, 2, 1% or less, e.g., about 10% or less, in the instruments described herein. In some embodiments, the fluorescence of the fluorescent moiety is such that it allows detection and/or quantitation of a molecule, e.g., a marker, at a limit of detection of less than about 5, 1, 0.5, 0.1, 0.05, 0.01, 0.005, 0.001 pg/ml and with a coefficient of variation of less than about 10%, in the instruments described herein. "Limit of detection," or LoD, as those terms are used herein, includes the lowest concentration at which one can identify a sample as containing a molecule of the substance of interest, e.g., the first non-zero value. It can be defined by the variability of zeros and the slope of the standard curve. For example, the limit of detection of an assay may be determined by running a standard curve, determining the standard curve zero value, and adding 2 standard deviations to that value. A concentration of the substance of interest that produces a signal equal to this value is the "lower limit of detection" concentration.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties that are preferred are fluorescent moieties, e.g., dye molecules that have a combination of 1) high absorption coefficient; 2) high quantum yield; 3) high photostability (low photobleaching); and 4) compatibility with labeling the molecule of interest (e.g., protein) so that it may be analyzed using the analyzers and systems of the invention (e.g., does not cause precipitation of the protein of interest, or precipitation of a protein to which the moiety has been attached).

Any suitable fluorescent moiety may be used. Examples include, but are not limited to, Alexa Fluor dyes (Molecular Probes, Eugene, Oreg.). The Alexa Fluor dyes are disclosed in U.S. Pat. Nos. 6,977,305; 6,974,874; 6,130,101; and 6,974,305 which are herein incorporated by reference in their entirety. Some embodiments of the invention utilize a dye chosen from the group consisting of Alexa Fluor 647, Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize a dye chosen from the group consisting of Alexa Fluor 488, Alexa Fluor 532, Alexa Fluor 647, Alexa Fluor 700 and Alexa Fluor 750. Some embodiments of the invention utilize a dye chosen from the group consisting of Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize the Alexa Fluor 647 molecule, which has an absorption maximum between about 650 and 660 nm and an emission maximum between about 660 and 670 nm. The Alexa Fluor 647 dye is used alone or in combination with other Alexa Fluor dyes.

In some embodiments, the fluorescent label moiety that is used to detect an indicator in a sample using the analyzer systems of the invention is a quantum dot. Quantum dots (QDs), also known as semiconductor nanocrystals or artificial atoms, are semiconductor crystals that contain anywhere between 100 to 1,000 electrons and range from 2-10 nm. Some QDs can be between 10-20 nm in diameter. QDs have high quantum yields, which makes them particularly useful for optical applications. QDs are fluorophores that fluoresce by forming excitons, which are similar to the excited state of traditional fluorophores, but have much longer lifetimes of up to 200 nanoseconds. This property provides QDs with low photobleaching. The energy level of QDs can be controlled by changing the size and shape of the QD, and the depth of the QDs' potential. One optical feature of small excitonic QDs is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the QD. Larger QDs have more energy levels which are more closely spaced, thus allowing the QD to absorb photons containing less energy, i.e., those closer to the red end of the spectrum. Because the emission frequency of a dot is dependent on the bandgap, it is possible to control the output wavelength of a dot with extreme precision. In some embodiments the protein that is detected with the single molecule analyzer system is labeled with a QD. In some embodiments, the single molecule analyzer is used to detect a protein labeled with one QD and using a filter to allow for the detection of different proteins at different wavelengths.

E. Isolated Macromolecular Indicators of Blood Glucose

1. Isolated Polypeptide Indicators

One aspect of the invention pertains to isolated indicator proteins and biologically active portions thereof, as well as polypeptide fragments suitable for use as immunogens to raise antibodies directed against an indicator protein or a fragment thereof. In one embodiment, the native indicator protein can be isolated from cells or tissue sources by an appropriate purification scheme using standard protein purification techniques. In another embodiment, a protein or peptide comprising the whole or a segment of the indicator protein is produced by recombinant DNA techniques. Alternative to recombinant expression, such protein or peptide can be synthesized chemically using standard peptide synthesis techniques. Recombinant proteins can be modified, e.g. glycated, to provide appropriate antigens for detection of HbA1c. Similarly, non-glycated fragments of hemoglobin can be used to raise antibodies that bind either non-glycated hemoglobin alone or total hemoglobin.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of an indicator protein include polypeptides comprising amino acid sequences sufficiently identical to or derived from the amino acid sequence of the indicator protein, which include fewer amino acids than the full length protein, and exhibit at least one activity of the corresponding full-length protein. Typically, biologically active portions comprise a domain or motif with at least one activity of the corresponding full-length protein. A biologically active portion of an indicator protein can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the indicator protein.

Preferred indicator proteins are encoded by nucleotide sequences provided in the sequence listing. Other useful proteins are substantially identical (e.g., at least about 40%, preferably 50%, 60%, 70%, 80%, 90%, 91%, 92%, 93%, 94%, 95%, 96%, 97%, 98% or 99%) to one of these sequences and retain the functional activity of the corresponding naturally-occurring indicator protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. Preferably, the percent identity between the two sequences is calculated using a global alignment. Alternatively, the percent identity between the two sequences is calculated using a local alignment. The percent identity between the two sequences is a function of the number of identical positions shared by the sequences (i.e., % identity=# of identical positions/total # of positions (e.g., overlapping positions)×100). In one embodiment the two sequences are the same length. In another embodiment, the two sequences are not the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the BLASTN and BLASTX programs of Altschul, et al. (1990) J. Mol. Biol. 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) Nucleic Acids Res. 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See ncbi.nlm.nih.gov. Another preferred, non-limiting example of a mathematical algorithm utilized for the comparison of sequences is the algorithm of Myers and Miller, (1988) CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) Proc. Natl. Acad. Sci. USA 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. In certain embodiments, the protein is post-translationally modified. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof. Methods of making polyclonal, monoclonal, and recombinant antibody and antibody fragments are well known in the art.

2. Isolated Nucleic Acid Indicators

One aspect of the invention pertains to isolated nucleic acid molecules, including nucleic acids which encode Eno1 or a portion thereof. Isolated nucleic acids of the invention also include nucleic acid molecules sufficient for use as hybridization probes to identify Eno1 nucleic acid molecules, and fragments thereof, e.g., those suitable for use as PCR primers for the amplification of a specific product or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. In one embodiment, an "isolated" nucleic acid molecule (preferably a protein-encoding sequences) is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. In another embodiment, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule that is substantially free of cellular material includes preparations having less than about 30%, 20%, 10%, or 5% of heterologous nucleic acid (also referred to herein as a "contaminating nucleic acid").

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., Molecular Cloning: A Laboratory Manual, 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises an Eno1 molecule which has a nucleotide sequence complementary to the nucleotide sequence of a marker nucleic acid or to the nucleotide sequence of a nucleic acid encoding Eno1. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises an Eno1 nucleic acid or which encodes an Eno1 protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 15, more preferably at least about 25, 50, 75, 100, 125, 150, 175, 200, 250, 300, 350, or 400 or more consecutive nucleotides of Eno1.

Probes based on the sequence of Eno1 can be used to detect transcripts or genomic sequences corresponding to Eno1. In certain embodiments, the probes hybridize to nucleic acid sequences that traverse splice junctions. The probe comprises a label group attached thereto, e.g., a radioisotope, a fluorescent compound, an enzyme, or an enzyme co-factor. Such probes can be used as part of a diagnostic test kit or panel for identifying cells, tissues, or individuals which express or mis-express the Eno1 protein, such as by measuring levels of a nucleic acid molecule encoding Eno1 in a sample from a subject, e.g., detecting mRNA levels or determining whether a gene encoding Eno1 or its translational control sequences have been mutated or deleted.

The invention further encompasses nucleic acid molecules that differ, due to degeneracy of the genetic code, from the nucleotide sequence of nucleic acids encoding Eno1 protein (e.g., protein having the sequence provided in the sequence listing), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to an indicator of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 15, 20, 25, 30, 40, 60, 80, 100, 150, 200, 250, 300, 350, 400, 450, 550, 650, 700, 800, or more nucleotides in length and hybridizes under stringent conditions to an Eno1 nucleic acid or to a nucleic acid encoding Eno1. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of Current Protocols in Molecular Biology, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

F. Indicator Applications

The invention provides methods for diagnosing elevated blood glucose, e.g., pre-diabetes, type 2 diabetes, type 1 diabetes, gestational diabetes, in a subject. The invention further provides methods for prognosing or monitoring progression or monitoring response of a subject with elevated blood glucose to a therapeutic treatment.

In one aspect, the present invention constitutes an application of diagnostic information obtainable by the methods of the invention in connection with analyzing, detecting, and/or measuring the level of Eno1 with at least one other indicator of blood glucose, e.g., blood glucose, e.g., fed blood glucose, fasting blood glucose, glucose tolerance, ketone level; and Hb1Ac levels.

For example, when executing the methods of the invention for detecting and/or measuring a polypeptide indicator, as described herein, one contacts a biological sample with a detection reagent, e.g, a monoclonal antibody, which selectively binds to the indicator of interest, forming a protein-protein complex, which is then further detected either directly (if the antibody comprises a label) or indirectly (if a secondary detection reagent is used, e.g., a secondary antibody, which in turn is labeled). Thus, the method of the invention transforms the polypeptide indicators of the invention to a protein-protein complex that comprises either a detectable primary antibody or a primary and further secondary antibody. Forming such protein-protein complexes is required in order to identify the presence of the biomarker of interest and necessarily changes the physical characteristics and properties of the indicator of interest as a result of conducting the methods of the invention.

The same principal applies when conducting the methods of the invention for detecting Eno1 nucleic acids. In particular, when amplification methods are used to detect an Eno1 mRNA, the amplification process, in fact, results in the formation of a new population of amplicons—i.e., molecules that are newly synthesized and which were not present in the original biological sample, thereby physically transforming the biological sample. Similarly, when hybridization probes are used to detect Eno1, a physical new species of molecules is in effect created by the hybridization of the probes (optionally comprising a label) to the target biomarker mRNA (or other nucleic acid), which is then detected. Such polynucleotide products are effectively newly created or formed as a consequence of carrying out the method of the invention.

The invention provides, in one embodiment, methods for diagnosing elevated blood glucose, e.g., pre-diabetes, diabetes, e.g., type 2 diabetes, type 1 diabetes, gestational diabetes. The methods of the present invention can be practiced in conjunction with any other method used by the skilled practitioner to prognose the occurrence or recurrence of elevated blood glucose and/or the response to a therapeutic intervention of a subject being treated for elevated blood glucose. The diagnostic and prognostic methods provided herein can be used to determine if additional and/or more complex or cumbersome tests or monitoring (e.g., glucose tolerance test, continuous glucose monitoring) should be performed on a subject. It is understood that a disease as complex as pre-diabetes or diabetes is rarely diagnosed using a single test. Therefore, it is understood that the diagnostic, prognostic, and monitoring methods provided herein are typically used in conjunction with other methods known in the art. For example, the methods for detection of the level of Eno1 as provided by the invention may be performed in conjunction with a detection of Hb1Ac levels, detection of blood glucose levels under fasting or fed conditions, or glucose tolerance test.

Methods for assessing the efficacy of a treatment regimen, e.g., drug treatment, behavior modification, surgery, or any other therapeutic approach useful for treating elevated blood glucose in a subject are also provided. In these methods the amount of Eno1 in a pair of samples (a first sample obtained from the subject at an earlier time point or prior to the treatment regimen and a second sample obtained from the subject at a later time point, e.g., at a later time point when the subject has undergone at least a portion of the treatment regimen) is assessed. It is understood that the methods of the invention include obtaining and analyzing more than two samples (e.g., 3, 4, 5, 6, 7, 8, 9, or more samples) at regular or irregular intervals for assessment of marker levels. Pair-wise comparisons can be made between consecutive or non-consecutive subject samples. Trends of marker levels and rates of change of marker levels can be analyzed for any two or more consecutive or non-consecutive subject samples. Measurement of Eno1 levels can be performed in conjunction with other methods for the detection an monitoring of blood glucose.

The methods of the invention may also be used to select a compound that is capable of modulating blood glucose by modulation of Eno1 expression or activity. In this method, a cell, preferably a cell with altered insulin sensitivity or altered glucose uptake is contacted with a test compound, and the ability of the test compound to modulate the expression and/or activity of Eno1 in the cell is determined, thereby selecting a compound that is capable of modulating Eno1 expression or activity, preferably increasing Eno1 expression or activity thereby increasing glucose uptake in the cell.

Using the methods described herein, a variety of molecules, may be screened in order to identify molecules which modulate, preferably increase the expression and/or activity of Eno1. Compounds so identified can be provided to a subject in order to normalize blood glucose by one or more of increasing glucose uptake, increasing insulin sensitivity, and/or decreasing insulin resistance thereby treating elevated blood glucose, e.g., pre-diabetes or diabetes, e.g., type 2 diabetes, type 1 diabetes, or gestational diabetes.

The present invention pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the level of expression of Eno1 protein or nucleic acid, in order to determine whether an individual is at risk of developing a disease or disorder related to elevated blood glucose, such as, without limitation, pre-diabetes or diabetes including type 2 diabetes, type 1 diabetes, or gestational diabetes. Such assays can be used for prognostic or predictive purposes to thereby prophylactically treat an individual prior to the onset of the disorder.

Yet another aspect of the invention pertains to monitoring the influence of agents (e.g., drugs or other therapeutic compounds) or behavioral and/or diet modifications on the expression or activity of Eno1 in clinical trials. These and other applications are described in further detail in the following sections.

1. Diagnostic Assays

An exemplary method for detecting the presence or absence or change of an indicator protein or nucleic acid in a biological sample involves obtaining a biological sample (e.g. blood or serum) from a test subject and contacting the biological sample with a compound or an agent capable of detecting the polypeptide or nucleic acid (e.g., mRNA or cDNA). The detection methods of the invention can thus be used to detect mRNA, cDNA, or protein including post-translationally modified proteins, for example, in a biological sample in vitro as well as in vivo.

Methods provided herein for detecting the presence, absence, change of the level of an indicator protein or nucleic acid in a biological sample include obtaining a biological sample from a subject that may or may not contain the marker protein or nucleic acid to be detected, contacting the sample with an indicator-specific binding agent (i.e., one or more marker-specific binding agents) that is capable of forming a complex with the indicator protein or nucleic acid to be detected, and contacting the sample with a detection reagent for detection of the indicator—indicator-specific binding agent complex, if formed. It is understood that the methods provided herein for detecting a level of an indicator in a biological sample includes the steps to perform the assay. In certain embodiments of the detection methods, the level of the indicator protein or nucleic acid in the sample is none or below the threshold for detection.

The methods include formation of either a transient or stable complex between the indicator and the indicator-specific binding agent. The methods require that the complex, if formed, be formed for sufficient time to allow a detection reagent to bind the complex and produce a detectable signal (e.g., fluorescent signal, a signal from a product of an enzymatic reaction, e.g., a peroxidase reaction, a phosphatase reaction, a beta-galactosidase reaction, or a polymerase reaction).

In certain embodiments, all of the indicators are detected using the same method. In certain embodiments, all of the indicators are detected using the same biological sample (e.g., same body fluid). In certain embodiments, different indicators are detected using different methods. In certain embodiments, indicators are detected in different biological samples (e.g., blood and serum).

2. Protein Detection

In certain embodiments of the invention, the indicator to be detected is a protein. In certain embodiments, the indicator to be detected is a post-translationally modified protein. Proteins are detected using a number of assays in which a complex between the indicator protein to be detected and the indicator specific binding agent would not occur naturally, for example, because one of the components is not a naturally occurring compound or the indicator for detection and the indicator specific binding agent are not from the same organism (e.g., human indicator proteins detected using indicator-specific binding antibodies from mouse, rat, or goat). In a preferred embodiment of the invention, the indicator protein for detection is a human indicator protein. In certain detection assays, the human indicators for detection are bound by indicator-specific, non-human antibodies, thus, the complex would not be formed in nature. The complex of the indicator protein can be detected directly, e.g., by use of a labeled indicator-specific antibody that binds directly to the indicator, or by binding a further component to the indicator—indicator-specific antibody complex. In certain embodiments, the further component is a second indicator-specific antibody capable of binding the indicator at the same time as the first indicator-specific antibody. In certain embodiments, the further component is a secondary antibody that binds to an indicator-specific antibody, wherein the secondary antibody preferably linked to a detectable label (e.g., fluorescent label, enzymatic label, biotin). When the secondary antibody is linked to an enzymatic detectable label (e.g., a peroxidase, a phosphatase, a beta-galactosidase), the secondary antibody is detected by contacting the enzymatic detectable label with an appropriate substrate to produce a colorimetric, fluorescent, or other detectable, preferably quantitatively detectable, product. Antibodies for use in the methods of the invention can be polyclonal, however, in a preferred embodiment monoclonal antibodies are used. An intact antibody, or a fragment or derivative thereof (e.g., Fab or $F(ab')_2$) can be used in the methods of the invention. Such strategies of indicator protein detection are used, for example, in ELISA, RIA, western blot, and immunofluorescence assay methods.

In certain detection assays, the indicator present in the biological sample for detection is an enzyme, e.g., Eno1, and the detection reagent is an enzyme substrate (e.g., 2-phosphoglycerate (2-PG) or phosphoenolpyruvate (PEP), or an analog of either of the compounds that produces a detectable product). In preferred embodiments, the substrate which forms a complex with the indicator enzyme to be detected is not the substrate for the enzyme in a human subject.

In certain embodiments, the indicator—indicator-specific binding agent complex is attached to a solid support for detection of the indicator. The complex can be formed on the substrate or formed prior to capture on the substrate. For example, in an ELISA, RIA, immunoprecipitation assay, western blot, immunofluorescence assay, in gel enzymatic assay the indicator for detection is attached to a solid support, either directly or indirectly. In an ELISA, RIA, or immunofluorescence assay, the indicator is typically attached indirectly to a solid support through an antibody or binding protein. In a western blot or immunofluorescence assay, the indicator is typically attached directly to the solid support. For in-gel enzyme assays, the indicator is resolved in a gel, typically an acrylamide gel, in which a substrate for the enzyme is integrated.

3. Nucleic Acid Detection

In certain embodiments of the invention, the indicator is a nucleic acid, e.g., an Eno1 nucleic acid. Nucleic acids are detected using a number of assays in which a complex between the indicator nucleic acid to be detected and an indicator-specific probe would not occur naturally, for example, because one of the components is not a naturally occurring compound. In certain embodiments, the analyte comprises a nucleic acid and the probe comprises one or more synthetic single stranded nucleic acid molecules, e.g., a DNA molecule, a DNA-RNA hybrid, a PNA, or a modified nucleic acid molecule containing one or more artificial bases, sugars, or backbone moieties. In certain embodiments, the synthetic nucleic acid is a single stranded is a DNA molecule that includes a fluorescent label. In certain embodiments, the synthetic nucleic acid is a single stranded oligonucleotide molecule of about 12 to about 50 nucleotides in length. In certain embodiments, the nucleic acid to be detected is an mRNA and the complex formed is an mRNA hybridized to a single stranded DNA molecule that is complementary to the mRNA. In certain embodiments, an RNA is detected by generation of a DNA molecule (i.e., a cDNA molecule) first from the RNA template using the single stranded DNA that hybridizes to the RNA as a primer, e.g., a general poly-T primer to transcribe poly-A RNA. The cDNA can then be used as a template for an amplification reaction, e.g., PCR, primer extension assay, using a marker-specific probe. In certain embodiments, a labeled single stranded DNA can be hybridized to the RNA present in the sample for detection of the RNA by fluorescence in situ hybridization (FISH) or for detection of the RNA by northern blot.

For example, in vitro techniques for detection of mRNA include northern hybridizations, in situ hybridizations, and rtPCR. In vitro techniques for detection of genomic DNA include Southern hybridizations. Techniques for detection of mRNA include PCR, northern hybridizations, and in situ hybridizations. Methods include both qualitative and quantitative methods.

A general principle of such diagnostic, prognostic, and monitoring assays involves preparing a sample or reaction mixture that may contain a nucleic acid for detection, and a probe, under appropriate conditions and for a time sufficient to allow the indicator nucleic acid and probe to interact and bind, thus forming a complex that can be removed and/or detected in the reaction mixture. These assays can be conducted in a variety of ways known in the art, e.g., PCR, FISH, northern blot.

4. Detection of Expression Levels

Eno1 levels can be detected based on the absolute expression level or a normalized or relative expression level. Detection of absolute Eno1 levels may be preferable when monitoring the treatment of a subject or in determining if there is a change in the blood glucose level or blood glucose regulation in a subject. For example, the expression level of Eno1 can be monitored in a subject undergoing treatment for abnormal blood glucose, e.g., at regular intervals, such a monthly intervals. A modulation in the level of Eno1 can be monitored over time to observe trends in changes in Eno1 levels. The expression level of Eno1 in the subject may be higher than the expression level of Eno1 in a normal sample, but may be higher than the prior expression level, thus indicating a benefit of the treatment regimen for the subject. Similarly, rates of change of an Eno1 level can be important in a subject who is being treated with behavior or diet modification rather than therapeutic interventions. Changes, or no changes, in Eno1 levels in an individual subject may be more relevant to treatment decisions for the subject than Eno1 levels present in the population. Rapid changes in Eno1 levels in a subject who otherwise appears to have a normal blood glucose may be indicative of an abnormal blood glucose or a predisposition to develop a condition related to abnormal blood glucose, even if the markers are within normal ranges for the population. Eno1 level can be determined or monitored in conjunction with one or more additional indicators of elevated blood glucose, e.g., HbA1c, increased blood glucose including one or more of increased fed or fasting blood glucose, or decreased rate of glucose clearance in a glucose tolerance test.

As an alternative to making determinations based on the absolute expression level of Eno1, determinations may be based on the normalized expression level of Eno1. Expression levels are normalized by comparing the absolute expression level of an indicator to the expression of a gene that is not an indicator, e.g., a housekeeping gene that is constitutively expressed. Suitable genes for normalization include housekeeping genes such as the actin gene and suitable proteins for normalization in blood or serum include albumin. This normalization allows the comparison of the expression level in one sample, e.g., a sample from a subject with normal blood glucose, to another sample, e.g., a sample from a subject suspected of having or having abnormal blood glucose, or between samples from different sources.

Alternatively, the expression level can be provided as a relative expression level as compared to an appropriate control, e.g., population control, earlier time point control, etc. Preferably, the samples used in the baseline determination will be from samples from subjects with normal blood glucose. The choice of the cell source is dependent on the use of the relative expression level. In addition, as more data is accumulated, the mean expression value can be revised, providing improved relative expression values based on accumulated data.

5. Monitoring Clinical Trials

Monitoring the influence of agents (e.g., drug compounds) on the level of an indicator of blood glucose can be applied not only in basic drug screening or monitoring the treatment of a single subject, but also in clinical trials. For example, the effectiveness of an agent to affect Eno1 expression can be monitored in clinical trials of subjects receiving treatment for elevated blood glucose. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of the indicator Eno1 and optionally one or more further indicators of blood glucose, e.g., blood glucose, ketone, or HbA1c in the pre-administration sample; (iii) obtaining one or more post-administration samples from the subject; (iv) detecting the level of expression of the indicator(s) in the post-administration samples; (v) comparing the level of indicator(s) in the pre-administration sample with the level of the indicator(s) in the post-administration sample or samples; and (vi) altering the administration of the agent to the subject accordingly. For example, decreased Eno1 expression and lack of normalization of other indicator(s) during the course of treatment may indicate ineffective dosage and the desirability of increasing the dosage. Conversely, increased expression of Eno1 and normalization of other indicator(s) may indicate efficacious treatment and no need to change dosage.

VI. Treatment of Impaired Blood Glucose Levels, Impaired Blood Glucose Level Control, and Diabetes As demonstrated herein, administration of Eno1 protein improves glucose uptake and response, normalizing blood glucose levels and control of blood glucose levels. The invention provides methods of treatment of subjects suffering from impaired glucose tolerance, increased blood glucose, insulin resistance, insulin insufficiency, and diabetes, e.g., type 2 diabetes, type 1 diabetes, pre-diabetes, and gestational diabetes by administering Eno1 to the subject to ameliorate at least one sign or symptom of the conditions. In certain embodiments, Eno1, preferably transcript variant 1 of Eno1, can be administered to a subject wherein at least one additional agent for the treatment of impaired glucose tolerance, increased blood glucose, insulin resistance, insulin insufficiency, or diabetes is administered to the subject. As used herein, the agents can be administered sequentially, in either order, or at the same time. Administration of multiple agents to a subject does not require co-formulation of the agents or the same administration regimen.

The method of treatment of impaired glucose tolerance, increased blood glucose, insulin resistance, insulin insufficiency, or diabetes, especially type 2 diabetes, using Eno1 can be combined with known methods and agents for the treatment of diabetes. Many agents and regimens are currently available for treatment of diabetes. The specific agent selected for treatment depends upon the subject, the specific symptoms and the severity of the disease state. For example, in certain embodiments, Eno1 can be administered in conjunction with dietary and/or behavior modification, e.g., caloric restriction, alone or in combination with bariatric surgery, and/or with increased physical activity. In certain embodiments, Eno1 can be administered with agents for the treatment of type 2 diabetes, e.g., metformin (Glucophage, Glumetza, others), glitazones, e.g., pioglitazone (Actos), glipizide (Glucotrol), glyburide (Diabeta, Glynase), glimepiride (Amaryl), acarbose (Precose), metformin (Glucophage), Sitagliptin (Januvia), Saxagliptin (Onglyza), Repaglinide (Prandin), Nateglinide (Starlix), Exenatide (Byetta), Liraglutide (Victoza), or insulin. Insulins are typically used only in treatment of later stage type 2 diabetes and include rapid-acting insulin (insulin aspart (NovoLog), insulin glulisine (Apidra), and insulin lispro (Humalog)); short-acting insulin (insulin regular (Humulin R, Novolin R)); intermediate-acting insulin (insulin NPH human (Humulin N, Novolin N)), and long-acting insulin (insulin glargine (Lantus) and insulin detemir (Levemir)). Treatments for diabetes can also include behavior modification including exercise and weight loss which can be facilitated by the use of drugs or surgery. Treatments for elevated blood glucose and diabetes can be combined. For example, drug therapy can be combined with behavior modification therapy. Insulins for use in treatment of type 1 diabetes include, but are not limited to Insulins are typically used only in treatment of later stage type 2 diabetes and include rapid-acting insulin (insulin aspart (NovoLog), insulin glulisine (Apidra), and insulin lispro (Humalog)); short-acting insulin (insulin regular (Humulin R, Novolin R)); intermediate-acting insulin (insulin NPH human (Humulin N, Novolin N)), and long-acting insulin (insulin glargine (Lantus) and insulin detemir (Levemir)).

Accordingly, in some aspects, the invention relates to a method of treating elevated blood glucose in a subject, comprising: (a) obtaining a biological sample from a subject suspected of having elevated blood glucose, (b) submitting the biological sample to obtain diagnostic information as to the level of Eno1, and (c) administering a therapeutically effective amount of an anti-diabetic therapy to the subject when the level of Eno1 in the sample is above a threshold level.

In some aspects, the invention relates to a method of treating elevated blood glucose in a subject, comprising: (a) obtaining diagnostic information as to the level of Eno1 in a biological sample from the subject, and (b) administering a therapeutically effective amount of an anti-diabetic therapy to the subject when the level of Eno1 in the sample is above a threshold level.

In some aspects, the invention relates to a method of treating elevated blood glucose in a subject, comprising: (a) obtaining a biological sample from a subject suspected of having elevated blood glucose for use in identifying diagnostic information as to the level of Eno1, (b) detecting the level of Eno1 in the biological sample, (c) recommending to a healthcare provider to administer a blood glucose lowering therapy to the subject when the level of Eno1 in the sample is below a threshold level.

The methods described above may further comprising obtaining diagnostic information as to the level of one or more additional indicators of elevated blood glucose. In some embodiments the methods further comprise measuring a level of one or more additional indicators of elevated blood glucose. The one or more additional indicators of elevated blood glucose may be selected from the group consisting of HbA1c level, fasting glucose level, fed glucose level, and glucose tolerance.

In some embodiments of the aforementioned methods, step (c) further comprises administering a therapeutically effective amount of a glucose lowering therapy to the subject if the level of Eno1 in the sample is below a threshold level and at least one of the additional indicators of elevated blood glucose is detected. In some embodiments step (c) further comprises recommending to a healthcare provider to administer a glucose lowering therapy to the subject if the level of Eno1 in the sample is below a threshold level and at least one of the additional indicators of elevated blood glucose is detected.

In some embodiments of the methods described above, the biological sample is blood or serum. In some embodiments, the level of Eno1 is determined by immunoassay or ELISA. In some embodiments, the level of Eno1 is determined by (i) contacting the biological sample with a reagent that selectively binds to the Eno1 to form a biomarker complex, and (ii) detecting the biomarker complex. In some embodiments, the reagent that selectively binds to the Eno1 to form a biomarker complex is an anti-Eno1 antibody that selectively binds to at least one epitope of Eno1.

In some embodiments of the methods described above, the level of Eno1 is detected by measuring the amount of Eno1 mRNA in the biological sample. The amount of Eno1 mRNA may be detected, for example, by an amplification reaction. In some embodiments, the amplification reaction is (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA).

In some embodiments, a hybridization assay is used for detecting the amount of Eno1 mRNA in the biological sample. In some embodiments, an oligonucleotide that is complementary to a portion of a Eno1 mRNA is used in the hybridization assay to detect the Eno1 mRNA.

VI. Animal Models of Diabetes and Insulin Resistance

A number of genetic and induced animal models of metabolic syndromes such as type 1 and type 2 diabetes, insulin resistance, hyperlipidemia, are well characterized in the art. Such animals can be used to demonstrate the effect of Eno1 in the treatment of insulin resistance and diabetes. Models of type 1 diabetes include, but are not limited to, NOD mice and streptozotocin-induced diabetes in rats and mice (models of type 1 diabetes). Genetic and induced models of type 2 diabetes include, but are not limited to, the leptin deficient ob/ob mouse, the leptin receptor deficient db/db mouse, and high fat fed mouse or rat models. In each of the models, the timeline for development of specific disease characteristics are well known. Eno1 can be administered before or after the appearance of symptoms of diabetes or insulin resistance to demonstrate the efficacy of Eno1 in the prevention or treatment of diabetes and/or insulin resistance in these animal models.

Depending on the specific animal model selected and the time of intervention, e.g., before or after the appearance of diabetes and/or insulin resistance, the animal models can be used to demonstrate the efficacy of the methods provide herein for the prevention, treatment, diagnosis, and monitoring of diabetes and/or insulin resistance.

VII. Drug Screening

Administration of Eno1 results in normalization of blood glucose in animals with induced diabetes, making Eno1 an attractive targets for identification of new therapeutic agents via screens to detect compounds or entities that enhance expression of Eno1. Accordingly, the present invention provides methods for the identification of compounds potentially useful for modulating blood glucose and diabetes. In particular, the present invention provides methods for the identification of compounds potentially useful for modulating Eno1 wherein the compounds modulate blood glucose and diabetes.

Such assays typically comprise a reaction between Eno1 and one or more assay components, e.g., test compounds. The other components may be either a test compound itself, or a combination of test compounds and a natural binding partner of Eno1. Compounds identified via assays such as those described herein may be useful, for example, for modulating, e.g., inhibiting, ameliorating, treating, or preventing the disease. Compounds identified for modulating the expression level of Eno1 are preferably further tested for activity useful in the treatment of abnormal blood glucose and/or diabetes, e.g., normalizing fed and/or fasting glucose, normalizing glucose clearance and/or insulin levels in a glucose tolerance test, normalizing HbA1c levels.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria and/or spores, (Ladner, U.S. Pat. No. 5,223,409), plasmids (Cull et al, 1992, Proc Natl Acad Sci USA 89:1865-1869) or on phage (Scott and Smith, 1990, Science 249:386-390; Devlin, 1990, Science 249:404-406; Cwirla et al, 1990, Proc. Natl. Acad. Sci. 87:6378-6382; Felici, 1991, J. Mol. Biol. 222:301-310; Ladner, supra.).

The screening methods of the invention comprise contacting a cell, e.g., a diseased cell, especially a cell with abnormal insulin response and/or glucose uptake, with a test compound and determining the ability of the test compound to modulate the expression and/or activity of Eno1 in the cell. The expression and/or activity of Eno1, optionally in combination with methods of detection of blood glucose levels, can be determined using any methods known in the art, such as those described herein.

In another embodiment, the invention provides assays for screening candidate or test compounds which are substrates of Eno1 or biologically active portions thereof. In yet another embodiment, the invention provides assays for screening candidate or test compounds which bind to Eno1 or biologically active portions thereof. Determining the ability of the test compound to directly bind to Eno1 can be accomplished, for example, by any method known in the art.

This invention further pertains to novel agents identified by the above-described screening assays. Accordingly, it is within the scope of this invention to further use an agent identified as described herein in an appropriate animal model. For example, an agent capable of modulating the expression and/or activity of Eno1 can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment as described above.

In certain embodiments, the screening methods are performed using cells contained in a plurality of wells of a multi-well assay plate. Such assay plates are commercially available, for example, from Stratagene Corp. (La Jolla, Calif.) and Corning Inc. (Acton, Mass.) and include, for example, 48-well, 96-well, 384-well and 1536-well plates.

Reproducibility of the results may be tested by performing the analysis more than once with the same concentration of the same candidate compound (for example, by incubating cells in more than one well of an assay plate). Additionally, since candidate compounds may be effective at varying concentrations depending on the nature of the compound and the nature of its mechanism(s) of action, varying concentrations of the candidate compound may be tested. Generally, candidate compound concentrations from 1 fM to about 10 mM are used for screening. Preferred screening concentrations are generally between about 10 pM and about 100 μm.

The screening methods of the invention will provide "hits" or "leads," i.e., compounds that possess a desired but not optimized biological activity. Lead optimization performed on these compounds to fulfill all physicochemical, pharmacokinetic, and toxicologic factors required for clinical usefulness may provide improved drug candidates. The present invention also encompasses these improved drug candidates and their use as therapeutics for modulating blood glucose and insulin response.

VIII. Kits/Panels

The invention also provides compositions and kits for diagnosing, prognosing, or monitoring a disease or disorder, recurrence of a disorder, or survival of a subject being treated for a disorder (e.g., abnormal blood glucose and/or diabetes). These kits include one or more of the following: a detectable antibody that specifically binds to Eno1, a detectable antibody that specifically binds to Eno1, reagents for obtaining and/or preparing subject tissue samples for staining, and instructions for use.

The invention also encompasses kits for detecting the presence of Eno1 protein or nucleic acid in a biological sample. Such kits can be used to determine if a subject is suffering from or is at increased risk of developing an abnormal blood glucose and/or diabetes. For example, the kit can comprise a labeled compound or agent capable of detecting Eno1 protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for use of the kit for practicing any of the methods provided herein or interpreting the results obtained using the kit based on the teachings provided herein. The kits can also include reagents for detection of a control protein in the sample not related to abnormal blood glucose, e.g., actin for tissue samples, albumin in blood or blood derived samples for normalization of the amount of the Eno1 present in the sample. The kit can also include the purified marker for detection for use as a control or for quantitation of the assay performed with the kit.

Kits include a panel of reagents for use in a method to diagnose abnormal blood glucose in a subject (or to identify a subject predisposed to developing abnormal blood glucose and/or diabetes), the panel comprising at least two detection reagents comprising a reagent for detection of Eno1 level and a reagent for detection of another indicator of blood glucose, e.g., HbA1c.

For antibody-based kits, the kit can comprise, for example: (1) a first antibody (e.g., attached to a solid support) which binds to a Eno1; and, optionally, (2) a second, different antibody which binds to either Eno1 or the first antibody and is conjugated to a detectable label. In certain embodiments, the kit includes (1) a second antibody (e.g., attached to a solid support) which binds to a second marker protein; and, optionally, (2) a second, different antibody which binds to either HbA1c or hemoglobin (either total or unmodified hemoglobin) or the second antibody and is conjugated to a detectable label. The first and second marker proteins are different.

For oligonucleotide-based kits, the kit can comprise, for example: (1) an oligonucleotide, e.g., a detectably labeled oligonucleotide, which hybridizes to a nucleic acid sequence encoding Eno1 or (2) a pair of primers useful for amplifying an Eno1 nucleic acid molecule. In certain embodiments, the kit includes a third primer specific for each nucleic acid marker to allow for detection using quantitative PCR methods. In certain embodiments, the kit further includes instructions to measure blood glucose in the subject, either directly or indirectly (e.g., using HbA1c levels).

For chromatography methods, the kit can include markers, including labeled markers, to permit detection and identification of one or more indicators of blood glucose, e.g., Eno1 and HbA1c by chromatography. In certain embodiments, kits for chromatography methods include compounds for derivatization of one or more blood glucose indicators. In certain embodiments, kits for chromatography methods include columns for resolving the indicators of the method.

Reagents specific for detection of Eno1 allow for detection and quantitation of the marker in a complex mixture, e.g., serum, blood. In certain embodiments, the reagents are species specific. In certain embodiments, the Eno1 reagents are not species specific. In certain embodiments, the Eno1 reagents are isoform specific. In certain embodiments, the Eno1 reagents are not isoform specific. In certain embodiments, the reagents detect total Eno1.

In certain embodiments, the kits for the diagnosis, monitoring, or characterization of elevated blood glucose and/or diabetes comprise at least one reagent specific for the detection of the level of expression of Eno1. In certain embodiments, the kits further comprise instructions to detect the level of blood glucose in a sample, either directly or indirectly, or both. In certain embodiments, the kit includes at least one reagent for detection of the level of HbA1c.

In certain embodiments, the kits can also comprise, e.g., a buffering agents, a preservative, a protein stabilizing agent, reaction buffers. The kit can further comprise components necessary for detecting the detectable label (e.g., an enzyme or a substrate). The kit can also contain a control sample or a series of control samples which can be assayed and compared to the test sample. The controls can be control serum samples or control samples of purified proteins or nucleic acids, as appropriate, with known levels of indicators. Each component of the kit can be enclosed within an individual container and all of the various containers can be within a single package, along with instructions for interpreting the results of the assays performed using the kit.

The kits of the invention may optionally comprise additional components useful for performing the methods of the invention.

For example, in some aspects the present invention relates to a kit for detecting Eno1 in a biological sample comprising at least one reagent for measuring the level of Eno1 in the biological sample, and a set of instructions for measuring the level of Eno1. In some embodiments, the reagent is an anti-Eno1 antibody. In some embodiments, the kit further comprises a means to detect the anti-Eno1 antibody. In some embodiments, the means to detect the anti-Eno1 antibody is a detectable secondary antibody. In some embodiments, the reagent for measuring the level of Eno1 is an oligonucleotide that is complementary to an Eno1 mRNA.

In some embodiments of the aforementioned kits, the instructions set forth an immunoassay or ELISA for detecting the Eno1 level in the biological sample. In some embodiments, the instructions set forth an amplification reaction for assaying the level of Eno1 mRNA in the biological sample. In some embodiments, the amplification reaction is used for detecting the amount of Eno1 mRNA in the biological sample. In some embodiments, the amplification reaction is (a) a polymerase chain reaction (PCR); (b) a nucleic acid sequence-based amplification assay (NASBA); (c) a transcription mediated amplification (TMA); (d) a ligase chain reaction (LCR); or (e) a strand displacement amplification (SDA).

In some embodiments of the aforementioned kits, the instructions set forth a hybridization assay for detecting the amount of Eno1 mRNA in the biological sample. In some embodiments, the kit further comprises at least one oligonucleotide that is complementary to a portion of an Eno1 mRNA.

The invention further provides panels of reagents for detection of one or more blood glucose indicators in a subject sample and at least one control reagent. In certain embodiments, the control reagent is to detect the indicator in the biological sample wherein the panel is provided with a control sample containing the indicator for use as a positive control and optionally to quantitate the amount of indicator present in the biological sample. In certain embodiments, the panel includes a detection reagent for a protein or nucleic acid not related to an abnormal blood glucose that is known to be present or absent in the biological sample to provide a positive or negative control, respectively. The panel can be provided with reagents for detection of a control protein in the sample not related to the abnormal blood glucose, e.g., albumin in blood or blood derived samples for normalization of the amount of the indicator present in the sample. The panel can be provided with a purified indicator, e.g., Eno1, for detection for use as a control or for quantitation of the assay performed with the panel.

In a preferred embodiment, the panel includes reagents for detection of Eno1, preferably in conjunction with a control reagent. In the panel, Eno1 is detected by a reagent specific for that Eno1. In certain embodiments, the panel further includes a reagent for the detection of HbA1c. In certain embodiments, the panel includes replicate wells, spots, or portions to allow for analysis of various dilutions (e.g., serial dilutions) of biological samples and control samples. In a preferred embodiment, the panel allows for quantitative detection of one or more indicators of blood glucose.

In certain embodiments, the panel is a protein chip for detection of one or more markers. In certain embodiments, the panel is an ELISA plate for detection of one or more markers. In certain embodiments, the panel is a plate for quantitative PCR for detection of one or more markers.

In certain embodiments, the panel of detection reagents is provided on a single device including a detection reagent for one or more markers of the invention and at least one control sample. In certain embodiments, the panel of detection reagents is provided on a single device including a detection reagent for two or more markers of the invention and at least one control sample. In certain embodiments, multiple panels for the detection of different markers of the invention are provided with at least one uniform control sample to facilitate comparison of results between panels.

In certain embodiments, panels and kits further include instructions or advice for measuring blood glucose in a subject. In certain embodiments, the kit or panel is provided with one or more reagents or devices for the measurement of blood glucose.

The invention also provides kits for treatment of at least one of diabetes, e.g., type 1 diabetes, type 2 diabetes, gestational diabetes, pre-diabetes, insulin resistance, glucose intolerance, abnormal blood glucose, and loss of blood glucose control. The kits include Eno1 and one or more of instructions for use and a device for administration, as appropriate.

This invention is further illustrated by the following examples which should not be construed as limiting. The contents of all references and published patents and patent applications cited throughout the application are hereby incorporated by reference.

EXAMPLES

Example 1—Employing Platform Technology to Identify Enolase 1 (Eno1) as an Important Node of Activity in the Etiology of Diabetes In this example, the platform technology described in detail in international Patent Application No. PCT/US2012/027615 was employed to integrate data obtained from a custom built diabetes model, and to identity novel proteins/pathways driving the pathogenesis of diabetes, particularly type 2 diabetes. Relational maps resulting from this analysis have identified Eno1 as an important node of activity in the etiology of diabetes. Therefore, Eno1 is an important diabetes treatment target, as well as a diagnostic/prognostic marker associated with diabetes.

Example 2—Eno1 Regulation of Glucose Uptake in Myotubes

Eno1 was recombinantly expressed in *E. coli* as a 6×HIS protein tag using a commercially available expression vector. The tagged Eno1 was purified using affinity chromatography methods known in the art. Preferably, the 6×HIS tag was cleaved to produce the protein for use in the methods provided herein.

Human skeletal muscle myoblasts (HSMM) were procured from PromoCell and were cultured in growth media recommended by the vendor. HSMM myoblasts (20,000 cells/well) were differentiated with 2% horse serum in 96 well plates for 7 days before experiment. Cells were treated with human Eno1 (500 ug/ml). Cells were washed twice with 200 µl MBSS modified balanced salt solution (MBSS) buffer containing 0.1% BSA, and then serum starved with 100 ul MBSS 0.1% BSA for 4 hours. Upon initiation of insulin stimulation, 100 ul 2× reagents in MBSS 0.1% BSA buffer was added to 100 ul starvation media to make 1× concentration for the experiment. The 2× reagents are: insulin (0, 20 nM, and 200 nM); a fluorescent glucose analog 2-NBDG (500 uM). Cells were treated with insulin and the fluorescent deoxy-glucose analog 2-NBDG for 30 min, then washed twice with MBSS buffer, then 50 ul MBSS buffer were added to wells. Glucose uptake was detected with fluorometer along with background detection with wells with no cells in them. After fluorometer readout, a fixative (formalin, 50 ul) was added to 50 ul MBSS in the wells, then 100 ul 1 uM DAPI was added to 100 ul formalin and MBSS mixture.

Figure 1B:
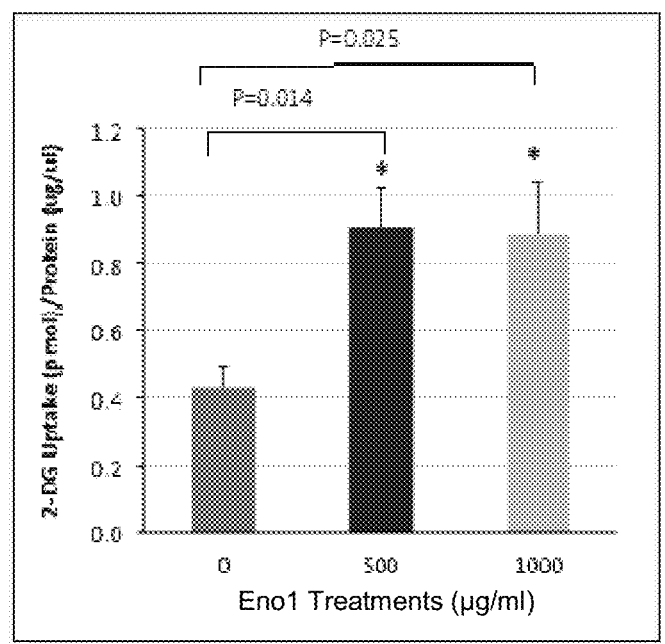
FIG. 1B shows glucose uptake in smooth muscle myoblasts treated with 0, 500, or 1000 µg/ml Eno1 without insulin treatment.

As shown in FIGS. 1A and 1B, treatment of myotubes with Eno1 significantly increased glucose uptake in both the absence and presence of insulin (p=0.025 insulin independent glucose uptake untreated vs. Eno1 treated). These results demonstrate a role for Eno1 in both insulin dependent and insulin independent glucose uptake. The insulin dependent glucose uptake induced by Eno1 demonstrates that Eno1 is intricately connected with the insulin signaling pathway in at least skeletal muscle in subjects sensitive to insulin. The results also demonstrate a role for Eno1 in insulin independent glucose uptake. This observation is important for treatment of subjects with both type 1 and type 2 diabetes who suffer from insulin resistance and who may also have hyper insulinemia, so that insulin action is compromised and hence a insulin independent. These results demonstrate that Eno1 is useful in stimulating glucose uptake even in individuals who no longer have normal insulin signaling.

Figure 2A:
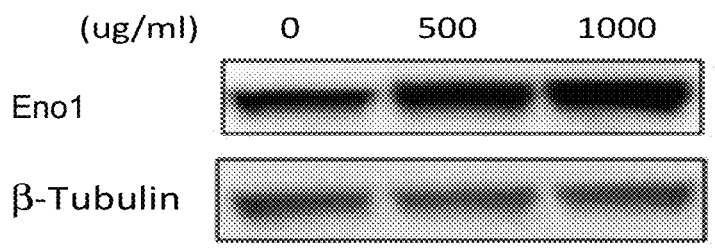
FIGS. 2A and 2B show Eno1 protein levels in human skeletal muscle myotubes treated with 0, 500 or 1000 µg/ml Eno1.
Figure 2B:
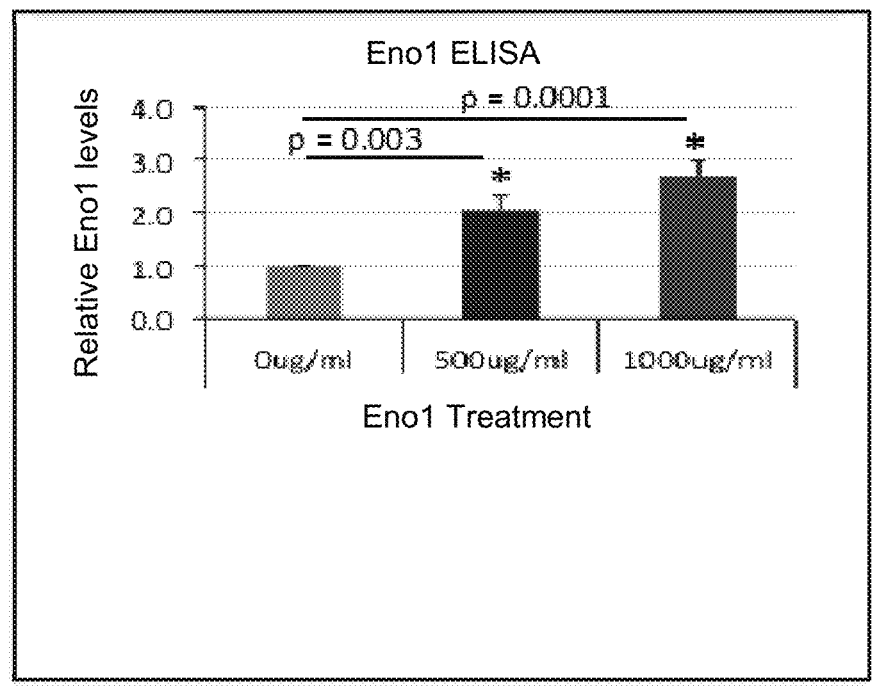
Figure 2C:
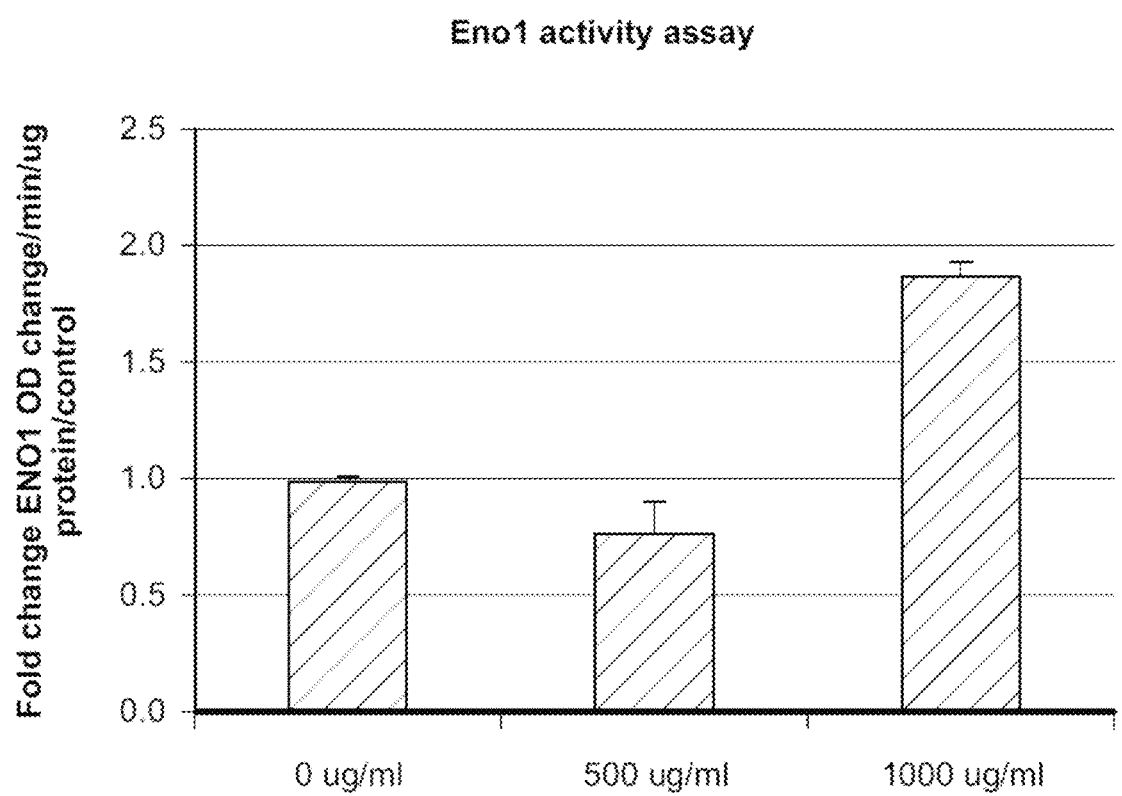
FIG. 2C shows Eno1 activity in human skeletal muscle myotubes treated with 0, 500 or 1000 µg/ml Eno1.

Cell cultures of human skeletal muscle myotubes were treated for 48 hours with the purified Eno1 protein described above to measure Eno1 uptake. Eno1 levels in the cells were then determined by Western blot. As shown in FIGS. 2A and 2B, Eno1 levels in cells treated with 500 μg/ml Eno1 or 1000 μg/ml Eno1 had significantly higher levels of Eno1 relative to untreated cells. Eno1 levels in cells treated with 1000 μg/ml Eno1 were also higher than in cells treated with 500 μg/ml Eno1. These results indicate that Eno1 is delivered into human skeletal muscle myotubes in a dose dependent manner.

Figure 3A:
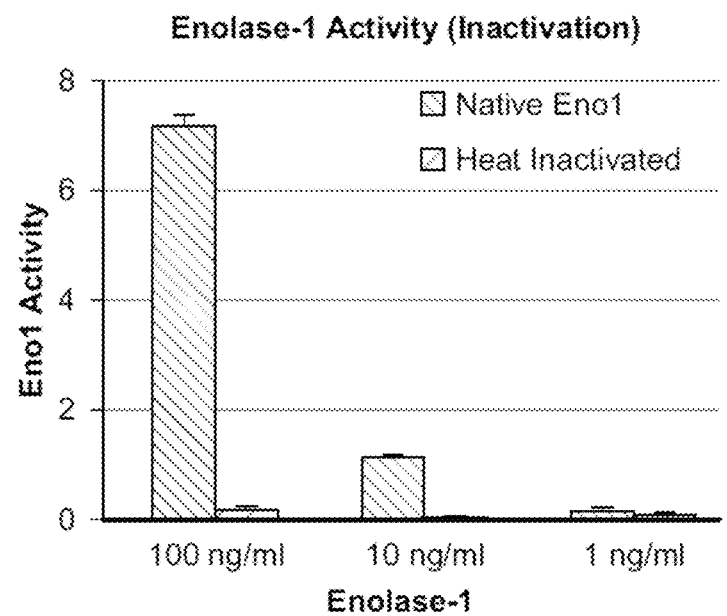
FIG. 3A shows Eno1 activity of native and heat inactivated Eno1.

To determine the role of Eno1 enzyme activity in glucose uptake, purified Eno1 was heat inactivated by treatment at 88° C. for 90 seconds, and activity levels of native and heat inactivated Eno1 were compared. Eno1 activity was determined by colorimetric assay using the Eno1 human activity assay kit from Abcam (Cambridge, Mass.; Cat. No. ab117994). As shown in FIG. 3A, heat inactivation greatly reduced Eno1 enzyme activity, but some residual activity remained.

Figure 3B:
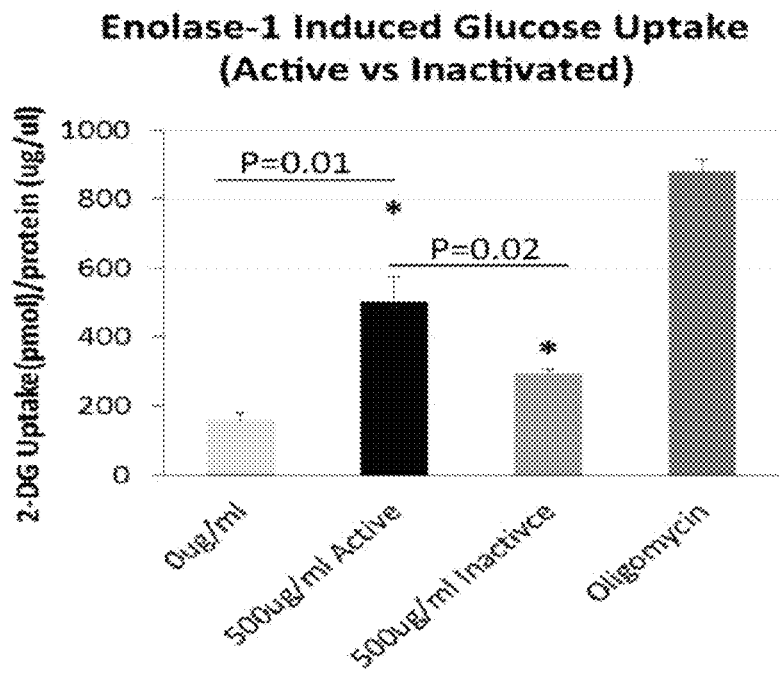
FIG. 3B shows induction of glucose uptake by active and heat inactivated Eno1.

The effect of native and heat inactivated Eno1 on glucose uptake was compared in human skeletal muscle myotubes following the methods described above. As shown in FIG. 3B, myotubes treated with native (active) Eno1 exhibited significantly higher glucose uptake relative to myotubes that were not treated with Eno1. Myotubes treated with heat inactivated Eno1 exhibited significantly lower glucose uptake compared to myotubes treated with active Eno1. These results indicate that the effect of Eno1 on glucose uptake is dependent on Eno1 enzyme activity. The increase in glucose uptake observed in the heat inactivated Eno1 relative to the control containing no Eno1 was likely due to the residual Eno1 activity of the heat inactivated enzyme.

Example 3—Mouse Models of Diet Induced Obesity (DIO) Mice

Two essentially equivalent models of diet induced obesity were used in the methods provided herein.

In the first method, male C57BL/6J mice were obtained from Jackson Laboratories (Bar Harbor, Me.) and initially housed 4-5 per cage at 22° C. on a 12:12 hr day-night cycle. Beginning at 6 weeks of age, mice were fed with a high-fat diet (Research Diets Cat #: D12492; 60 kcal % fat, 20 kcal % protein, and 20 kcal % carbohydrate). Lean control mice were also obtained and fed a standard diet. Body weight of DIO mice before experiments was significantly heavier than that of lean control mice. In one study, DIO mice weighed 38.4±0.6 g whereas lean mice weighed 29.9±0.5 g ($p<0.05$).

In the second method, diet induced obese male C57BL/6J mice (12 week old) and control lean mice (12 week old) were obtained from Jackson Laboratories (Bar Harbor, Me.) and initially housed 4-5 per cage at 22° C. on a 12:12 hr day-night cycle. Mice were acclimated in animal facility for one week before treatments and maintained with a high-fat diet for DIO group (Research Diets Cat #: D12492; 60 kcal % fat, 20 kcal % protein, and 20 kcal % carbohydrate) or a low fat diet (10% kcal % fat) for lean group.

Example 4—Treatment of Glucose Intolerance with Eno1 in Diet Induced Obesity (DIO) Mice The experimental protocol was started when the mice (n=10 per group) were obese after being maintained for 7 weeks on a high fat diet. Osmotic minipumps (Model 1004, Alzet, Cupertino, Calif.) were filled following manufacturer's guidelines with 0.1 ml of the Eno1 peptide or vehicle (phosphate buffered saline (PBS), pH 7.0). The pumps were primed in sterile saline at 4° C. overnight. Mice were anesthetized with isoflurane (1-3% in 100% oxygen) and scrubbed with 70% isopropanol and betadine solutions before surgery. A small subcutaneous incision was made in the midscapular region, the pump was inserted and the wound was sutured. Animals were allowed to recover before returning to their home cages. The implantation of the subcutaneous osmotic minipumps continuously infused peptide at a constant rate of 0.11 μl/hr for four weeks. Pump-exchange surgeries were performed every 4 weeks. The purified Eno1 treatment doses calculated by pump infusion rate was 10 mg/kg body weight.

Figure 4A:
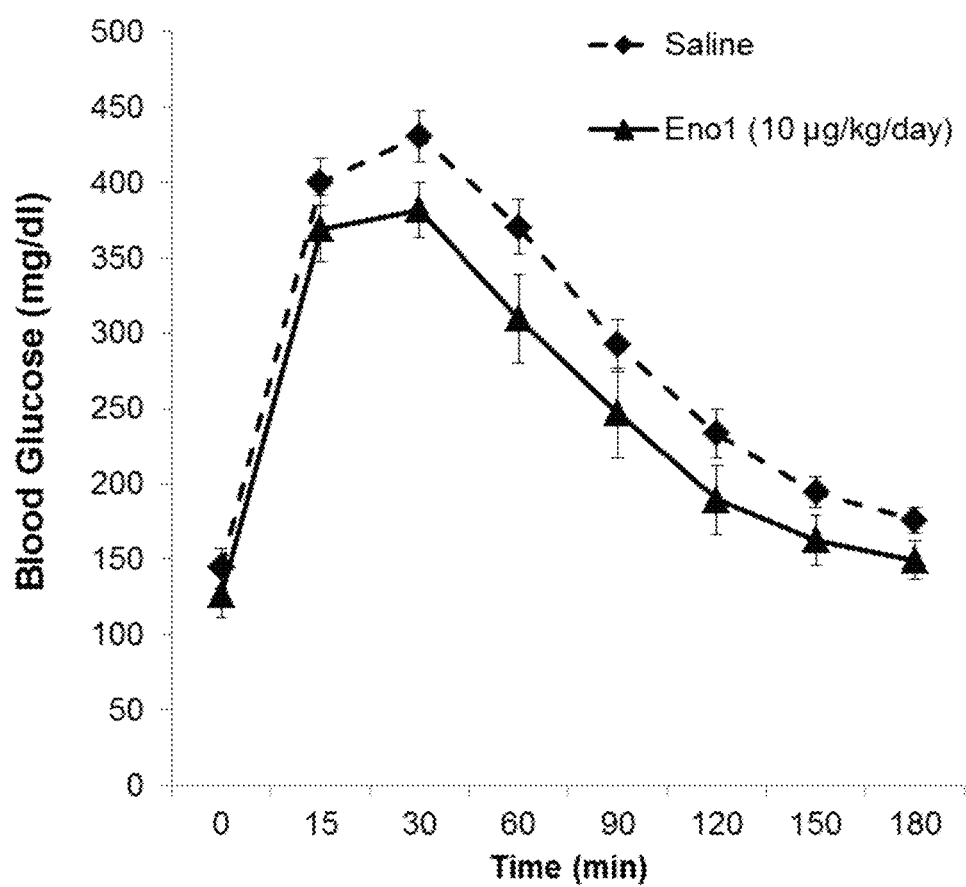
FIGS. 4A and 4B show (A) a time course and (B) the area under the curve (AUC) of glucose clearance in a glucose tolerance test in a mouse model of diet induced obesity (DIO) after treatment with or without Eno1 protein.
Figure 4B:
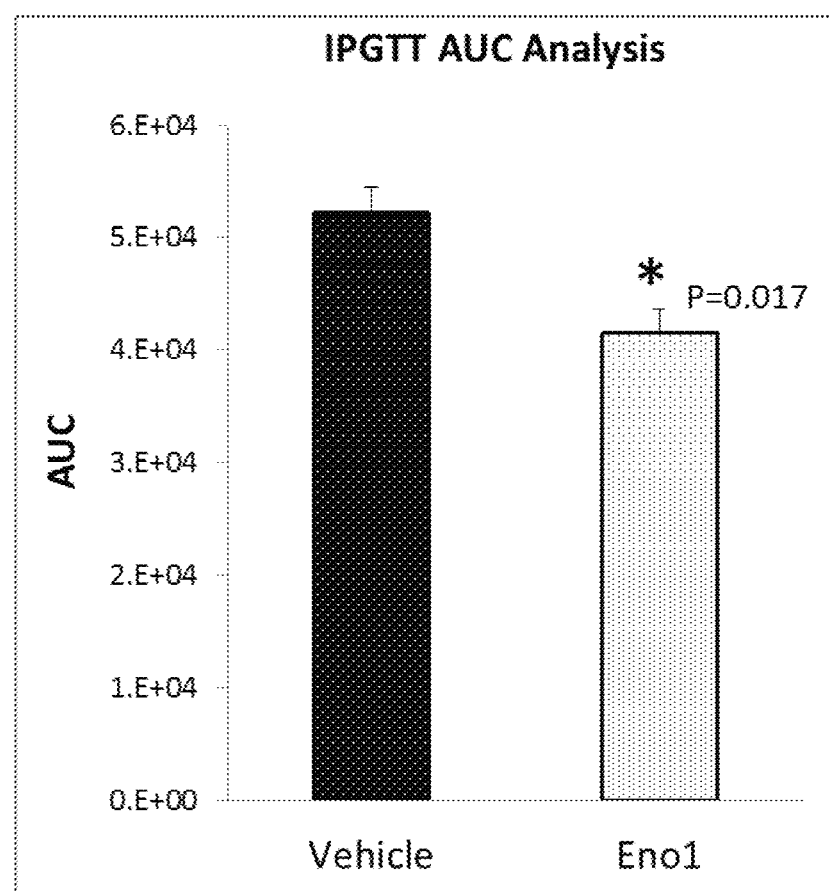

Glucose tolerance tests (GTT) were performed after 6 h of fasting using routine methods. Briefly, initial fasting blood glucose levels were determined, followed by intraperitoneal (ip) injection of 20% dextrose solution at a dose of 1.5 g/kg body weight. Blood glucose levels were measured from the tail vein at 15, 30, 60, 90, and 120 minutes after the glucose injection using an ACCU-CHEK® Advantage glucometer (ROCHE® Diagnostics, Indianapolis, Ind.). The area under the curve (AUC) during the GTT was calculated with Graphpad Prism® software, and student t-tests were performed for significance between different treatment groups. The results are shown in FIGS. 4A and 4B.

As can readily be observed, mice treated with Eno1 had a significant decrease in blood glucose area under the curve as compared to untreated mice (p=0.017). These data demonstrate that treatment of obese mice with Eno1 protein increases glucose tolerance as demonstrated by a glucose tolerance test and indicate that Eno1 is effective in the treatment of insulin resistance, glucose intolerance, and type 2 diabetes.

Example 5—Generation of a PAMAM Dendrimer, Muscle Targeted Eno1

Having demonstrated the efficacy of Eno1 in increasing glucose uptake in myotubes and increasing glucose tolerance upon systemic administration, a muscle targeted Eno1 was generated to analyze its efficacy in increasing glucose tolerance. Detectably labeled G5-PAMAM dendrimers containing the muscle targeting peptide (MTP) ASSLNIA (SEQ ID NO: 12) and/or Eno1 were generated using the methods described below. A range of different ratios of MTP to dendrimer were evaluated, including MTP containing dendrimers which contained about 10 MTP peptides per dendrimer, about 3 MTP peptides per dendrimer, or about 1 MTP peptide per dendrimer.

The process of preparing Eno1 dendrimer complexes includes the identification of optimal ratios and concentrations of the reagents. Stock solutions of Eno1 were prepared in buffer and the protein solution was mixed with G5 dendrimer-muscle targeting peptide (MTP) conjugate in different ratios. A range of different ratios of dendrimer to Eno1 were also evaluated, including Eno1 containing dendrimers which contained about one dendrimer per molecule of Eno1 protein or about five dendrimers per molecule of Eno1 protein.

The stability of the Eno1-dendrimer-SMTP complex was evaluated at different temperatures, and stability was determined over a 3-4 month time period by measuring Eno1 activity using a commercially available Eno1 assay. The selected conjugates were also evaluated using biophysical techniques, including Dynamic Light Scattering (DLS) and UV-Vis spectroscopy to confirm complexation between the dendrimer-peptide conjugate and Eno1.

Determination of the Purity of Eno1:

The purity of a 5.32 mg/mL solution of Eno1 protein was checked by Coomassie and Silver staining and Western blotting. Several dilutions of the Eno1 protein ranging from 10 µg/well to 100 ng/well were prepared and loaded on a 12-well, 4-12% mini-PROTEAN® TGX gel [BIO-RAD Cat #456-1095 Lot #4000 79200]. The lane assignments were as follows; Lane 1: Ladder (Precision Plus Protein Standard Dual Color [BIO-RAD Cat #161-0374]; Lane 2: Eno1 (10.0 µg); Lane 3: Eno1 (1.0 µg); Lane 4: Eno1 (0.1 µg); Lane 5: Ladder (Precision Plus Protein Standard Dual Color [BIO-RAD Cat #161-0374]; Lane 6: Eno1 (10.0 µg); Lane 7: Eno1 (1.0 µg); Lane 8: Eno1 (0.1 µg); Lane 9: Ladder (Precision Plus Protein Standard Dual Color [BIO-RAD Cat #161-0374]; Lane 10: Eno1 (10.0 µg); Lane 11: Eno1 (1.0 µg); Lane 12: Eno1 (0.1 µg). The SDS-PAGE was run at 200 V for 20-25 min.

Coomassie Staining:

After the gel was run, the gel was split into 3 equal parts. One of the parts was stained with Coomassie Stain. Briefly, the gel was soaked in 100 mL of Coomassie Stain solution (0.025% Coomassie Stain in 40% Methanol and 7% Acetic Acid) and heated for one minute in a microwave. Then the gel was left to stain with gentle agitation for 45 minutes. After the staining was complete, the gel was destained using destaining solution (40% Methanol and 7% Acetic Acid) until the background staining was acceptable.

Figure 5:
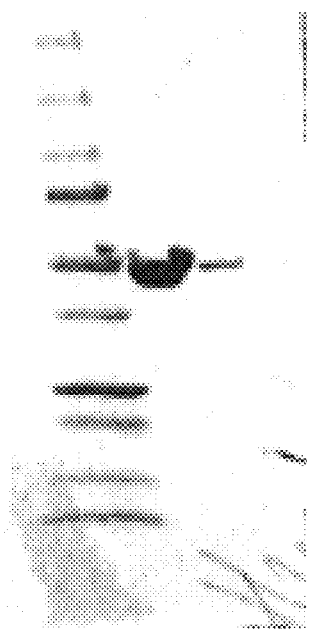
FIG. 5 shows Coomassie Staining of a polyacrylamide gel containing various concentrations of Eno1 analyzed by SDS-PAGE. L1: Precision Plus Protein Standard Dual Color, L2: Eno1 (10.0 µg), L3: Eno1 (1.0 µg), L4: Eno1 (0.1 µg).

As shown in FIG. 5, the protein ran as a single band of about 47 KDa, which is consistent with the size of Eno1.

Silver Staining:

Since Coomassie Staining is not a sensitive method for visualization of the protein bands, another portion of the gel was stained with Silver Stain using BIO-RAD's Silver Staining Kit [BIO-RAD Cat #161-0443]. The Modified Silver Stain Protocol was followed.

Figure 6:
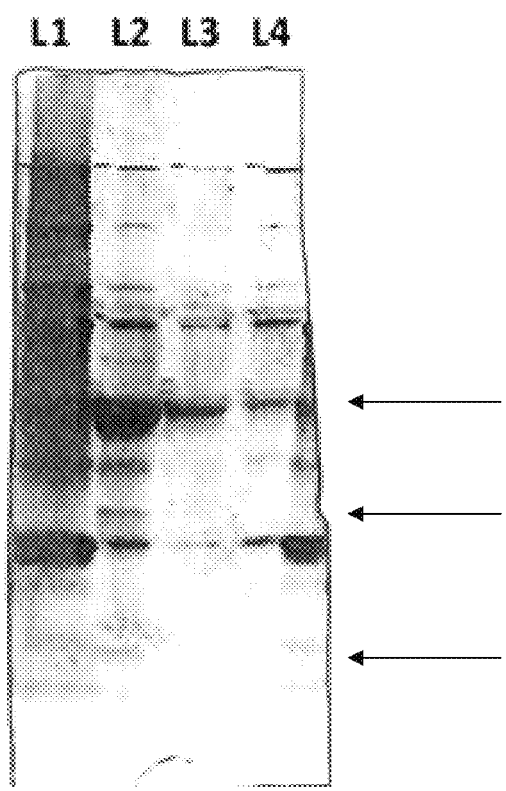
FIG. 6 shows silver staining of a polyacrylamide gel containing various concentrations of Eno1 analyzed by SDS-PAGE. L1: Precision Plus Protein Standard Dual Color, L2: Eno1 (10.0 µg), L3: Eno1 (1.0 µg), L4: Eno1 (0.1 µg).

As shown in FIG. 6, extra bands can be seen in each lane, which correspond to the bands of the ladder. This is due to the leakage of the ladder into the neighboring lanes. The three bands marked with an arrow are not from the ladder. The most prominent band is about 47 kDa, which is consistent with the size of Eno1. There are two extra bands in the purified protein but these bands are faint, indicating that overall purity of the Eno1 was relatively high.

Western Blot Analysis:

The identity of Eno1 was further confirmed by Western blot. For this purpose, the final portion of the gel was transferred into 100 mL of Tris-Glycine buffer and transferred onto 0.2 µm PVDF membrane (BIO-RAD) using a transblot SD semi-dry transfer apparatus (BIO-RAD) at 20 V for 2.0 h. The efficiency of the transfer was checked by observing the presence of the pre-stained ladder bands on the membrane. The membrane was dried for 1.0 h. The membrane was then wetted with methanol for 1.0 min and blocked with 15.0 mL ODYSSEY® Blocking Buffer (LI-COR) at room temperature for 2.0 h.

Figure 7:
FIG. 7 shows Western Blot analysis of Eno1. L1: Precision Plus Protein Standard Dual Color, L2: Eno1 (10.0 µg), L3: Eno1 (1.0 µg), L4: Eno1 (0.1 µg).

After the blocking was complete, the membrane was incubated with 15.0 mL ODYSSEY® Blocking Buffer containing 30 µL of anti-ENOA-1 m-Ab (mouse) (purchased from ABNOVA) overnight at 4° C. Then the membrane was washed with 3×30 mL of 1×PBS-T with shaking for 5 minutes each. The membrane was incubated with 15.0 mL ODYSSEY® Blocking Buffer containing 5 µL of Goat anti-mouse secondary antibody labeled with IRDye® 800CW (purchased from LICOR) for 2.0 h at room temperature. After the incubation, the membrane was washed with 3×30 mL of 1×PBS-T followed by 2×30 mL of 1×PBS with shaking for 5 minutes each. Finally, the membrane was imaged using the LICOR ODYSSEY Infrared Imager. As shown in FIG. 7, Western Blot analysis confirmed that the dominant band at 47 kDa was Eno1.

Zeta (ζ)-Potential Characterization of Enolase-I/G5-PAMAM-SMTP:

Eno1 and Generation 5 PAMAM dendrimers decorated with 2-3 Skeletal Muscle Targeting Peptides (SMTPs) were complexed at varied ratios to form Eno1/G5-SMTP protein/dendrimer complexes. The concentration of the dendrimer was kept constant at 1.0 µM and the Eno1 concentration was varied between 0.1 µM-10.0 µM. Table 2 below describes how the Enolase-I/G5-dendrimer/SMTP mixtures were prepared.

TABLE 2

Various combinations of Eno1 and G5-dendrimer/SMTP for formation of dendrimer complexes.

| Eno1/Dendrimer Molar Ratio | Eno1 (5.32 mg/mL) | G5-Dendrimer SMTP (30.0 mg/mL) | PBS buffer pH = 7.40 |
| --- | --- | --- | --- |
| 10:1 | 88.3 µL | 1.03 µL | 910.67 µL |
| 5:1 | 44.15 µL | 1.03 µL | 954.82 µL |
| 2:1 | 17.66 µL | 1.03 µL | 981.31 µL |
| 1:1 | 8.83 µL | 1.03 µL | 990.14 µL |
| 1:2 | 4.42 µL | 1.03 µL | 994.55 µL |
| 1:5 | 1.77 µL | 1.03 µL | 997.2 µL |
| 1:10 | 0.88 µL | 1.03 µL | 998.09 µL |

Each sample was prepared by adding G5-dendrimer/SMTP to the respective amount of PBS. Enolase was then added to the G5-dendrimer/SMTP solution in a drop wise fashion while vortexing at low speed. The sample was then incubated at room temperature for 20 minutes prior to analysis.

Figure 8:
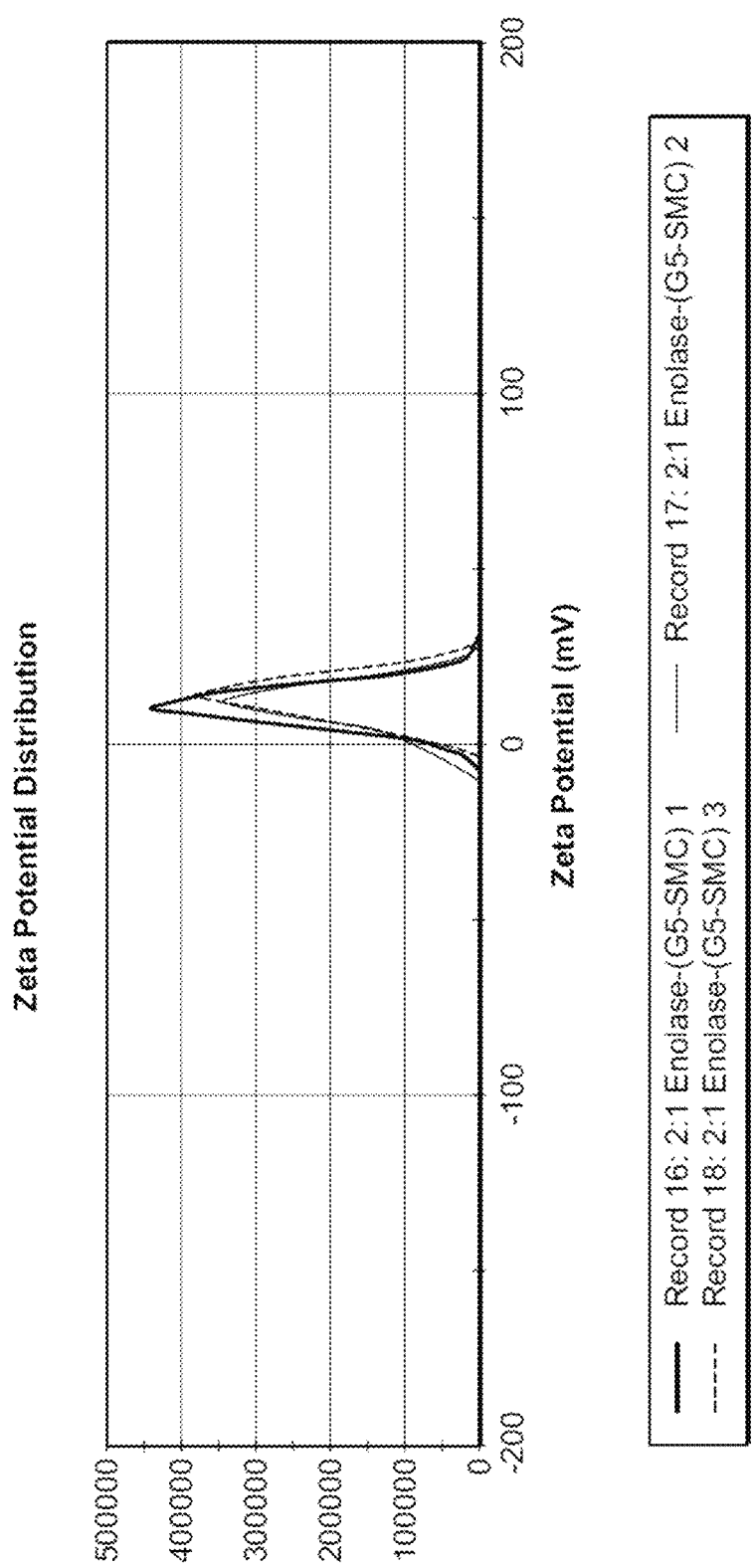
FIG. 8 shows Zeta ($\zeta$)-Potential measurement of Eno1/G5-dendrimer/SMTP complexes made with a 2:1 ratio of Eno1 to dendrimer SMTP.

Size measurements were made using the Zetasizer Nano Z90s instrument from Malvern Instruments. The default parameters were used for the measurements and three separate measurements of each sample were collected. FIG. 8 shows representative Zeta (ζ)-Potential data for three samples of Eno1/G5-dendrimer/SMTP complexes having a 2:1 molar ratio of Eno1 to dendrimer/SMTP. Zeta (ζ)-Potential was measured using Dynamic Light Scattering. As shown in FIG. 8, the peaks of the three samples are matching, indicating a uniform charge distribution of the Enolase-SMTP dendrimer complex.

Stability of Enolase-I/G5-SMTP Complexes:

The stability of the Enolase-I/G5-dendrimer/SMTP conjugates was measured by using the ENO1 Human Activity Assay Kit (ABCAM, Cambridge, Mass.; Catalogue No. ab117994). Briefly, the sample was added to a microplate containing a monoclonal mouse antibody specific to Eno1. The microplate was incubated at room temperature for 2 hours, and Eno1 was immunocaptured within the wells of the microplate. The wells of the microplate were washed to remove all other enzymes. Eno1 activity was determined by following the consumption of NADH in an assay buffer that included pyruvate kinase (PK), lactate dehydrogenase (LDH) and the required substrates 2-phospho-D-glycerate (2PG) and NADH. Eno1 converts 2PG to phosphoenolpyruvate, which is converted to pyruvate by PK. Pyruvate is converted to lactate by LDH, and this reaction requires NADH. The consumption of NADH was monitored as decrease of absorbance at 340 nm.

Figure 9:
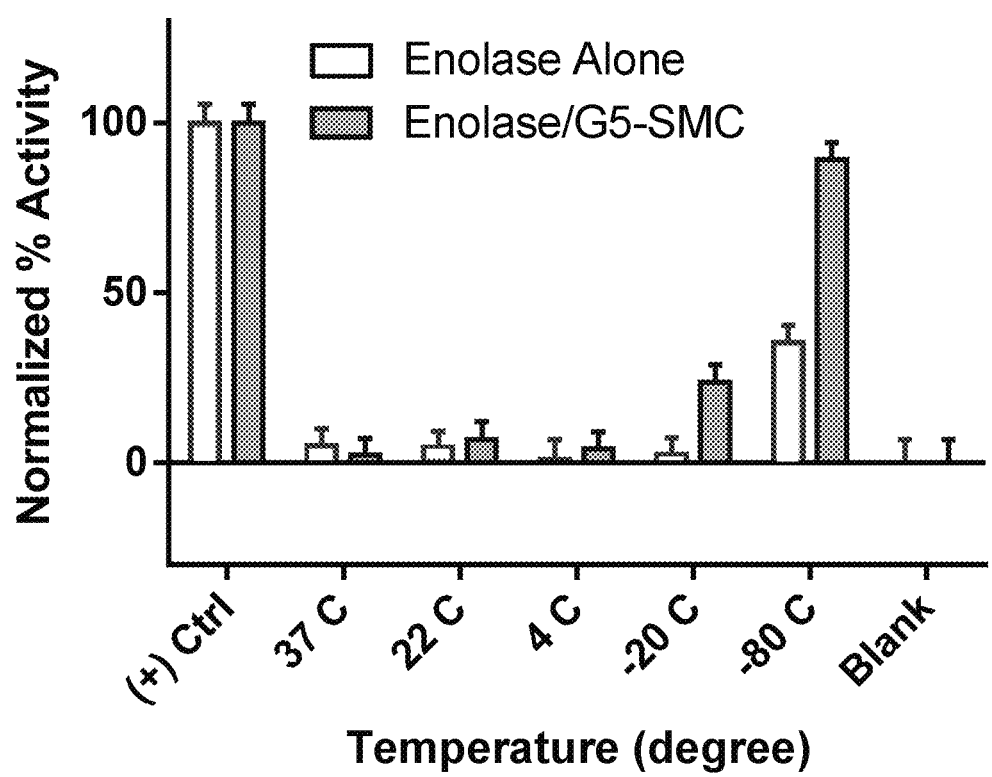
FIG. 9 shows normalized activities of Eno1 alone (Enolase Alone) and Eno1/G5-dendrimer/SMTP (Enolase/G5-SMC) solutions after storage at various temperatures.

The activity of Enolase-I/G5-dendrimer/SMTP conjugates that were stored at different temperatures at different time points was measured using the assay described above. A concentration of 500 ng of Eno1 was selected for testing because this concentration falls in the middle of the dynamic range of the assay kit. Two different sets of solutions were prepared. One set (control) contained Eno1 alone (i.e. unconjugated Eno1) and the other set contained Eno1/G5-dendrimer/SMTP mixtures. These mixtures were then kept at −80° C., −20° C., 4° C., 22° C., and 37° C. The results showed that in the first week all of the samples were active, and the Eno1/G5-dendrimer/SMTP conjugates seemed to have a slightly higher activity than Eno1 alone. However, the activities of the solutions, regardless of whether or not they contained dendrimers, steadily decreased in the next two weeks. By week 3, the solutions that were stored at 4° C., 22° C., and 37° C. showed no activity, while the solutions that were stored at −80° C., and −20° C. showed significant stability. At the end of the study (Week 10), The Eno1/G5-dendrimer/SMTP solution that was kept at −80° C. retained about 90% of its activity whereas Eno1 alone was only 35% active. On the other hand, Eno1/G5-dendrimer/SMTP solution that was kept at −20° C. was about 24% active, whereas Eno1 alone stored at −20° C. was not active (FIG. 9).

Example 6—In Vivo Eno1 Targeting Studies with G5 PAMAM Dendrimers

Figure 10A:
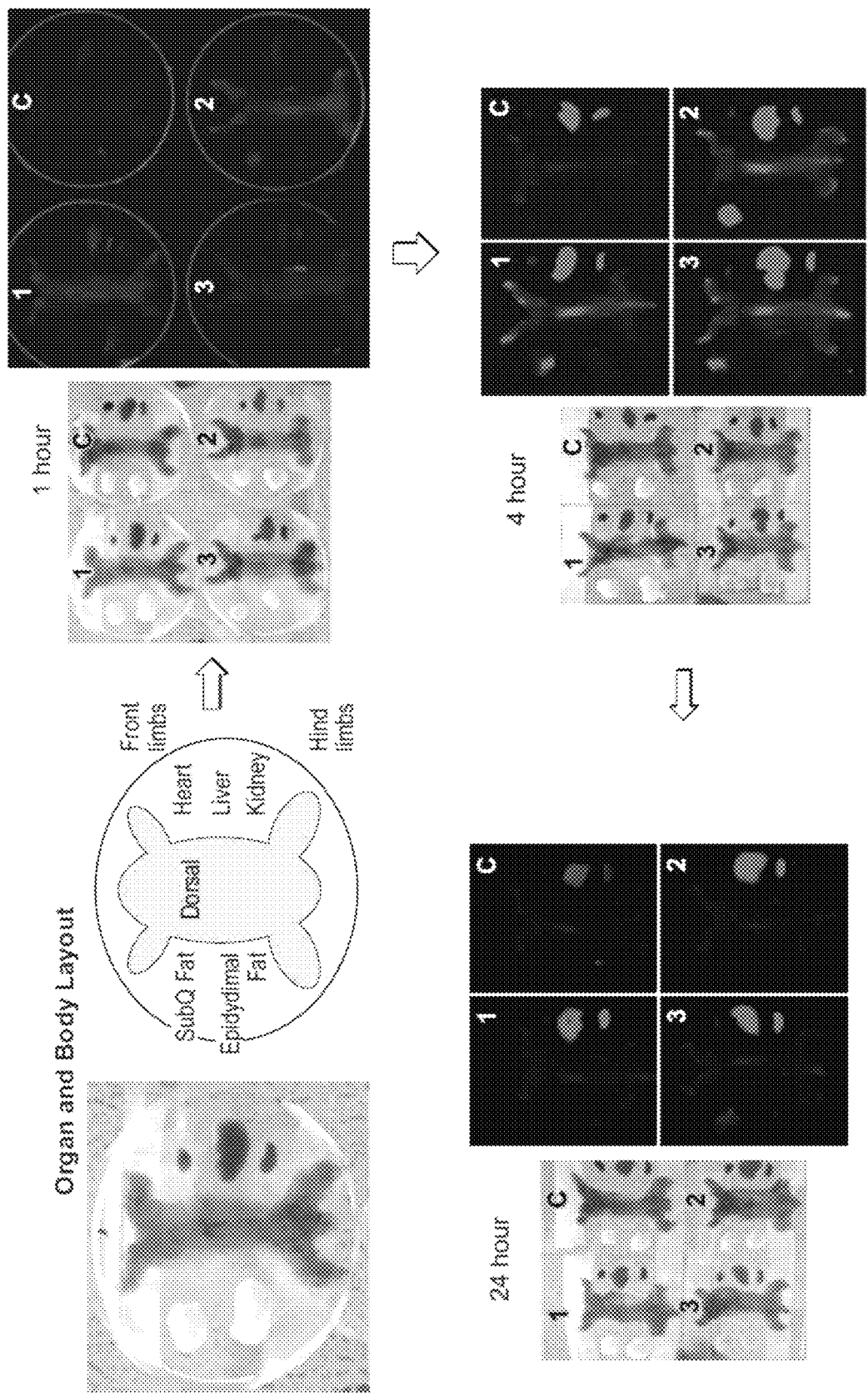
FIGS. 10A and 10B are representative fluorescent images of the tissue distribution in mice of (A) a fluorescently-labeled Eno1-G5-PAMAM dendrimer complex and (B) a fluorescently-labeled, muscle targeted Eno-1-G5-PAMAM dendrimer complex.

A detectably labeled PAMAM dendrimer complex containing Eno1 was prepared using the method provided in the prior example and analyzed for tissue distribution in mice after subcutaneous injection. Specifically, for 72 hours prior to injection mice were fed alfalfa free food to limit background fluorescence. Mice were injected with 3 µg ENO1/mouse subcutaneously 150 µl total (750 left laterally, 75 µl right laterally). The molar ratio of dendrimer to Eno1 in the complex was 5:1. One, 4, and 24 hours post injection animals were sacrificed, skinned, and organs removed in preparation for LI-COR imaging. The results are shown in FIG. 10A.

As shown, at 1 hour, general systemic distribution of the Eno1-PAMAM dendrimer was observed. After 4 hours, significant accumulation of the Eno1-PAMAM dendrimer was observed in liver, kidney, and subcutaneous fat, as well as in the upper torso. After 24 hours, the Eno1-dendrimer complex was substantially cleared and observed substantially in the liver and kidney.

Figure 10B:
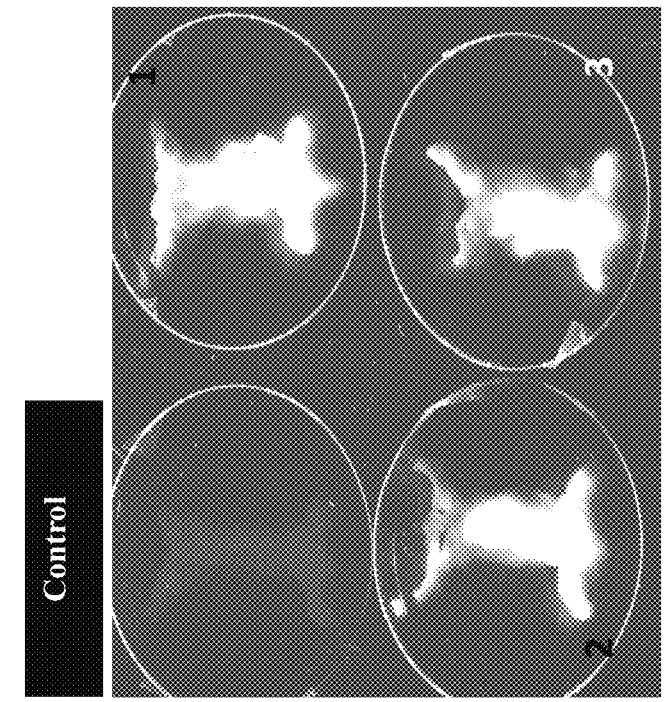
Figure 10B:
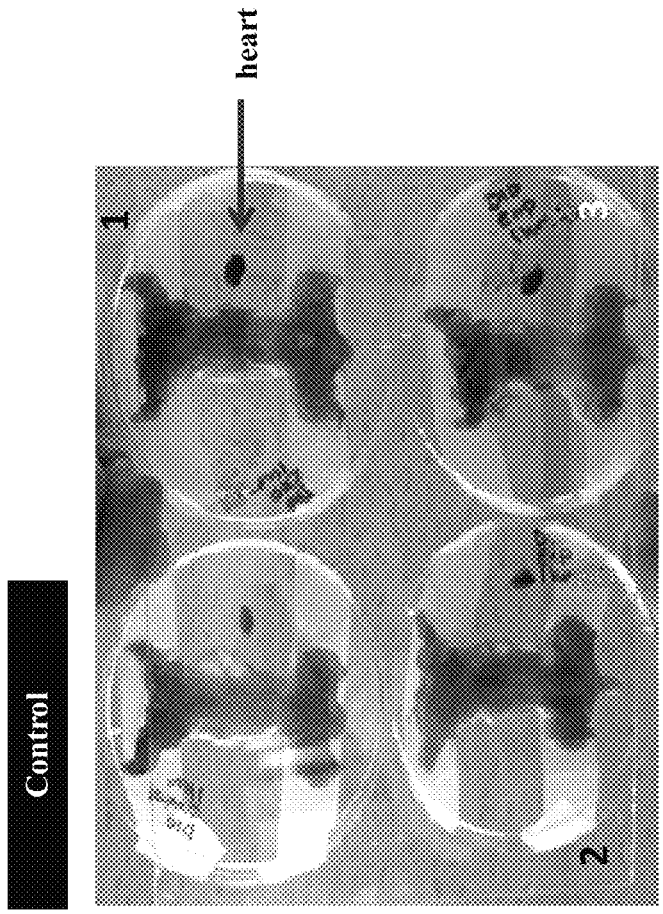

A follow-up study was performed using the skeletal muscle targeted Eno1-PAMAM dendrimer complex containing the SMTP "ASSLNIA" (SEQ ID NO: 12). A detectably labeled PAMAM dendrimer complex containing Eno1 and SMTP ((Enolase-Vivo Tag680xl)-(G5-SMTP)) was prepared using the method provided in the prior example. The molar ratio of dendrimer to SMTP in the complex was 1:1. The experiments were performed essentially as described above. The skeletal muscle targeted Eno1-PAMAM dendrimer complex was administered at a dose of 50 mg/kg body weight. These images in FIG. 10B were taken after 1 hr of injection. Organs, other than the heart, were retained in the body. As can be readily observed, the muscle-targeted Eno1 dendrimer complex was targeted to skeletal muscle, not heart. These results demonstrate that the skeletal muscle targeted Eno1-PAMAM dendrimer complex can be used for the delivery of Eno1 to skeletal muscle cells.

Example 7—Treatment of Glucose Intolerance with Muscle Targeted Eno1 in Diet Induced Obesity (DIO) Mice Diet induced obese male C57BL/6J mice (12 week old) and control lean mice (12 week old) were obtained from Jackson Laboratories (Bar Harbor, Me.) and initially housed 4-5 per cage at 22° C. on a 12:12 hr day-night cycle. Mice were acclimated in animal facility for one week before treatments and maintained with a high-fat diet for DIO group (Research Diets Cat #: D12492; 60 kcal % fat, 20 kcal % protein, and 20 kcal % carbohydrate) or a low fat diet (10% kcal % fat) for lean group.

Beginning at 13 weeks of age, all mice received daily subcutaneous injections of either saline or different complexes with combinations of G5 dendrimer, skeletal muscle targeting peptide (SMTP), and purified Eno1 (50 mg/kg body weight) for duration of 4 weeks. During the 4 weeks of the treatment portion of the experiment, intraperitoneal glucose tolerance tests (IPGTT) were performed weekly. Body weight, fed glucose, and fasted glucose were measured weekly during treatment period. The treatment groups are shown below:
1. LFD—Lean Controls—no injection
2. HFD—saline control (volume equivalent to G5+SMTP+Eno1)
3. HFD—G5 only (equivalent to 50 µg/kg of G5+SMTP+Eno1)
4. HFD—G5+SMTP (equivalent to 50 µg/kg of G5+SMTP+Eno1)
5. HFD—G5+Eno1 (50 µg/kg body weight)
6. HFD—G5+SMTP+Eno1 (50 µg/kg body weight)

The molar ratio of dendrimer to Eno1 in the complexes was 5:1, the molar ratio of dendrimer to SMTP in the complexes was 1:1, and the dendrimer was acetylated. Results from the study are provided in FIGS. 11, 12, 13, 14 and 15.

Figure 11:
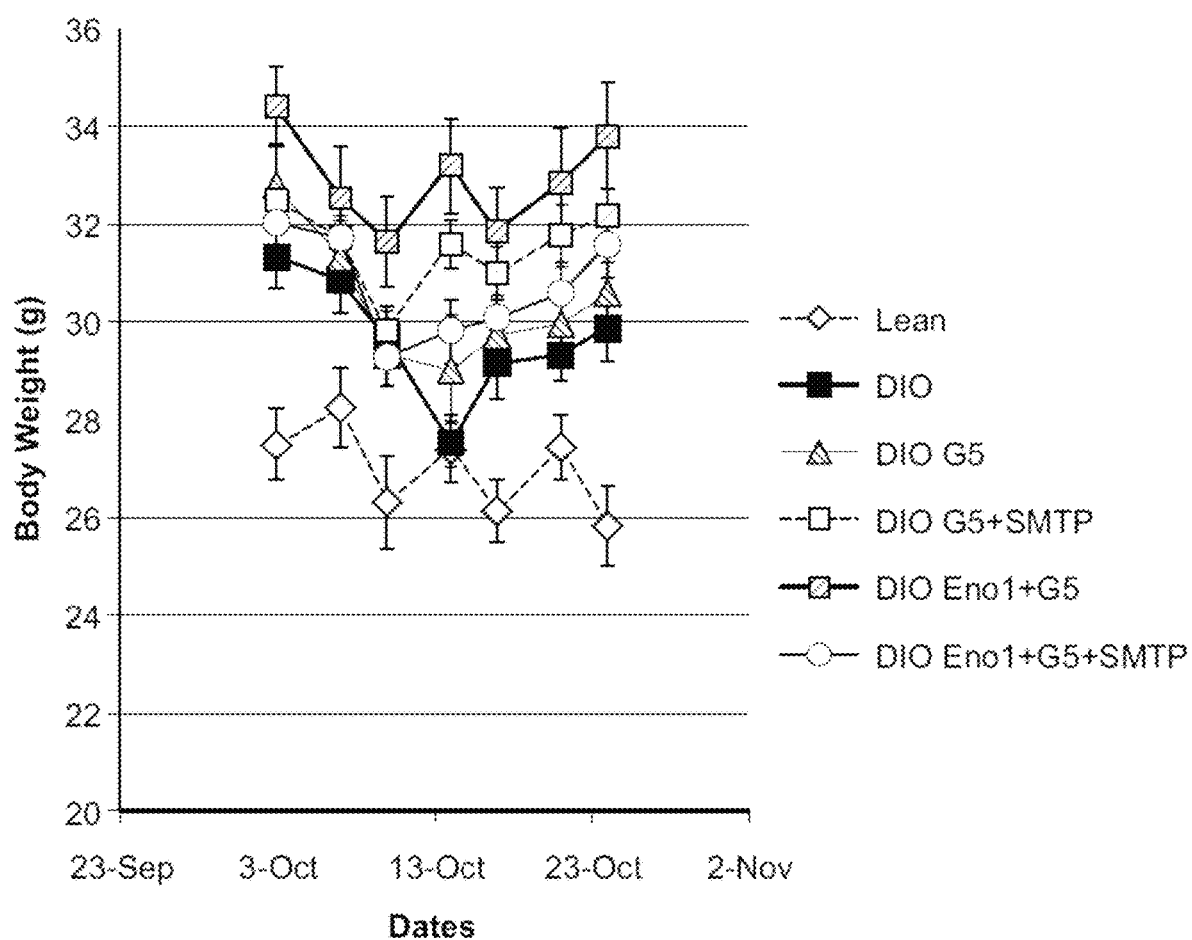
FIG. 11 is a graph of the body weights of lean mice or DIO mice treated with one of vehicle, G5-PAMAM dendrimer, G5-PAMAM dendrimer+SMTP, G5-PAMAM dendrimer+Eno1, G5-PAMAM dendrimer+Eno1+SMTP.

In this small cohort, none of the treatment regimens were found to have a significant effect on body weight in the DIO mice at any time during the study (see FIG. 11).

Figure 12:
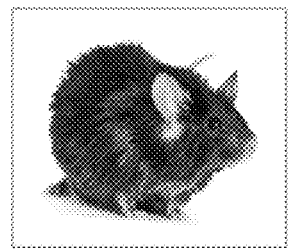
FIG. 12 is a graph showing blood glucose levels in mice with diet induced obesity after injection of saline or G5-PAMAM dendrimer+Eno1+SMTP (50 ug/kg) at 1, 4, and 24 hours after injection.
Figure 12:
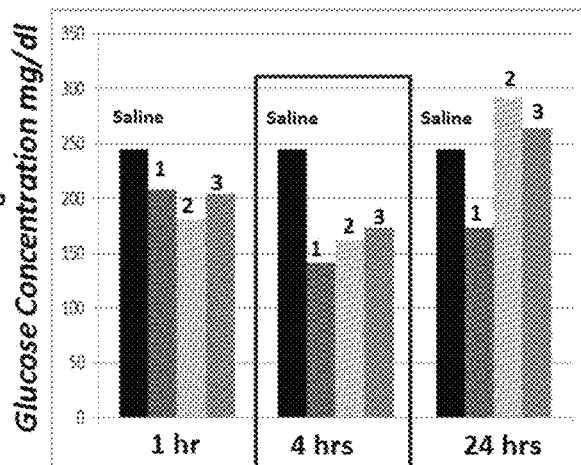

Treatment of mice with a single dose of the dendrimer bound muscle targeted Eno1 was demonstrated to have an effect on blood glucose levels at the earliest time points tested. As shown in FIG. 12, one hour after administration of 50 µg/kg of G5+SMTP+Eno1, a reduction of blood glucose was observed as compared to a saline control, with the maximum reduction observed at 4 hours. The effect was no longer observed at 24 hours after the single injection.

Figure 13A:
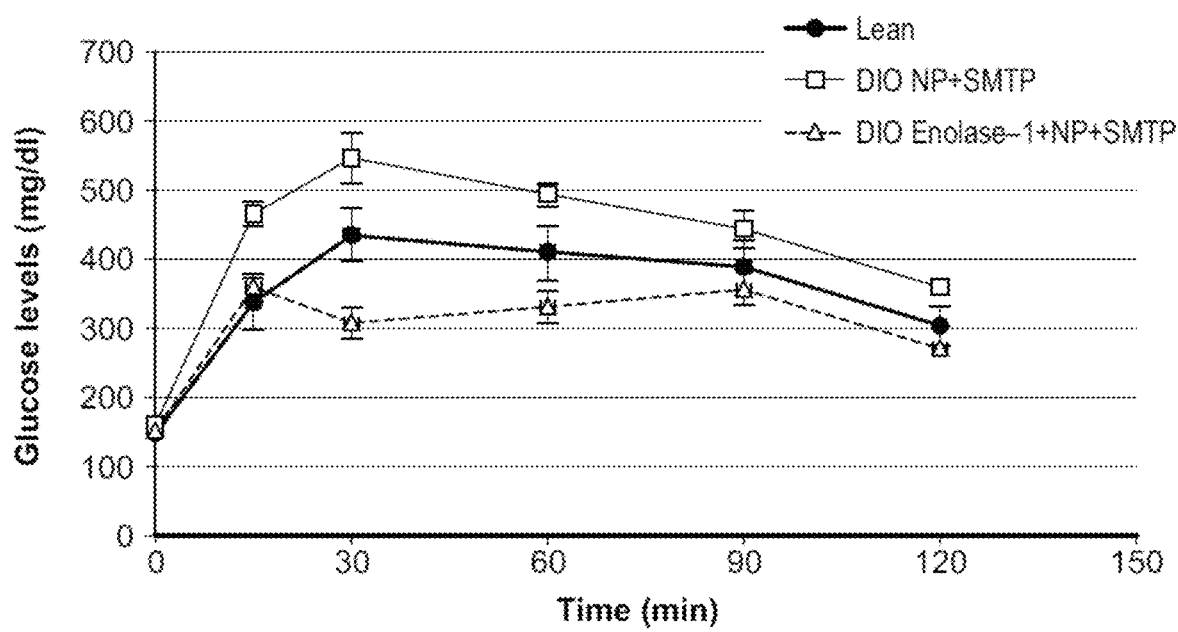
FIG. 13A shows the results of a glucose tolerance test in lean mice and a diet-induced obesity (DIO) mouse model of diabetes after 1 week of treatment with G5-PAMAM dendrimer+SMTP (DIO NP+SMTP) or G5-PAMAM dendrimer+Eno1+SMTP (DIO Enolase-1+NP+SMTP).
Figure 13B:
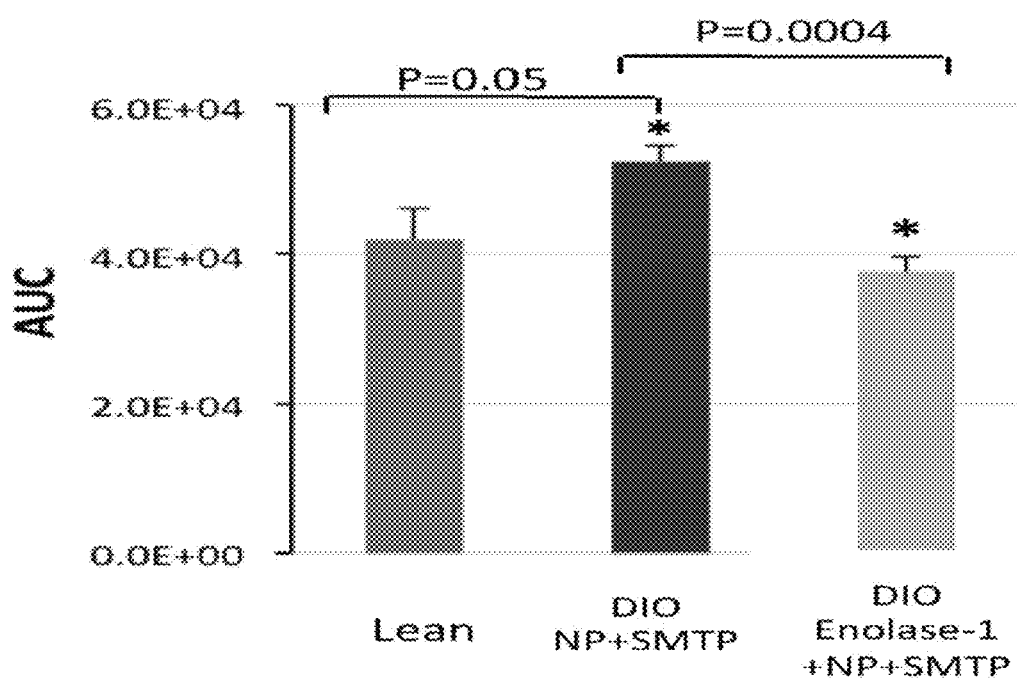
FIG. 13B shows the area under the curve (AUC) for each treatment group in FIG. 13A.
Figure 13C:
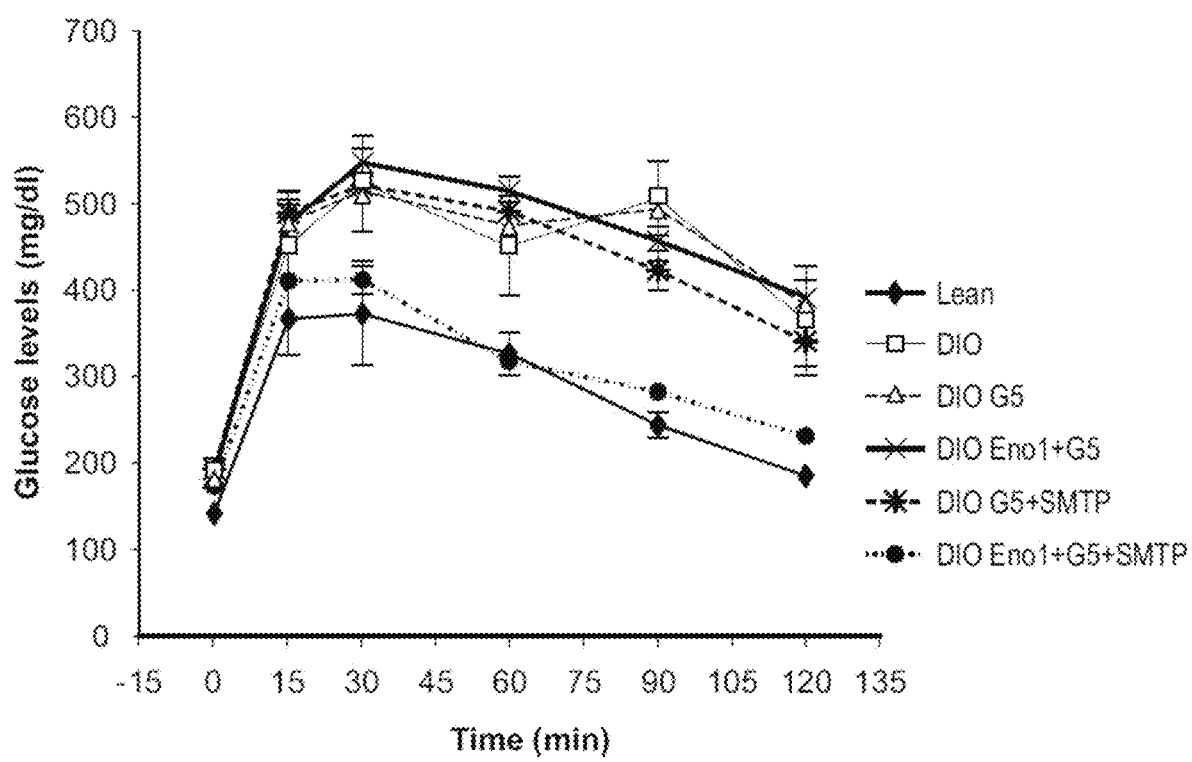
FIGS. 13C and 13D show (C) a time course and (D) the area under the curve (AUC) of glucose clearance in a glucose tolerance test in lean mice or in DIO mice after two weeks treatment with one of vehicle, G5-PAMAM dendrimer (G5), G5-PAMAM dendrimer+SMTP, G5-PAMAM dendrimer+Eno1, G5-PAMAM dendrimer+Eno1+SMTP.
Figure 13D:
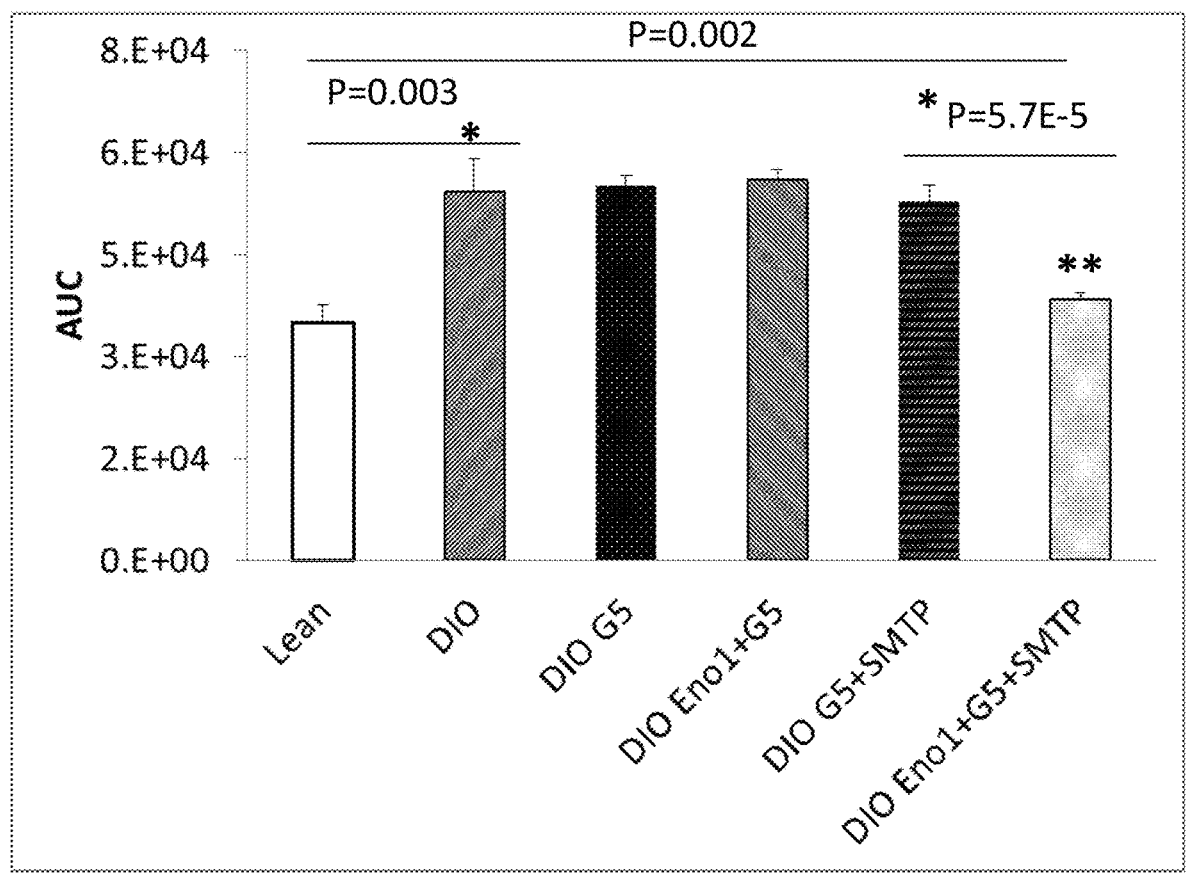

At one week after initiation of administration of the dendrimer bound muscle targeted Eno1, glucose tolerance in the DIO mice treated with the Eno1 dendrimer SMTP complex (DIO Enolase-1+NP+SMTP) were significantly lower than glucose tolerance in DIO mice treated with the dendrimer SMTP complex alone (DIO NP+SMTP) (see FIGS. 13A and 13B).

At two weeks after initiation of administration of the dendrimer bound muscle targeted Eno1, glucose tolerance in the DIO mice was still significantly improved (see FIGS. 6C and 6D). The improvement of glucose tolerance was dependent on the presence of Eno1 in the dendrimer complex (DIO G5+SMTP vs. DIO Eno1 G5+SMTP, $p=5.7\times10^{-5}$, $p=0.002$). The effect was no longer observed 23 hours after the single injection (data not shown).

Figure 14A:
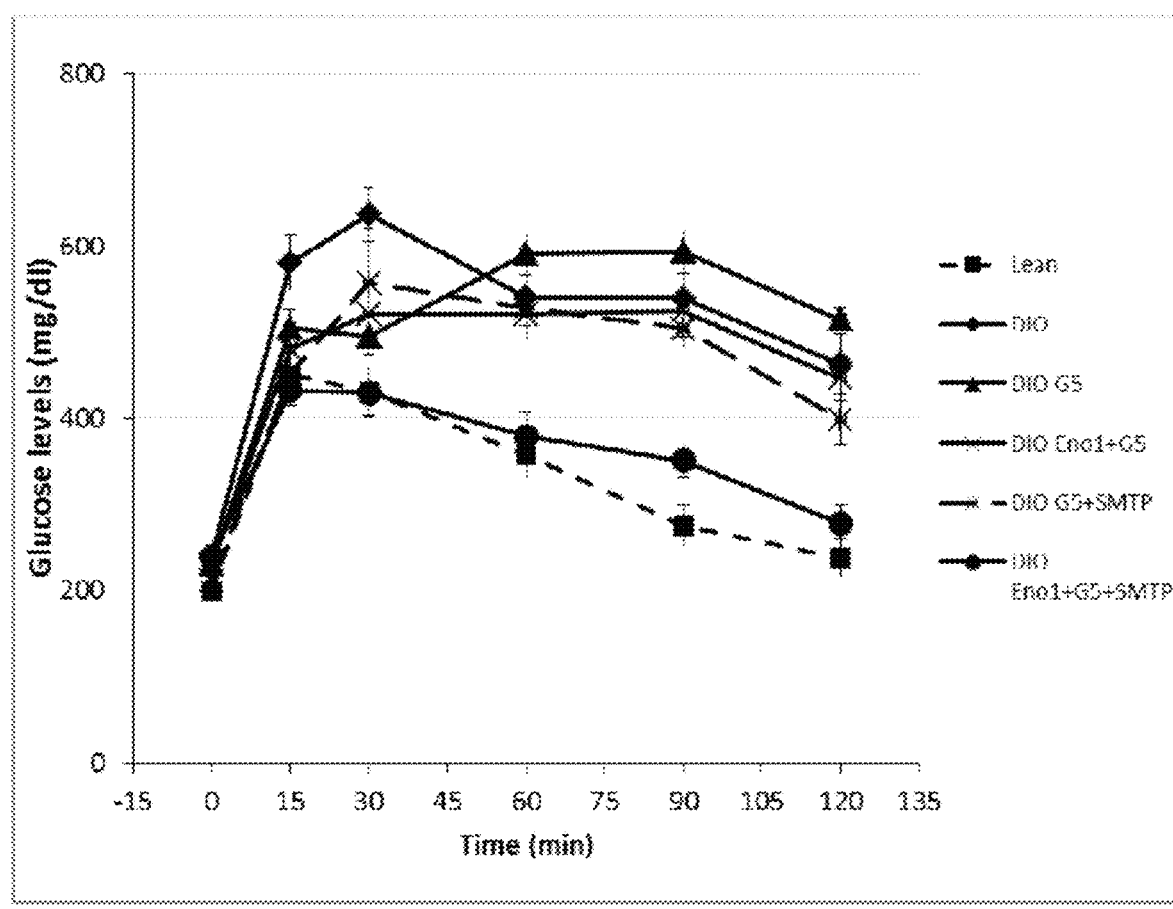
FIGS. 14A and 14B show (A) a time course and (B) the area under the curve (AUC) of glucose clearance in a glucose tolerance test in lean mice or in DIO mice after four weeks treatment with one of vehicle, G5-PAMAM dendrimer, G5-PAMAM dendrimer+SMTP, G5-PAMAM dendrimer+Eno1, G5-PAMAM dendrimer+Eno1+SMTP.
Figure 14B:
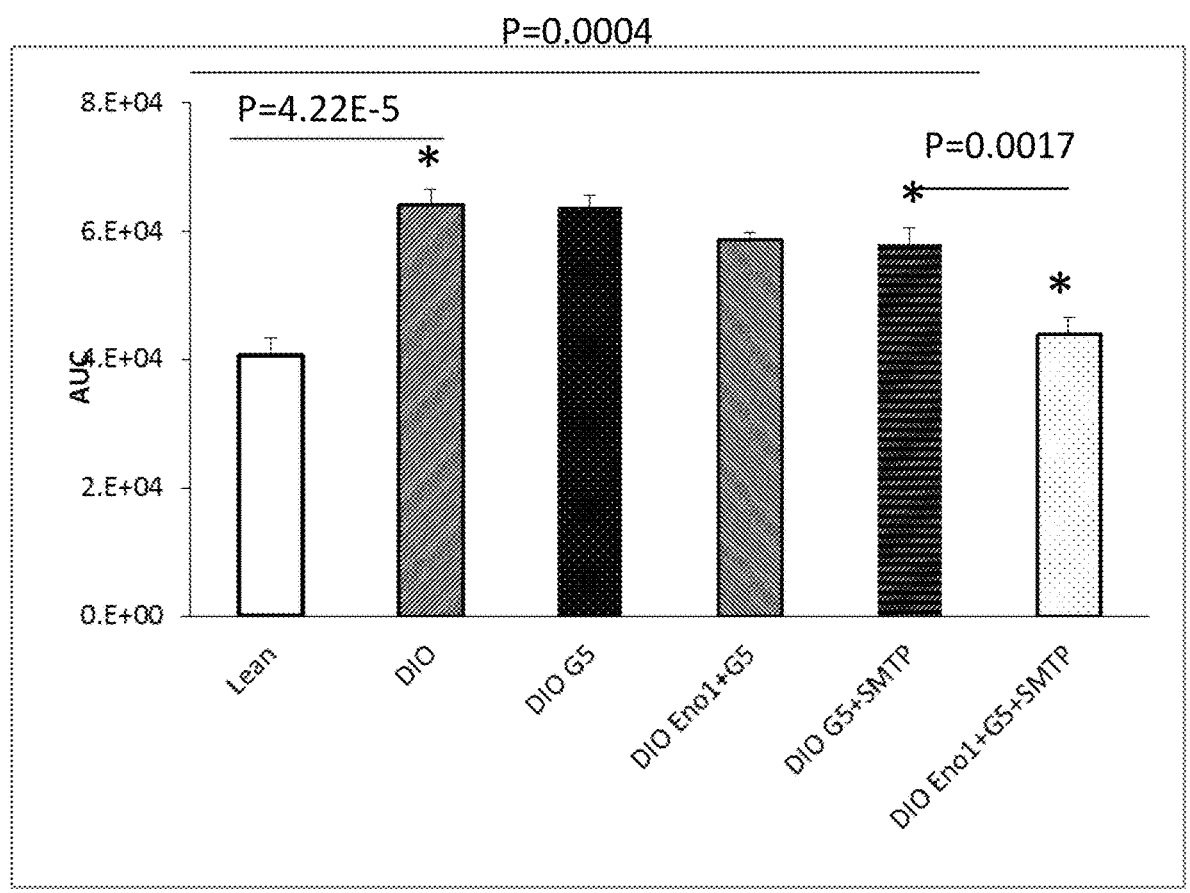

The beneficial effect of G5+SMTP+Eno1 treatment observed at weeks 1 and 2 was sustained through week 4 (see FIGS. 14A and 14B). Specifically glucose tolerance in the DIO Eno1 G5+SMTP treated mice was similar to that in lean mice. The improvement of glucose tolerance was significant and dependent on the presence of Eno1 in the dendrimer complex (DIO G5+SMTP vs. DIO Eno1 G5+SMTP, p=0.0017). The effect was no longer observed 23 hours after the single injection (data not shown).

These results show that dendrimer bound, muscle targeted Eno1 is effective in increasing glucose tolerance in a model of diet induced obesity, and that G5+SMTP+Eno1 is effective in normalizing blood glucose in a mouse model of diet induced obesity. These results demonstrate that Eno1 is useful in the treatment of elevated blood glucose, glucose intolerance, and diabetes, particularly type 2 diabetes.

Figure 15:
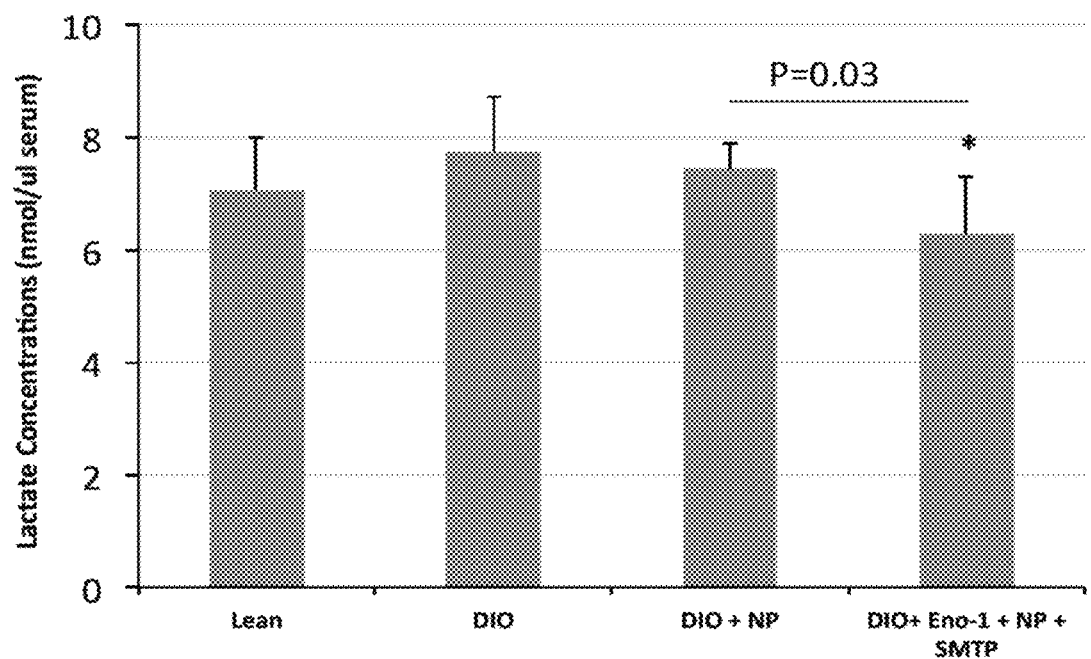
FIG. 15 shows serum lactate levels in lean mice, diet induced obesity (DIO) mice, DIO mice treated with G5-dendrimer (DIO+NP), and DIO mice treated with Eno1/G5-dendrimer/SMTP complex (DIO+Eno-1+NP+SMTP) after 8 weeks of treatment.

The mice were treated as described above for an additional 4 weeks (8 weeks treatment in total), and serum lactate levels were determined in lean mice, diet induced obesity (DIO) mice, DIO mice treated with G5-dendrimer, and DIO mice treated with Eno1/G5-dendrimer/SMTP complex after 8 weeks of treatment. Lactate levels in serum were measured using a lactate colorimetric assay kit from Biovision (Milpitas, Calif.). As shown in FIG. 15, Eno1/G5-dendrimer/SMTP complex significantly reduced lactate serum levels. This result suggests that the reduced glucose levels observed in the DIO mice treated with the Eno1/G5-dendrimer/SMTP complex is due to increased glucose oxidation, rather than shunting of glycolysis to lactate. This would minimize the undesirable effects of lactate acidosis.

Example 8—Treatment of Glucose Intolerance with Muscle Targeted Eno1 in a Genetic Model of Obesity, Db/Db Mice Male obese and diabetic db/db mice (male BKS.Cg-m+/+Lepr$^{db}$/J) mice were obtained from a commercial vendor. All mice were housed 2-3 per cage at 22° C. on a 12:12 hr day-night cycle and are acclimated for 3 weeks at animal facility on a standard chow diet. At 8 weeks of age, the following subcutaneous injections of either saline or different complexes with combinations of G5 dendrimer, skeletal muscle targeting peptide (SMTP), and purified Eno1 were administered once daily by subcutaneous administration (n=6 per group). The treatment groups are as follows:
1. db/db with saline injection
2. db/db with G5+SMTP (volume equivalent to Eno1+G5+SMTP at 25 ug/kg dose)
3. db/db with Eno1 (25 ug/kg body weight)+G5+SMTP
4. db/db with Eno1 (50 ug/kg body weight)+G5+SMTP The molar ratio of dendrimer to Eno1 in the complexes was 5:1, and the molar ratio of dendrimer to SMTP in the complexes was 1:1, and the dendrimer was acetylated.

Figure 16A:
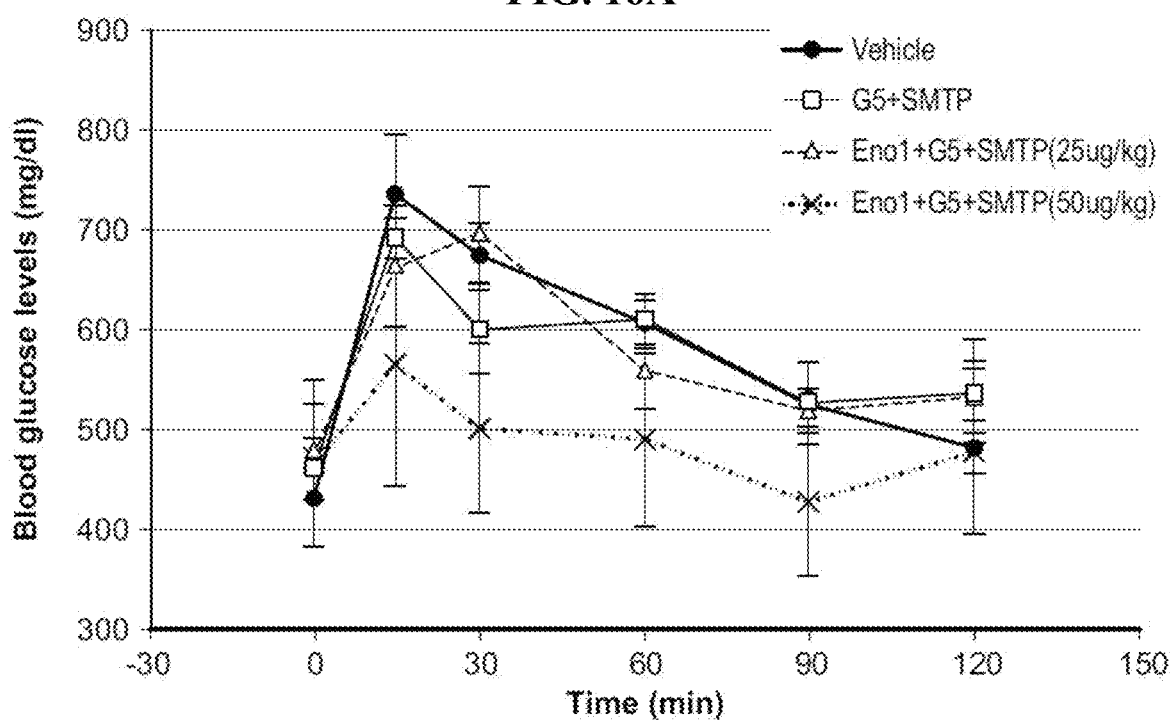
FIGS. 16A and 16B show (A) a time course and (B) the area under the curve (AUC) of glucose clearance in an intraperitoneal glucose tolerance test in db/db mice (BKS.Cg-m+1+Leprdb/J) after one week treatment with one of vehicle, G5-PAMAM dendrimer (G5)+SMTP, and G5-PAMAM dendrimer+Eno1+SMTP at 25 ug/kg or 50 ug/kg.
Figure 16B:
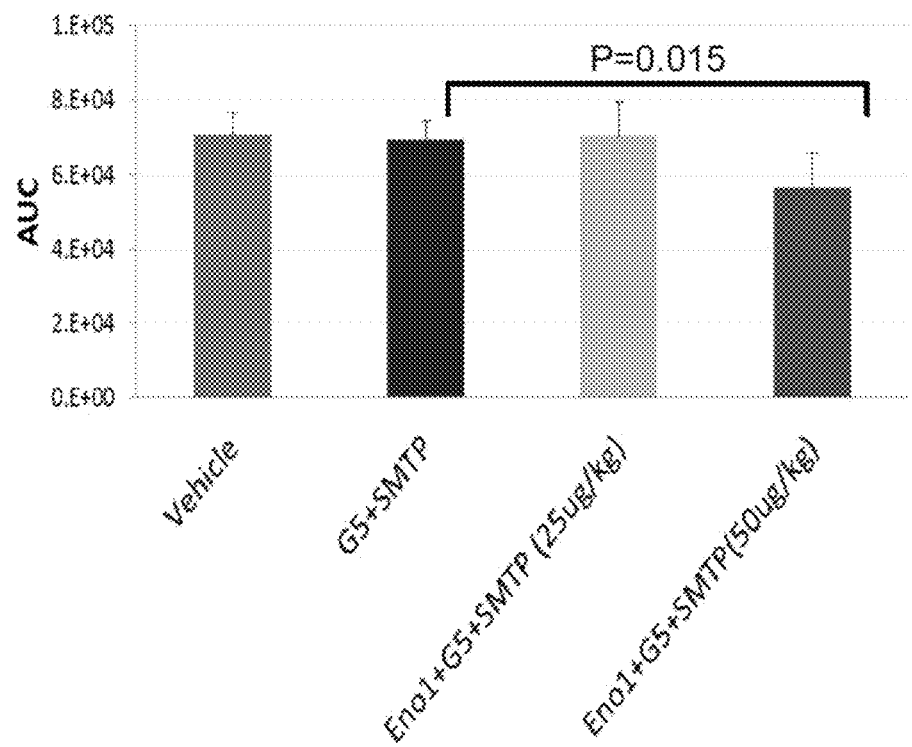

At day 7, the mice were administered the appropriate agent and returned to the cage for 6 hours without food prior to administration of an IPGTT as described in the Example above. The results are shown in FIGS. 16A and 16B. As can be readily observed, treatment of mice with Eno1+G5+SMTP resulted in an increase in glucose tolerance after glucose challenge with a significant increase in glucose clearance observed in the mice treated with Eno1 (50 ug/kg body weight)+G5+SMTP as compared to the mice treated with G5+SMTP (p=0.015).

Figure 17A:
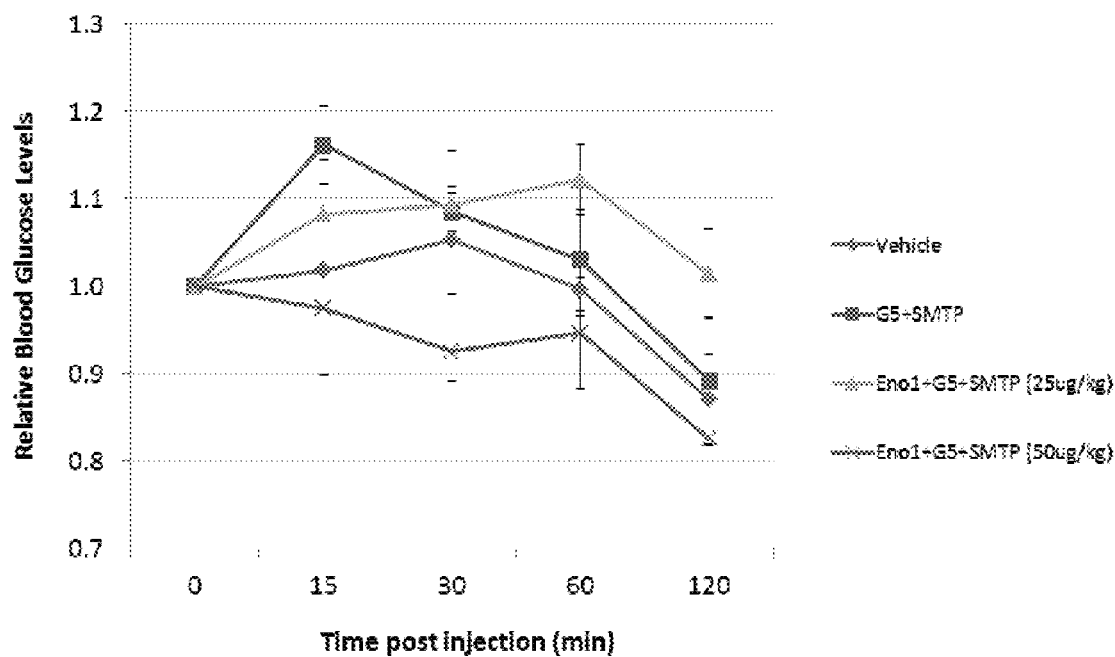
FIGS. 17A and 17B show a time course of glucose levels in db/db mice (BKS.Cg-m+1+Leprdb/J) after two weeks of treatment with one of vehicle, G5-PAMAM dendrimer (G5)+SMTP, and G5-PAMAM dendrimer+Eno1+SMTP at 25 ug/kg or 50 ug/kg obtained in a time course initiated immediately after injection with the vehicle, G5-PAMAM dendrimer+SMTP, and G5-PAMAM dendrimer+Eno1+SMTP at the indicated doses.
Figure 17B:
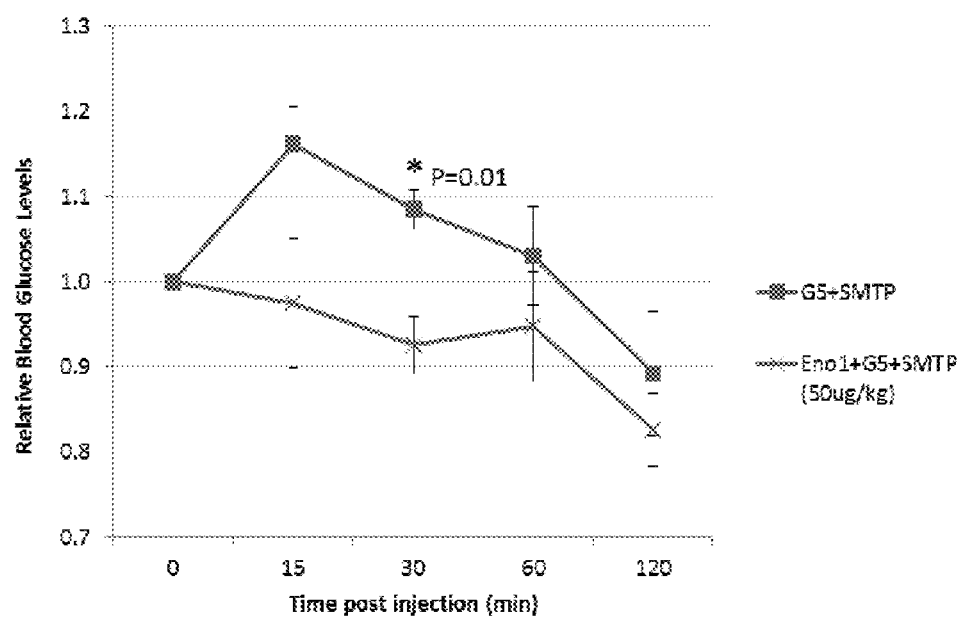
Figure 18:
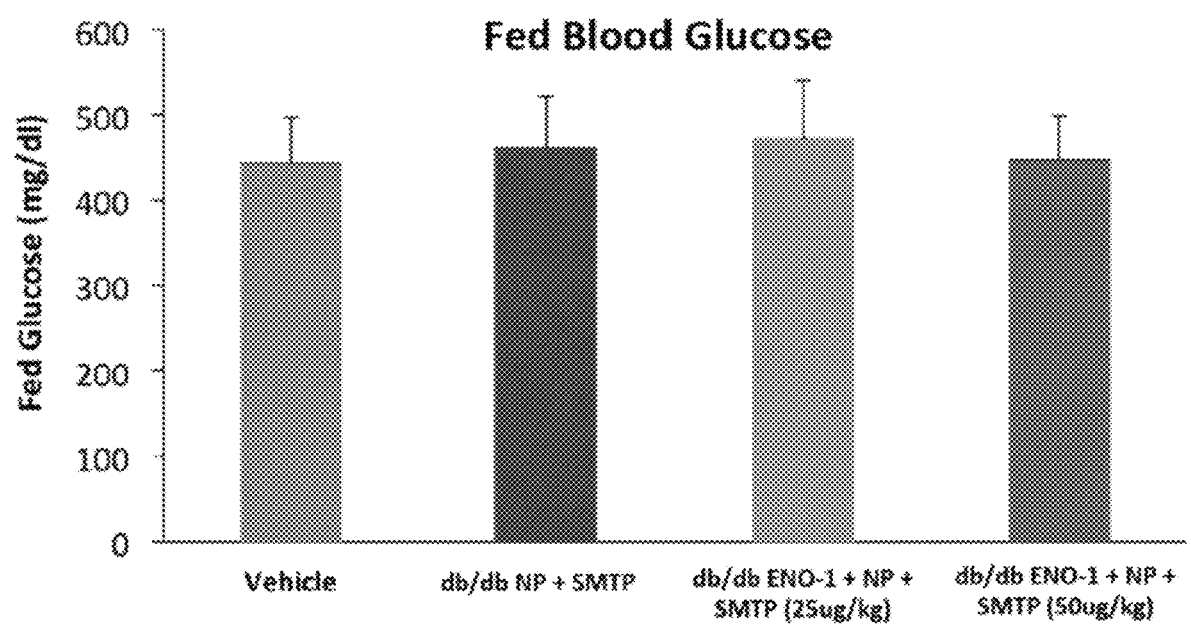
FIG. 18 shows the effect of once daily subcutaneous injection of 25 µg/kg body weight or 50 µg/kg body weight of Eno1/G5-dendrimer/SMTP complex on fed blood glucose levels in a db/db diabetic mouse model after two weeks of treatment. Fed glucose was measured 24 hours after Eno1 injection without fasting. "NP" is the G5-dendrimer.

The study was continued with three out of the six mice in each of the treatment groups listed above. Mice were administered the indicated agent for an additional week (2 weeks total). The effect of Eno1 on lowering fed blood glucose was tested. Specifically, without controlling the intake of food, blood glucose levels in mice were assessed for two hours immediately after administration of the active agent. The results are shown in FIGS. 17A and 17B. As shown, administration of Eno1 (50 ug/kg body weight)+G5+SMTP was demonstrated to decrease fed blood glucose and resulted in a statistically significant reduction in blood glucose 30 minutes after administration as compared to administration of G5+SMTP. However, the reduced blood glucose observed 30 minutes after Eno1+G5+SMTP treatment were not maintained at 24 hours after Eno1 injection (FIG. 18).

Accordingly, the effect of twice daily dosing of Eno1+G5+SMTP on blood glucose levels was also evaluated in the db/db mice. Treatments were administered by subcutaneous injection twice daily, once in the morning and once in the evening, for four weeks. The treatment groups were as follows:
1. PBS
2. 100 μg/kg body weight Eno1+G5+SMTP
3. 200 μg/kg body weight Eno1+G5+SMTP The molar ratio of dendrimer to Eno1 in the Eno1+G5+SMTP complex was 5:1, and the molar ratio of dendrimer to SMTP in the Eno1+G5+SMTP complex was 1:1, and the dendrimer was acetylated.

Figure 19:
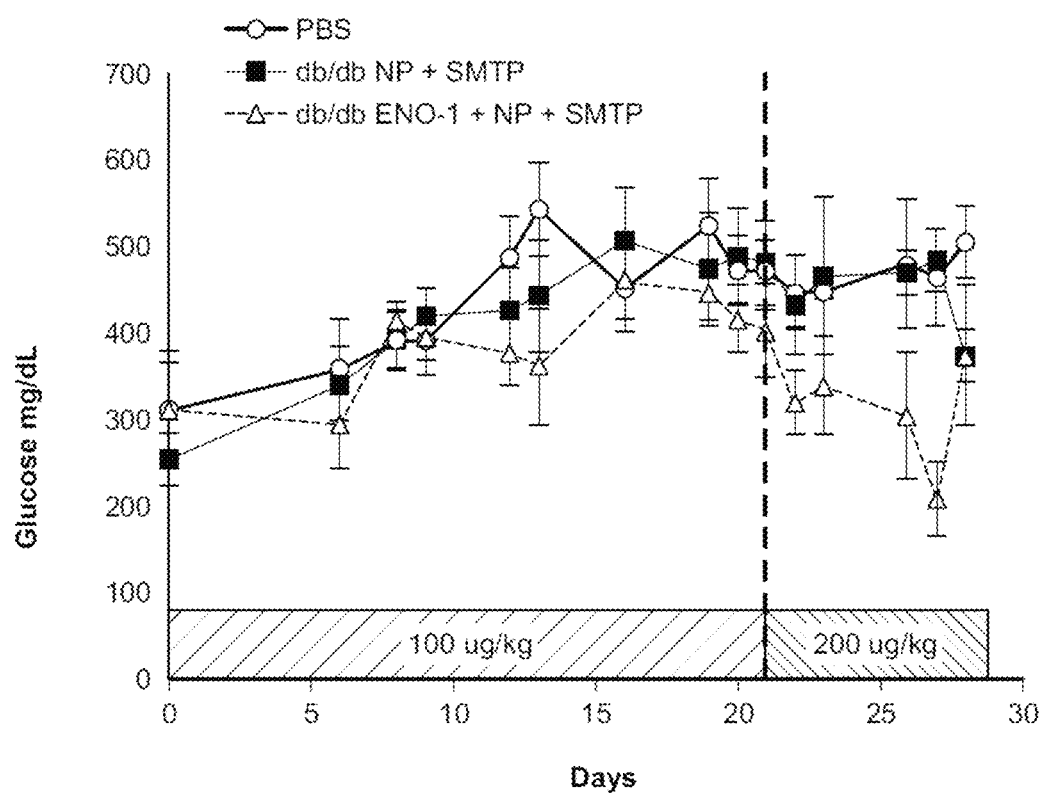
FIG. 19 shows the effect of twice daily (morning and evening) subcutaneous injection of 100 µg/kg body weight or 200 µg/kg body weight of Eno1/G5-dendrimer/SMTP complex on fed blood glucose levels in a db/db diabetic mouse model.

The total daily dose for treatment group 2 was 200 μg/kg body weight Eno1+G5+SMTP and the total daily dose for treatment group 3 was 400 μg/kg body weight Eno1+G5+SMTP. Without controlling the intake of food, fed blood glucose levels were assessed in the mice 16 hours after the evening injection (i.e. before the morning injection). As shown in FIG. 19, twice daily injection of 200 μg/kg body weight Eno1+G5+SMTP decreased fed blood glucose levels relative to the control PBS treatment.

Thus, treatment of mice with Eno1 G5+SMTP was shown to normalize glucose response in db/db mice. The data described in Examples 7 and 8 together demonstrate that Eno1 is effective in increasing glucose tolerance in both an induced and a genetic model of type 2 diabetes.

Figure 20:
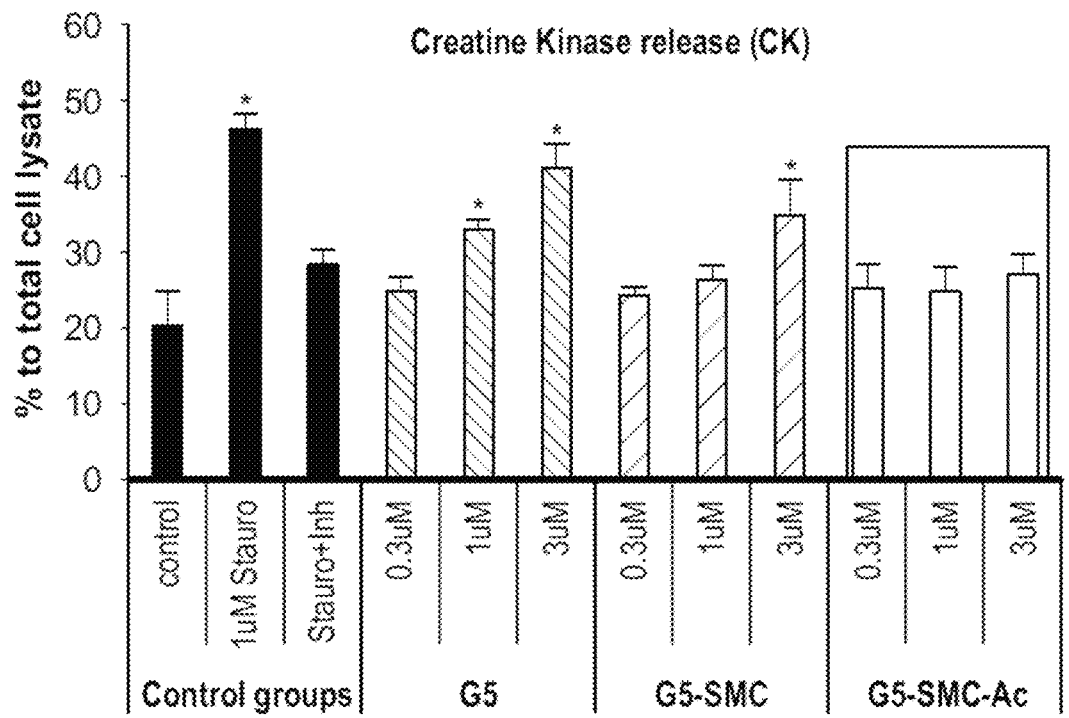
FIG. 20 shows creatine kinase and caspase 3 activity detected after treatment with G5-PAMAM dendrimer (G5), G5-PAMAM dendrimer+SMTP (G5-SMC), and acylated G5-PAMAM dendrimer+SMTP (G5-SMC-Ac).
Figure 20:
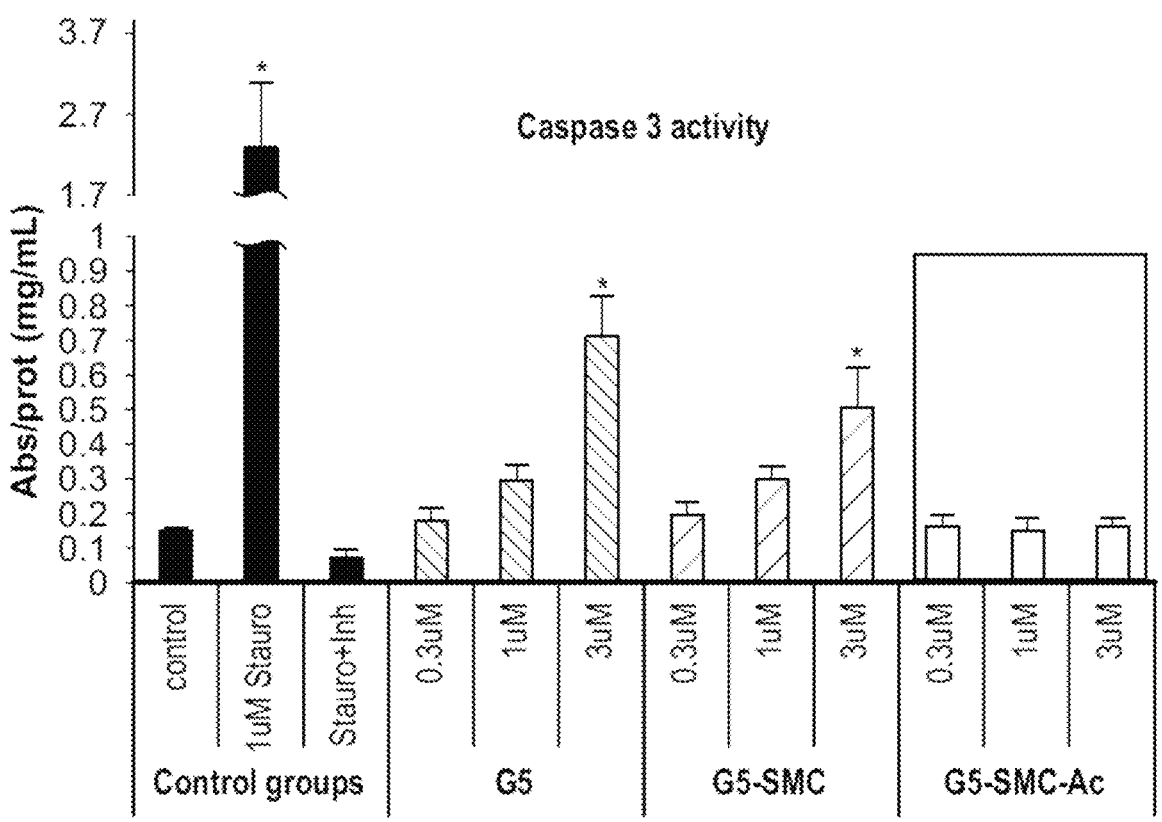

Example 9—Comparative Toxicity of Acylated Vs. Non-Acylated SMTP Containing Dendrimers The toxicity of acylated and non-acylated dendrimers containing SMTP were compared using creatine kinase and caspase 3 assays. Mice were injected with one of staurosporine (positive control), staurosporine+inhibitor (negative control); G5 PAMAM dendrimers, SMTP-G5 PAMAM dendrimers, and acylated SMTP-G5 PAMAM dendrimers. The molar ratio of dendrimer to Eno1 in the complexes was 5:1, and the molar ratio of dendrimer to SMTP in the complexes was 1:1. After injection samples were collected and assayed for the creatine kinase levels as a percent of total cell lysate and caspase 3 activity using commercially available kits. The results are shown in FIG. 20. As shown in FIG. 20, administration of the G5 PAMAM dendrimers at both 1 uM and 3 uM concentrations and administration of SMTP-G5 PAMAM dendrimers at 3 uM concentration resulted in a significant increase in creatine kinase activity. No such effect was observed with the acylated SMTP-G5 PAMAM dendrimers. Similarly, a significant increase in caspase 3 activity was observed after administration of 3 uM G5 PAMAM dendrimers and SMTP-G5 PAMAM dendrimers. However, no increase in caspase 3 activity was observed upon administration of the acylated SMTP-G5 PAMAM dendrimers. These results demonstrate that acylation of SMTP-G5 PAMAM dendrimers reduces toxicity.

Example 10—Treatment of Glucose Intolerance with Muscle Targeted Eno1 in a Genetic and Induced Models of Type 2 and Type 1 Diabetes Male obese mice, diabetic db/db mice (male BKS.Cg-m+/+Lepr$^{db}$/J), NOD1 mice, or streptazocin treated mice are obtained or generated. All mice are housed 2-3 per cage at 22° C. on a 12:12 hr day-night cycle and are acclimated for at least 1 week at animal facility on an appropriate chow diet (i.e., high fat diet for obese mice, normal chow for other mice). At an appropriate age, typically about 8 weeks of age, subcutaneous injections of either saline or different complexes with combinations of G5 dendrimer, skeletal muscle targeting peptide (SMTP), and purified Eno1 (25 or 50 mg/kg body weight) are administered daily for duration of 1-2 weeks. Implantable pumps (e.g., ALZET pumps) as described above can be used for administration on a daily or continuous basis. Alternatively, the agents can be administered intramuscularly in various formulations. Intramuscular injections are typically performed on a less frequent basis than subcutaneous injections (e.g., typically about once per week).

During the 2 weeks of time-course, intraperitoneal glucose tolerance tests (IPGTT) are performed and fasting and fed blood glucose is monitored, either randomly or in a time course after administration of the agent. Body weight is measured weekly during treatment period. The treatment groups include at least one control (e.g., 1 or 2) and at least one Eno1 treatment from the list shown below:
1. Saline injection
2. G5+SMTP (volume equivalent to Eno1+G5+SMTP at 25 ug/kg body weight/day)
3. Eno1 (25 ug/kg body weight/day)+G5+SMTP
4. Eno1 (50 ug/kg body weight/day)+G5+SMTP
5. Eno1 (25 ug/kg body weight/day)
6. Eno1 (50 ug/kg body weight/day)

Dosages provided are exemplary and are not to be considered limiting.

Treatment of mice with Eno1 G5+SMTP is demonstrated to normalize glucose response in the diabetic mice.

Example 11—Assessment of Glucose Levels and Glucose Response in Mice

The intraperitoneal glucose tolerance test (IPGTT) is described above and routinely used to assess glucose tolerance and insulin response. Other exemplary methods that can be used to confirm the efficacy of Eno1 in normalizing blood glucose and insulin response are provided below. Methods to assess body composition and metabolism are also provided below.

Intraperitoneal Insulin Tolerance Test (IPITT)

Insulin tolerance test (ITT) is performed after 1 hour fasting to assess pyruvate metabolism. Initial blood glucose levels is determined, followed by injection (ip) of human insulin (1-2 U/kg; Humulin R; Eli Lilly, Indianapolis, Ind.). Blood glucose levels are measured from the tail vein as described above at 15, 30, 60, 90, and 120 min after the insulin injection. The insulin injection amount is determined empirically by insulin response due to the onset of the hepatic insulin resistance in the mice subjected to the high fat diet.

Intraperitoneal Pyruvate Tolerance Test (IPPTT)

Pyruvate challenge test is administered after 6 h of fasting. Initial blood glucose levels are determined, followed by injection (ip) of pyruvate dissolved in saline (2 g/kg; Sigma, St. Louis, Mo.). Blood glucose levels are measured from the tail vein as described above at 15, 30, 60, 90, and 120 min after the pyruvate injection. The area under the curve (AUC) during the test is calculated.

Fed Blood Glucose Levels

Blood samples are obtained from mice fed ad libitum either randomly or at a defined time or time interval after administration of an agent of interest. Blood glucose levels are measured.

Fasting Blood Glucose Levels

Blood samples are obtained from mice after a fast of a predefined time period (typically about 6-8 hours) at a defined time or time interval after administration of an agent of interest. Blood glucose levels are measured.

Assessment of Indicator Levels to Assess Blood Glucose Levels

Mouse models of type 1 or type 2 diabetes are treated with one or more agents of the invention and appropriate controls. Levels of HbA1c and/or Eno1 protein and/or RNA are monitored to determine blood glucose levels over a sustained period.

Dual-Energy X-Ray Absorptiometry (DEXA)

The body mass composition of different treatment groups is determined by dual-energy x-ray absorptiometry (DEXA) scanning using LUNAR PIXImus® mouse densitometer following the procedures recommended by the manufacturer. Lean body mass, fat body mass, total body tissue weight, bone density, and bone mineral content are recorded and analyzed.

Comprehensive Lab Animal Monitoring System (CLAMS)

The CLAMS (Columbus Instruments, Columbus, Ohio, USA) metabolic monitoring cages are used to simultaneously monitor horizontal and vertical activity, feeding and drinking, oxygen consumption, and $CO_2$ production. ASO injected and control mice are individually placed in CLAMS cages and monitored over a 4-day period after acclimation to the cages for 1-2 days. The various parameters are recorded in both fasted and fed conditions. Food and water consumption are measured directly as accumulated data. Hourly files display all measurements for each parameter: volume of oxygen consumed, ml/kg per h ($VO_2$), volume of carbon dioxide produced, ml/kg per h ($VCO_2$), respiratory exchange ratio, heat (kcal/h), accumulated food (g), accumulated drink (g), XY total activity (all horizontal beam breaks in counts), XY ambulatory activity (minimum three different, consecutive horizontal beam breaks in counts), and Z activity (all vertical beam breaks in counts). The data are recorded during the 30-s sampling period. The CLAMS data are analyzed by normalizing with lean body mass.

Figure 21:
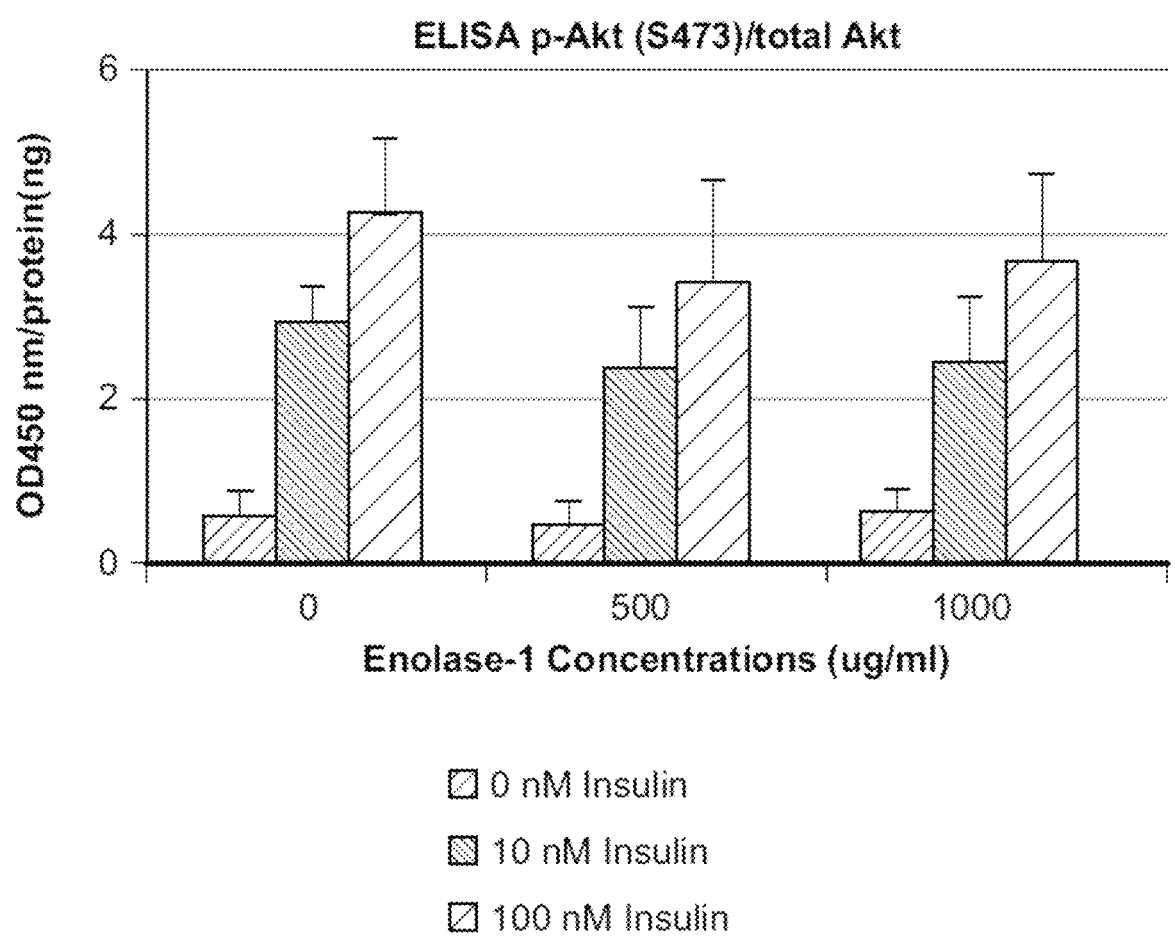
FIG. 21 shows p-Akt protein levels in human skeletal muscle myotubes with or without Eno1 and insulin treatment.

Example 12—Effect of Eno1 on Insulin Stimulated p-Akt in Human Skeletal Muscle Myotubes The effect of purified Eno-1 on insulin stimulated p-Akt (S473) protein levels was determined in cell cultures of human skeletal muscle myotubes with our without insulin treatment. p-Akt protein levels were measured by ELISA. As shown in FIG. 21, insulin treatment increased p-Akt protein levels in the absence of Eno1 treatment, and the effect of insulin on p-Akt protein levels was similar with or without Eno1 treatment. These results indicate that Eno1 does not influence insulin stimulation of p-Akt protein levels, suggesting that the effects of Eno1 on glucose uptake in muscle cells are independent of insulin and would occur in cells exhibiting insulin resistance.

Example 13—Eno1 is Associated with Increased Glucose Flux in Human Skeletal Muscle Myotubes Glucose transporter 1 (Glut1) and Glucose transporter 4 (Glut4) are involved in the transport of glucose across the plasma membrane and are the predominant facilitative glucose transporters within skeletal muscle (Jones et al., 1998, Journal of Applied Physiology, Vol. 84, pp. 1661-1666). Glut4 is responsible for insulin-regulated glucose transport into the cell. Myogenin is a muscle specific transcription factor that may be involved in regulating Glut1 and Glut4 expression (see Jones et al., above). Hexokinase 2 (HK2) phosphorylates glucose to form glucose-6-phosphate (G6P) and is the predominant hexokinase in skeletal muscle.

Figure 22A:
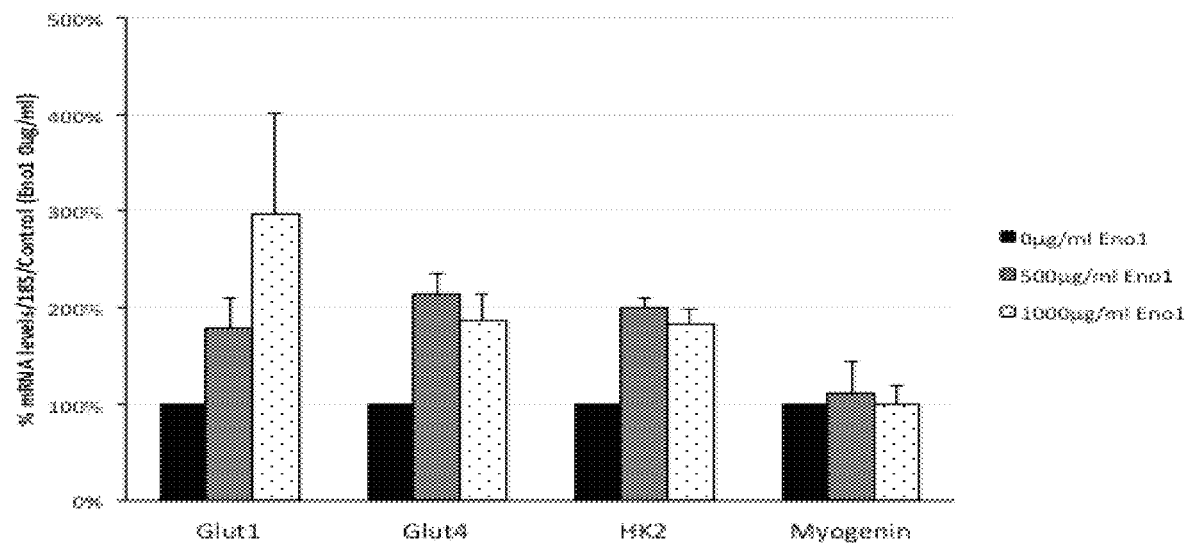
FIG. 22A shows Glut1, Glut4, HK2 and Myogenin mRNA levels in human skeletal muscle myotubes with or without treatment with purified Eno1.
Figure 22B:
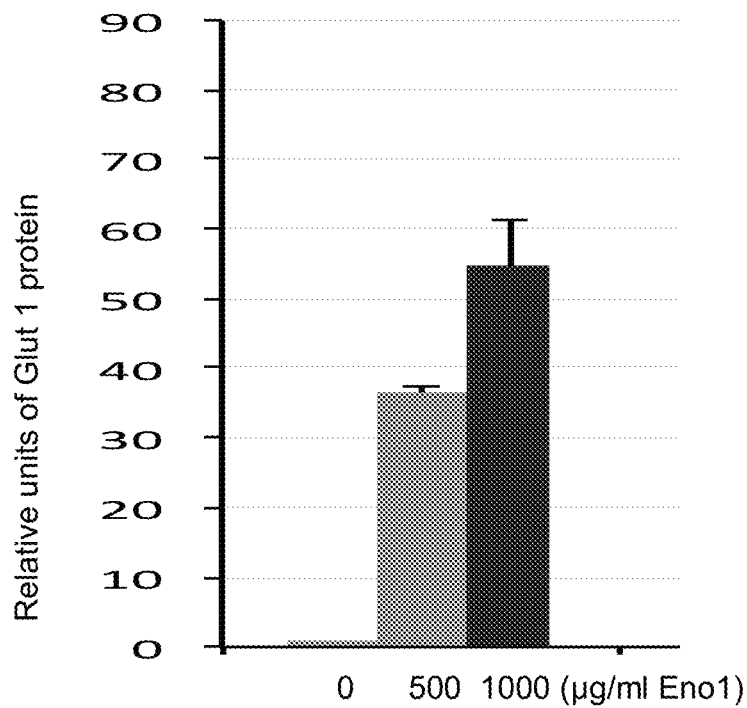
FIG. 22B shows Glut1 protein levels in human skeletal muscle myotubes with or without treatment with purified Eno1. Glut 1 protein levels are relative units normalized by the ribosomal proteins median.

Expression of Glut1, Glut 4, HK2 and myogenin was measured in cell cultures of human skeletal muscle myotubes with or without Eno1 treatment. The myotubes were treated with purified Eno1 which was prepared as described in Example 2. Glut1, Glut4, HK2 and myogenin mRNA levels were determined by quantitative PCR. Glut1 protein levels were determined by MS proteomics analysis. As shown in FIGS. 22A and 22B, Eno1 treatment increased Glut1, Glut4 and HK2 mRNA levels, and Glut1 protein levels. Because these proteins are involved in glucose transport and metabolism, these results indicate that Eno1 treatment is associated with increased glucose flux in skeletal muscle.

Figure 23:
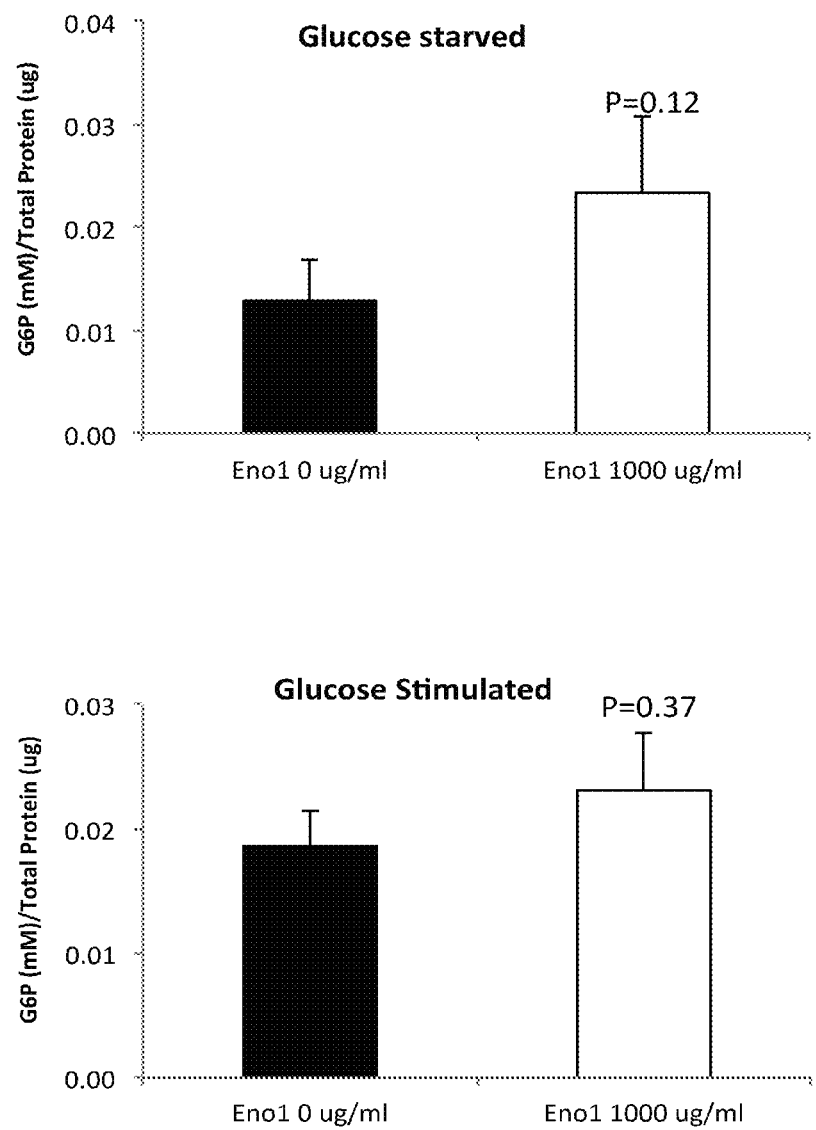
FIG. 23 shows glucose-6-phosphate (G6P) levels in glucose starved (top panel) and glucose stimulated (bottom panel) human skeletal muscle myotubes with or without treatment with purified Eno1.
Figure 24:
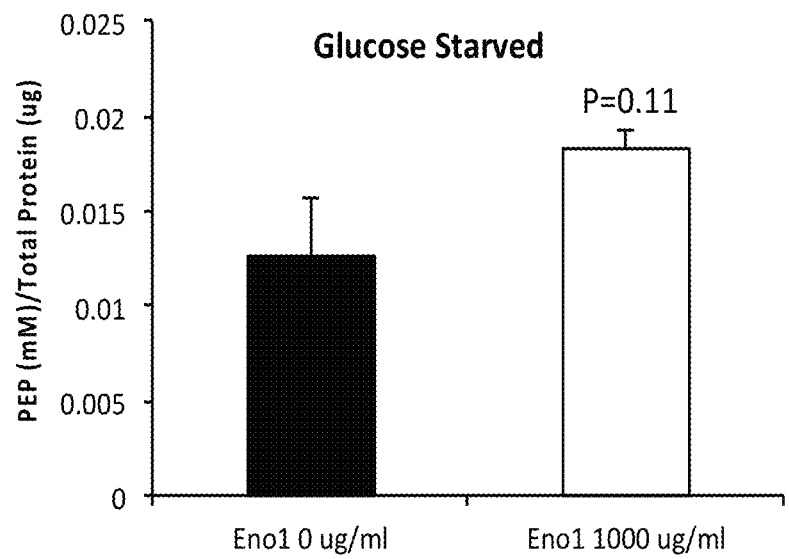
FIG. 24 shows phosphoenol pyruvate (PEP) levels in glucose starved (top panel) and glucose stimulated (bottom panel) human skeletal muscle myotubes with or without treatment with purified Eno1.
Figure 24:
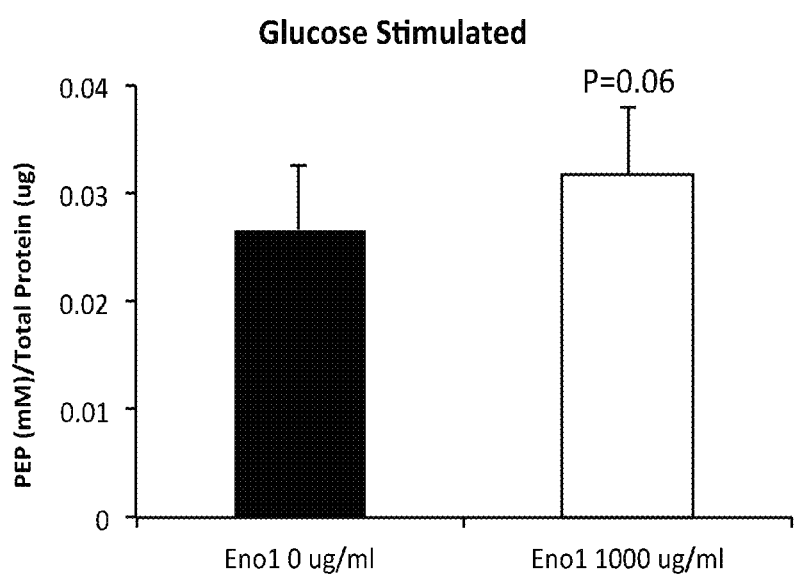

To further investigate the role of Eno1 in glucose flux, G6P and phosphoenol pyruvate (PEP) levels were measured in glucose starved and glucose stimulated human skeletal muscle myotubes with or without treatment with purified Eno1. Glucose starving was performed by incubating the myotubes in glucose free DMEM for 15 min. Glucose stimulation was performed by treating the myotubes with 5 mM glucose for 15 min. G6P and PEP levels were measured using assay kits from Biovision (Milpitas, Calif.; Cat. Nos. K657-100 and K365-100). As shown in FIGS. 23 and 24, Eno1 treatment increased G6P and PEP levels in both glucose starved and glucose stimulated human skeletal muscle myotubes, further indicating that Eno1 treatment is associated with increased glucose flux in skeletal muscle.

Example 14—Eno1 Mode of Action

To further investigate the mode of action of Eno1 in glucose uptake, the oxygen consumption rate (OCR) and extracellular acidification rate (ECAR) were measured in human skeletal muscle myotube cells. OCR is an indicator of mitochondrial respiration and ECAR is an indicator of glycolysis.

Figure 25:
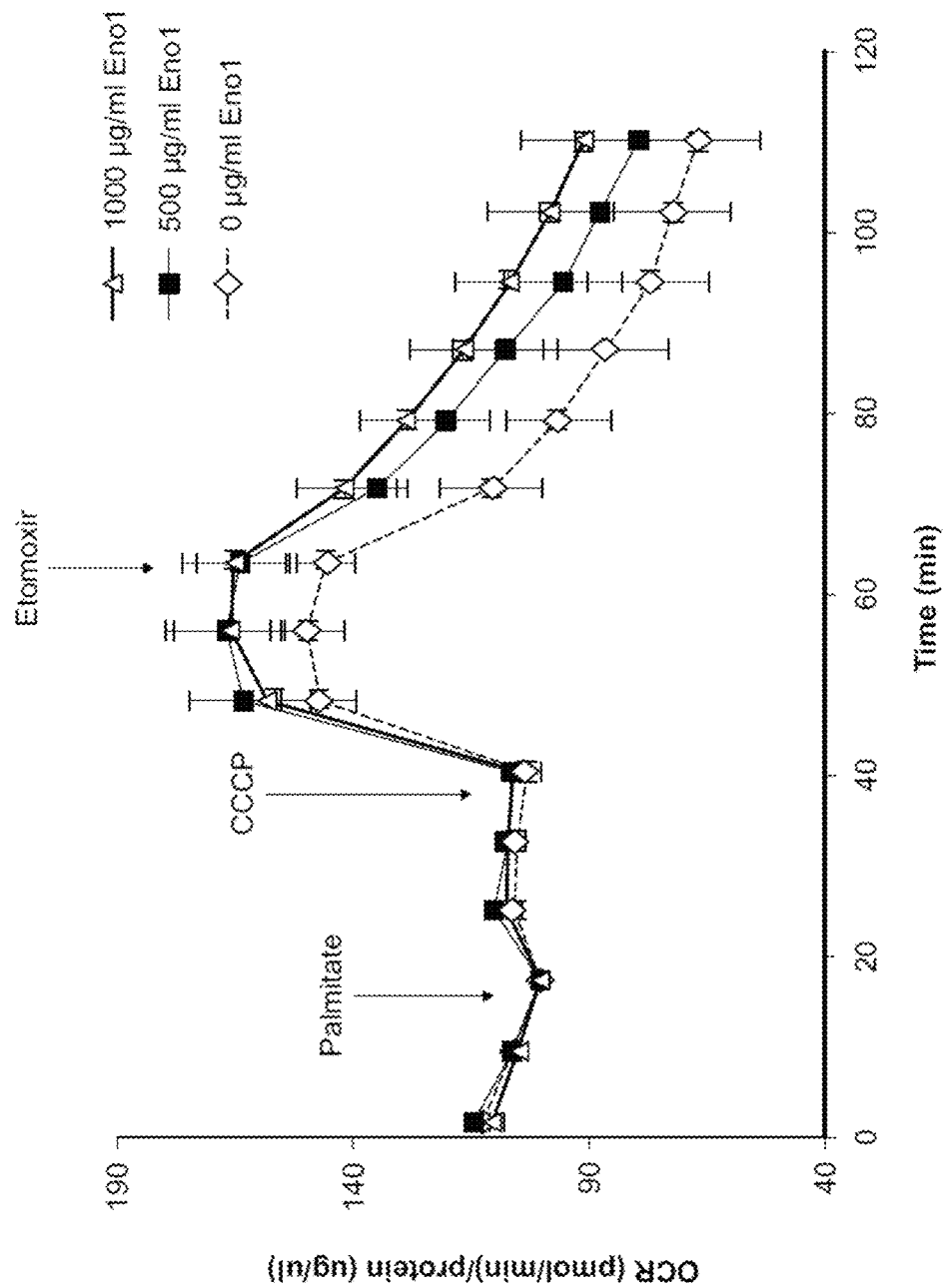
FIG. 25 shows the oxygen consumption rate (OCR) in human skeletal muscle myotube (HSMM) cultures treated sequentially with palmitate, CCCP and etomoxir with or without treatment with purified Eno1.

For OCR experiments, various compounds were added sequentially to the cells to induce changes in OCR. For example palmitate and carbonyl cyanide m-chlorophenylhydrazone (CCCP, an uncoupler of oxidative phosphorylation) were added to increase OCR and etomoxir (a fatty acid oxidation inhibitor) was added to decrease OCR. KHB buffer (pH 7.4) was added to each well and measurements were performed every 3 min with 2 min intermeasurement mixing. BSA-conjugated palmitate (final concentration 200 mmol/L), CCCP (final concentration 2 µM) and etomoxir (final concentration 50 mmol/L) were injected sequentially. As shown in FIG. 25, Eno1 treatment increased OCR. These results indicate that Eno1 treatment is associated with increased mitochondrial free fatty acid oxidation in human skeletal muscle myotubes.

Figure 26:
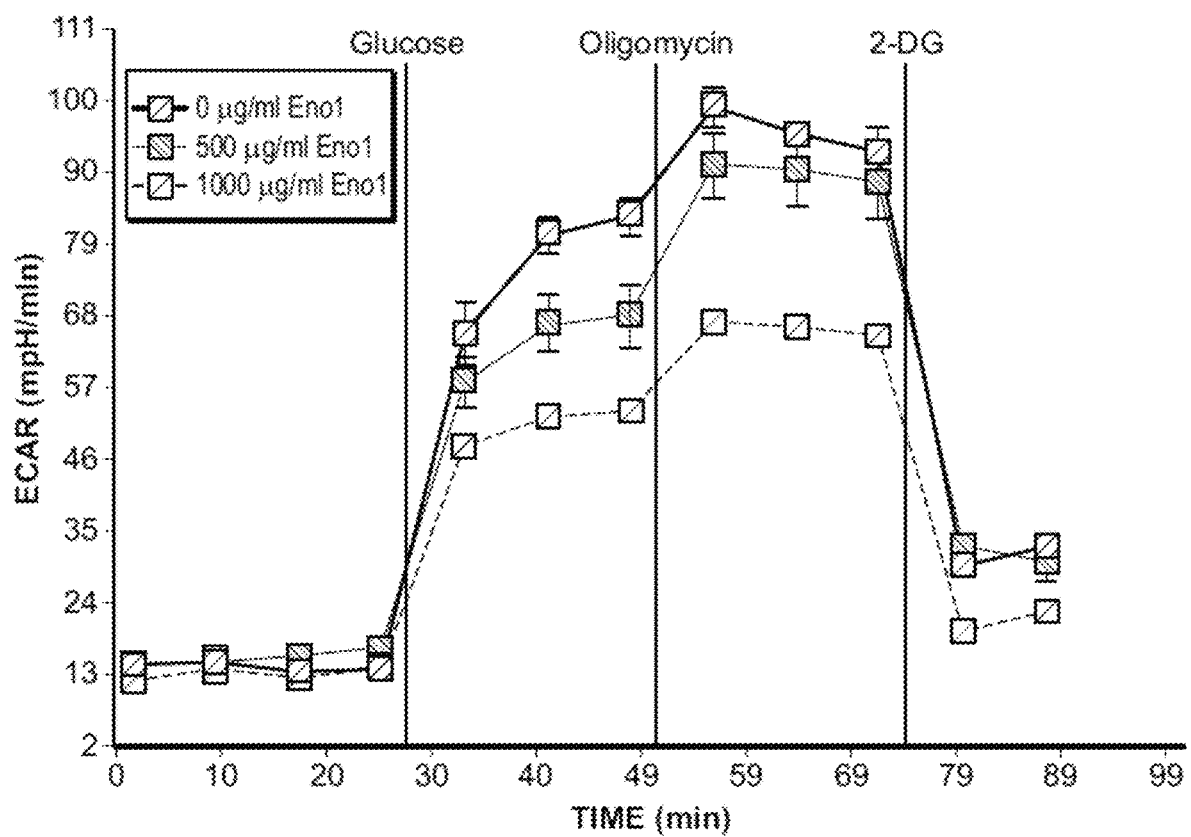
FIG. 26 shows the extracellular acidification rate (ECAR) in human skeletal muscle myotube (HSMM) cultures treated sequentially with glucose, oligomycin and 2-DG with or without treatment with purified Eno1.

For ECAR experiments with glucose as a substrate, sodium carbonate and glucose/pyruvate-free DMEM were used. Glucose, oligomycin and 2-DG were injected sequentially to give final concentrations of 25 mmol/L. As shown in FIG. 26, Eno1 treatment increased ECAR, indicating that Eno1 treatment is associated with increased glycolytic activity and capacity.

Figure 27A:
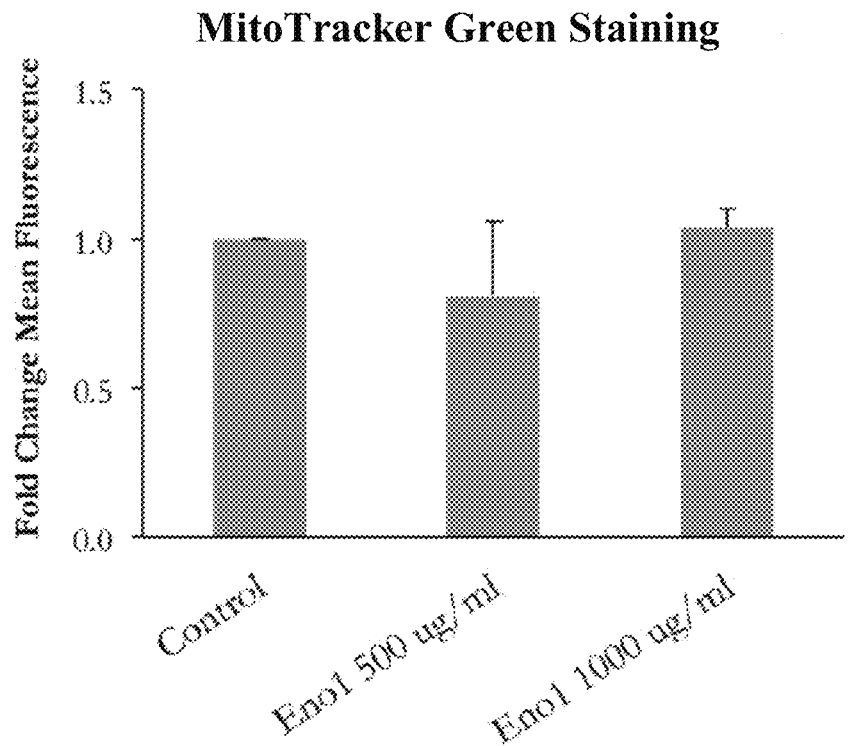
FIG. 27A shows mitochondrial content in human skeletal muscle myotubes treated with 500 µg/ml or 1000 µg/ml Eno1 relative to untreated control human skeletal muscle myotubes. Mitochondrial content was determined by adding Mitotracker Green, a green fluorescent mitochondrial stain, to the cells after 48 hours of Eno1 treatment.

To determine the mitochondrial content of human skeletal muscle myotubes treated with Eno1, myotubes were treated with 500 ug/ml or 1000 µg/ml Eno1 for 48 hours and then Mitotracker green (Invitrogen), a green fluorescent mitochondrial stain, was added. After 15 min of staining, the myotubes were trypsinized, washed, and subjected to flow cytometry to determine mitochondrial content. As shown in FIG. 27A, Eno1 treatment does not influence mitochondrial content.

Figure 27B:
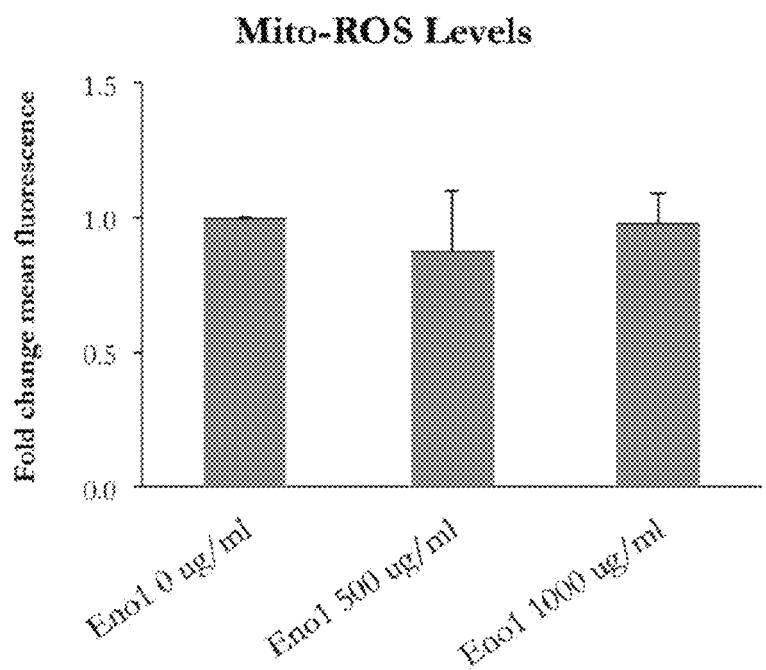
FIG. 27B shows mitochondrial reactive oxygen species (Mito-ROS) production in human skeletal muscle myotubes treated with 500 ug/ml or 1000 µg/ml Eno1 relative to untreated control human skeletal muscle myotubes (Eno1 0 ug/ml). Mito-ROS was determined by treating cells with Dihydrorhodamin 123, an uncharged and nonfluorescent reactive oxygen species (ROS) indicator that can passively diffuse across membranes where it is oxidized to cationic rhodamine 123 which localizes in the mitochondria and exhibits green fluorescence. After dihydrorhodamin 123 treatment, myotubes were trypsinized, washed, and subjected to flow cytometry to determine Mito-ROS levels.

Mitochondrial ROS was also detected in the Eno1 treated human skeletal muscle myotubes described above. Mitochondrial ROS was determined by treating cells with Dihydrorhodamin 123 (Life Technologies), an uncharged and nonfluorescent reactive oxygen species (ROS) indicator that can passively diffuse across membranes where it is oxidized to cationic rhodamine 123 which localizes in the mitochondria and exhibits green fluorescence. The myotubes were then trypsinized, washed, and subjected to flow cytometry. Treatment of human skeletal muscle myotubes with Eno1 did not affect mitochondrial reactive oxygen species production (FIG. 27B).

These results indicate that the mode of action of Eno1 is not due to changes in mitochondrial content or ROS production.

Figure 28A:
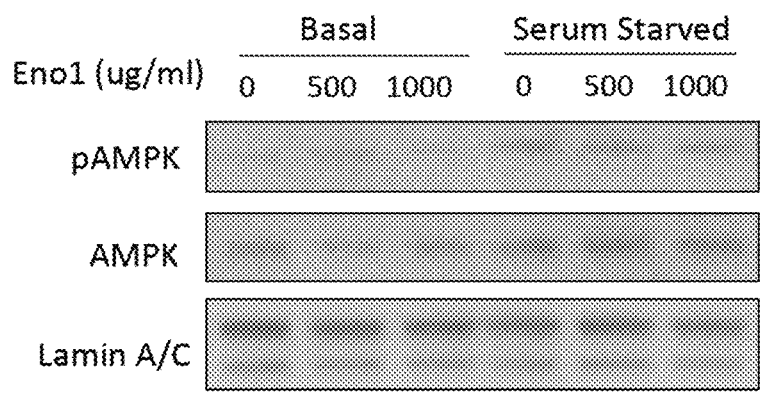
FIG. 28A shows 5' AMP activated protein kinase (AMPK) and phosphorylated AMPK (pAMPK) levels in skeletal muscle myotubes treated with 0, 500, or 1000 µg/ml Eno1. Lamin A/C was used as the loading control.
Figure 28B:
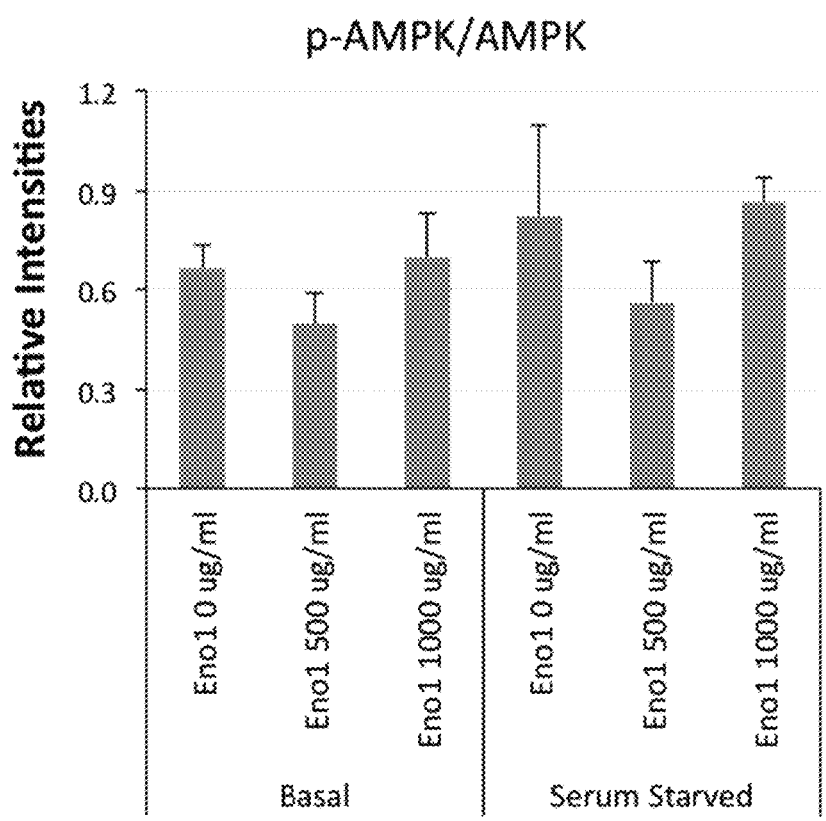
FIG. 28B shows the ratio of pAMPK (p-AMPK) to AMPK in basal and serum starved skeletal muscle myotubes treated with 0, 500, or 1000 µg/ml Eno1.

To further investigate the mode of action for Eno1, non-phosphorylated 5' AMP activated protein kinase (AMPK) and phosphorylated AMPK (pAMPK) levels were measured in basal and serum starved human skeletal muscle myotubes treated with 0, 500, or 1000 µg/ml Eno1. Basal human skeletal muscle myotubes were treated with normal differentiation medium containing 2% horse serum, while serum-starved myotubes were starved with serum free DMEM containing 0.5% BSA for 3 hours before lysis of the myotubes. AMPK and pAMPK levels were determined by Western blot using antibodies specific to the phosphorylated or non-phosphorylated form of the kinase. An antibody specific to Lamin A/C was used to confirm even loading among samples. As shown in FIGS. 28A and 28B, Eno1 treatment did not affect pAMPK levels in basal or serum starved myotubes. AMPK activation or phosphorylation is one of the major insulin independent pathways that regulate glucose uptake in skeletal muscle, for example during muscle contraction. Accordingly, the lack of an effect of Eno1 on pAMPK levels suggest a novel mode of action for Eno1 beyond conventional signal transduction.

Example 15—Eno1 Binding Partners in Human Skeletal Muscle Myotubes

To further investigate the mode of action for Eno1, the binding partners of Eno1 were compared in untreated human skeletal muscle myotubes (containing endogenous Eno1) and human skeletal muscle myotubes treated with 50 µg/ml or 100 µg/ml of 6×Histidine tagged exogenous Eno1. Endogenous Eno1 was immunoprecipitated in the untreated myotubes using an antibody specific to Eno1. The exogenous Eno1 was immunoprecipitated using the 6×Histidine Tag antibody. The binding partners of endogenous Eno1 and exogenous Eno1 were identified by quantitative proteomics, and the identity of the binding partners was confirmed by Western blot and/or reverse immunoprecipitation.

Figure 29:
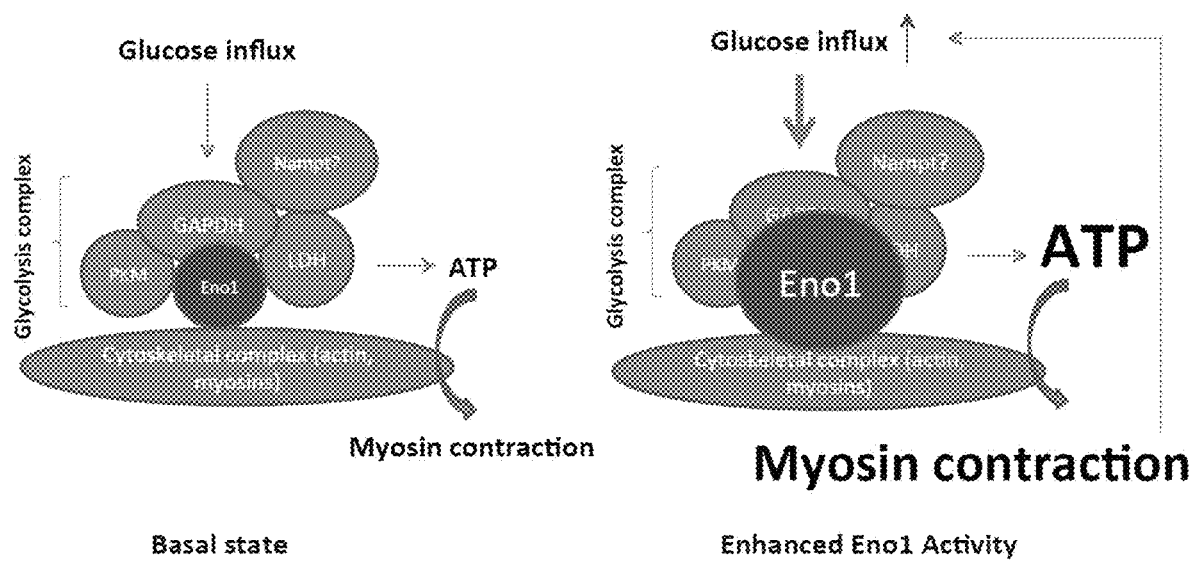
FIG. 29 shows a schematic of a working model describing the potential role of Nampt in the mode of action for Eno1.

Nicotinamide phosphoribosyltransferase (Nampt) was identified as a binding partner of both endogenous and exogenous Eno1. Nampt catalyzes the synthesis of nicotinamide mononucleotide (NMN) from nicotinamide and is involved in muscle contraction and secretion. Eno1 may interact with Nampt as part of the glycolysis complex, as depicted in FIG. 29.

Example 16—Interaction of Eno1 and Nampt

Figure 30:
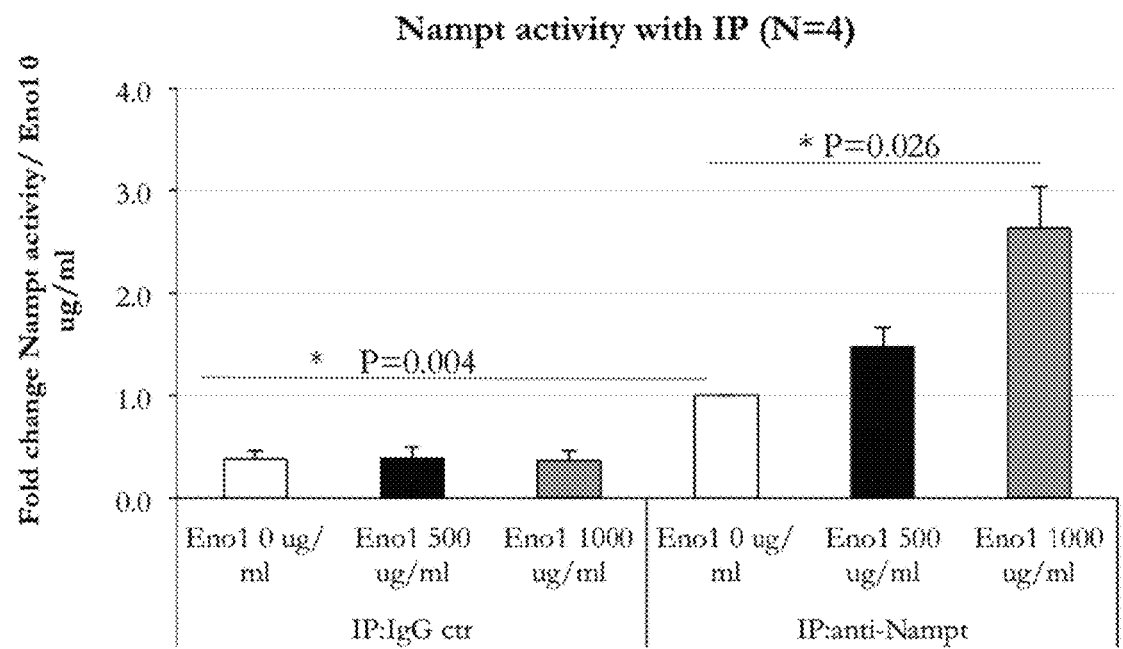
FIG. 30 shows Nampt activity in human skeletal muscle myotubes treated with 500 ug/ml or 1000 µg/ml Eno1 in differentiation medium for 48 hours after 4 days of differentiation relative to untreated control human skeletal muscle myotubes (Eno1 0 ug/ml).

Nampt activity was determined in human skeletal muscle myotubes treated with 500 ug/ml or 1000 µg/ml Eno1 in differentiation medium for 48 hours after 4 days of differentiation. Myotube lysates were subjected to immunoprecipitation using either IgG or anti-Nampt antibody (Clone AF-1E12) from Cyclex (Nagano, Japan). The immunoprecipitated myotube lysates were subjected to Nampt activity assay using Cyclex Nampt activity assay kit (#CY-1251). As shown in FIG. 30, Eno1 treatment increased Nampt activity. Eno1 treatment also increased secretion of Nampt (eNampt) in human skeletal muscle myotubes (data not shown).

Figure 31:
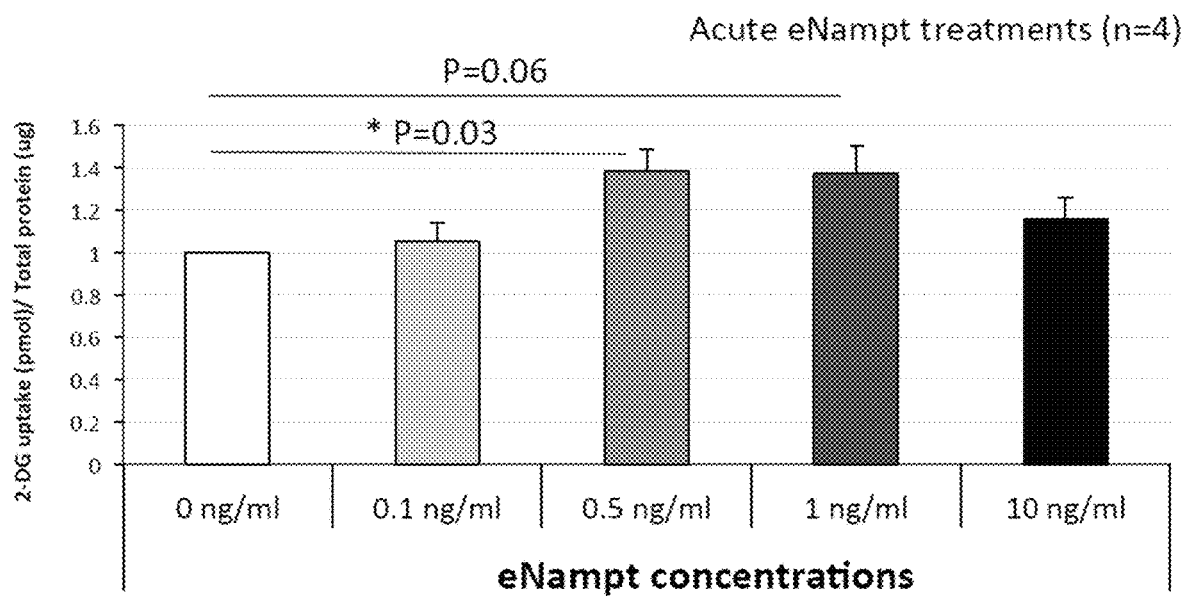
FIG. 31 shows 2-DG uptake in serum starved human skeletal muscle myotubes treated with recombinant extracellular Nampt (eNampt).

2-DG uptake was measured in human skeletal muscle myotubes which had been serum starved for 3 hours and then treated with recombinant extracellular Nampt (eNampt) from Abcam (Cambridge, Mass.). 2-DG uptake was measured using a fluorometric glucose uptake assay kit from Abcam (Cat. No. ab136956). As shown in FIG. 31, addition of eNampt increased 2-DG uptake.

Figure 32:
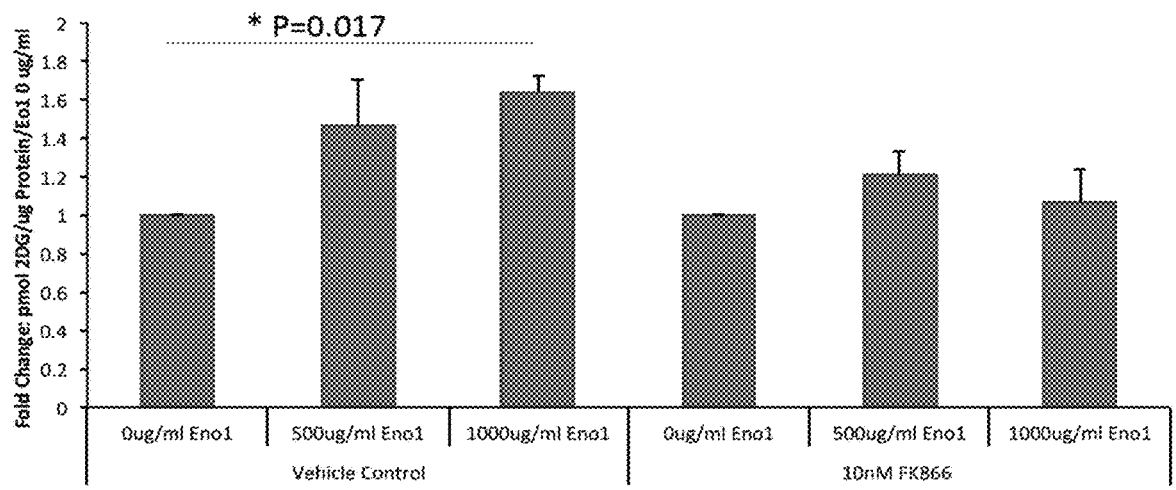
FIG. 32 shows glucose uptake in human skeletal muscle myotube cultures treated with 0, 500 or 1000 µg/ml Eno1 in differentiation medium for 48 hours after 4 days of differentiation in the presence or absence of the Nampt inhibitor FK866. FK866 was added 24 hours after initiation of Eno1 treatment, and the myotubes were treated with FK866 for 24 hours. 2-DG uptake was measured after 3 hours serum starvation. Nampt inhibition by FK866 abolished Eno1 induced glucose uptake.

To determine the role of Nampt in Eno1 induced glucose uptake, human skeletal muscle myotubes were treated with Eno1 for 48 hours as described above, and the Nampt inhibitor FK866 was added 24 hours after initiation of Eno1 treatment, for a total FK866 treatment time of 24 hours. 2-DG uptake was measured after 3 hours serum starvation using the Abcam glucose uptake assay kit described above. As shown in FIG. 32, Nampt inhibition by FK866 abolished Eno1 induced glucose uptake. This result indicates that Nampt plays a role in Eno1 induced glucose uptake.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

Each reference, patent, patent application, and GenBank number referred to in the instant application is hereby incorporated by reference as if each reference were noted to be incorporated individually.

DESCRIPTION OF SEQUENCES

| SEQ ID NO: | Sequence | Description |
| --- | --- | --- |
| 1 | DNA | Human Eno1, transcript variant 1. |
| 2 | AA | Human Eno1, transcript variant 1. |
| 3 | DNA | Human Eno1, transcript variant 2. |
| 4 | AA | Human Eno1, transcript variant 2, also referred to as c-myc promoter-binding protein-1 (MBP-1). |
| 5 | DNA | Human Eno2. |
| 6 | AA | Human Eno2. |
| 7 | DNA | Human Eno3, transcript variant 1. Encodes isoform 1 of Eno3. |
| 8 | DNA | Human Eno3, transcript variant 2. Encodes isoform 1 of Eno3. |
| 9 | AA | Human Eno3, isoform 1. |
| 10 | DNA | Human Eno3, transcript variant 3. Encodes isoform 2 of Eno3. |
| 11 | AA | Human Eno3, isoform 2. |

The invention claimed is:

1. A pharmaceutical composition comprising:
   (a) a therapeutically effective amount of an enolase 1 (Eno1) polypeptide or a fragment thereof; and
   (b) a muscle targeting moiety,
   wherein the muscle targeting moiety and the Eno1 polypeptide or a fragment thereof are in a complex.

2. The pharmaceutical composition of claim 1, wherein the Eno1 polypeptide is human Eno1 polypeptide.

3. The pharmaceutical composition of claim 1, wherein the composition further comprises a microparticle, a nanoparticle, an in situ forming composition, or a liposome.

4. The pharmaceutical composition of claim 1, wherein the muscle targeting moiety is a skeletal muscle targeting moiety.

5. The pharmaceutical composition of claim 1, wherein the composition is formulated for parenteral administration.

6. The pharmaceutical composition of claim 1, wherein the composition is formulated for oral administration.

7. The pharmaceutical composition of claim 1, wherein the composition is formulated for intramuscular administration, intravenous administration, or subcutaneous administration.

8. A method of decreasing blood glucose in a subject with elevated blood glucose, the method comprising administering to the subject the pharmaceutical composition of claim 1, thereby decreasing blood glucose in the subject.

9. A method of treating diabetes in a subject, the method comprising administering to the subject the pharmaceutical composition of claim 1, thereby treating diabetes in the subject.

10. The method of claim 9, wherein the diabetes is type 2 diabetes or type 1 diabetes.

11. The method of claim 8, wherein the Eno1 polypeptide is administered parenterally.

12. The method of claim 11, wherein the Eno1 polypeptide is administered by a route selected from the group consisting of intramuscular, intravenous, and subcutaneous.

13. The method of claim 8, wherein the subject is human.

14. The method of claim 9, wherein the Eno1 polypeptide is administered parenterally.

15. The method of claim 14, wherein the Eno1 polypeptide is administered by a route selected from the group consisting of intramuscular, intravenous, and subcutaneous.

16. The method of claim 9, wherein the subject is human.

* * * * *

SEQUENCE LISTING

```
<160> NUMBER OF SEQ ID NOS: 16

<210> SEQ ID NO 1
<211> LENGTH: 2204
<212> TYPE: DNA
<213> ORGANISM: Homo sapiens

<400> SEQUENCE: 1
gtggggcccc agagcgacgc tgagtgcgtg cgggactcgg agtacgtgac ggagcccga       60 gctctcatgc ccgccacgcc gccccgggcc atccccgga gccccggctc cgcacacccc      120
agttcggctc accggtccta tctggggcca gagtttcgcc cgcaccacta cagggccgct     180
ggggagtcgg ggccccccag atctgcccgc ctcaagtccg cgggacgtca ccccccttc     240 cacgctactg cagccgtcgc agtcccaccc ctttccggga ggtgagggaa tgagtgacgg     300
ctctcccgac gaatggcgag gcggagctga ggggcgtgc cccggaggcg ggaagtgggt      360
ggggctcgcc ttagctaggc aggaagtcgg cgcgggcggc gcggacagta tctgtgggta     420
cccggagcac ggagatctcg ccggctttac gttcacctcg gtgtctgcag caccctccgc     480
ttcctctcct aggcgacgag acccagtggc tagaagttca ccatgtctat tctcaagatc     540
catgccaggg agatctttga ctctcgcggg aatcccactg ttgaggttga tctcttcacc     600
tcaaaaggtc tcttcagagc tgctgtgccc agtggtgctt caactggtat ctatgaggcc     660
```

```
ctagagctcc gggacaatga taagactcgc tatatgggga agggtgtctc aaaggctgtt    720
gagcacatca ataaaactat tgcgcctgcc ctggttagca agaaactgaa cgtcacagaa    780
caagagaaga ttgacaaact gatgatcgag atggatggaa cagaaaataa atctaagttt    840
ggtgcgaacg ccattctggg ggtgtccctt gccgtctgca aagctggtgc cgttgagaag    900
ggggtccccc tgtaccgcca catcgctgac ttggctggca actctgaagt catcctgcca    960
gtcccggcgt tcaatgtcat caatggcggt tctcatgctg caacaagct  ggccatgcag   1020 gagttcatga tcctcccagt cggtgcagca aacttcaggg aagccatgcg cattggagca   1080
gaggtttacc acaacctgaa gaatgtcatc aaggagaaat atgggaaaga tgccaccaat   1140 gtggggatg aaggcgggtt tgctcccaac atcctggaga ataagaagg cctggagctg    1200 ctgaagactg ctattgggaa agctggctac actgataagg tggtcatcgg catggacgta   1260
gcggcctccg agttcttcag gtctgggaag tatgacctgg acttcaagtc tcccgatgac   1320
cccagcaggt acatctcgcc tgaccagctg gctgacctgt acaagtcctt catcaaggac   1380
tacccagtgg tgtctatcga agatcccttt gaccaggatg actggggagc ttggcagaag   1440
ttcacagcca gtgcaggaat ccaggtagtg ggggatgatc tcacagtgac caacccaaag   1500
aggatcgcca aggccgtgaa cgagaagtcc tgcaactgcc tcctgctcaa agtcaaccag   1560
attggctccg tgaccgagtc tcttcaggcg tgcaagctgg cccaggccaa tggttggggc   1620
gtcatggtgt ctcatcgttc ggggagact gaagataccct tcatcgctga cctggttgtg   1680
gggctgtgca ctgggcagat caagactggt gccccttgcc gatctgagcg cttggccaag   1740
tacaaccagc tcctcagaat tgaagaggag ctgggcagca aggctaagtt tgccggcagg   1800
aacttcagaa accccttggc caagtaagct gtgggcaggc aagcccttcg gtcacctgtt   1860
ggctacacag acccctcccc tcgtgtcagc tcaggcagct cgaggccccc gaccaacact   1920
tgcaggggtc cctgctagtt agcgccccac cgccgtggag ttcgtaccgc ttccttagaa   1980
cttctacaga agccaagctc cctggagccc tgttggcagc tctagctttg cagtcgtgta   2040
attggcccaa gtcattgttt ttctcgcctc actttccacc aagtgtctag agtcatgtga   2100
gcctcgtgtc atctccgggg tggccacagg ctagatcccc ggtggttttg tgctcaaaat   2160
aaaaagcctc agtgacccat gagaataaaa aaaaaaaaa aaaa                    2204
```

<210> SEQ ID NO 2
<211> LENGTH: 434
<212> TYPE: PRT
<213> ORGANISM: Homo sapiens

<400> SEQUENCE: 2

```
Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95
```

Met Asp Gly Thr Glu Asn Lys Ser Lys Phe Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
            165                 170                 175

Asn Phe Arg Glu Ala Met Arg Ile Gly Ala Glu Val Tyr His Asn Leu
        180                 185                 190

Lys Asn Val Ile Lys Glu Lys Tyr Gly Lys Asp Ala Thr Asn Val Gly
    195                 200                 205

Asp Glu Gly Gly Phe Ala Pro Asn Ile Leu Glu Asn Lys Glu Gly Leu
210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
            245                 250                 255

Tyr Asp Leu Asp Phe Lys Ser Pro Asp Asp Pro Ser Arg Tyr Ile Ser
        260                 265                 270

Pro Asp Gln Leu Ala Asp Leu Tyr Lys Ser Phe Ile Lys Asp Tyr Pro
    275                 280                 285

Val Val Ser Ile Glu Asp Pro Phe Asp Gln Asp Asp Trp Gly Ala Trp
290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
            325                 330                 335

Cys Asn Cys Leu Leu Leu Lys Val Asn Gln Ile Gly Ser Val Thr Glu
        340                 345                 350

Ser Leu Gln Ala Cys Lys Leu Ala Gln Ala Asn Gly Trp Gly Val Met
    355                 360                 365

Val Ser His Arg Ser Gly Glu Thr Glu Asp Thr Phe Ile Ala Asp Leu
370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
            405                 410                 415

Leu Gly Ser Lys Ala Lys Phe Ala Gly Arg Asn Phe Arg Asn Pro Leu
        420                 425                 430

Ala Lys

<210> SEQ ID NO 3
<211> LENGTH: 2567
<212> TYPE: DNA
<213> ORGANISM: Homo sapiens

<400> SEQUENCE: 3
aactaaagaa aagtttcccc atctcccagg agggttctgt gggccctcca gagatcatca     60
gcctcttcac gggctagaaa ggatccaggg aaggtctaac caatgacctg ccctgaatgg    120
tgagctgcag gtgtgtcatt tagtgtgatt ttcctgttga ctgactcata ggagccctgc    180

```
tctgtggcag agctagcctc tgctgtatt caaattgact tagtgtgtgt gcaacattga      240
cctttctaga gatagaacat gtggccaaat tacagaaaag cataggggc tagatcacgc      300 attctcagtg gggcacccgg aaaactccaa aaaggctgca gggaggggac aatgatgaaa      360
tcaggttgtg aaacactggg ctggtgtcgc agtggtggtg ctgggtgttc agtcccgctt      420
taatgctgta agaagcactc tacacacacg aacatgttac catttgaccg ttgtttaatg      480
gcgtacgtgg ggacttagcc ggagcaggat gatgctgtgc cttgatggta atgagtgctc      540
agtaagtaag catttgtgga agattgaacg catggcccct gaaatgctct cctctgcttt      600
cctgccccct cactgtctct cactcgcagt ccttaatcac cggttctctt ctgagtctct      660 ctcattttc cttcttcatc ctctgctggg caggcgtctc cagacccatt aagtatatta      720
atgagttcct ggcaccagcc ctgtgcactc aggtaactga ttgaacagcc tttagtctgc      780
agttggcgtt tccagtgcat ggtcttgcaa actaacctcc agtcagatcg ttctgagcca      840
gctgctgttt tgtgtggctc taaccctctg gggtcctagg taggagcact cagactgggc      900
cggaaagtcc tccgattctg gggggaaagg ggagaggggg aagaggtccc acagaaggtc      960
ccttggtggg cttccgcgtc ggcctcaaca gtggttctct ctaacaatgc tgctcaagcc     1020
tgttttaaag ttaatgtcag taatttgatt tgattgttcc ttccaggtgt ctcaaaggct     1080
gttgagcaca tcaataaaac tattgcgcct gccctggtta gcaagaaact gaacgtcaca     1140
gaacaagaga agattgacaa actgatgatc gagatggatg gaacagaaaa taaatctaag     1200
tttggtgcga acgccattct gggggtgtcc cttgccgtct gcaaagctgg tgccgttgag     1260 aaggggggtcc ccctgtaccg ccacatcgct gacttggctg gcaactctga agtcatcctg     1320
ccagtcccgg cgttcaatgt catcaatggc ggttctcatg ctggcaacaa gctggccatg     1380
caggagttca tgatcctccc agtcggtgca gcaaacttca gggaagccat gcgcattgga     1440
gcagaggttt accacaacct gaagaatgtc atcaaggaga aatatgggaa agatgccacc     1500
aatgtggggg atgaaggcgg gtttgctccc aacatcctgg agaataaaga aggcctggag     1560
ctgctgaaga ctgctattgg gaaagctggc tacactgata aggtggtcat cggcatggac     1620
gtagcggcct ccgagttctt caggtctggg aagtatgacc tggacttcaa gtctcccgat     1680
gaccccagca ggtacatctc gcctgaccag ctggctgacc tgtacaagtc cttcatcaag     1740
gactacccag tggtgtctat cgaagatccc tttgaccagg atgactgggg agcttggcag     1800
aagttcacag ccagtgcagg aatccaggta gtggggatg atctcacagt gaccaaccca     1860
aagaggatcg ccaaggccgt gaacgagaag tcctgcaact gcctcctgct caaagtcaac     1920
cagattggct ccgtgaccga gtctcttcag gcgtgcaagc tgcccaggc caatggttgg     1980 ggcgtcatgt gtctcatcg ttcggggag actgaagata ccttcatcgc tgacctggtt     2040
gtggggctgt gcactgggca gatcaagact ggtgccccctt gccgatctga gcgcttggcc     2100
aagtacaacc agctcctcag aattgaagag gagctgggca gcaaggctaa gtttgccggc     2160
aggaacttca gaaacccctt ggccaagtaa gctgtgggca ggcaagccct tcggtcacct     2220
gttggctaca cagacccctc ccctcgtgtc agctcaggca gctcgaggcc cccgaccaac     2280
acttgcaggg gtccctgcta gttagcgcca ccgccgtg gagttcgtac cgcttcctta     2340
gaacttctac agaagccaag ctccctggag ccctgttggc agctctagct ttgcagtcgt     2400
gtaattggcc caagtcattg tttttctcgc ctcactttcc accaagtgtc tagagtcatg     2460
tgagcctcgt gtcatctccg gggtggccac aggctagatc cccggtggtt ttgtgctcaa     2520
aataaaaagc ctcagtgacc catgagaata aaaaaaaaa aaaaaaa                    2567
```

<210> SEQ ID NO 4
<211> LENGTH: 341
<212> TYPE: PRT
<213> ORGANISM: Homo sapiens

<400> SEQUENCE: 4

Met Ile Glu Met Asp Gly Thr Glu Asn Lys Ser Lys Phe Gly Ala Asn
1               5                   10                  15

Ala Ile Leu Gly Val Ser Leu Ala Val Cys Lys Ala Gly Ala Val Glu
            20                  25                  30

Lys Gly Val Pro Leu Tyr Arg His Ile Ala Asp Leu Ala Gly Asn Ser
        35                  40                  45

Glu Val Ile Leu Pro Val Pro Ala Phe Asn Val Ile Asn Gly Gly Ser
    50                  55                  60

His Ala Gly Asn Lys Leu Ala Met Gln Glu Phe Met Ile Leu Pro Val
65              70                  75                  80

Gly Ala Ala Asn Phe Arg Glu Ala Met Arg Ile Gly Ala Glu Val Tyr
                85                  90                  95

His Asn Leu Lys Asn Val Ile Lys Glu Lys Tyr Gly Lys Asp Ala Thr
            100                 105                 110

Asn Val Gly Asp Glu Gly Gly Phe Ala Pro Asn Ile Leu Glu Asn Lys
        115                 120                 125

Glu Gly Leu Glu Leu Leu Lys Thr Ala Ile Gly Lys Ala Gly Tyr Thr
    130                 135                 140

Asp Lys Val Val Ile Gly Met Asp Val Ala Ala Ser Glu Phe Phe Arg
145                 150                 155                 160

Ser Gly Lys Tyr Asp Leu Asp Phe Lys Ser Pro Asp Pro Ser Arg
                165                 170                 175

Tyr Ile Ser Pro Asp Gln Leu Ala Asp Leu Tyr Lys Ser Phe Ile Lys
            180                 185                 190

Asp Tyr Pro Val Val Ser Ile Glu Asp Pro Phe Asp Gln Asp Asp Trp
        195                 200                 205

Gly Ala Trp Gln Lys Phe Thr Ala Ser Ala Gly Ile Gln Val Val Gly
    210                 215                 220

Asp Asp Leu Thr Val Thr Asn Pro Lys Arg Ile Ala Lys Ala Val Asn
225                 230                 235                 240

Glu Lys Ser Cys Asn Cys Leu Leu Leu Lys Val Asn Gln Ile Gly Ser
                245                 250                 255

Val Thr Glu Ser Leu Gln Ala Cys Lys Leu Ala Gln Ala Asn Gly Trp
            260                 265                 270

Gly Val Met Val Ser His Arg Ser Gly Glu Thr Glu Asp Thr Phe Ile
        275                 280                 285

Ala Asp Leu Val Val Gly Leu Cys Thr Gly Gln Ile Lys Thr Gly Ala
    290                 295                 300

Pro Cys Arg Ser Glu Arg Leu Ala Lys Tyr Asn Gln Leu Leu Arg Ile
305                 310                 315                 320

Glu Glu Glu Leu Gly Ser Lys Ala Lys Phe Ala Gly Arg Asn Phe Arg
                325                 330                 335

Asn Pro Leu Ala Lys
            340

<210> SEQ ID NO 5
<211> LENGTH: 2423
<212> TYPE: DNA

<213> ORGANISM: Homo sapiens

<400> SEQUENCE: 5

```
acccgcgctc gtacgtgcgc ctccgccggc agctcctgac tcatcggggg ctccgggtca      60
catgcgcccg cgcggcccta taggcgcctc ctccgcccgc cgcccgggag ccgcagccgc     120
cgccgccact gccactcccg ctctctcagc gccgcgtcg ccaccgccac cgccaccgcc     180
actaccaccg tctgagtctg cagtcccgag atcccagcca tcatgtccat agagaagatc     240
tgggcccggg agatcctgga ctcccgcggg aaccccacag tggaggtgga tctctatact     300
gccaaaggtc ttttccgggc tgcagtgccc agtggagcct ctacgggcat ctatgaggcc     360
ctggagctga gggatggaga caaacagcgt tacttaggca aaggtgtcct gaaggcagtg     420
gaccacatca actccaccat cgcgccagcc ctcatcagct caggtctctc tgtggtggag     480
caagagaaac tggacaacct gatgctggag ttggatggga ctgagaacaa atccaagttt     540
ggggccaatg ccatcctggg tgtgtctctg gccgtgtgta aggcagggc agctgagcgg     600
gaactgcccc tgtatcgcca cattgctcag ctggccggga actcagacct catcctgcct     660
gtgccggcct tcaacgtgat caatggtggc tctcatgctg caacaagct ggccatgcag     720
gagttcatga tcctcccagt gggagctgag agctttcggg atgccatgcg actaggtgca     780
gaggtctacc atacactcaa gggagtcatc aaggacaaat acggcaagga tgccaccaat     840
gtgggggatg aaggtggctt tgcccccaat atcctggaga acagtgaagc cttggagctg     900
gtgaaggaag ccatcgacaa ggctggctac acggaaaaga tcgttattgg catggatgtt     960
gctgcctcag agtttatcg tgatggcaaa tatgacttgg acttcaagtc tcccactgat    1020
ccttcccgat acatcactgg ggaccagctg ggggcactct accaggactt tgtcagggac    1080
tatcctgtgg tctccattga ggacccattt gaccaggatg attgggctgc ctggtccaag    1140
ttcacagcca atgtagggat ccagattgtg ggtgatgacc tgacagtgac caacccaaaa    1200
cgtattgagc gggcagtgga agaaaaggcc tgcaactgtc tgctgctcaa ggtcaaccag    1260
atcggctcgg tcactgaagc catccaagcg tgcaagctgg cccaggagaa tggctgggg    1320
gtcatggtga gtcatcgctc aggagagact gaggacacat tcattgctga cctggtggtg    1380
gggctgtgca caggccagat caagactggt gccccgtgcc gttctgaacg tctggctaaa    1440
tacaaccagc tcatgagaat tgaggaagag ctggggatg aagctcgctt tgccggacat    1500
aacttccgta atcccagtgt gctgtgattc ctctgcttgc ctggagacgt ggaacctctg    1560
tctcatcctc ctggaacctt gctgtcctga tctgtgatag ttcaccccct gagatcccct    1620
gagcccagg gtgcccagaa cttccctgat tgacctgctc cgctgctcct tggcttacct    1680
gacctcttgc tgtctctgct cgccctcctt tctgtgccct actcattggg gttccgcact    1740
ttccacttct tcctttctct ttctctcttc cctcagaaac tagaaatgtg aatgaggatt    1800
attataaaag ggggtccgtg gaagaatgat cagcatctgt gatgggagcg tcagggttgg    1860
tgtgctgagg tgttagagag ggaccatgtg tcacttgtgc tttgctcttg tcccacgtgt    1920
cttccacttt gcatatgagc cgtgaactgt gcatagtgct gggatggagg ggagtgttgg    1980
gcatgtgatc acgcctggct aataaggctt tagtgtattt attatttat ttattttatt    2040
tgtttttcat tcatcccatt aatcatttcc ccataactca atggcctaaa actgcctga    2100
cttggggaa cgatgtgtct gtatttcatg tggctgtaga tcccaagatg actggggtgg    2160
gaggtcttgc tagaatggga agggtcatag aaagggcctt gacatcagtt cctttgtgtg    2220
tactcactga agcctgcgtt ggtccagagc ggaggctgtg tgcctggggg agttttcctc    2280
```

```
tatacatctc tccccaaccc taggttccct gttcttcctc cagctgcacc agagcaacct    2340
ctcactcccc atgccacgtt ccacagttgc caccacctct gtggcattga aatgagcacc    2400
tccattaaag tctgaatcag tgc                                            2423
```

<210> SEQ ID NO 6
<211> LENGTH: 434
<212> TYPE: PRT
<213> ORGANISM: Homo sapiens

<400> SEQUENCE: 6

```
Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60

Ala Val Asp His Ile Asn Ser Thr Ile Ala Pro Ala Leu Ile Ser Ser
65                  70                  75                  80

Gly Leu Ser Val Val Glu Gln Glu Lys Leu Asp Asn Leu Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Thr Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
```

```
                    340                 345                 350
Ala Ile Gln Ala Cys Lys Leu Ala Gln Glu Asn Gly Trp Gly Val Met
                355                 360                 365

Val Ser His Arg Ser Gly Glu Thr Glu Asp Thr Phe Ile Ala Asp Leu
            370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu

<210> SEQ ID NO 7
<211> LENGTH: 1536
<212> TYPE: DNA
<213> ORGANISM: Homo sapiens

<400> SEQUENCE: 7
```

| | | | | | |
|---|---|---|---|---|---|
| ataaatgcgc | agcctgagag | ggggtgagct | gacactgtcc | cagctgccac | ctagactcgg | 60 |
| agctccatcc | aaacctccag | cgaagacatc | ccaggtcggg | tgaatcttcc | agccctgggg | 120 |
| gtggaggtag | taaggccat | ggccatgcag | aaaatctttg | cccgggaaat | cttggactcc | 180 |
| aggggcaacc | ccacggtgga | ggtggacctg | cacacggcca | agggccgatt | ccgagcagct | 240 |
| gtgcccagtg | gggcttccac | gggtatctat | gaggctctgg | aactaagaga | cggagacaaa | 300 |
| ggccgctacc | tggggaaagg | agtcctgaag | gctgtggaga | acatcaacaa | tactctgggc | 360 |
| cctgctctgc | tgcaaaagaa | actaagcgtt | gtggatcaag | aaaaagttga | caaatttatg | 420 |
| attgagctag | atgggaccga | gaataagtcc | aagtttgggg | ccaatgccat | cctgggcgtg | 480 |
| tccttggccg | tgtgtaaggc | gggagcagct | gagaaggggg | tcccccctgta | ccgccacatc | 540 |
| gcagatctcg | ctgggaaccc | tgacctcata | ctcccagtgc | cagccttcaa | tgtgatcaac | 600 |
| gggggctccc | atgctggaaa | caagctggcc | atgcaggagt | tcatgattct | gcctgtggga | 660 |
| gccagctcct | tcaaggaagc | catgcgcatt | ggcgccgagg | tctaccacca | cctcaagggg | 720 |
| gtcatcaagg | ccaagtatgg | gaaggatgcc | accaatgtgg | gtgatgaagg | tggcttcgca | 780 |
| cccaacatcc | tggagaacaa | tgaggccctg | gagctgctga | agacggccat | ccaggcggct | 840 |
| ggttacccag | acaaggtggt | gatcggcatg | gatgtggcag | catctgagtt | ctatcgcaat | 900 |
| gggaagtacg | atcttgactt | caagtcgcct | gatgatcccg | cacggcacat | cactggggag | 960 |
| aagctcggag | agctgtataa | gagctttatc | aagaactatc | ctgtggtctc | catcgaagac | 1020 |
| ccctttgacc | aggatgactg | gccactttgg | acctccttcc | tctcgggggt | gaacatccag | 1080 |
| attgtggggg | atgacttgac | agtcaccaac | cccaagagga | ttgcccaggc | cgttgagaag | 1140 |
| aaggcctgca | actgtctgct | gctgaaggtc | aaccagatcg | gctcggtgac | cgaatcgatc | 1200 |
| caggcgtgca | aactggctca | gtctaatggc | tggggggtga | tggtgagcca | ccgctctggg | 1260 |
| gagactgagg | acacattcat | tgctgacctt | gtggtgggc | tctgcacagg | acagatcaag | 1320 |
| actggcgccc | cctgccgctc | ggagcgtctg | gccaaataca | accaactcat | gaggatcgag | 1380 |
| gaggctcttg | ggacaaggc | aatctttgct | ggacgcaagt | tccgtaaccc | gaaggccaag | 1440 |
| tgagaagctg | gaggctccag | gactccactg | gacagaccca | ggtcttccag | acctgcttcc | 1500 |
| tgaaataaac | actggtgcca | accaagaaaa | aaaaaa | | | 1536 |

<210> SEQ ID NO 8
<211> LENGTH: 1494
<212> TYPE: DNA
<213> ORGANISM: Homo sapiens

<400> SEQUENCE: 8

```
ataaatgcgc agcctgagag ggggtgagct gacactgtcc cagctgccac ctagactcgg      60
agctccatcc aaacctccag cgaagacatc ccagccatgg ccatgcagaa aatctttgcc     120
cgggaaatct tggactccag gggcaacccc acggtggagg tggacctgca cacggccaag     180
ggccgattcc gagcagctgt gcccagtggg gcttccacgg gtatctatga ggctctggaa     240
ctaagagacg gagacaaagg ccgctacctg gggaaaggag tcctgaaggc tgtggagaac     300
atcaacaata ctctgggccc tgctctgctg caaaagaaac taagcgttgt ggatcaagaa     360
aaagttgaca aatttatgat tgagctagat gggaccgaga ataagtccaa gtttggggcc     420
aatgccatcc tgggcgtgtc cttggccgtg tgtaaggcgg gagcagctga aaggggggtc     480
cccctgtacc gccacatcgc agatctcgct gggaaccctg acctcatact cccagtgcca     540
gccttcaatg tgatcaacgg gggctcccat gctggaaaca gctggccat gcaggagttc     600
atgattctgc ctgtgggagc cagctccttc aaggaagcca tgcgcattgg cgccgaggtc     660
taccaccacc tcaagggggt catcaaggcc aagtatggga aggatgccac caatgtgggt     720
gatgaaggtg gcttcgcacc caacatcctg agaacaatg aggccctgga gctgctgaag     780
acggccatcc aggcggctgg ttacccagac aaggtggtga tcggcatgga tgtggcagca     840
tctgagttct atcgcaatgg gaagtacgat cttgacttca gtcgcctga tgatcccgca     900
cggcacatca ctggggagaa gctcggagag ctgtataaga gctttatcaa gaactatcct     960
gtggtctcca tcgaagaccc ctttgaccag atgactgggg ccacttggac ctccttcctc    1020
tcggggtga acatccagat tgtgggggat gacttgacag tcaccaaccc caagaggatt    1080
gcccaggccg ttgagaagaa ggcctgcaac tgtctgctgc tgaaggtcaa ccagatcggc    1140
tcggtgaccg aatcgatcca ggcgtgcaaa ctggctcagt ctaatggctg ggggtgatg    1200
gtgagccacc gctctgggga gactgaggac acattcattg ctgaccttgt ggtggggctc    1260
tgcacaggac agatcaagac tggcgccccc tgccgctcgg agcgtctggc caaatacaac    1320
caactcatga ggatcgagga ggctcttggg gacaaggcaa tctttgctgg acgcaagttc    1380
cgtaacccga aggccaagtg agaagctgga ggctccagga ctccactgga cagacccagg    1440
tcttccagac ctgcttcctg aaataaacac tggtgccaac caagaaaaaa aaaa          1494
```

<210> SEQ ID NO 9
<211> LENGTH: 434
<212> TYPE: PRT
<213> ORGANISM: Homo sapiens

<400> SEQUENCE: 9

```
Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gly Arg Tyr Leu Gly Lys Gly Val Leu Lys
    50                  55                  60

Ala Val Glu Asn Ile Asn Asn Thr Leu Gly Pro Ala Leu Leu Gln Lys
```

```
              65                  70                  75                  80
Lys Leu Ser Val Val Asp Gln Glu Lys Val Asp Lys Phe Met Ile Glu
                      85                  90                  95

Leu Asp Gly Thr Glu Asn Lys Ser Lys Phe Gly Ala Asn Ala Ile Leu
                100                 105                 110

Gly Val Ser Leu Ala Val Cys Lys Ala Gly Ala Ala Glu Lys Gly Val
            115                 120                 125

Pro Leu Tyr Arg His Ile Ala Asp Leu Ala Gly Asn Pro Asp Leu Ile
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Lys Glu Ala Met Arg Ile Gly Ala Glu Val Tyr His His Leu
                180                 185                 190

Lys Gly Val Ile Lys Ala Lys Tyr Gly Lys Asp Ala Thr Asn Val Gly
            195                 200                 205

Asp Glu Gly Gly Phe Ala Pro Asn Ile Leu Glu Asn Asn Glu Ala Leu
        210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
                245                 250                 255

Tyr Asp Leu Asp Phe Lys Ser Pro Asp Asp Pro Ala Arg His Ile Thr
                260                 265                 270

Gly Glu Lys Leu Gly Glu Leu Tyr Lys Ser Phe Ile Lys Asn Tyr Pro
            275                 280                 285

Val Val Ser Ile Glu Asp Pro Phe Asp Gln Asp Trp Ala Thr Trp
        290                 295                 300

Thr Ser Phe Leu Ser Gly Val Asn Ile Gln Ile Val Gly Asp Asp Leu
305                 310                 315                 320

Thr Val Thr Asn Pro Lys Arg Ile Ala Gln Ala Val Glu Lys Lys Ala
                325                 330                 335

Cys Asn Cys Leu Leu Leu Lys Val Asn Gln Ile Gly Ser Val Thr Glu
                340                 345                 350

Ser Ile Gln Ala Cys Lys Leu Ala Gln Ser Asn Gly Trp Gly Val Met
            355                 360                 365

Val Ser His Arg Ser Gly Glu Thr Glu Asp Thr Phe Ile Ala Asp Leu
        370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
                405                 410                 415

Leu Gly Asp Lys Ala Ile Phe Ala Gly Arg Lys Phe Arg Asn Pro Lys
            420                 425                 430

Ala Lys

<210> SEQ ID NO 10
<211> LENGTH: 1365
<212> TYPE: DNA
<213> ORGANISM: Homo sapiens

<400> SEQUENCE: 10
ataaatgcgc agcctgagag ggggtgagct gacactgtcc cagctgccac ctagactcgg    60
```

```
agctccatcc aaacctccag cgaagacatc ccagccatgg ccatgcagaa aatctttgcc    120
cgggaaatct tggactccag gggcaacccc acggtggagg tggacctgca cacggccaag    180
ggccgattcc gagcagctgt gcccagtggg gcttccacgg gtatctatga ggctctggaa    240
ctaagagacg gagacaaagg ccgctacctg gggaaagcca agtttggggc caatgccatc    300
ctgggcgtgt ccttggccgt gtgtaaggcg ggagcagctg agaagggggt ccccctgtac    360
cgccacatcg cagatctcgc tgggaaccct gacctcatac tcccagtgcc agccttcaat    420
gtgatcaacg ggggctccca tgctggaaac aagctggcca tgcaggagtt catgattctg    480
cctgtgggag ccagctcctt caaggaagcc atgcgcattg gcgccgaggt ctaccaccac    540
ctcaaggggg tcatcaaggc caagtatggg aaggatgcca ccaatgtggg tgatgaaggt    600
ggcttcgcac ccaacatcct ggagaacaat gaggccctgg agctgctgaa gacggccatc    660
caggcggctg gttacccaga caaggtggtg atcggcatgg atgtggcagc atctgagttc    720
tatcgcaatg ggaagtacga tcttgacttc aagtcgcctg atgatcccgc acggcacatc    780
actggggaga agctcggaga gctgtataag agctttatca gaactatcc tgtggtctcc    840 atcgaagacc cctttgacca ggatgactgg gccacttgga cctccttcct ctcgggggtg    900
aacatccaga ttgtggggga tgacttgaca gtcaccaacc ccaagaggat tgcccaggcc    960
gttgagaaga aggcctgcaa ctgtctgctg ctgaaggtca accagatcgg ctcggtgacc   1020
gaatcgatcc aggcgtgcaa actggctcag tctaatggct gggggtgat ggtgagccac   1080 cgctctgggg agactgagga cacattcatt gctgaccttg tggtggggct ctgcacagga   1140
cagatcaaga ctggcgcccc ctgccgctcg agcgtctgg ccaaatacaa ccaactcatg   1200
aggatcgagg aggctcttgg ggacaaggca atctttgctg gacgcaagtt ccgtaacccg   1260
aaggccaagt gagaagctgg aggctccagg actccactgg acagacccag gtcttccaga   1320
cctgcttcct gaaataaaca ctggtgccaa ccaagaaaaa aaaaa                   1365
```

<210> SEQ ID NO 11
<211> LENGTH: 391
<212> TYPE: PRT
<213> ORGANISM: Homo sapiens

<400> SEQUENCE: 11

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gly Arg Tyr Leu Gly Lys Ala Lys Phe Gly
    50                  55                  60

Ala Asn Ala Ile Leu Gly Val Ser Leu Ala Val Cys Lys Ala Gly Ala
65                  70                  75                  80

Ala Glu Lys Gly Val Pro Leu Tyr Arg His Ile Ala Asp Leu Ala Gly
                85                  90                  95

Asn Pro Asp Leu Ile Leu Pro Val Pro Ala Phe Asn Val Ile Asn Gly
            100                 105                 110

Gly Ser His Ala Gly Asn Lys Leu Ala Met Gln Glu Phe Met Ile Leu
        115                 120                 125

Pro Val Gly Ala Ser Ser Phe Lys Glu Ala Met Arg Ile Gly Ala Glu
    130                 135                 140

```
Val Tyr His His Leu Lys Gly Val Ile Lys Ala Lys Tyr Gly Lys Asp
145                 150                 155                 160

Ala Thr Asn Val Gly Asp Glu Gly Gly Phe Ala Pro Asn Ile Leu Glu
                165                 170                 175

Asn Asn Glu Ala Leu Glu Leu Leu Lys Thr Ala Ile Gln Ala Ala Gly
            180                 185                 190

Tyr Pro Asp Lys Val Val Ile Gly Met Asp Val Ala Ala Ser Glu Phe
        195                 200                 205

Tyr Arg Asn Gly Lys Tyr Asp Leu Asp Phe Lys Ser Pro Asp Asp Pro
    210                 215                 220

Ala Arg His Ile Thr Gly Glu Lys Leu Gly Leu Tyr Lys Ser Phe
225                 230                 235                 240

Ile Lys Asn Tyr Pro Val Val Ser Ile Glu Asp Pro Phe Asp Gln Asp
                245                 250                 255

Asp Trp Ala Thr Trp Thr Ser Phe Leu Ser Gly Val Asn Ile Gln Ile
            260                 265                 270

Val Gly Asp Asp Leu Thr Val Thr Asn Pro Lys Arg Ile Ala Gln Ala
        275                 280                 285

Val Glu Lys Lys Ala Cys Asn Cys Leu Leu Lys Val Asn Gln Ile
290                 295                 300

Gly Ser Val Thr Glu Ser Ile Gln Ala Cys Lys Leu Ala Gln Ser Asn
305                 310                 315                 320

Gly Trp Gly Val Met Val Ser His Arg Ser Gly Glu Thr Glu Asp Thr
                325                 330                 335

Phe Ile Ala Asp Leu Val Val Gly Leu Cys Thr Gly Gln Ile Lys Thr
            340                 345                 350

Gly Ala Pro Cys Arg Ser Glu Arg Leu Ala Lys Tyr Asn Gln Leu Met
        355                 360                 365

Arg Ile Glu Glu Ala Leu Gly Asp Lys Ala Ile Phe Ala Gly Arg Lys
    370                 375                 380

Phe Arg Asn Pro Lys Ala Lys
385                 390

<210> SEQ ID NO 12
<211> LENGTH: 7
<212> TYPE: PRT
<213> ORGANISM: Artificial Sequence
<220> FEATURE:
<223> OTHER INFORMATION: muscle targeting peptide

<400> SEQUENCE: 12

Ala Ser Ser Leu Asn Ile Ala
1               5

<210> SEQ ID NO 13
<211> LENGTH: 7
<212> TYPE: PRT
<213> ORGANISM: Artificial Sequence
<220> FEATURE:
<223> OTHER INFORMATION: muscle targeting peptide

<400> SEQUENCE: 13

Trp Asp Ala Asn Gly Lys Thr
1               5

<210> SEQ ID NO 14
<211> LENGTH: 7
<212> TYPE: PRT
```

```
<213> ORGANISM: Artificial Sequence
<220> FEATURE:
<223> OTHER INFORMATION: muscle targeting peptide

<400> SEQUENCE: 14

Gly Glu Thr Arg Ala Pro Leu
1               5

<210> SEQ ID NO 15
<211> LENGTH: 9
<212> TYPE: PRT
<213> ORGANISM: Artificial Sequence
<220> FEATURE:
<223> OTHER INFORMATION: muscle targeting peptide

<400> SEQUENCE: 15

Cys Gly His His Pro Val Tyr Ala Cys
1               5

<210> SEQ ID NO 16
<211> LENGTH: 7
<212> TYPE: PRT
<213> ORGANISM: Artificial Sequence
<220> FEATURE:
<223> OTHER INFORMATION: muscle targeting peptide

<400> SEQUENCE: 16

His Ala Ile Tyr Pro Arg His
1               5
```